(12) United States Patent
Akselrod

(10) Patent No.: US 11,419,703 B2
(45) Date of Patent: Aug. 23, 2022

(54) ORTHODONTIC BRACES AND FEET ORTHOTICS WITH BACKSCATTER BASED SENSORS

(71) Applicant: David Akselrod, Burlington (CA)

(72) Inventor: David Akselrod, Burlington (CA)

( * ) Notice: Subject to any disclaimer, the term of this patent is extended or adjusted under 35 U.S.C. 154(b) by 199 days.

(21) Appl. No.: 16/714,446

(22) Filed: Dec. 13, 2019

(65) Prior Publication Data

US 2020/0113654 A1    Apr. 16, 2020

Related U.S. Application Data

(63) Continuation-in-part of application No. 15/653,461, filed on Jul. 18, 2017, now Pat. No. 10,758,153, which is a continuation-in-part of application No. 15/607,673, filed on May 29, 2017, which is a continuation-in-part of application No. 15/418,414, filed on Jan. 27, 2017.

(60) Provisional application No. 62/779,748, filed on Dec. 14, 2018.

(51) Int. Cl.
*A61C 7/08* (2006.01)
*A61B 5/0534* (2021.01)
*A61B 5/00* (2006.01)
*H02J 50/20* (2016.01)

(52) U.S. Cl.
CPC ............. *A61C 7/08* (2013.01); *A61B 5/0031* (2013.01); *A61B 5/0534* (2013.01); *A61B 5/6847* (2013.01); *A61B 2562/046* (2013.01); *A61B 2562/08* (2013.01); *H02J 50/20* (2016.02)

(58) Field of Classification Search
CPC ....... A61C 7/08; A61C 19/063; A63B 71/085; A61B 2562/08; A61B 2562/085; A61B 2562/046; H02J 50/05; H02J 50/10; H02J 50/20; H02J 50/23; H02J 50/27; H02J 50/30
See application file for complete search history.

(56) References Cited

U.S. PATENT DOCUMENTS

| 5,251,635 A | 10/1993 | Dumoulin |
|---|---|---|
| 5,791,350 A | 8/1998 | Morton |
| 6,239,705 B1 | 5/2001 | Glen |

(Continued)

*Primary Examiner* — Jacqueline T Johanas
*Assistant Examiner* — Shannel Nicole Belk
(74) *Attorney, Agent, or Firm* — Eric Kelly

(57) ABSTRACT

Inventions herein include at least mostly optically clear orthodontic braces and feet orthotics (collectively referred to as "appliances") with backscatter based sensors. These two categories of appliances share a common property requiring that the given appliance must be correctly custom manufactured to fit a patient's own particular geometry and dimensions of their teeth and/or feet in order to perform as intended. Incorporating such appliances with backscatter based sensors enables simple, easy, fast, efficient, and cost effective measurements, in real-time or near real-time, of stresses, forces, structural changes, and/or the like in the given appliance; which in turn can aid in determining if adjustments or re-manufacture of the appliance may be needed or desired; and/or wherein such measurements may aid in evaluating performance of the given appliance. In some embodiments, such measurements may also be taken remotely away from a practitioner; and then communicated to a remotely located practitioner.

19 Claims, 63 Drawing Sheets

(56) References Cited

U.S. PATENT DOCUMENTS

| | | |
|---|---|---|
| 7,978,074 B2 | 7/2011 | Nikitin |
| 10,265,017 B1 | 4/2019 | Myslinski |
| 2005/0201450 A1 | 9/2005 | Volpi |
| 2006/0134580 A1 | 6/2006 | Raby |
| 2006/0166157 A1* | 7/2006 | Rahman ............... A61B 5/4833 433/6 |
| 2006/0180647 A1 | 8/2006 | Hansen |
| 2006/0187044 A1 | 8/2006 | Fabian |
| 2006/0232408 A1 | 10/2006 | Nycz |
| 2007/0106138 A1 | 5/2007 | Beiski |
| 2008/0117021 A1 | 5/2008 | Brunski |
| 2008/0119698 A1* | 5/2008 | Tricca ................. A61B 5/4839 600/309 |
| 2008/0204240 A1 | 8/2008 | Hilgers |
| 2009/0237236 A1 | 5/2009 | Maassarani |
| 2009/0155744 A1 | 6/2009 | Jandali |
| 2009/0231101 A1 | 9/2009 | Hyde |
| 2009/0286195 A1* | 11/2009 | Sears ..................... A61C 7/14 433/8 |
| 2010/0001841 A1 | 1/2010 | Cardullo |
| 2010/0007469 A1 | 1/2010 | Cardullo |
| 2010/0097194 A1 | 4/2010 | Killian |
| 2010/0105011 A1 | 4/2010 | Karkar |
| 2010/0143871 A1 | 6/2010 | Berger |
| 2011/0034912 A1 | 2/2011 | de Graff |
| 2011/0136076 A1 | 6/2011 | Li |
| 2012/0126948 A1 | 5/2012 | Brunski |
| 2012/0220986 A1 | 8/2012 | Wolff |
| 2013/0181048 A1 | 7/2013 | Liu |
| 2013/0274563 A1 | 10/2013 | Duesterhoft |
| 2014/0062717 A1 | 3/2014 | Mudumbai |
| 2014/0246917 A1 | 9/2014 | Proud |
| 2014/0248574 A1 | 9/2014 | Koon |
| 2014/0276603 A1 | 9/2014 | Magee |
| 2014/0335469 A1* | 11/2014 | Boyden ................. A61C 7/20 433/215 |
| 2015/0141268 A1 | 5/2015 | Rothberg |
| 2015/0216641 A1 | 8/2015 | Popa-Simil |
| 2015/0260498 A1 | 9/2015 | Soohoo |
| 2015/0374469 A1* | 12/2015 | Konno ................... A61B 5/228 433/27 |
| 2016/0084894 A1 | 3/2016 | Govindaraj |
| 2016/0135917 A1 | 5/2016 | Mickle |
| 2016/0220330 A1 | 8/2016 | Lemchen |
| 2016/0354012 A1 | 12/2016 | Zeng |
| 2017/0056131 A1* | 3/2017 | Alauddin ............... A61C 19/04 |
| 2017/0128168 A1 | 5/2017 | Bindayel |
| 2017/0252140 A1* | 9/2017 | Murphy ............... A61B 5/4833 |
| 2017/0286820 A1 | 10/2017 | Nikunen |
| 2018/0000565 A1* | 1/2018 | Shanjani ............... A61C 7/002 |
| 2018/0008378 A1 | 1/2018 | Raghavan |
| 2018/0078334 A1* | 3/2018 | Lotan ................... A61B 5/1111 |
| 2018/0153450 A1 | 6/2018 | Routh |
| 2018/0271401 A1 | 9/2018 | Greene |
| 2018/0368767 A1 | 12/2018 | Albalat Estela |
| 2019/0117339 A1 | 4/2019 | Bolzan |
| 2019/0192259 A1* | 6/2019 | Kopelman ........... A61B 5/1111 |
| 2019/0223751 A1 | 7/2019 | Weinstein |
| 2019/0243997 A1 | 8/2019 | Danaei-Moghaddam |
| 2020/0187860 A1 | 6/2020 | Myslinski |
| 2020/0188164 A1 | 6/2020 | Myslinski |
| 2020/0188708 A1 | 6/2020 | Myslinski |

* cited by examiner

ORTHODONTIC BRACES AND FEET ORTHOTICS WITH BACKSCATTER BASED SENSORS

PRIORITY NOTICE

The present application claims priority under 35 U.S.C. § 119(e) to U.S. Provisional Patent Application Ser. No. 62/779,748 filed on Dec. 14, 2018, the disclosure of which is incorporated herein by reference in its entirety.

The present patent application is a continuation-in-part (CIP) of U.S. non-provisional patent application Ser. No. 15/607,673 filed on May 29, 2017, and claims priority to said U.S. non-provisional patent application under 35 U.S.C. § 120. The above-identified patent application is incorporated herein by reference in its entirety as if fully set forth below.

The present patent application is a continuation-in-part (CIP) of U.S. non-provisional patent application Ser. No. 15/653,461 filed on Jul. 18, 2017, and claims priority to said U.S. non-provisional patent application under 35 U.S.C. § 120. The above-identified patent application is incorporated herein by reference in its entirety as if fully set forth below.

The present patent application is a continuation-in-part (CIP) of U.S. non-provisional patent application Ser. No. 15/418,414 filed on Jan. 27, 2017, and claims priority to said U.S. non-provisional patent application under 35 U.S.C. § 120. The above-identified patent application is incorporated herein by reference in its entirety as if fully set forth below.

TECHNICAL FIELD OF THE INVENTION

The present invention relates in general to monitoring states of substantially optically clear orthodontic braces and foot orthotics and, more specifically, to monitoring states of substantially optically clear orthodontic braces and foot orthotics using backscatter sensor tags that are part of the substantially optically clear orthodontic braces and/or part of the foot orthotics.

The present invention also relates in general to manufacturing, adjusting or re-manufacturing medical, orthodontic, dental, podiatric or orthopedic appliances via measuring or monitoring physical states of materials of interest constituting the said appliances and, more specifically, to monitoring physical states of materials of interest using wireless sensor tags and where the materials of interest may have uses in dental, medical, and/or construction fields.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

Prior art imaging techniques, such as, X-ray, CT-scan, MRI, ultrasound, radar, and/or the like generally involve expensive (expensive to buy, lease, use, train, maintain, etc.), specialized, complicated equipment, and/or equipment that may occupy a relatively large footprint. And in many applications the electromagnetic energy emitted for imaging purposes from some prior art imaging systems may be dangerous or destructive to the object being imaged and thus such imaging must be minimized to prevent problems from overexposure. A prime example of this is the use of X-rays to image hard (dense) structures in biologic samples, such as teeth and bones in vertebrates; where overexposure to X-rays may lead to undesirable mutations and cancers. And even in the case of inanimate objects, such objects may also still be prone to deterioration (e.g., becoming brittle) resulting from overexposure to emitted high energy imaging electromagnetic radiation, such as X-rays. In many instances, if overexposure was not a problem, practitioners would then prefer to utilize such imaging techniques more frequently thus significantly increasing probability of discovering issues earlier in time. In some instances, such as with cancer patients or with pregnant women, use of X-rays is necessarily restricted.

There is a need in the art for imaging techniques that in comparison to preexisting imaging techniques of X-ray, CT-scan, MRI, ultrasound, radar, and/or the like would be comparatively less expensive to implement; and/or would require a smaller equipment footprint to utilize. Additionally, there is a need in the art for a non-invasive, contactless, imaging techniques that may utilize comparatively less energetic electromagnetic spectra, such as radio waves to communicate information that upon analysis may yield imaging results and other state information of a given material-of-interest (e.g., one or more orthodontic-elements) to be imaged.

It is to these ends that the present invention has been developed. Embodiments of the present invention may provide novel ways of analyzing (monitoring and/or tracking) current states, structural integrity, and various qualities of various materials-of-interest; with applications in medical care, dentistry, and construction and engineering without use of preexisting imaging techniques that may use X-ray, CT-scan, MRI, ultrasound, and/or a reliance upon dangerous imaging techniques utilizing ionizing radiation. Examples of materials-of-interest may include, but may not be limited to: dental fillings, root canals, dental crowns, dental sealants and resins, dental and other medical implants, and other structures used in medicine, dentistry and/or construction and/or engineering.

Using minimization advances in microelectronics and process manufacturing techniques, negligibly-sized micro-sensors may be implanted in the material-of-interest to be analyzed (monitored and/or tracked). In some applications, implantation of such negligibly-sized micro-sensors may be done prior to the given material-of-interest curing and/or hardening, e.g., a dental filling. Using the disclosed imaging technology, subsequent to the completion of such curing or hardening, the current state, e.g., the structural integrity, may be scanned (imaged) to determine possible problems in the material-of-interest such as, but not limited to, possible fracturing, cracking, bending, twisting, torsion, excessive pressure, shear stress, tension, compression, abnormal temperature, foreign materials or liquids penetration, and/or the like. And such analysis may be done non-invasively, without use of ionizing radiation in some applications, and reading of the implanted negligibly-sized micro-sensors may be remotely measured. Thus, such scanning (i.e., reading or imaging) may be done comparatively much more frequently that would be permitted if the practitioner had to rely upon using X-ray imaging.

The disclosed imaging techniques may not require a power source in the implanted negligibly-sized micro-sensors. Energy required for the operation of the implanted negligibly-sized micro-sensors may be harvested from external electromagnetic energy sources during the reading (scanning) process.

Embodiments of the present invention may also establish locations (e.g., positions or coordinates) of backscatter-devices with the implanted negligibly-sized micro-sensors. Such location determination may utilize well-known LPS (local positioning systems) techniques, that may involve use of triangulation, trilateration, multilateration, combinations thereof, and the like; as well as involve solving various nonlinear equations using various well-known techniques. Embodiments of the present invention may provide contactless ways of determining real-time locations as well as real-time sensor readings of and from these implanted negligibly-sized backscatter-devices with sensors, which over time and over differently placed implanted negligibly-sized backscatter-devices with sensors may yield information as to the various current states and changes in state of the given material-of-interest that is being monitored (e.g., one or more orthodontic-elements).

These backscatter-devices (with sensors or without sensors) may be referred to as RFID tags or Near-Field Communication (NFC) devices. Distances (ranges) between these backscatter-devices (with sensors or without sensors) and various readers may readily be determined. The reader may emit various electromagnetic signals and may receive back "backscattered" (returned) electromagnetic signals from the backscatter-devices (with sensors or without sensors). And from such returning backscattered electromagnetic signals, distances (ranges) as well as location determination and readings from sensors may then be utilized to analyze various states of the material-of-interest being monitored.

Localization (location determination) of backscatter-devices using well-known LPS (local positioning systems) techniques, that may involve use of triangulation, trilateration, multilateration, combinations thereof, and/or the like is well understood in the relevant art. For example, range measurements between readers and backscatter-devices may be based on a number of prior art techniques, among them determining ranges based on phase differences between transmitted and backscattered (returned) signals, Returned Signal Strength (RSSI), and/or other means. For example, trilateration may be a well-known technique of determining three-dimensional (3D) coordinates of an object using the measured ranges (distances) from that object to three or more other objects with known three-dimensional (3D) coordinates. Triangulation may another well-known technique in this context.

Prior art techniques used for applying medical, orthodontic, dental, podiatric or orthopedic appliances, once said appliances are manufactured, do not make use of ongoing feedback to evaluate their effectiveness and make respective changes. Specifically, no adjustments are made based on the measurements, made during the active usage of the appliances, of one or more of: structural integrity of a current state of the appliances; structural integrity changes of the appliances; pressure received at the appliances; force received at the appliances; stress received at the appliances; torsion received at the appliances; deformation received at the appliances; temperature at some portion of the appliances; and/or the like.

An example of this may be the process of using existing podiatric appliances such as orthotic insoles. Once the patient undergoes evaluation and orthotic insoles are manufactured, no adjustments of the said orthotic insoles are usually made based on measurements during the active usage of the insoles. Changes in a patient's gate, physical changes in his/her feet, physical changes in the said orthotic insoles or other changes may diminish the effectiveness of the treatment. However, even if a patient were to request an additional re-evaluation, it would be done based on external scans of his/her feet and not based on the forces acting on his/her orthotic insoles during an active usage of the said insoles. In this respect, mistakes in manufacturing of the said orthotic insoles may not be discovered and corrected.

Another example may be an application of the orthodontic appliances such as an orthodontic-braces (such as a teeth tray or teeth aligner), an orthodontic-bracket, an orthodontic-archwire, an orthodontic-spring, an orthodontic-expander, an orthodontic elastic-band, an orthodontic-power-chain, an orthodontic-band, and/or the like. It is only during orthodontist or dentist visits and only by means of imaging scans or manual examination that the orthodontist or dentist may observe the need to make corrections in said orthodontic appliances. For example, an orthodontic-archwire or an orthodontic expander may not be exerting correct force on some teeth due to variety of reasons such as miscalculation, different from expected changes in teeth development, materials fatigue, and/or other reasons. Even during orthodontists appointments, the adjustments are not done based on the actual forces acting on the said orthodontic appliances during their active use but rather based on the measurements or examination done on patients teeth.

There is a need in the art for techniques that in comparison to preexisting techniques of applying and manufacturing medical, orthodontic, dental, podiatric or orthopedic appliances would enable ongoing monitoring and ongoing adjustment or re-manufacturing of the said appliances based on either changes in the said appliances and/or based on the changes in the patient. For example, based on such monitoring, changes to the said appliances should be done or new appliances should be manufactured to account for changes that took place since the original appliances were made or adjusted, and/or based on the actual forces and/or effects of said appliance on the patient during their usage.

Additionally, there is a need in the art for the said techniques to be comparatively less expensive to implement; and/or would require a smaller equipment footprint to utilize.

Additionally, there is a need in the art for a non-invasive, contactless, imaging techniques that may utilize comparatively less energetic electromagnetic spectra, such as radio waves to communicate information that upon analysis may yield imaging results and other state information of a given material-of-interest (e.g., one or more orthodontic-elements) to be imaged.

It is to these ends that the present invention has been developed. Embodiments of the present invention may provide novel ways of analyzing (monitoring and/or tracking) current states, structural integrity, various qualities and forces acting on materials-of-interest used in appliances utilized in medical care, dentistry, podiatry or construction. Examples of materials-of-interest may include, but may not be limited to those used in manufacturing of: medical, orthodontic, dental, podiatric or orthopedic appliances, dental and other medical implants, corrective appliances, and other structures used in medicine, dentistry and/or construction and/or engineering.

Using minimization advances in microelectronics and process manufacturing techniques, negligibly-sized micro-sensors may be implanted in the material-of-interest used to manufacture the said medical, orthodontic, dental, podiatric or orthopedic appliances or implanted or placed in the said appliances to be analyzed (monitored and/or tracked).

In some cases, such as orthotic insoles manufacturing, a bigger-sized (e.g., an order of a number of millimeters or centimeters) sensors may be used.

In some applications, implantation of such negligibly-sized micro-sensors may be done prior to the given material-of-interest curing and/or hardening, e.g., orthodontic corrective devices. Using the disclosed imaging technology, subsequent to the completion of such curing or hardening, the current state, e.g., the structural integrity, may be scanned (imaged) to determine possible problems in the material-of-interest such as, but not limited to, possible fracturing, cracking, bending, twisting, torsion, excessive pressure, shear stress, tension, compression, abnormal temperature, foreign materials or liquids penetration, and/or the like. And such analysis may be done non-invasively, without use of ionizing radiation in some applications, and reading of the implanted negligibly-sized micro-sensors may be remotely measured. Thus, such scanning (i.e., reading or imaging) may be done comparatively much more frequently that would be permitted if the practitioner had to rely upon using X-ray imaging.

The disclosed imaging techniques may not require a power source in the implanted sensors. Energy required for the operation and communication with the implanted sensors may be harvested from external electromagnetic energy sources during the reading (scanning) process. Examples of such devices could be electromagnetic induction-based devices, backscatter devices, among others.

The said backscatter-devices (with sensors or without sensors) may be referred to as RFID tags or Near-Field Communication (NFC) devices. The reader, which in some instances could be integrated in the cellular smartphone or other devices, may emit various electromagnetic signals and may receive back "backscattered" (returned) electromagnetic signals from the backscatter-devices (with sensors or without sensors). And from such returning backscattered electromagnetic signals, readings from sensors may then be utilized to analyze various states of the material-of-interest or appliances-of-interest being monitored.

BRIEF SUMMARY OF THE INVENTION

To minimize the limitations in the prior art, and to minimize other limitations that will be apparent upon reading and understanding the present specification, embodiments of the present invention describe devices (tags), systems, and methods to determine structural integrity and other states of materials-of-interest, such as dental fillings, implants, root canal posts, and various orthodontic-elements, to name a few, in a non-invasive and contactless way; and using comparatively safe and/or low energy electromagnetic radiation, such as, but not limited to, radio waves.

For example, and without limiting the scope of the present invention, in some embodiments, such a system may comprise one or more monitoring-sensor-tags and one or more readers. The one or more monitoring-sensor-tags may be attached to the material-of-interest, such as the one or more orthodontic-elements. The one or more orthodontic-elements may be selected from an orthodontic-bracket, an orthodontic-bracket-hook, an orthodontic-bracket-receiving-cavity, an orthodontic-bracket-lock, an orthodontic-archwire, an orthodontic-spring, an orthodontic-expander, an orthodontic elastic-band, an orthodontic-power-chain, an orthodontic-band, and/or the like. The one or more monitoring-sensor-tags may comprise at least one electric circuit, at least one antenna (a first-antenna), and at least one sensor. The at least one electric circuit may be in communication with the at least one antenna (the first-antenna) and the at least one sensor. The one or more readers may comprise one or more second-antennas. The one or more readers using the one or more second-antennas may transmit electromagnetic radiation of a predetermined characteristic. The first-antenna may receive this electromagnetic radiation of the predetermined characteristic as an input. This input may cause the at least one electric circuit to take one or more readings from the at least one sensor; and may then transmit the one or more readings using the first-antenna back to the one or more second-antennas. At least one of the second-antennas selected from the one or more second-antennas may then receive the one or more readings. The one or more readers or a device (e.g., a computer) in communication with the one or more readers may then use the one or more readings to determine the current state of the material-of-interest, such as the one or more orthodontic-elements.

Present inventions discussed herein may include substantially optically clear orthodontic braces and feet orthotics (collectively referred to as "appliances") with backscatter based sensors. These two categories of otherwise different appliances share a common property requiring that the given appliance must be correctly custom manufactured to fit the patient's own particular geometry and dimensions of their teeth and/or feet in order to perform as intended. Incorporating such appliances with backscatter based sensors enables simple, easy, fast, efficient, and cost effective measurements, in real-time or near real-time, of stresses, forces, structural changes, and/or the like in the given appliance; which in turn can aid in determining if adjustments or re-manufacture of appliance may be needed or desired; and/or wherein such measurements may aid in evaluating performance of the given appliance. In some embodiments, such measurements may also be taken remotely away from the practitioner (e.g., away from the orthodontist or away from the pediatrist); and the remotely generated measurement data may be communicated to the practitioner via standard network communication technology.

It is an objective of the present invention to provide an imaging system and an imaging method that may be comparatively less expensive to use and implement as compared against traditional X-ray, CT-scan, MRI, ultrasound, radar, or the like imaging systems.

It is another objective of the present invention to provide an imaging system and an imaging method that may be comparatively easy and simple to use and implement as compared against traditional X-ray, CT-scan, MRI, ultrasound, radar, or the like imaging systems.

It is another objective of the present invention to provide an imaging system and imaging method that comparatively utilizes as smaller equipment footprint as compared against traditional X-ray, CT-scan, MRI, ultrasound, radar, or the like imaging systems.

It is another objective of the present invention to provide devices (tags), systems, and methods to determine structural integrity and other states of a given orthodontic-element in a non-invasive and contactless way.

It is another objective of the present invention to provide devices (tags), systems, and methods to determine structural integrity and other states of a given orthodontic-element using comparatively safe and/or low energy electromagnetic radiation, such as radio waves.

It is another objective of the present invention to provide backscatter-tags with sensors (monitoring-sensor-tags) that may be implantable into a given type of orthodontic-element as discussed herein.

It is another objective of the present invention to provide backscatter-tags with sensors wherein the sensors may be of different types for measuring different qualities, properties, and/or characteristics.

It is another objective of the present invention to determine locations of backscatter-tags with sensors (monitoring-sensor-tags), that may be implantable into a given type of orthodontic-element, over time in the same monitoring-sensor-tag and/or as compared against different implanted monitoring-sensor-tags.

It is another objective of the present invention to provide a substantially optically clear orthodontic braces fitted with one or more backscatter tags (with sensor(s)).

It is another objective of the present invention to provide feet orthotics fitted with one or more backscatter tags (with sensor(s)).

It is another objective of the present invention to provide a system for monitoring data measurements from one or more backscatter tags (with sensor(s)) that may be fitted/incorporated to substantially optically clear orthodontic braces.

It is another objective of the present invention to provide a system for manufacturing, or/and re-adjusting substantially optically clear orthodontic braces based on monitoring or obtaining data measurements from one or more backscatter tags (with sensor(s)) that may be fitted/incorporated to said substantially optically clear orthodontic braces.

It is another objective of the present invention to provide a system for manufacturing, or/and re-adjusting feet orthotics based on monitoring or obtaining data measurements from one or more backscatter tags (with sensor(s)) that may be fitted/incorporated to said feet orthotics.

It is yet another objective of the present invention to provide a system for monitoring data measurements from one or more backscatter tags (with sensor(s)) that may be fitted/incorporated to feet orthotics.

These and other advantages and features of the present invention are described herein with specificity so as to make the present invention understandable to one of ordinary skill in the art, both with respect to how to practice the present invention and how to make the present invention.

BRIEF DESCRIPTION OF THE SEVERAL VIEWS OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention.

Figure 1A:
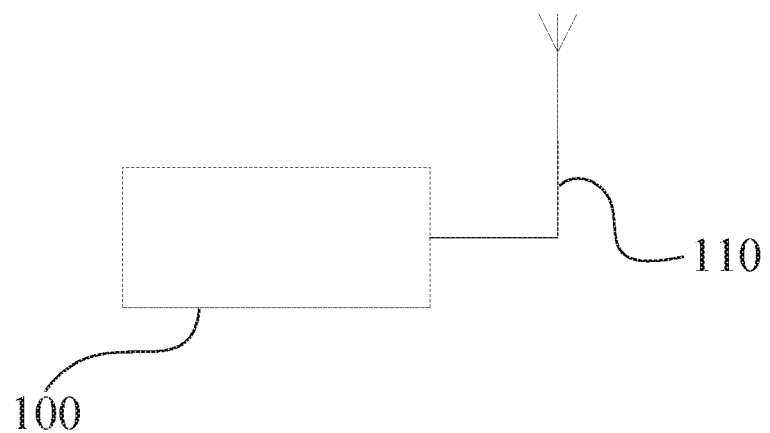
FIG. 1A may depict a schematic block diagram of a reader.

REFERENCE NUMERAL SCHEDULE 100 reader 100
110 antenna 110 (second-antenna 110)
120 monitoring-sensor-tag 120
130 antenna 130 (first-antenna 130)
140 electric circuit 140
202 capacitive-based sensor 202
203 resistance-based sensor 203
204 processing circuitry 204
205 capacitance measurement circuit 205
206 resistance measurement circuit 206
207 backscatter-receiver-and-transmitter 207
208 inductance-based-sensor 208
209 inductance measurement circuit 209
300 load capacitor 300
310 digital inventor 310 (e.g., a C-MOS pair 310)
340 capacitive-based sensor 340
350 ring oscillator 350
400 plate 400
401 dielectric material 401
402 conductive surface type "A" 402
403 substrate 403
404 conductive surface type "B" 404
405 conductive surface type "C" 405
406 conductive surface type "D" 406
407 conductive surface type "E" 407
408 conductive surface type "F" 408
500 ring oscillator 500
501 switch 501
502 P-MOS transistor 502
503 N-MOS transistor 503
600 ring oscillator 600
601 load resistor 601
602 strain-influenced resistor 602
700 strain-influenced resistor 700
701 thin-film-coating 701
702 substrate 702
703 spiral-formed-electric-conductor 703
801 sensor-portion 801
802 processing-portion 802
930 CLOCK 930
931 RESTART_COUNT signal 931
932 COUNTER 932
933 COUNTER OVERFLOW signal 933
934 zero value 934
935 0-to-1 transition of Pulse of Counter Overflow signal 935
936 1-to-0 transition of Pulse of Counter Overflow signal 936
937 maximal value 937
938 Pulse of RESTART_COUNT signal 938
1000 tooth 1000
1001 dental-filling 1001
1002 gum 1002
1003 root-canal-cavity 1003
1004 root-canal-post 1004
1005 dental-crown 1005

1006 standalone-strain-sensor 1006
1007 dental-implant 1007
1008 implant-post 1008
1020 first-sensor-tag 1020
1021 second-sensor-tag 1021
1023 lattice-of-sensors 1023
1025 initial predetermined spacing 1025
1026 sensor-spacing 1026
1028 material-of-interest 1028
1102 reference-sensor-tags 1102
1107 reference-housing-member 1107
1108 reader-housing-member 1108
1109 reader-and-calibration-member 1109
1110 member-separation-distance 1110
1111 reader-tag-separation-distance 1111
1112 reader-antenna-tag-separation-distance 1112
1113 reader-antenna-tag-separation-distance 1113
1115 antenna-interface 1115
1203 position-reference-tag 1203
1204 position-reference-member 1204
1320 Imaginary x-axis 1320
1321 Imaginary y-axis 1321
1322 Imaginary z-axis 1322
1325 origin 1325
1326 translating-scan-member 1326
1327 patient-fixation-member 1327
1328 patient 1328
1329 support 1329
1400 direction-of-motion 1400
1500 method 1500
1530 calibrate readers step 1530
1531 determine location of readers step 1531
1532 reader interrogation of monitoring-sensor-tags step 1532
1533 authentication step 1533
1534 determine location of monitoring-sensor-tags step 1534
1535 reader instructs monitoring-sensor-tags step 1535
1536 reader transmit "restart counting" command step 1536
1537 determine if additional measurements to be taken step 1537
1538 determine if reader location to be re-determined step 1538
1539 determine if different measurement types to be taken step 1539
1540 transmit received monitoring-sensor-tag transmission step 1540
1600 method 1600
1680 choose set of calibration reference-sensor-tags step 1680
1681 select particular calibration method and settings step 1681
1682 perform calibration reference-sensor-tags measurements step 1682
1683 process calibration reference-sensor-tags measurements step 1683
1700 method 1700
1772 measuring ranges of monitoring-sensor tags step 1772
1773 applying calibration-based corrections step 1773
1777 process results step 1777
1800 system 1800
1801 processor 1801
1803 memory 1803
1805 display 1805
1807 device 1807
1828 material-of-interest 1828
1900 orthodontic-bracket 1900

1901 tooth-surface 1901
1903 base 1903
1905 head 1905
1907 orthodontic-bracket-receiving-cavity 1907
1909 upper-head 1909
1911 lower-head 1911
1913 upper-base 1913
1915 lower-base 1915
1917 interior-side 1917
1919 orthodontic-bracket-lock 1919
1921 top-interior 1921
1923 interior-seam 1923
1924 substrate 1924
2001 bottom-interior 2001
2003 lock-interior 2003
2005 top-base 2005
2007 bottom-base 2007
2301 orthodontic-bracket-hook 2301
2303 hook-stop 2303
2401 orthodontic-archwire 2401
2403 orthodontic-spring 2403
2501 orthodontic-elastic-band 2501
2901 isolation-layer 2901
3000 orthodontic-expander 3000
3001 orthodontic-band 3001
3003 expander-arm 3003
3005 force-generating-means 3005
3007 direction-of-force 3007
3100 orthodontic-power-chain 3100
3101 capture-portion 3101
3103 linkage-portion 3103
3300 aligner 3300
3301 tooth-well 3301
3400 aligner 3400
3401 tooth-well 3401
3410 finger 3410
3450 mobile-computing-device 3450
3460 visual interpretation of sensor information 3460
3501 orthotic 3501
3503 shoe 3503
3505 foot 3505
3507 wired connection 3507
3508 wired connection 3508
3509 reader 3509
3511 mat-reader 3511
3513 WiFi-antenna 3513
3515 wireless charging source 3515
3517 power source 3517
3519 memory 3519
3521 WiFi-antenna 3521
3523 wireless charging device 3523
3525 power source 3525
3527 memory 3527
3529 ball-region 3529
3531 arch-region 3531
3533 heal-region 3533
3535 lateral spacing 3535
3540 visual interpretation of sensor information 3540
3600 method for initial manufacturing of given appliance of interest 3600
3601 step of scanning organ or objects 3601
3603 step of manufacturing the appliance of interest 3603
3605 step of performing readouts of sensors 3605
3607 step of determining if adjustments in appliance of interest needed or desired 3607
3609 step of performing required (or desired) adjustments of the appliance of interest 3609

3610 step of pre-use readout-and-adjustment loop 3610
3611 step of performing readouts of sensors when the appliance of interest may be in use 3611
3613 step of determining if adjustments in the appliance of interest needed or desired 3613
3615 step of performing required (or desired) adjustments of the appliance of interest 3615
3616 step of readout-and-adjustment loop 3616—readout-and-adjustment loop
3617 appliance of interest is ready for its intended use 3617
3700 method of assessing performance of the given appliance of interest in the presence or proximity of practitioner 3700
3701 step of collecting accumulated data 3701
3800 method of assessing performance of the given appliance of interest remotely from practitioner 3800
3801 step of determining if adjustments in the appliance of interest needed or desired 3801
3813 keep using existing appliance of interest 3813

DETAILED DESCRIPTION OF THE INVENTION

In the following discussion that addresses a number of embodiments and applications of the present invention, reference is made to the accompanying drawings that form a part thereof, where depictions are made, by way of illustration, of specific embodiments in which the invention may be practiced. It is to be understood that other embodiments may be utilized and changes may be made without departing from the scope of the invention.

Note, "fixed" as used herein may be with respect positional locations that are non-variable and/or non-self-moving; i.e., "fixed" as used herein may not refer to something being affixed or attached to something.

FIG. 1A may depict a schematic block diagram of a reader 100. In some embodiments, reader 100 may comprise antenna 110. In some embodiments, reader 100 may comprise at least one antenna 110. In some embodiments, reader 100 may comprise one or more antennas 110.

Figure 1B:
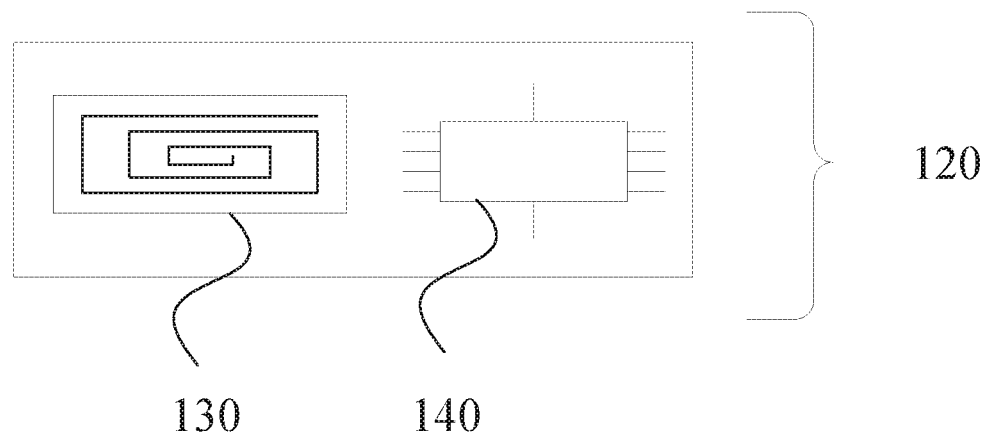
FIG. 1B may depict a schematic block diagram of a monitoring-sensor-tag.

FIG. 1B may depict a schematic block diagram of a monitoring-sensor-tag 120. In some embodiments, monitoring-sensor-tag 120 may comprise at least one electric circuit 140. In some embodiments, monitoring-sensor-tag 120 may comprise at least one antenna 130 in communication with the at least one electric circuit 140. In some embodiments, at least one electric circuit 140 may be in communication with at least one sensor. In some embodiments, monitoring-sensor-tag 120 may comprise the at least one sensor. In some embodiments, at least one electric circuit 140 may comprise the at least one sensor. In some embodiments, this at least one sensor may be sensor 202, sensor 203, sensor 340, sensor 406, sensor 407, and/or other sensors discussed herein and/or sensors discussed in U.S. patent application Ser. No. 15/653,461. In some embodiments, this at least one sensor may be designated/termed, "tag-sensor."

In some embodiments, at least one electric circuit 140 may be an integrated circuit. In some embodiments, the at least one sensor (e.g., 202, 203, and/or other sensors discussed herein) may be located inside of and integral with such an integrated circuit and in electrical communication with the integrated circuit. In some embodiments, the at least one sensor (e.g., 202, 203, 1006, and/or other sensors discussed herein) may be located outside of such an integrated circuit and in electrical communication with the integrated circuit.

In some embodiments, a given monitoring-sensor-tag 120 may be a backscatter sensor tag. In some embodiments, a given monitoring-sensor-tag 120 may be a RFID (radio frequency identification) sensor tag. In some embodiments, a given monitoring-sensor-tag 120 may be a NFC (near field communication) sensor tag.

In some embodiments, a given monitoring-sensor-tag 120 may communicate with a given reader 100. In some embodiments, such communication may be wireless. In some embodiments, such wireless communication may be via a predetermined wavelength or via predetermined wavelengths of electromagnetic radiation. For example, and without limiting the scope of the present invention, such a wavelength may be wavelengths associated with radio waves. For example, and without limiting the scope of the present invention, a given reader 100 may "interrogate" monitoring-sensor-tags 120 at a number of predetermined frequencies.

In some embodiments, upon at least one antenna 130 receiving electromagnetic radiation of a predetermined characteristic as an input from at least one antenna 110, this input may cause at least one electric circuit 140 to take one or more readings from the at least one sensor and to then transmit such one or more readings using at least one antenna 130. Then, at least one antenna 110 may receive these one or more readings being broadcast from at least one antenna 130. Hence, reader 100 may be "reading" from (i.e., scanning for) signals broadcast from a given monitoring-sensor-tag 120.

In some embodiments, when the at least one electric circuit 140 may cause the at least one antenna 130 to transmit the one or more readings, the at least one electric circuit 140 may also cause the at least one antenna 130 to transmit "additional information." In some embodiments, this "additional information" may comprise one or more of: identification information for a given monitoring-sensor-tag 120 that is transmitting (e.g., an ID for each monitoring-sensor-tag 120 that is transmitting); model number for the given monitoring-sensor-tag 120 that is transmitting; serial number for the given monitoring-sensor-tag 120 that is transmitting; manufacturer of the given monitoring-sensor-tag 120 that is transmitting; year of manufacture of the given monitoring-sensor-tag 120 that is transmitting; or a request for a security code associated with that given monitoring-sensor-tag 120 that is transmitting; a cyclic redundancy check code for the information that the given monitoring-sensor-tag 120 that is transmitting; a parity check code for information that the given monitoring-sensor-tag 120 that is transmitting; and receipt of a disable instruction for the given monitoring-sensor-tag 120 that is transmitting; wherein the given monitoring-sensor-tag 120 that is transmitting is selected from the one or more monitoring-sensor-tags 120.

In some embodiments, monitoring-sensor-tag 120 may be passive and receive power wirelessly transmitted from a given reader 100. That is, electrical power required to operate a given monitoring-sensor-tag 120 may be provided wirelessly from at least one antenna 110 from a given reader 100 that may be broadcasting and sufficiently close to at least one antenna 130 of given monitoring-sensor-tag 120.

In some embodiments, at least one of the one or more monitoring-sensor-tags 120 may be from substantially six inches to substantially 1.0 micrometer in a largest dimension of the at least one of the one or more monitoring-sensor-tags 120. In some embodiments, "substantially" in this context may mean plus or minus 10% of the given unit of measurement; i.e., plus or minus 10% of an inch and plus or minus 10% of a micrometer. In application, the size of a given monitoring-sensor-tag 120 may be negligible with respect to any impact the given monitoring-sensor-tag 120 may have on the associated material-of-interest; i.e., the sizes of the utilized monitoring-sensor-tags 120 may not negatively affect the associated material-of-interest.

In some embodiments, each monitoring-sensor-tag 120 may be attached to a given material-of-interest. Note, such materials-of-interest are not shown in FIG. 1A and in FIG. 1B. In some embodiments, a given material-of-interest may be selected from: a dental-filling 1001 (see e.g., FIG. 10A), a root-canal-post 1004 (see e.g., FIG. 10B), a root-canal-cavity 1003 (see e.g., FIG. 10B), a dental-crown 1005 (see e.g., FIG. 10B), a dental-implant 1007 (see e.g., FIG. 10C), an article implantable within a body of an organism, the article attachable to the body of the organism, specific tissue of the organism, a construction member, one or more orthodontic-elements (see e.g., FIG. 19 through FIG. 32), and/or the like. See also FIG. 10D for material-of-interest 1028, which in some embodiments may be any of the above identified given materials-of-interest. See also FIG. 13C showing monitoring-sensor-tag 120 located within a leg of a patient 1328; wherein in that example a portion of the leg (e.g., tissue, bone, an implant, or the like) may be given material-of-interest. See also FIG. 18 for material-of-interest 1828, which in some embodiments may be any of the above identified given materials-of-interest.

In some embodiments, the given material-of-interest may be an article. In some embodiments, the article may be selected from: a medical device; a tissue graft; a bone graft; an artificial tissue; a bolus with time-release medication; a medication; and/or the like. In some embodiments, the medical device may be selected from one or more of: a dental-implant 1007, an implantable device, an implantable organ (e.g., may include from a cadaver), implantable tissue (e.g., may include from a cadaver), an artificial organ, artificial tissue, an artificial joint, an artificial limb, an artificial valve, a suture, and/or the like.

In some embodiments, the construction member (of the given material-of-interest) may be selected from one or more of: concrete; cement; plaster; mortar; resin; brick; block; drywall; particle board; plywood; wood framing member (e.g., a stud); posts; beams; girders; engineered structural members; and/or the like.

In some embodiments, one or more monitoring-sensor-tags 120 being "attached to" the given material-of-interest, at an initial time of "attachment," may comprise one or more of the following locations: on a surface of the given material-of-interest; within the given material-of-interest; partially on the surface of the given material-of-interest and partially within the given material-of-interest; and/or the like. In some embodiments, the one or more monitoring-sensor-tags 120 may be immersed entirely within the material-of-interest. In some embodiments, the one or more monitoring-sensor-tags 120 may be immersed at least partially within the material-of-interest. That is, in some embodiments, "attached to" may comprise "immersion." In some embodiments, one or more monitoring-sensor-tags 120 may associate with the given material-of-interest; such as, but not limited to, translating with the given material-of-interest.

In some embodiments, an importance of attaching one or more monitoring-sensor-tags 120 with the given material-of-interest, may be that the at least one sensor of a given monitoring-sensor-tag 120 may then convey state information from readings of that at least one given sensor. That is, by using the monitoring-sensor-tags 120 attached to the given material-of-interest, information (e.g., various states) of the given material-of-interest may be monitored and/or tracked. In some embodiments, such monitoring and/or tracking may be accomplished with using radio waves as opposed to ionizing imaging radiation like x-rays; which may provide for increased safety to patients 1328 when the given material-of-interest is associated with a given patient 1328. Additionally, because of this, more frequent monitoring and/or tracking of the given material-of-interest may be utilized, resulting in increased efficacy and minimization of problems that may arise to due to infrequent monitoring, as there may be minimal need to minimize patient 1328 exposure to ionizing imaging radiation since embodiments of the present invention may communicate over radio waves between monitoring-sensor-tags 120 and various readers 100.

For example, and without limiting the scope of the present invention, in some embodiments, such state information of the given material-of-interest that may be monitored and/or tracked by using one or more monitoring-sensor-tags 120 attached to the given material-of-interest may be one or more of: structural integrity of a current state of the material-of-interest; structural integrity changes of the material-of-interest; pressure received at the material-of-interest; force received at the material-of-interest; stress received at the material-of-interest; shear-stress in the material-of-interest; twisting in the material-of-interest; torsion received at the material-of-interest; compression of the material-of-interest; tension in the material-of-interest; deformation received at the material-of-interest; temperature at some portion of the material-of-interest; positional changes of a given monitoring-sensor-tag 120 attached to the material-of-interest with respect to position of another monitoring-sensor-tag 120 attached to the material-of-interest, wherein the given monitoring-sensor-tag 120 and the other monitoring-sensor-tag are 120 selected from the one or more monitoring-sensor-tags 120 attached to the material-of-interest; or positional changes of at least one monitoring-sensor-tag 120 attached to the material-of-interest with respect to time, wherein the at least one monitoring-sensor-tag 120 is selected from the one or more monitoring-sensor-tags 120.

Figure 2A:
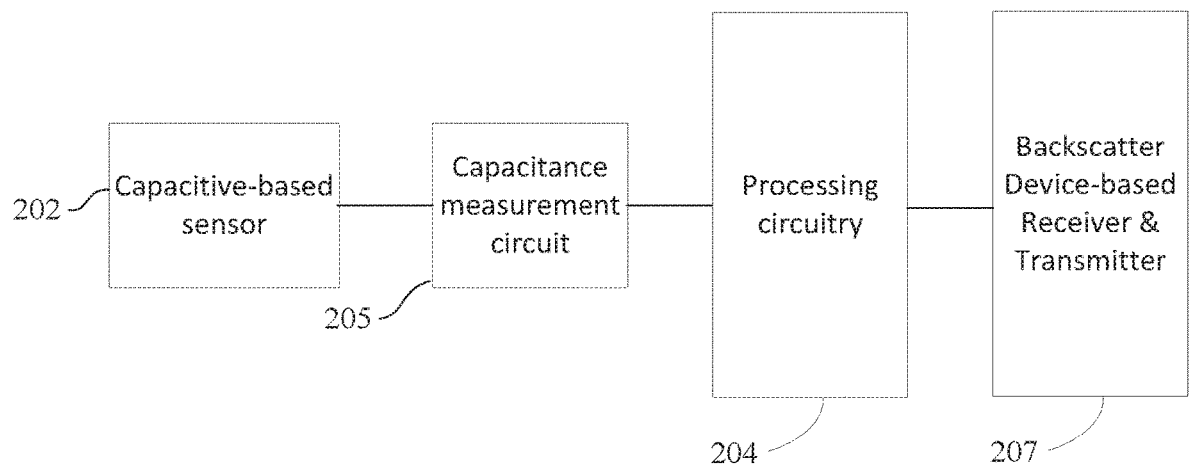
FIG. 2A may depict a schematic block diagram of a monitoring-sensor-tag comprising a capacitive-based sensor.

FIG. 2A may depict a schematic block diagram of monitoring-sensor-tag 120 comprising a capacitive-based sensor 202. In some embodiments, a given monitoring-sensor-tag 120 may comprise backscatter-receiver-and-transmitter 207, processing circuitry 204, capacitance measurement circuit 205, and capacitive-based sensor 202. In some embodiments, processing circuitry 204 may be in communication with capacitance measurement circuit 205. In some embodiments, processing circuitry 204 may be in communication with backscatter-receiver-and-transmitter 207. In some embodiments, capacitance measurement circuit 205 may be in communication with capacitive-based sensor 202.

In some embodiments, capacitance measurement circuit 205 may measure the capacitance of capacitive-based sensor 202 to quantify a current state reading of material-of-interest that monitoring-sensor-tag 120 may be attached to. In some embodiments, processing circuitry 204 may control capacitance measurement circuit 205 and process the one or more readings (the obtained results) for radio-frequency transmission (or for other electromagnetic transmission). In some embodiments, backscatter-receiver-and-transmitter 207 may transmit the one or more readings (the obtained results) to reader 100. In some embodiments, backscatter-receiver-and-transmitter 207 may receive instructions from reader 100 using electromagnetic waves; such as, but not limited to radio wavelength electromagnetic waves. See e.g., FIG. 2A.

In some embodiments, at least one antenna 130 (of monitoring-sensor-tag 120) may comprise backscatter-receiver-and-transmitter 207. In some embodiments, at least one electric circuit 140 (of monitoring-sensor-tag 120) may comprise processing circuitry 204. In some embodiments, at least one electric circuit 140 (of monitoring-sensor-tag 120) may comprise processing circuitry 204 and capacitance measurement circuit 205. In some embodiments, at least one electric circuit 140 (of monitoring-sensor-tag 120) may comprise processing circuitry 204, capacitance measurement circuit 205, and capacitive-based sensor 202.

Figure 2B:
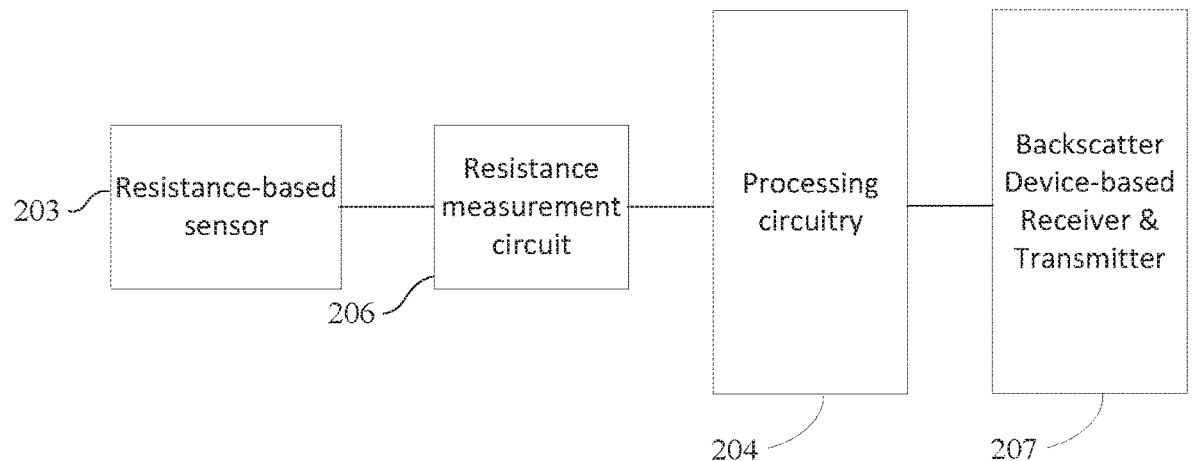
FIG. 2B may depict a schematic block diagram of a monitoring-sensor-tag comprising a resistance-based sensor.

FIG. 2B may depict a schematic block diagram of monitoring-sensor-tag 120 comprising a resistance-based sensor 203. In some embodiments, a given monitoring-sensor-tag 120 may comprise backscatter-receiver-and-transmitter 207, processing circuitry 204, resistance measurement circuit 206, and resistance-based sensor 203. In some embodiments, processing circuitry 204 may be in communication with resistance measurement circuit 206. In some embodiments, processing circuitry 204 may be in communication with backscatter-receiver-and-transmitter 207. In some embodiments, resistance measurement circuit 206 may be in communication with resistance-based sensor 203.

In some embodiments, resistance measurement circuit 206 may measure the resistance of resistance-based sensor 203 to quantify a current state reading of material-of-interest that monitoring-sensor-tag 120 may be attached to. In some embodiments, processing circuitry 204 may control resistance measurement circuit 206 and process the one or more readings (the obtained results) for radio-frequency transmission (or for other electromagnetic transmission). In some embodiments, backscatter-receiver-and-transmitter 207 may transmit the one or more readings (the obtained results) to reader 100. In some embodiments, backscatter-receiver-and-transmitter 207 may receive instructions from reader 100 using electromagnetic waves; such as, but not limited to radio wavelength electromagnetic waves. See e.g., FIG. 2B.

In some embodiments, at least one antenna 130 (of monitoring-sensor-tag 120) may comprise backscatter-receiver-and-transmitter 207. In some embodiments, at least one electric circuit 140 (of monitoring-sensor-tag 120) may comprise processing circuitry 204. In some embodiments, at least one electric circuit 140 (of monitoring-sensor-tag 120) may comprise processing circuitry 204 and resistance measurement circuit 206. In some embodiments, at least one electric circuit 140 (of monitoring-sensor-tag 120) may comprise processing circuitry 204, resistance measurement circuit 206, and resistance-based sensor 203.

Figure 2C:
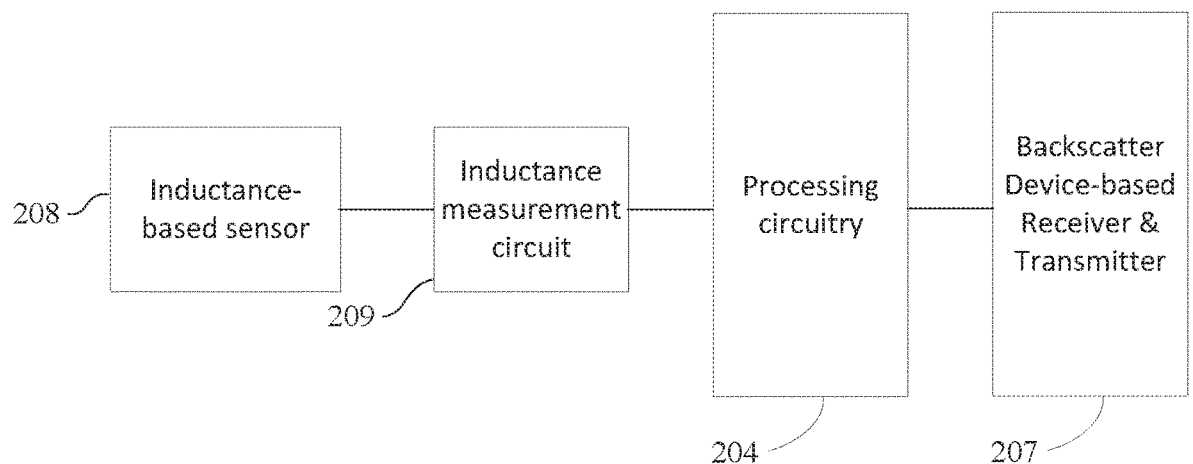
FIG. 2C may depict a schematic block diagram of a monitoring-sensor-tag comprising an inductance-based sensor.

FIG. 2C may depict a schematic block diagram of monitoring-sensor-tag 120 comprising an inductance-based-sensor 208. In some embodiments, a given monitoring-sensor-tag 120 may comprise backscatter-receiver-and-transmitter 207, processing circuitry 204, inductance measurement circuit 209, and inductance-based-sensor 208. In some embodiments, processing circuitry 204 may be in communication with inductance measurement circuit 209. In some embodiments, processing circuitry 204 may be in communication with backscatter-receiver-and-transmitter 207. In some embodiments, inductance measurement circuit 209 may be in communication with inductance-based-sensor 208.

In some embodiments, inductance measurement circuit 209 may measure the inductance of inductance-based-sensor 208 to quantify a current state reading of material-of-interest that monitoring-sensor-tag 120 may be attached to. In some embodiments, processing circuitry 204 may control inductance measurement circuit 209 and process the one or more readings (the obtained results) for radio-frequency transmission (or for other electromagnetic transmission). In some embodiments, backscatter-receiver-and-transmitter 207 may transmit the one or more readings (the obtained results) to reader 100. In some embodiments, backscatter-receiver-and-transmitter 207 may receive instructions from reader 100 using electromagnetic waves; such as, but not limited to radio wavelength electromagnetic waves. See e.g., FIG. 2C.

In some embodiments, at least one antenna 130 (of monitoring-sensor-tag 120) may comprise backscatter-receiver-and-transmitter 207. In some embodiments, at least one electric circuit 140 (of monitoring-sensor-tag 120) may comprise processing circuitry 204. In some embodiments, at least one electric circuit 140 (of monitoring-sensor-tag 120) may comprise processing circuitry 204 and inductance measurement circuit 209. In some embodiments, at least one electric circuit 140 (of monitoring-sensor-tag 120) may comprise processing circuitry 204, inductance measurement circuit 209, and inductance-based-sensor 208.

Figure 2D:
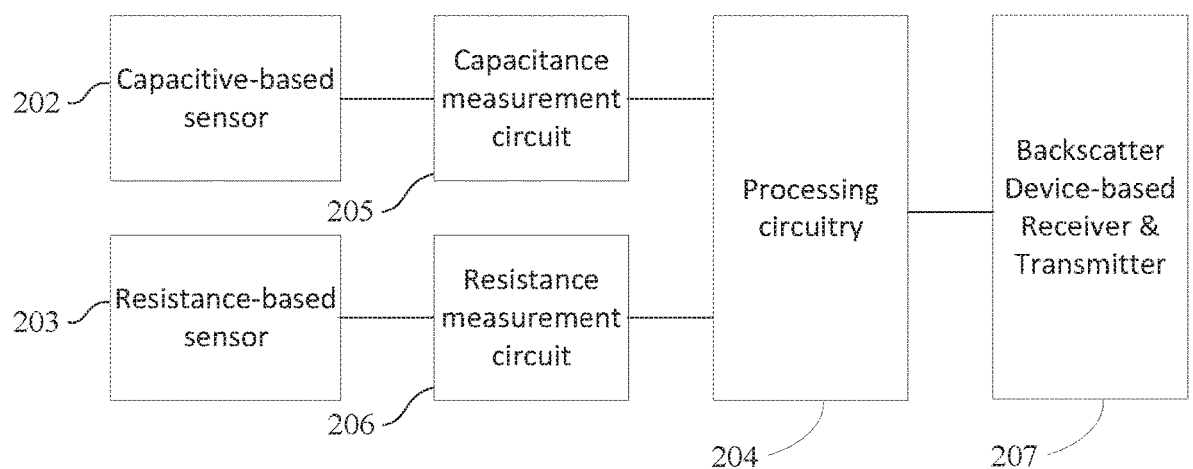
FIG. 2D may depict a schematic block diagram of a monitoring-sensor-tag comprising a capacitive-based sensor and a resistance-based-sensor.

FIG. 2D may depict a schematic block diagram of a monitoring-sensor-tag comprising a capacitive-based sensor 202 and a resistance-based-sensor 203. In some embodiments, a given monitoring-sensor-tag 120 may comprise backscatter-receiver-and-transmitter 207, processing circuitry 204, capacitance measurement circuit 205, capacitive-based sensor 202, resistance measurement circuit 206, and resistance-based sensor 203. In some embodiments, processing circuitry 204 may be in communication with capacitance measurement circuit 205. In some embodiments, processing circuitry 204 may be in communication with resistance measurement circuit 206. In some embodiments, processing circuitry 204 may be in communication with backscatter-receiver-and-transmitter 207. In some embodiments, capacitance measurement circuit 205 may be in communication with capacitive-based sensor 202. In some embodiments, resistance measurement circuit 206 may be in communication with resistance-based sensor 203.

In some embodiments, capacitance measurement circuit 205 may measure the capacitance of capacitive-based sensor 202 to quantify a current state reading of material-of-interest that monitoring-sensor-tag 120 may be attached to. In some embodiments, resistance measurement circuit 206 may measure the resistance of resistance-based sensor 203 to quantify another current state reading of material-of-interest that monitoring-sensor-tag 120 may be attached to. In some embodiments, processing circuitry 204 may control capacitance measurement circuit 205 and may control resistance measurement circuit 206 and process the one or more readings (the obtained results) for radio-frequency transmission (or for other electromagnetic transmission). In some embodiments, backscatter-receiver-and-transmitter 207 may transmit the one or more readings (the obtained results) to reader 100. In some embodiments, backscatter-receiver-and-transmitter 207 may receive instructions from reader 100 using electromagnetic waves; such as, but not limited to radio wavelength electromagnetic waves. See e.g., FIG. 2D.

In some embodiments, at least one antenna 130 (of monitoring-sensor-tag 120) may comprise backscatter-receiver-and-transmitter 207. In some embodiments, at least one electric circuit 140 (of monitoring-sensor-tag 120) may comprise processing circuitry 204. In some embodiments, at least one electric circuit 140 (of monitoring-sensor-tag 120) may comprise processing circuitry 204, capacitance measurement circuit 205, and resistance measurement circuit 206. In some embodiments, at least one electric circuit 140 (of monitoring-sensor-tag 120) may comprise processing circuitry 204, capacitance measurement circuit 205, capacitive-based sensor 202, resistance measurement circuit 206, and resistance-based sensor 203.

Figure 2E:
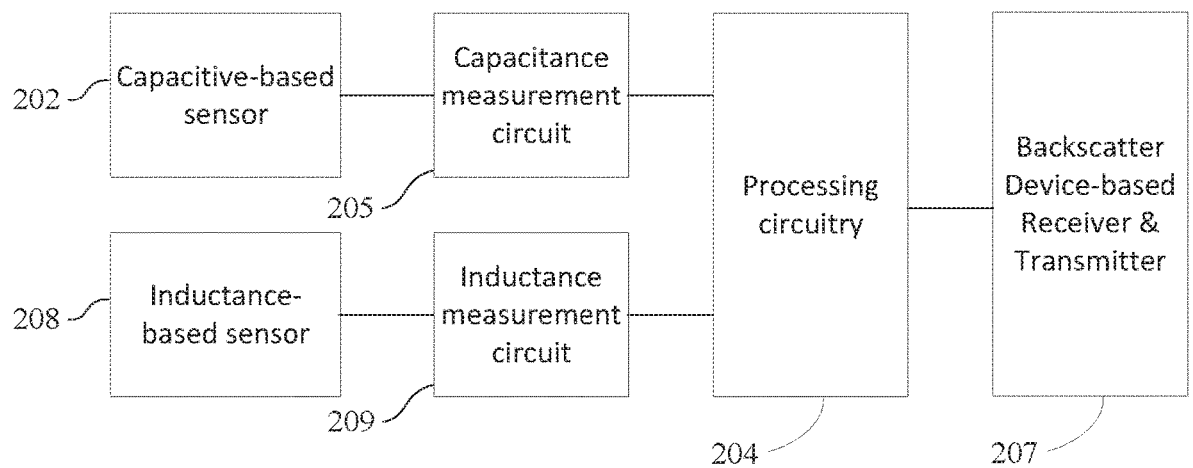
FIG. 2E may depict a schematic block diagram of a monitoring-sensor-tag comprising a capacitive-based sensor and an inductance-based-sensor.

FIG. 2E may depict a schematic block diagram of a monitoring-sensor-tag comprising a capacitive-based sensor 202 and an inductance-based-sensor 208. In some embodiments, a given monitoring-sensor-tag 120 may comprise backscatter-receiver-and-transmitter 207, processing circuitry 204, capacitance measurement circuit 205, capacitive-based sensor 202, inductance measurement circuit 209, and inductance-based-sensor 208. In some embodiments, processing circuitry 204 may be in communication with capacitance measurement circuit 205. In some embodiments, processing circuitry 204 may be in communication with inductance measurement circuit 209. In some embodiments, processing circuitry 204 may be in communication with backscatter-receiver-and-transmitter 207. In some embodiments, capacitance measurement circuit 205 may be in communication with capacitive-based sensor 202. In some embodiments, inductance measurement circuit 209 may be in communication with inductance-based-sensor 208.

In some embodiments, capacitance measurement circuit 205 may measure the capacitance of capacitive-based sensor 202 to quantify a current state reading of material-of-interest that monitoring-sensor-tag 120 may be attached to. In some embodiments, inductance measurement circuit 209 may measure the inductance of inductance-based-sensor 208 to quantify another current state reading of material-of-interest that monitoring-sensor-tag 120 may be attached to. In some embodiments, processing circuitry 204 may control capacitance measurement circuit 205 and may control inductance measurement circuit 209 and process the one or more readings (the obtained results) for radio-frequency transmission (or for other electromagnetic transmission). In some embodiments, backscatter-receiver-and-transmitter 207 may transmit the one or more readings (the obtained results) to reader 100. In some embodiments, backscatter-receiver-and-transmitter 207 may receive instructions from reader 100 using electromagnetic waves; such as, but not limited to radio wavelength electromagnetic waves. See e.g., FIG. 2E.

In some embodiments, at least one antenna 130 (of monitoring-sensor-tag 120) may comprise backscatter-receiver-and-transmitter 207. In some embodiments, at least one electric circuit 140 (of monitoring-sensor-tag 120) may comprise processing circuitry 204. In some embodiments, at least one electric circuit 140 (of monitoring-sensor-tag 120) may comprise processing circuitry 204, capacitance measurement circuit 205, and inductance measurement circuit 209. In some embodiments, at least one electric circuit 140 (of monitoring-sensor-tag 120) may comprise processing circuitry 204, capacitance measurement circuit 205, capacitive-based sensor 202, inductance measurement circuit 209, and inductance-based-sensor 208.

Figure 2F:
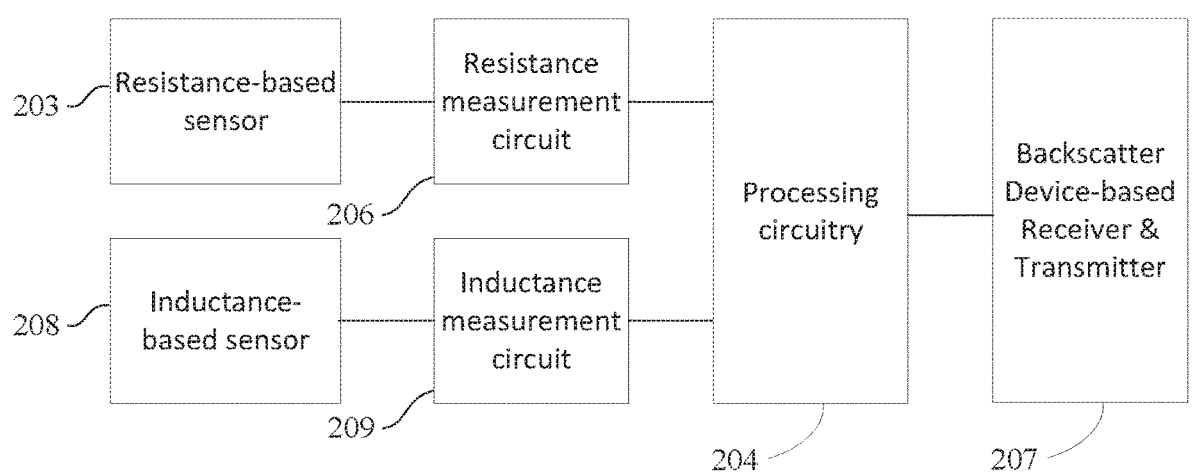
FIG. 2F may depict a schematic block diagram of a monitoring-sensor-tag comprising a resistance-based sensor and an inductance-based-sensor.

FIG. 2F may depict a schematic block diagram of a monitoring-sensor-tag comprising a resistance-based sensor 203 and an inductance-based-sensor 208.

In some embodiments, a given monitoring-sensor-tag 120 may comprise backscatter-receiver-and-transmitter 207, processing circuitry 204, resistance measurement circuit 206, resistance-based sensor 203, inductance measurement circuit 209, and inductance-based-sensor 208. In some embodiments, processing circuitry 204 may be in communication with resistance measurement circuit 206. In some embodiments, processing circuitry 204 may be in communication with inductance measurement circuit 209. In some embodiments, processing circuitry 204 may be in communication with backscatter-receiver-and-transmitter 207. In some embodiments, resistance measurement circuit 206 may be in communication with resistance-based sensor 203. In some embodiments, inductance measurement circuit 209 may be in communication with inductance-based-sensor 208.

In some embodiments, resistance measurement circuit 206 may measure the resistance of resistance-based sensor 203 to quantify a current state reading of material-of-interest that monitoring-sensor-tag 120 may be attached to. In some embodiments, inductance measurement circuit 209 may measure the inductance of inductance-based-sensor 208 to quantify another current state reading of material-of-interest that monitoring-sensor-tag 120 may be attached to. In some embodiments, processing circuitry 204 may control resistance measurement circuit 206 and may control inductance measurement circuit 209 and may process the one or more readings (the obtained results) for radio-frequency transmission (or for other electromagnetic transmission). In some embodiments, backscatter-receiver-and-transmitter 207 may transmit the one or more readings (the obtained results) to reader 100. In some embodiments, backscatter-receiver-and-transmitter 207 may receive instructions from reader 100 using electromagnetic waves; such as, but not limited to radio wavelength electromagnetic waves. See e.g., FIG. 2F.

In some embodiments, at least one antenna 130 (of monitoring-sensor-tag 120) may comprise backscatter-receiver-and-transmitter 207. In some embodiments, at least one electric circuit 140 (of monitoring-sensor-tag 120) may comprise processing circuitry 204. In some embodiments, at least one electric circuit 140 (of monitoring-sensor-tag 120) may comprise processing circuitry 204, resistance measurement circuit 206, and inductance measurement circuit 209. In some embodiments, at least one electric circuit 140 (of monitoring-sensor-tag 120) may comprise processing circuitry 204, resistance measurement circuit 206, resistance-based sensor 203, inductance measurement circuit 209, and inductance-based-sensor 208.

Figure 2G:
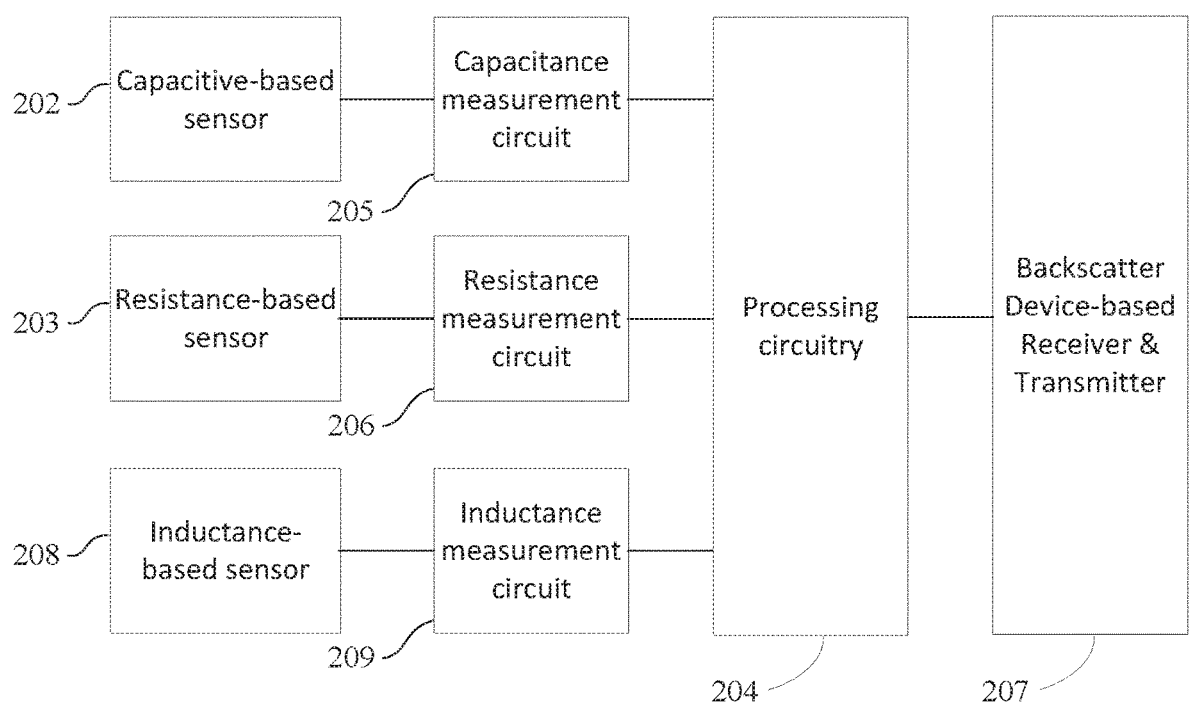
FIG. 2G may depict a schematic block diagram of a monitoring-sensor-tag comprising a capacitive-based sensor, a resistance-based sensor, and an inductance-based-sensor.

FIG. 2G may depict a schematic block diagram of a monitoring-sensor-tag comprising a capacitive-based sensor 202, a resistance-based sensor 203, and an inductance-based-sensor 208.

In some embodiments, a given monitoring-sensor-tag 120 may comprise backscatter-receiver-and-transmitter 207, processing circuitry 204, capacitance measurement circuit 205, capacitive-based sensor 202, resistance measurement circuit 206, resistance-based sensor 203, inductance measurement circuit 209, and inductance-based-sensor 208. In some embodiments, processing circuitry 204 may be in communication with capacitance measurement circuit 205. In some embodiments, processing circuitry 204 may be in communication with resistance measurement circuit 206. In some embodiments, processing circuitry 204 may be in communication with inductance measurement circuit 209. In some embodiments, processing circuitry 204 may be in communication with backscatter-receiver-and-transmitter 207. In some embodiments, capacitance measurement circuit 205 may be in communication with capacitive-based sensor 202. In some embodiments, resistance measurement circuit 206 may be in communication with resistance-based sensor 203. In some embodiments, inductance measurement circuit 209 may be in communication with inductance-based-sensor 208.

In some embodiments, capacitance measurement circuit 205 may measure the capacitance of capacitive-based sensor 202 to quantify a current state reading of material-of-interest that monitoring-sensor-tag 120 may be attached to. In some embodiments, resistance measurement circuit 206 may measure the resistance of resistance-based sensor 203 to quantify another current state reading of material-of-interest that monitoring-sensor-tag 120 may be attached to. In some embodiments, inductance measurement circuit 209 may measure the inductance of inductance-based-sensor 208 to quantify yet another current state reading of material-of-interest that monitoring-sensor-tag 120 may be attached to. In some embodiments, processing circuitry 204 may control capacitance measurement circuit 205, may control resistance measurement circuit 206, and may control inductance measurement circuit 209. In some embodiments, processing circuitry 204 may process the one or more readings (i.e., the obtained results) for radio-frequency transmission (or for other electromagnetic transmission). In some embodiments, backscatter-receiver-and-transmitter 207 may transmit the one or more readings (the obtained results) to reader 100. In some embodiments, backscatter-receiver-and-transmitter 207 may receive instructions from reader 100 using electromagnetic waves; such as, but not limited to radio wavelength electromagnetic waves. See e.g., FIG. 2G.

In some embodiments, at least one antenna 130 (of monitoring-sensor-tag 120) may comprise backscatter-receiver-and-transmitter 207. In some embodiments, at least one electric circuit 140 (of monitoring-sensor-tag 120) may comprise processing circuitry 204. In some embodiments, at least one electric circuit 140 (of monitoring-sensor-tag 120) may comprise processing circuitry 204, capacitance measurement circuit 205, resistance measurement circuit 206, and inductance measurement circuit 209. In some embodiments, at least one electric circuit 140 (of monitoring-sensor-tag 120) may comprise processing circuitry 204, capacitance measurement circuit 205, capacitive-based sensor 202, resistance measurement circuit 206, resistance-based sensor 203, inductance measurement circuit 209, and inductance-based-sensor 208.

As noted above in the FIG. 1B discussion of monitoring-sensor-tag 120, monitoring-sensor-tag 120 may comprise the at least one sensor. In some embodiments, the at least one sensor may be selected from one or more of: capacitive-based sensor 202, resistance-based sensor 203, and/or inductance-based-sensor 208. See e.g., FIG. 2A through and including FIG. 2G.

As noted above in the FIG. 1B discussion of monitoring-sensor-tag 120, at least one electric circuit 140 (of monitoring-sensor-tag 120) may comprise the at least one sensor. In some embodiments, the at least one sensor may be selected from one or more of: capacitive-based sensor 202, resistance-based sensor 203, and/or inductance-based-sensor 208. See e.g., FIG. 2A through and including FIG. 2G.

Figure 10A:
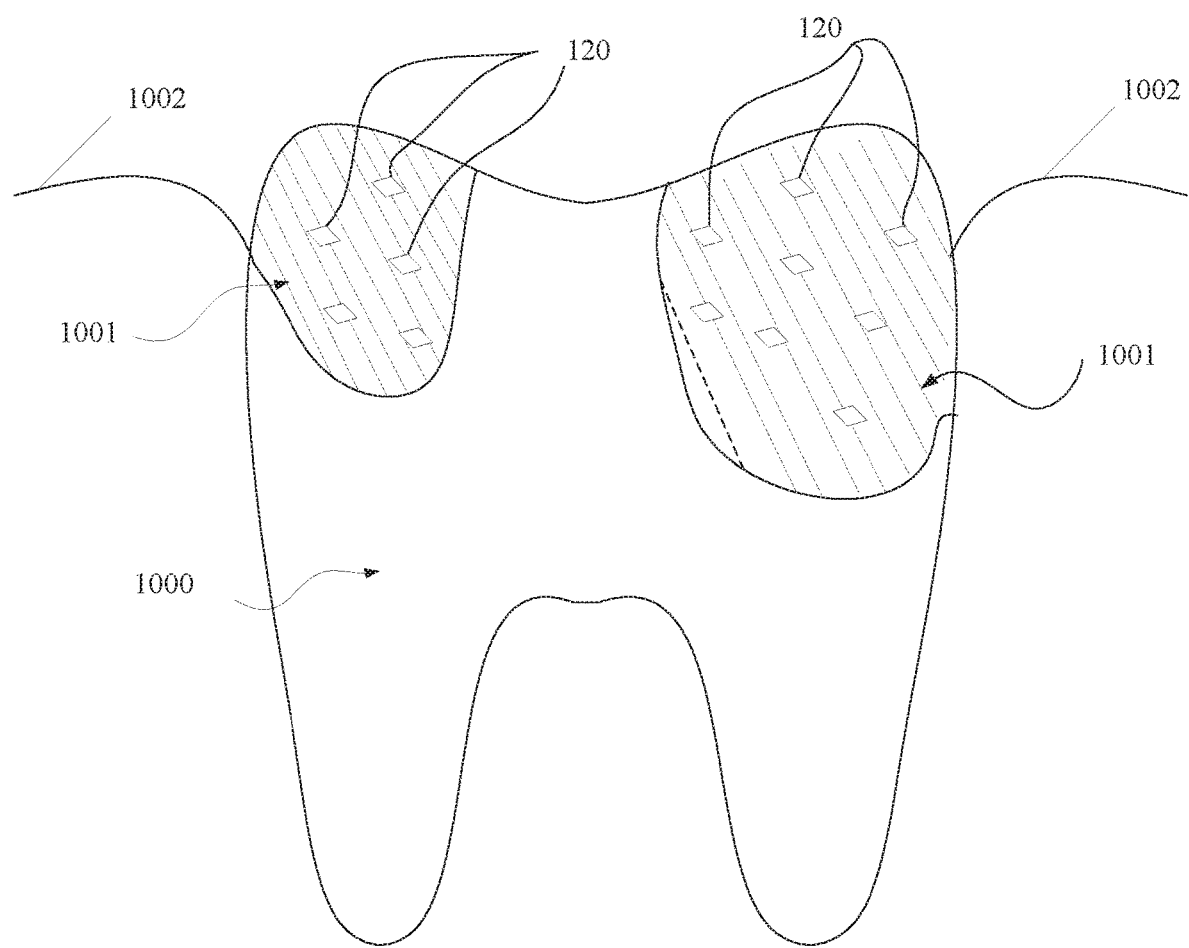
FIG. 10A may be a diagram of a patient's tooth with one or more monitoring-sensor-tags placed in dental-filling as a material-of-interest, in accordance with some embodiments of the present invention.
Figure 10B:
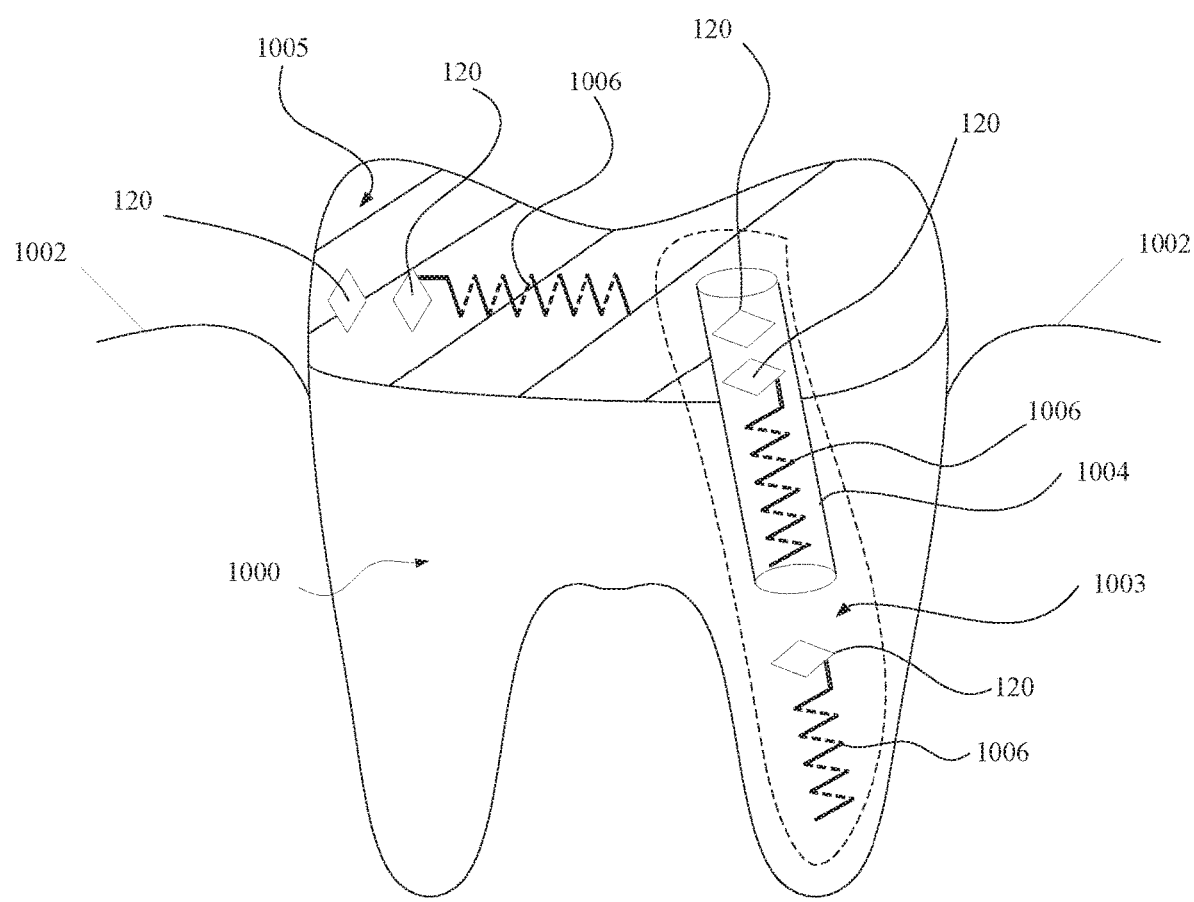
FIG. 10B may be a diagram of a patient's tooth with one or more monitoring-sensor-tags placed in: a root-canal-cavity, in a root-canal-post, and/or in a dental-crown; in accordance with some embodiments of the present invention.
Figure 10C:
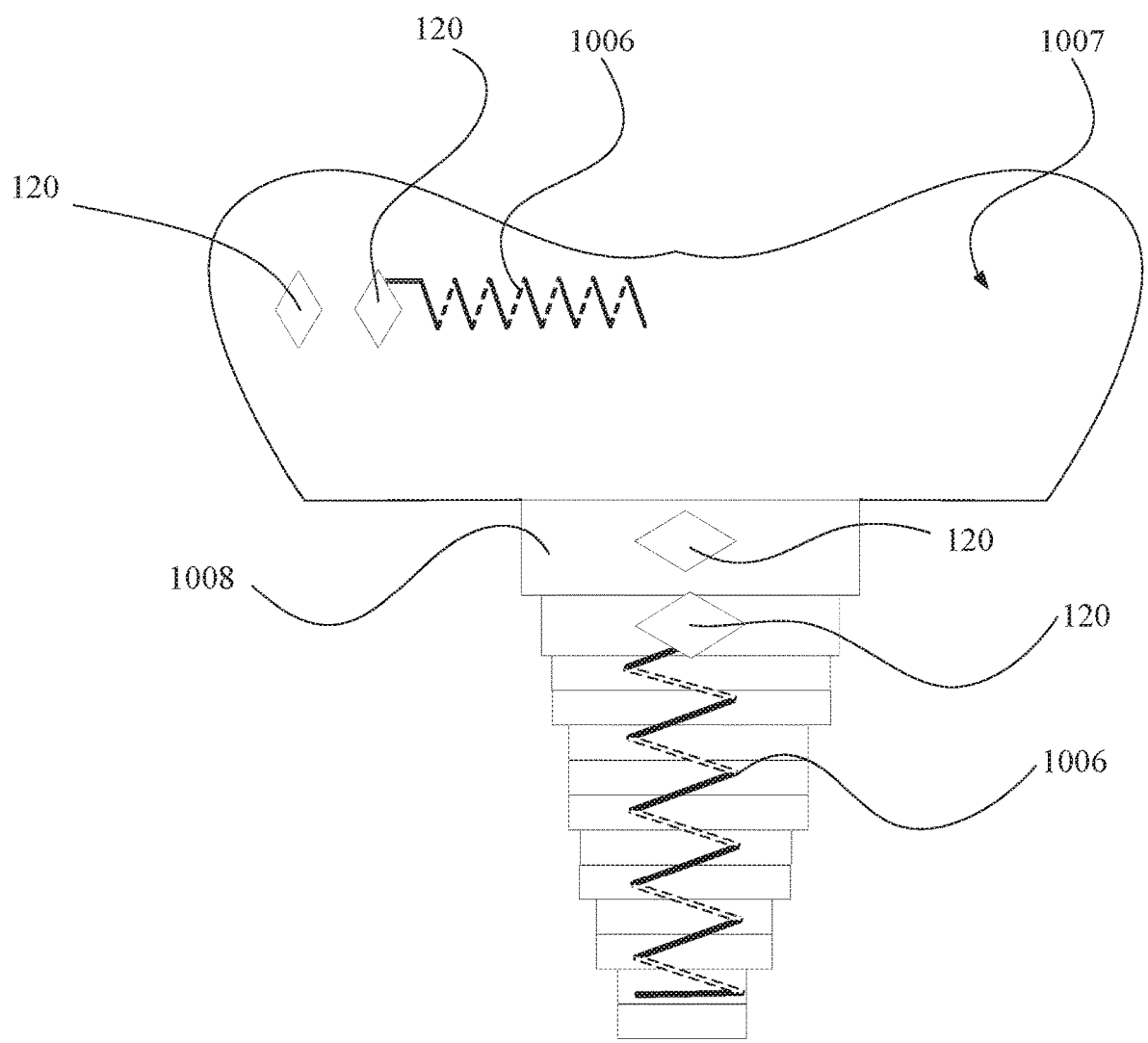
FIG. 10C may be a diagram of a patient's tooth dental-implant with one or more monitoring-sensor-tags, in accordance with some embodiments of the present invention.
Figure 10D:
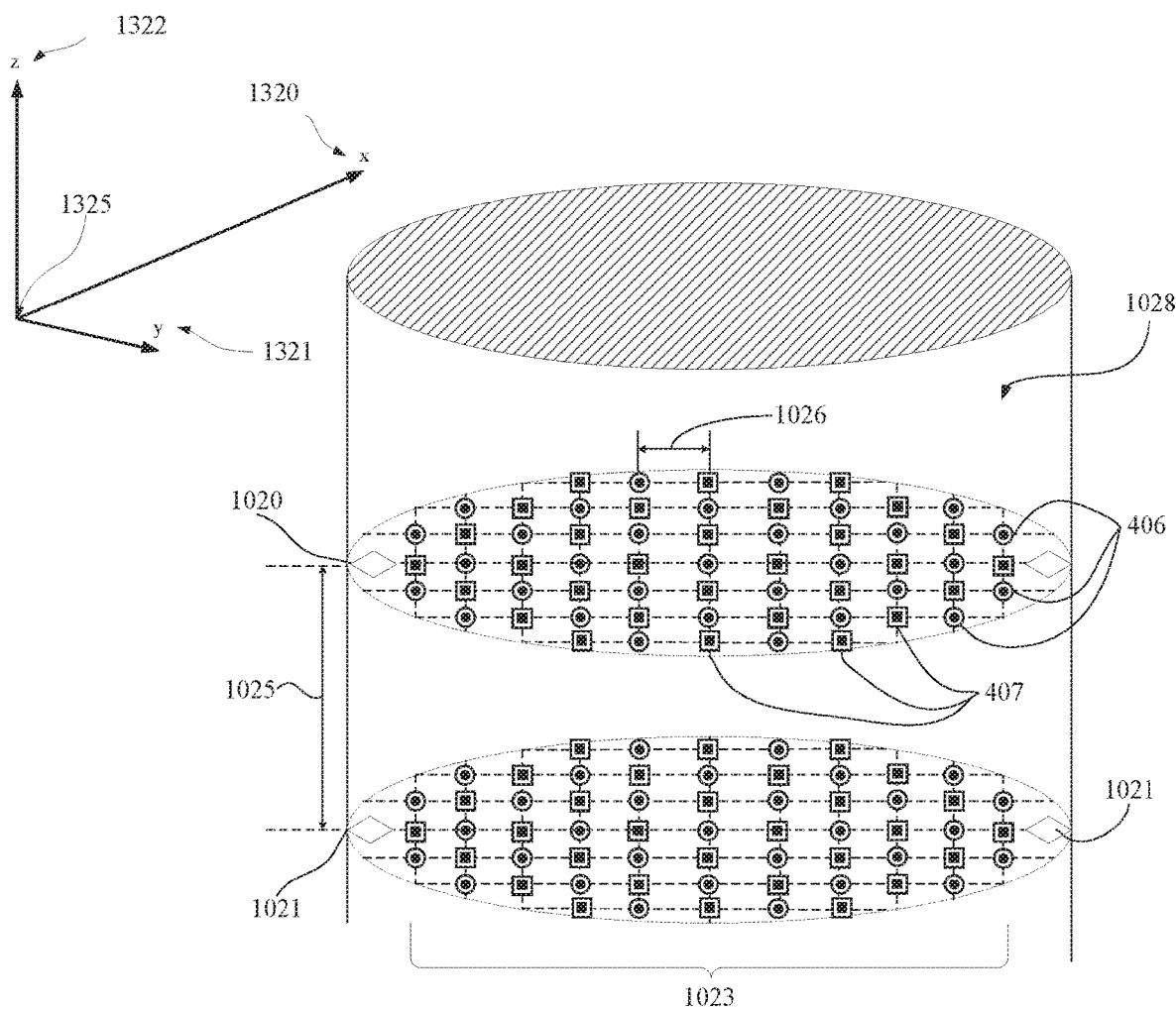
FIG. 10D may be a diagram of a first-sensor-tag and a second-sensor-tag arranged in a material-of-interest with an initial predetermined spacing between the first-sensor-tag and the second-sensor-tag in this material-of-interest.

In some embodiments, at least one electric circuit 140 (of monitoring-sensor-tag 120) may be attached to and in communication with the at least one sensor, such as, but not limited to: spiral-formed-electric-conductor 703 (see e.g., FIG. 7C); standalone-strain-sensor 1006 (see e.g., FIG. 10B, FIG. 10C, and FIG. 18); and lattice-of-sensors 1023 (see e.g., FIG. 10D).

In some embodiments, the one or more readings taken from the at least one sensor may be readings of one or more of: inductance from one or more inductance-based-sensors 208; capacitance from one or more capacitive-based sensors 202; and/or resistance from one or more resistance-based sensors 203. See e.g., FIG. 2A through and including FIG. 2G. In some embodiments, such one or more readings of current values, over time, of one or more of inductance, capacitance, or resistance may determine changes in such properties. In some embodiments, initial current value readings may function as baseline readings that future current value readings may be monitored against to determine changes.

In some embodiments, these one or more readings may provide status information to determine one or more of: structural integrity of a current state of the material-of-interest; structural integrity changes of the material-of-interest; pressure received at the material-of-interest; force received at the material-of-interest; stress received at the material-of-interest; torsion received at the material-of-interest; deformation received at the material-of-interest; temperature at some portion of the material-of-interest; positional changes of a given monitoring-sensor-tag 120 attached to the material-of-interest with respect to position of another monitoring-sensor-tag 120 attached to the material-of-interest, wherein the given monitoring-sensor-tag 120 and the other monitoring-sensor-tag are 120 selected from the one or more monitoring-sensor-tags 120 attached to the material-of-interest; or positional changes of at least one monitoring-sensor-tag 120 attached to the material-of-interest with respect to time, wherein the at least one monitoring-sensor-tag 120 is selected from the one or more monitoring-sensor-tags 120. In some embodiments, readings from one or more of capacitive-based sensor 202, resistance-based sensor 203, and/or inductance-based-sensor 208 may yield such current status information as noted above.

In some embodiments, structural integrity changes of the material-of-interest may comprise monitoring for liquid penetration into the given material-of-interest. In some embodiments, liquid as used herein may comprise viscous fluids, slurries, and/or slow flow films. In some embodiments, liquid as used herein may comprise viscous fluids, slurries, and/or slow flow films that may harden and/or become cured into a hardened state (with no to minimal flow). In some embodiments, structural integrity changes of the material-of-interest may comprise monitoring for liquid penetration to the at least one sensors (e.g., 202 and/or 203) located within the given material-of-interest. For example, and without limiting the scope of the present invention, the at least one sensors (e.g., 202, 203, and/or 1006) may monitor for liquid penetration into filling 1001, see e.g., FIG. 10A; for liquid penetration beneath dental-crowns 1005, see e.g., FIG. 10B; for liquid penetration into root-canal-cavity 1003, see e.g., FIG. 10B; or monitor for liquid penetration into other materials-of-interest. Such liquid penetration may indicate an increased likelihood of infection and/or of structural integrity failures and/or detachment of the given material-of-interest (e.g., detachment of: dental-filling 1001, dental-crown 1005, root-canal-post 1004, and/or dental-implant 1007). In some embodiments, such at least one sensors (e.g., 202, 203, and/or 1006) may monitor for liquid penetration at the at least one sensors (e.g., 202, 203, and/or 1006), in at least some portion of the given material-of-interest, and/or within hollow space within the given material-of-interest. In some embodiments, such at least one sensors (e.g., 202, 203, and/or 1006) may monitor for liquid penetration without the at least one sensors (e.g., 202, 203, and/or 1006) coming in physical contact with the liquid.

It should be appreciated by those of ordinary skill in the relevant art that capacitive-based sensor 202 and capacitance measurement circuits 205 may be used to implement configurations depicted in FIG. 2A, FIG. 2D, FIG. 2E, and/or FIG. 2G to quantify, measure, track, monitor, and/or analyze various states and changes in states of materials-of-interest with one or more monitoring-sensor-tag 120 processing the one or more reading originating from such capacitive-based sensor 202.

Figure 3:
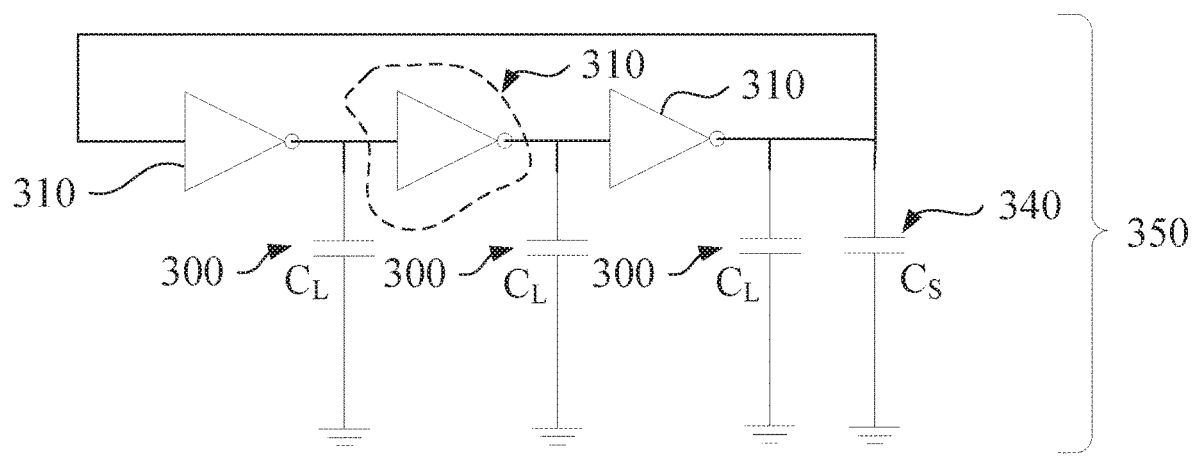
FIG. 3 may be a circuit diagram of a ring oscillator implementing a capacitance measurement circuit.

FIG. 3 may be a circuit diagram of a ring oscillator 350 implementing a capacitance measurement circuit 205 with capacitive-based sensor 202. In some embodiments, capacitance measurement circuit 205 with capacitive-based sensor 202 may be carried out via ring oscillator 350. In some embodiments, ring oscillator circuit 350 may measure values of capacitive-based sensor 202, transferring such values of capacitive-based sensor 202 into frequency of oscillations of said ring oscillator 350.

Continuing discussing FIG. 3, in some embodiments, ring oscillator 350 may comprise an odd number of stages. In some embodiments, each such stage may comprise a respective digital invertor 310 and load capacitor 300. In some embodiments, digital invertor 310 may be C-MOS pair 310, which for example may be a combination of p-type and n-type field-effect transistors depicted in FIG. 5B. In some embodiments, ring oscillator 350 may also comprise capacitive-based sensor 340 (located in some embodiments, after a last stage). In some embodiments, an oscillation frequency of ring oscillator circuit 350 man be found using expression (1):

$$F = \frac{1}{2N\tau} \quad (1)$$

where N may be a number of stages and τ may be a delay of each stage, and where τ can be expressed as:

$$\tau = \frac{CV_T}{I_t} \quad (2)$$

where C is a capacitance of each stage, $V_T$ is a threshold voltage of a C-MOS pair 310, and $I_t$ is an average charging current of the load capacitor C of each stage. If the capacitance of the capacitive-based sensor 340 changes, the oscillation frequency of ring oscillator circuit 350 may change as well, according to the expressions above.

Figure 4A:
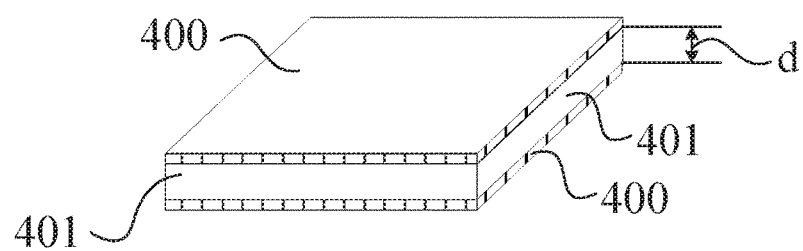
FIG. 4A may be a perspective view of a basic capacitor.
Figure 4B:
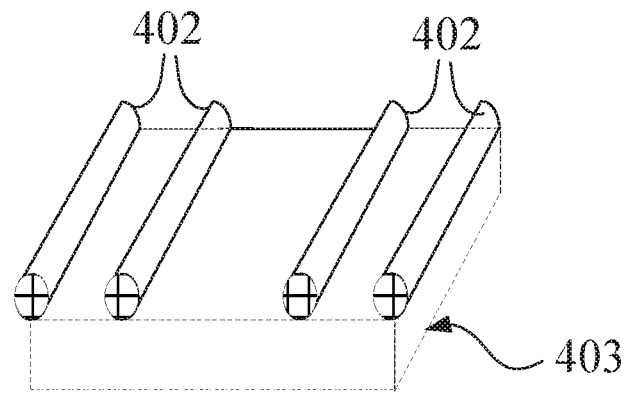
FIG. 4B may be a perspective view of a capacitor with substantially parallel regions of a conductive surface of type "A."
Figure 4C:
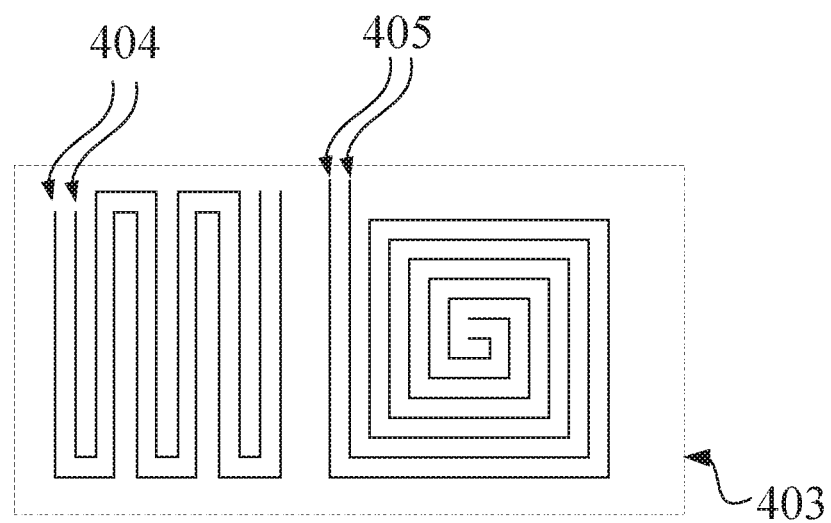
FIG. 4C may be a top view of a capacitor; with substantially parallel regions of a conductive surface of type "B"; and with substantially parallel regions of a conductive surface of type "C."
Figure 4D:
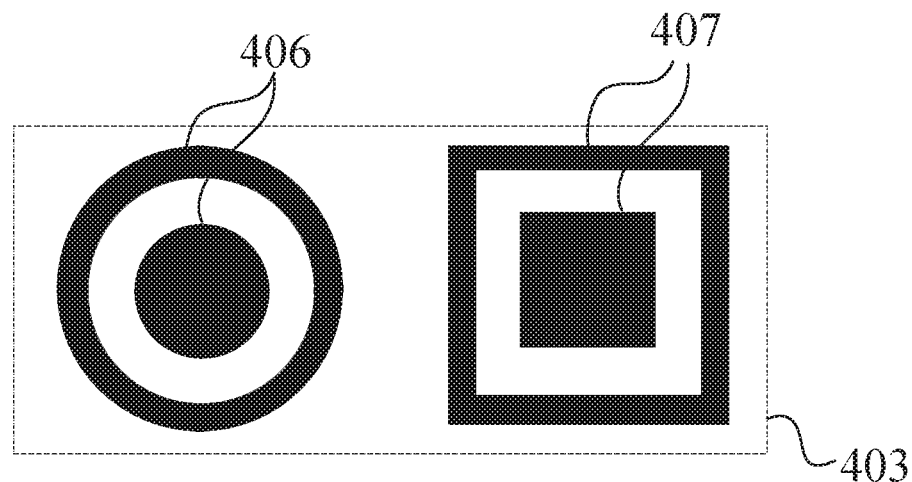
FIG. 4D may be a top view of a capacitor; with regions of a conductive surface of type "D"; and with regions of a conductive surface of type "E."
Figure 4E:
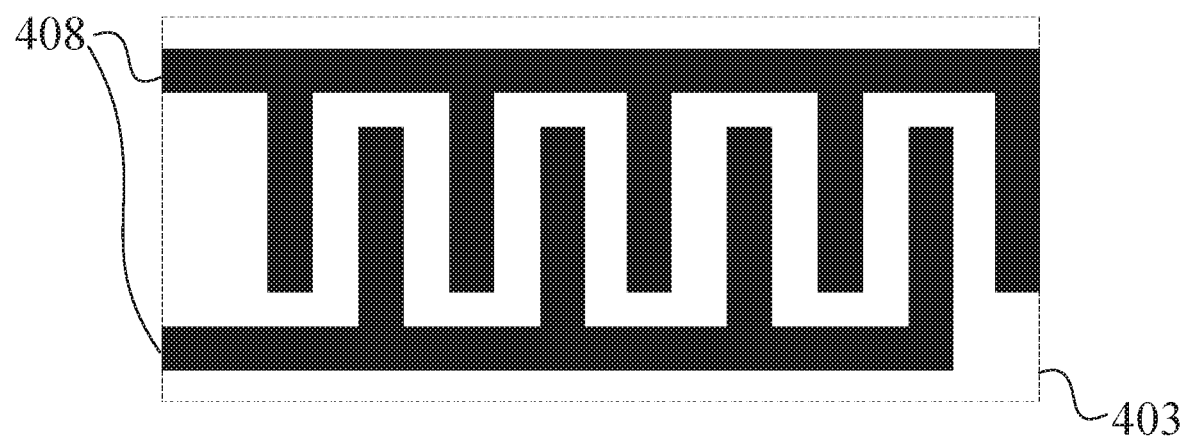
FIG. 4E may be a top view of a capacitor, with regions of a conductive surface of type "F."

FIG. 4A through and including FIG. 4E may depict various capacitors, which may be used as capacitors in at least some of the circuit diagrams shown in the figures. FIG. 4A through and including FIG. 4E may depict various capacitors, which may be used as components in capacitive-based sensors 202.

FIG. 4A may be a perspective view of a basic capacitor. In some embodiments, this basic capacitor may comprise two substantially parallel plates 400 that may be separated by dielectric material 401. In some embodiments, such plates 400 may be separated from each by a distance of d. In some embodiments, plates 400 may be constructed from substantially conductive materials. In some embodiments, the capacitance of this basic capacitor may be found from the following expression (3):

$$C = \frac{\varepsilon_0 \varepsilon_r A}{d} \quad (3)$$

where A is an area of each of the conductive plates 400, d is a width of the dielectric material 401 between the conductive plates 400, $\varepsilon_r$ is the relative permittivity of the dielectric material 401, and $\varepsilon_0 \approx 8.85 \cdot 10^{-12}$ F/m is vacuum permittivity constant.

FIG. 4B may be a perspective view of a capacitor with substantially parallel regions of a conductive surface of type "A" 402 mounted to substrate 403. In some embodiments, substrate 403 may be a dielectric material. In some embodiments, the capacitor of FIG. 4B may comprise two pairs of substantially parallel regions of conductive surface of type "A" 402 mounted to substrate 403. In some embodiments, conductive surface of type "A" 402 may be constructed from electrically conductive materials of construction.

FIG. 4C may be a top view of a capacitor; with substantially parallel regions of a conductive surface of type "B" 404; and with substantially parallel regions of a conductive surface of type "C" 405. In some embodiments, conductive surface of type "B" 404 and conductive surface of type "C" 405 may be mounted to a same substrate 403. In some embodiments, substrate 403 may be a dielectric material. In some embodiments, conductive surface of type "B" 404 and conductive surface of type "C" 405 may be constructed from electrically conductive materials of construction. In some embodiments, conductive surface of type "C" 405 may be arranged in a pair of substantially parallel rows in a spiral fashion with substrate 403 disposed between or/and under such substantially parallel rows; for example, and without limiting the scope of the present invention, arranged as conductive wires in concentric circles on a dielectric substrate.

FIG. 4D may be a top view of a capacitor; with regions of a conductive surface of type "D" 406; and with regions of a conductive surface of type "E" 407. In some embodiments, conductive surface of type "D" 406 and conductive surface of type "E" 407 may be mounted to a same substrate 403. In some embodiments, substrate 403 may be a dielectric material. In some embodiments, conductive surface of type "D" 406 and conductive surface of type "E" 407 may be constructed from electrically conductive materials of construction. In some embodiments, conductive surface of type "D" 406 may be arranged in concentric circles (in a bull's eye fashion) with substrate 403 disposed between such concentric circles. In some embodiments, conductive surface of type "E" 407 may be arranged in concentric squares with substrate 403 disposed between or/and under such concentric squares.

FIG. 4E may be a top view of a capacitor, with regions of a conductive surface of type "F" 408. In some embodiments, the capacitor of FIG. 4E may have regions of conductive surface of type "F" 408 mounted to substrate 403. In some embodiments, substrate 403 may be a dielectric material. In some embodiments, conductive surface of type "F" 408 may be constructed from electrically conductive materials of construction.

FIG. 4B, FIG. 4C, FIG. 4D, and FIG. 4E may depict examples of various capacitors that may be used in some capacitive-based sensors 202 embodiments. Such capacitors may form at least part of capacitive-based sensors 202 that may be the at least one sensor of a given monitoring-sensor-tag 120. In some embodiments, capacitive-based sensors 202 may comprise one or more of: plates 400, conductive surface type "A" 402, conductive surface type "B" 404, conductive surface type "C" 405, conductive surface type "D" 406, conductive surface type "E" 407, and/or conductive surface type "F" 408; placed (e.g., mounted, installed, immersed, implanted, and/or the like) on a dielectric substrate 403 (and/or onto dielectric material 401 in some embodiments).

Continuing discussing FIG. 4B, FIG. 4C, FIG. 4D, and FIG. 4E, in some embodiments, the given material-of-interest that may be the object of analysis, monitoring, and/or tracking may be the dielectric substrate 403. Thus in use, material-of-interest, acting as dielectric substrate 403, may substantially fill in and/or substantially cover one or more of: plates 400, conductive surface type "A" 402, conductive surface type "B" 404, conductive surface type "C" 405, conductive surface type "D" 406, conductive surface type "E" 407, and/or conductive surface type "F" 408. Use of such capacitors in capacitive-based sensor 202 may permit monitoring and/or detection of structural defects in the material-of-interest (such as, but not limited to, cracks or changes in structure of material-of-interest). Because changes in structure of the material-of-interest acting as the dielectric substrate 403 may change the relative permittivity $\varepsilon_r$, which, in turn, may change the capacitance of capacitive-based sensor 202 in communication with capacitance measurement circuit 205.

For example, and without limiting the scope of the present invention, a change in the relative permittivity $\varepsilon_r$ of material-of-interest due to a structural change may be detected (registered) by capacitive-based sensor 340 in ring oscillator 350, which may be one possible implementation of capacitance measurement circuit 205 with capacitive-based sensor 202. That is, this change may register as a change in the frequency of ring oscillator 350. Such frequency changes may be measured, monitored, tracked, and/or analyzed to provide strong indications of structural defects and/or of structural changes in the given material-of-interest. For example, and without limiting the scope of the present invention, the relative permittivity of concrete is approximately 4.5 times higher than the relative permittivity of air. Accordingly, any appearance of a crack in the concrete, that may permit air ingress, may then alter the capacitance of the implanted monitoring-sensor-tag 120 into the given material-of-interest, which in this example may be a section of concrete. A same concept may be applied to liquid ingress into structural defects and/or structural changes of other materials-of-interest, such as, but not limited to, dental-filling 1001.

Capacitive-based, resistance-based, inductance-based or other types of sensors as part of a given monitoring-sensor-tag 120, that may be implanted to (i.e., attached to) the given material-of-interest, may also be used to measure temperature of the analyzed given material-of-interest, according to various embodiments of the present invention.

Figure 5A:
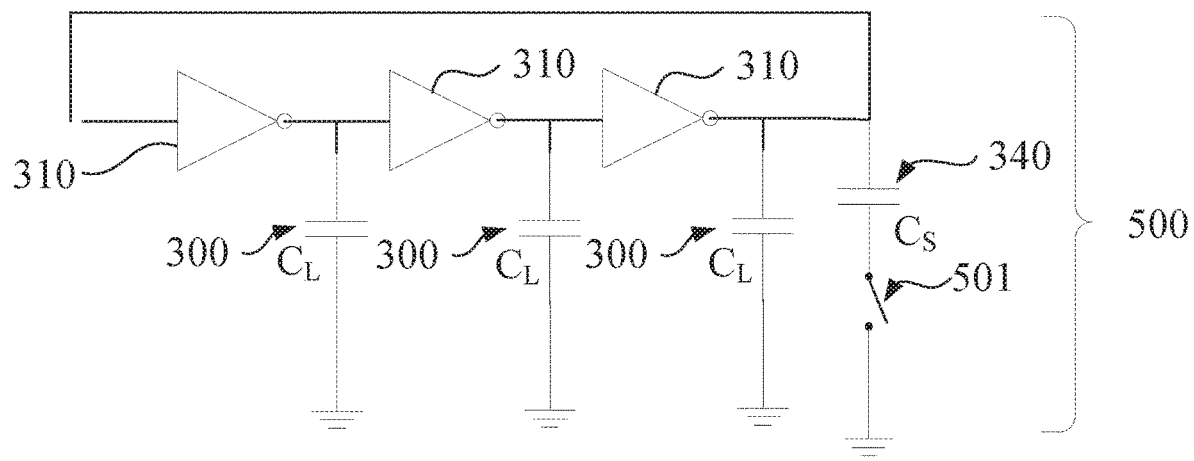
FIG. 5A may be a circuit diagram of a ring oscillator implementing a capacitance measurement circuit.

FIG. 5A may be a circuit diagram of a ring oscillator 500 implementing a capacitance measurement circuit 205 with capacitive-based sensor 202. In some embodiments, capacitance measurement circuit 205 with capacitive-based sensor 202 may be carried out via ring oscillator 500. In some embodiments, ring oscillator circuit 500 may measure values of capacitive-based sensor 202, transferring such values of capacitive-based sensor 202 into frequency of oscillations of said ring oscillator 500. In some embodiments, ring oscillator 500 may be used to monitor, track, and/or analyze temperature changes to the given material-of-interest where ring oscillator 500 may be implanted to (i.e., attached to).

Continuing discussing FIG. 5A, in some embodiments, ring oscillator 500 may comprises an odd number of stages. In some embodiments, each such stage may comprise a respective digital invertor 310 and load capacitor 300. In some embodiments, digital invertor 310 may be C-MOS pair 310. In some embodiments, ring oscillator 500 may also comprise capacitive-based sensor 340 (located in some embodiments, after a last stage) and a switch 501 in series with capacitive-based sensor 340.

Figure 5B:
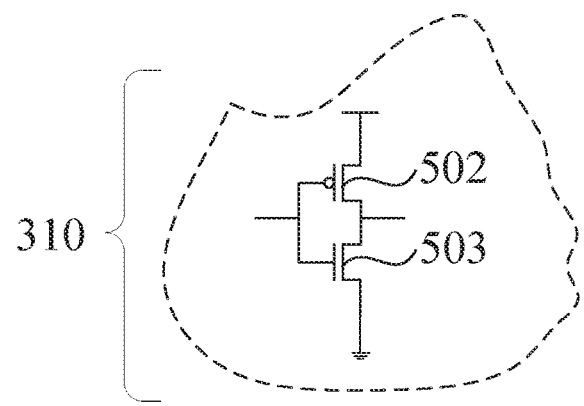
FIG. 5B may be a circuit diagram of a C-MOS pair digital invertor.

FIG. 5B may be a circuit diagram of C-MOS pair 310 (digital invertor 310). In some embodiments, C-MOS pair 310 (digital invertor 310) may comprise P-MOS transistor 502 and N-MOS transistor 503.

Continuing discussing FIG. 5A and FIG. 5B, in some embodiments, ring oscillator 500 may comprise switch 501. In some embodiments, switch 501 may connect or disconnect capacitive-based sensor 340 from ring oscillator 500. Accordingly, the oscillation frequency of ring oscillator 500 may depend on an ambient temperature of the surrounding material-of-interest. Current I flowing through P-MOS transistor 502 and N-MOS transistor 503, forming digital invertor 310, may affect a delay of each stage, depending on the ambient temperature of the surrounding material-of-interest. In this manner, the ring oscillator 500, with the switchable capacitive-based sensor 340, may function as a temperature sensor for the monitored given material-of-interest. With switch 501 in a disconnected state, capacitive-based sensor 340 may not influence the oscillation frequency of ring oscillator 500; therefore the oscillation frequency of ring oscillator 500 may correlate with the ambient temperature of the surrounding material-of-interest.

It should be appreciated by those of ordinary skill in the relevant art that resistance-based sensors 203 and resistance measurement circuits 206 may be used to implement configurations depicted in FIG. 2B, FIG. 2D, FIG. 2F, and/or FIG. 2G to quantify, measure, track, monitor, and/or analyze various states and changes in states of materials-of-interest with one or more monitoring-sensor-tag 120 processing the one or more reading originating from such resistance-based sensors 203.

Figure 6:
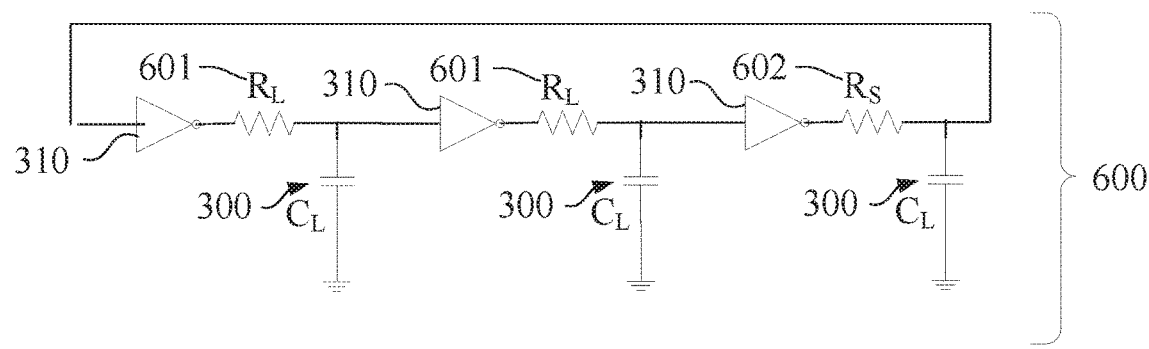
FIG. 6 may be a circuit diagram of a ring oscillator implementing a resistance measurement circuit.

FIG. 6 may be a circuit diagram of a ring oscillator 600 implementing a resistance measurement circuit 206 with resistance-based sensor 203. In some embodiments, ring oscillator 600 may be used to sense, measure, monitor, track, and/or analyze strains, force, torsion, and/or pressure in portions of material-of-interest with monitoring-sensor-tag 120; wherein the at least one sensor (of monitoring-sensor-tag 120) may comprise ring oscillator 600. In the embodiment implemented and depicted in FIG. 6, ring oscillator 600 (e.g., implemented as resistance measurement circuit 206 with resistance-based sensor 203) may comprise resistance-based sensor 203, an example of a strain-influenced resistor 602; wherein monitoring-sensor-tag 120 may comprise ring oscillator 600 and the at least one sensor (of monitoring-sensor-tag 120) may comprise a strain-influenced resistor 602. Thus, ring oscillator 600 may be used to sense, measure, monitor, track, and/or analyze deformations, structural defects, and/or structural changes in material-of-interest.

Continuing discussing FIG. 6, in some embodiments, ring oscillator circuit 600 may comprise an odd number of stages. In some embodiments, each such stage may comprise digital invertor 310 and an "RC pair." In some embodiments, each such RC pair (except a final stage) may comprise a load capacitor 300 and a load resistor 601. In some embodiments, a final stage RC pair may comprise a load capacitor 300 and a strain-influenced resistor 602. In some embodiments, an oscillation frequency F of ring oscillator 600 may be determined from the expression (4):

$$F = \frac{1}{2N\tau} = \frac{1}{2N \cdot f(RC, V_t)} \qquad (4)$$

where N may be a number of stages, $\tau$ may be a delay of each stage, $f(RC, V_t)$ may be a function of the RC value of each stage, and of the threshold voltage of CMOS invertor (digital inventor 310) $V_r$. In some embodiments, strain-influenced resistor 602 (denoted as $R_s$ in FIG. 6) may be a strain-influenced resistor. In some embodiments, ring oscillator 600 may be a component of the least one sensor of monitoring-sensor-tag 120 that may be attached to (i.e., implanted, immersed, and/or the like) to the given material-of-interest. And changes (e.g., strains, forces, torsion, pressure, structural changes, deformations, and/or the like) in the given material-of-interest may then translate into changes in the oscillation frequency F that ring oscillator 600 may be sensing, measuring, monitoring, tracking, and/or analyzing.

Figure 7A:
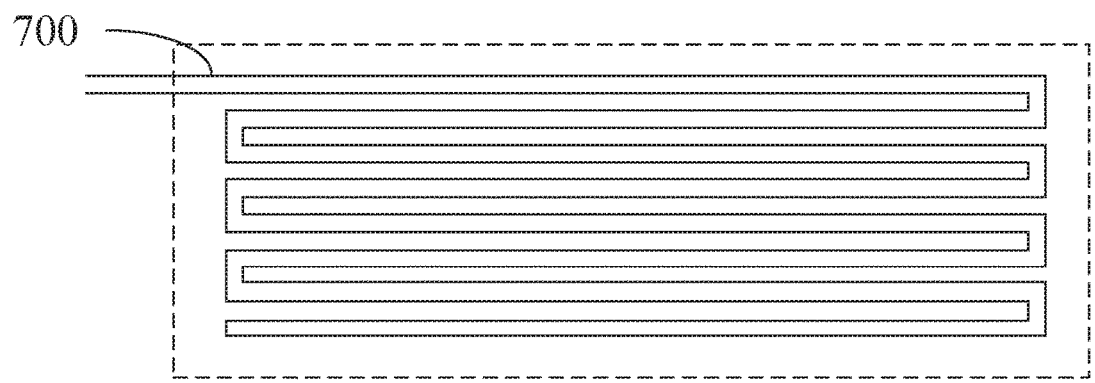
FIG. 7A may be a top view of an example of a stress sensor used in some embodiments of the present invention.

FIG. 7A may be a top view of an example of a stress sensor used in some embodiments of the present invention. In some embodiments, such a stress sensor may be the at least one sensor of monitoring-sensor-tag 120. In some embodiments, the stress sensor depicted in FIG. 7A may be strain-influenced resistor 700. In some embodiments, strain-influenced resistor 700 may be a part of an implementation of ring oscillator 600, strain-influenced resistor 602; thus strain-influenced resistor 700 may be a type of resistance-based sensor 203 used to sense, measure, monitor, track, and/or analyze changes (e.g., strains, forces, torsion, pressure, structural changes, deformations, and/or the like) in the given material-of-interest by such changes to the material-of-interest may translate into changes in the oscillation frequency F that ring oscillator 600 may be sensing, measuring, monitoring, tracking, and/or analyzing.

Figure 7B:
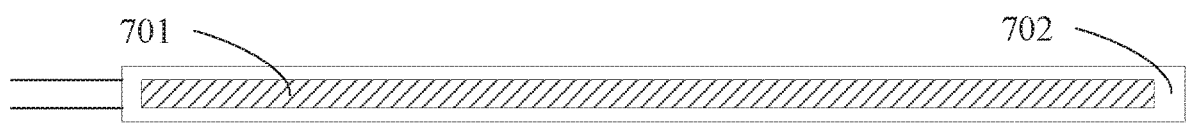
FIG. 7B may be a top view of an example of a stress sensor used in some embodiments of the present invention.

FIG. 7B may be a top view of an example of a stress sensor used in some embodiments of the present invention. In some embodiments, such a stress sensor may be the at least one sensor of monitoring-sensor-tag 120. In some embodiments, this stress sensor depicted in FIG. 7B may be an example of a resistance-based sensor 203. In some embodiments, this stress sensor depicted in FIG. 7B may comprise thin-film-coating 701 and substrate 702. In some embodiments, thin-film-coating 701 may be an electrically resistive compound. When monitoring-sensor-tag 120 with the stress sensor shown in FIG. 7B may be attached to (e.g., implanted, immersed, touching, and/or the like) the given material-of-interest, changes (e.g., strains, forces, torsion, pressure, structural changes, deformations, and/or the like) in the given material-of-interest may translate into changes in the resistance of thin-film-coating 701 which may be registered, sensed, measured, monitored, tracked, and/or analyzed by resistance-based sensor 203. In some embodiments, substrate 702 may be a flexible non-conductive material upon which the thin-film-coating 701 may be attached or set upon. Physical forces acting on and causing various changes such as, but not limited to, possible fracturing, cracking, bending, twisting, excessive pressure, abnormal temperature, and/or the like, of substrate 702 may also change monitorable conductive qualities of thin-film coating 701.

Figure 7C:
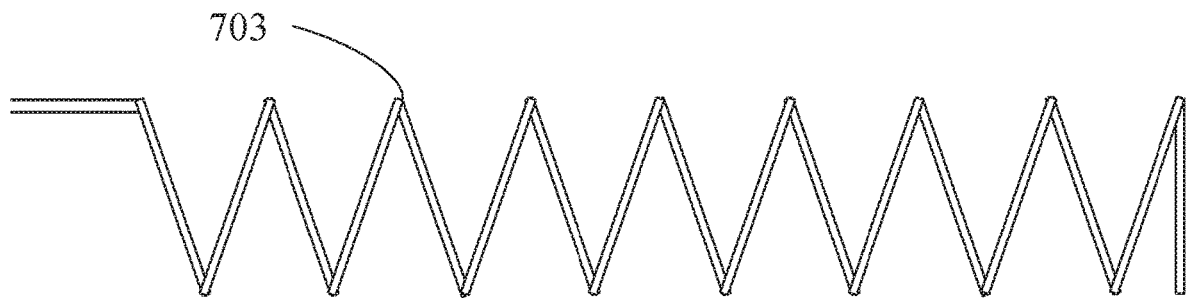
FIG. 7C may be a top view of an example of a stress sensor used in some embodiments of the present invention.

FIG. 7C may be a top view of an example of a stress sensor used in some embodiments of the present invention. In some embodiments, such a stress sensor may be the at least one sensor of monitoring-sensor-tag 120. In some embodiments, this stress sensor depicted in FIG. 7B may be an example of a resistance-based sensor 203. In some embodiments, the stress sensor depicted in FIG. 7C may be spiral-formed-electric-conductor 703. In some embodiments, spiral-formed-electric-conductor 703 may be a type of resistance-based sensor 203. In some embodiments, spiral-formed-electric-conductor 703 may be substantially spiral shaped. When monitoring-sensor-tag 120 with the stress sensor (e.g., spiral-formed-electric-conductor 703) shown in FIG. 7C may be attached to (e.g., implanted, immersed, touching, and/or the like) the given material-of-interest, changes (e.g., strains, forces, torsion, pressure, structural changes, deformations, and/or the like) in the given material-of-interest may translate into changes in the resistance of spiral-formed-electric-conductor 703 which may be registered, sensed, measured, monitored, tracked, and/or analyzed by resistance-based sensor 203.

Figure 8:
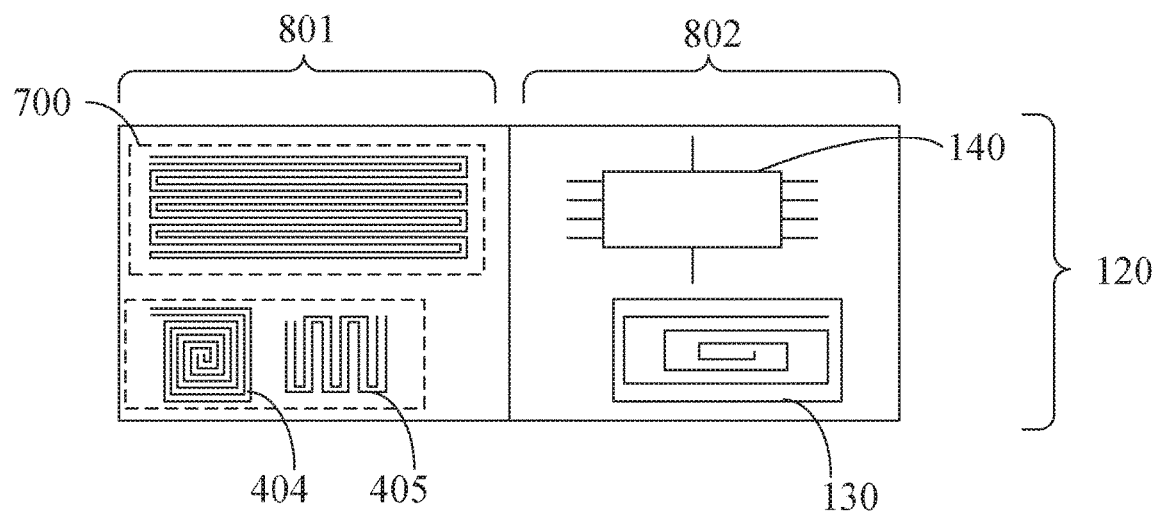
FIG. 8 may be a diagrammatical top view of a monitoring-sensor-tag's structure and components, as used in some embodiments of the present invention.

FIG. 8 may be a diagrammatical top view of a monitoring-sensor-tag's 120 structure and components, as used in some embodiments of the present invention. In some embodiments, a given monitoring-sensor-tag 120 may be divided functionally and/or structurally into sensor-portion 801 and processing-portion 802. While sensor-portion 801 and processing-portion 802 may be shown as distinct portions in FIG. 8, in some embodiments, sensor-portion 801 and processing-portion 802 may overlap. In some embodiments, sensor-portion 801 may comprise the at least one sensor. In some embodiments, processing-portion 802 may comprise at least one antenna 130 and at least one electric circuit 140; wherein at least one electric circuit 140 and at least one antenna 130 may be in communication with each other. In some embodiments, at least one electric circuit 140 may be in communication with sensor-portion 801. In some embodiments, at least one electric circuit 140 may be in communication with sensor-portion with the at least one sensor. In some embodiments, at least one electric circuit 140 may comprise processing circuitry 204. In some embodiments, at least one electric circuit 140 may comprise processing circuitry 204 and may further comprise one or more of capacitive measurement circuit 205, resistance measurement circuit 206, and/or inductance measurement circuit 209.

Continuing discussing FIG. 8, as shown in FIG. 8 the at least one sensor of sensor-portion 801 may comprise three distinct sensors: conductive surface type "B" 404, conductive surface type "C" 405, and strain-influenced resistor 700 (which may be a part [component] of an implementation of ring oscillator 600). See e.g., FIG. 4C, FIG. 6, and FIG. 7A; as well as their respective discussions above. Continuing discussing FIG. 8, in some embodiments, strain-influenced resistor 700 may be strain influenced sensor. In some embodiments, conductive surface type "B" 404 and conductive surface type "C" 405 may function as compound integrity sensors that may allow for structural integrity analysis of the given material-of-interest where the given sensor may be implanted. In some embodiments, these three distinct sensors may be in communication with at least one electric circuit 140. In some embodiments, at least one electric circuit 140 may provide control logic for controlling these three distinct sensors. In some embodiments, at least one electric circuit 140 may provide control logic for controlling these three distinct sensors by taking one or more readings from these three distinct sensors and instructing at least one antenna 130 in the transmission of such one or more readings for pickup by one or more readers 100.

Continuing discussing FIG. 8, while three distinct sensors may be shown in FIG. 8, it is expressly contemplated the at least one sensor of sensor-portion 801 may comprise one or more of the sensors discussed and shown in the accompanying figures.

Continuing discussing FIG. 8, in some embodiments, sensor-portion 801 and processing-portion 802 may be manufactured as single and distinct articles of manufacture, that once assembled may be in communication with each other. In some embodiments, sensor-portion 801 and processing-portion 802 may be manufactured by printing as single and distinct articles of manufacture, that once assembled may be in communication with each other.

Continuing discussing FIG. 8, in some embodiments, sensor-portion 801 and processing-portion 802 may be manufactured as a single integrated article of manufacture. In some embodiments, sensor-portion 801 and processing-portion 802 may be printed as a single integrated article of manufacture.

Figure 9:
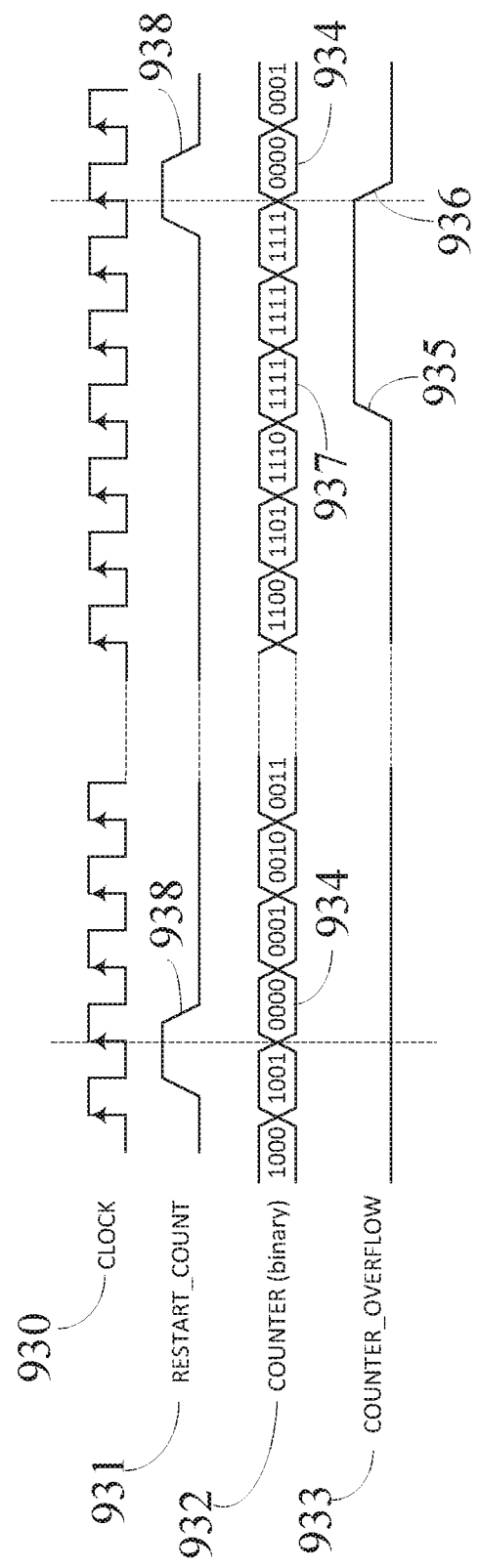
FIG. 9 may be a diagram of control and status signals, in accordance with some embodiments of the present invention.

As noted above, in some embodiments, upon at least one antenna 130 receiving electromagnetic radiation of a predetermined characteristic as an input from at least one antenna 110 of reader 100, this input may cause at least one electric circuit 140 to take one or more readings from the at least one sensor and to then transmit such one or more readings using at least one antenna 130. FIG. 9 may be a diagram of control and status signals, in accordance with some embodiments of the present invention. In some embodiments, electric circuit 140 (or processing circuitry 204 in some embodiments) may be executing the functions shown in FIG. 9.

Continuing discussing FIG. 9, in some embodiments, electric circuit 140 and/or processing circuitry 204 may be event-driven (or input-driven) and digital CLOCK 930 may implement events which condition time and orchestrate the functionality of electric circuit 140 and/or processing circuitry 204. In some embodiments, CLOCK 930 may be digital clock. In some embodiments, CLOCK 930 may be a binary clock. In some embodiments, RESTART_COUNT signal 931 may change to binary value 1 for at least one CLOCK 930 cycle by electric circuit 140 (or processing circuitry 204 in some embodiments) receiving respective instruction(s) from reader 100, as indicated at Pulse of RESTART_COUNT signal 938. That is, Pulse of RESTART_COUNT signal 938 may be a response to at least one antenna 130 receiving electromagnetic radiation of a predetermined characteristic as an input from at least one antenna 110 of reader 100, where this input may then cause at least one electric circuit 140 to take the one or more readings from the at least one sensor. In some embodiments, a RESTART_COUNT signal 931 may trigger resetting of a COUNTER 932. In some embodiments, COUNTER 932 may store values from the at least one sensor; such as, the one or more readings. In some embodiments, COUNTER 932 may store values of a number of ring oscillator (e.g., ring oscillator 350 or ring oscillator 600) oscillations. In some embodiments, COUNTER 932 may be a digital register. In some embodiments, COUNTER 932 may be a binary counter. In some embodiments, COUNTER 932 may represent a state of a digital ripple counter, input of which may be connected to the last stage of ring oscillator (e.g., ring oscillator 350 or ring oscillator 600). In some embodiments, COUNTER 932 may have its value set to a zero value, as indicated at zero value 934; which may be triggered by Pulse of RESTART_COUNT signal 938 that may in turn trigger RESTART_COUNT signal 931, which may in turn result in zero value 934 for COUNTER 932. In some embodiments, if COUNTER 932 may reach a maximal value 937, then a COUNTER OVERFLOW signal 933 may be triggered; wherein this COUNTER OVERFLOW signal 933 changes its binary value from 0 to 1, as indicated at "0-to-1 transition of Pulse of Counter Overflow signal 935." In that case, COUNTER OVERFLOW signal 933 may stay at binary value 1 until a next change of RESTART_COUNT signal 931 from binary value 0 to 1 for at least one CLOCK 930 cycle, as indicated at "1-to-0 transition of Pulse of Counter Overflow signal 936."

Optionally, in some embodiments, a value Y, stored in a divider register, may advance COUNTER 932 to the next value every Y CLOCK 930 cycles. That may prevent COUNTER 932 reaching its maximal value 937 too soon.

FIG. 10A may be a diagram of a patient 1328 tooth 1000 with one or more monitoring-sensor-tags 120 placed in a dental-filling 1001 as a material-of-interest, in accordance with some embodiments of the present invention. FIG. 10A may depict a schematic diagram of tooth 1000. Tooth 1000 may comprise one or more dental-fillings 1001. FIG. 10A may also depict gum 1002, so as to schematically indicate a gum 1002 line in relation to tooth 1000 (for demonstration purposes).

In FIG. 10A, dental-filling(s) 1001 may be the material-of-interest. For example, and without limiting the scope of the present invention, dental-fillings 1001 may be selected from filling materials used in the practice of dentistry, such as, but not limited to "fill" cavities and/or to "seal" undesirable surface geometry on teeth 1000. For example, and without limiting the scope of the present invention, dental-fillings 1001 may be selected from one or more of: composite resins; glass ionomer cements; resin-ionomer cements; porcelain (and/or ceramics); porcelain fused to a metal; and/or the like.

Continuing discussing FIG. 10A, in some embodiments, one or more monitoring-sensor-tags 120 may be attached to, located on, located in, immersed, implanted, and/or the like in the one or more dental-fillings 1001 of tooth 1000. Note, characteristics (e.g., one or more readings) of such one or more monitoring-sensor-tags 120 placement with respect to one or more dental-fillings 1001 may change over time as the given one or more dental-fillings 1001 may cure and/or harden. In some embodiments, placement of one or more monitoring-sensor-tags 120 with respect to one or more dental-fillings 1001 may be random. In some embodiments, placement of one or more monitoring-sensor-tags 120 with respect to one or more dental-fillings 1001 may be substantially uniform. In some embodiments, placement of one or more monitoring-sensor-tags 120 with respect to one or more dental-fillings 1001 may be approximately uniform. In some embodiments, placement of one given monitoring-sensor-tags 120 (e.g., a first-sensor-tag 1020) with respect to another different monitoring-sensor-tags 120 (e.g., a second-sensor-tag 1021) may be specified (e.g., at a fixed distance such as at an initial predetermined spacing 1025) within the given material-of-interest, such as dental-filling 1001 (see e.g., FIG. 10D discussed below). Thus, placement of such one or more monitoring-sensor-tag 120 with respect to one or more dental-fillings 1001 may be used to obtain various information about one or more dental-fillings 1001 and may do so in a non-invasive manner and in a manner that does not require use of ionizing imaging radiation.

FIG. 10B may be a diagram of a patient 1328 tooth 1000 with one or more monitoring-sensor-tags 120 placed in: a root-canal-cavity 1003, in a root-canal-post 1004, and/or in a dental-crown 1005; in accordance with some embodiments of the present invention. In FIG. 10B the material-of-interest may be selected from one or more of: root-canal-cavity 1003, root-canal-post 1004, dental-crown 1005, and/or the like. In some embodiments, one or more monitoring-sensor-tags 120 may be attached to, located on, located in, immersed, implanted, and/or the like in the root-canal-cavity 1003, the root-canal-post 1004, and/or the dental-crown 1005. In some embodiments, one or more monitoring-sensor-tags 120 may further comprise a standalone-strain-sensor 1006. In some embodiments, standalone-strain-sensor 1006 may be an external sensor structure attached to a given monitoring-sensor-tag 120. In some embodiments, standalone-strain-sensor 1006 may be a strain-influenced resistor 700 or a spiral-formed-electric-conductor 703. In some embodiments, standalone-strain-sensor 1006 may be capacitive-based sensor 202 or a resistance-based sensor 203. In some embodiments, standalone-strain-sensor 1006 may be in communication with one or more of: electric circuit 140, processing circuitry 204, capacitance measurement circuit 205, and/or resistance measurement circuit 206.

FIG. 10C may be a diagram of a patient 1328 tooth dental-implant 1007 with one or more monitoring-sensor-tags 120, in accordance with some embodiments of the present invention. In some embodiments, dental-implant 1007, which may be an artificial tooth, may comprise implant-post 1008; wherein implant-post 1008 may be anchored to patient 1328. In FIG. 10C, the material-of-interest may be dental-implant 1007 and/or implant-post 1008. in some embodiments, one or more monitoring-sensor-tags 120 may be attached to, located on, located in, immersed, implanted, and/or the like in the dental-implant 1007 and/or in the implant-post 1008. In some embodiments, one or more monitoring-sensor-tags 120 may further comprise a standalone-strain-sensor 1006. In some embodiments, standalone-strain-sensor 1006 may be an external sensor structure attached to a given monitoring-sensor-tag 120. In some embodiments, standalone-strain-sensor 1006 may be a strain-influenced resistor 700 or a spiral-formed-electric-conductor 703. In some embodiments, standalone-strain-sensor 1006 may be capacitive-based sensor 202 or a resistance-based sensor 203. In some embodiments, standalone-strain-sensor 1006 may be in communication with one or more of: electric circuit 140, processing circuitry 204, capacitance measurement circuit 205, and/or resistance measurement circuit 206.

FIG. 10D may be a diagram of a first-sensor-tag 1020 and a second-sensor-tag 1021 arranged in a material-of-interest with an initial predetermined spacing 1025 between the first-sensor-tag 1020 and the second-sensor-tag 1021 in the material-of-interest 1028. Note, in some embodiments, material-of-interest 1028 shown in FIG. 10D may be any material-of-interest noted herein. For example, and without limiting the scope of the present invention, in some embodiments, material-of-interest 1028 may be selected from one or more of: dental-filling 1001, root-canal-cavity 1003, root-canal-post 1004, dental-crown 1005, dental-implant 1007, implant-post 1008, an article implantable within a body of an organism (e.g., where the organism is patient 1328), the article attachable to the body of the organism, specific tissue of the organism, tooth 1000, orthodontic-bracket 1900, tooth-surface 1901, orthodontic-bracket-lock 1919, orthodontic-bracket-hook 2301, orthodontic-archwire 2401, orthodontic-spring 2403, orthodontic-elastic-band 2501, orthodontic-expander 3000, orthodontic-band 3001, orthodontic-power-chain 3100, aligner 3400, tooth-well 3401, orthotic 3501, foot 3505, ball-region 3529, arch-region 3531, heal-region 3533, a construction member, portions thereof, combinations thereof, and/or the like.

Continuing discussing FIG. 10D, in some embodiments, each of first-sensor-tag 1020 and/or of second-sensor-tag 1021 may comprise a lattice-of-sensors 1023 (e.g., sensors such as, 202, 203, 406, 407, 700, 703, and/or 1006); wherein each respective lattice-of-sensors 1023 may be separated from other lattice-of-sensors 1023 by initial predetermined spacing 1025. And in some embodiments, sensors within a given lattice (e.g., lattice-of-sensors 1023) may be separated by sensor-spacing 1026. Because initial predetermined spacing 1025 may be known, then positional locations of the other one or more monitoring-sensor-tags 120 may be determined. Likewise, because initial predetermined spacing 1026 may be known, then positional locations of the sensors within a given lattice (e.g., lattice-of-sensors 1023) may be determined. In some embodiments, each lattice-of-sensors 1023 (e.g., of each first-sensor-tag 1020 and/or of each second-sensor-tag 1021) may comprise a plurality of sensors. In some embodiments, a sensor selected from this plurality of sensors may be one or more of: sensor 202, sensor 203, sensor 406, sensor 407, sensor 700, sensor 703, sensor 1006, sensors from U.S. patent application Ser. No. 15/653,461, and/or the like; wherein this plurality of sensors may be attached to the given sensor-tag, such as first-sensor-tag 1020 and/or second-sensor-tag 1021. In some embodiments, each such sensor-tag (e.g., first-sensor-tag 1020 and/or second-sensor-tag 1021) may comprise their own electric circuit 140 (or processing circuitry 204). In some embodiments, the plurality of sensors (e.g., 202, 203, 406, 407, 700, 703, and/or 1006) of each lattice-of-sensors 1023 may be in communication with such an electric circuit 140 (or processing circuitry 204) but located outside of such an electric circuit 140. In some embodiments, this communication of the plurality of sensors may be electrical communication via wired connections among from the plurality of sensors to first-sensor-tag 1020 and/or of second-sensor-tag 1021. In some embodiments, the lattice-of-sensors (e.g., the plurality of sensors) may not have their own antennas for wireless communications; instead relying upon antenna(s) of first-sensor-tag 1020 and/or of second-sensor-tag 1021 (such as antenna 130) for wireless communications. See e.g., FIG. 10D. In some embodiments, first-sensor-tag 1020 and second-sensor-tag 1021 may be types of monitoring-sensor-tags 120 with initial predetermined spacing 1025 known between them. Also, in some embodiments, there may be a plurality of first-sensor-tag 1020 and a plurality of second-sensor-tag 1021.

Continuing discussing FIG. 10D, the plurality of sensors (e.g., 202, 203, 406, 407, 700, 703, and/or 1006) of each lattice-of-sensors 1023 may be in communication between individual sensors of said plurality of sensors. See e.g., the dashed vertical and horizontal lines in FIG. 10D connecting individual sensors from said plurality of sensors. Such embodiments may have an advantage in smaller overall circuit area, sensor data transmission speed, ease of configuration, and/or ease of sensor interrogation, among others, over connecting individual sensors directly to first-sensor-tag 1020 and/or to second-sensor-tag 1021.

Note, initial predetermined spacing 1025 may change over time. For example, as the given material-of-interest 1028 may cure and/or harden, initial predetermined spacing 1025 may alter. In some embodiments, initial predetermined spacing 1025 may be calibrated before and after such curing and/or hardening of material-of-interest 1028.

Note, FIG. 10D may also depict a known coordinate system and known origin 1325 (i.e., origin 1325 of chosen coordinate system). Origin 1325 and a chosen coordinate system may be further discussed in the FIG. 13A discussion below.

In some embodiments, lattice-of-sensors 1023 may comprise a plurality of sensors, at least one antenna, and at least one processing circuitry. In some embodiments, the plurality of sensors may be sensors that are physically interconnected with each other. In some embodiments, the plurality of sensors may be a matrix sensors that are physically interconnected with each other. In some embodiments, a given sensor selected from the plurality of sensors may be in physical contact with at least three other different sensors. In some embodiments, a given sensor selected from the plurality of sensors may be in physical contact with at least four other different sensors. In some embodiments, the plurality of sensors may be comprised of sensors of different types.

Any sensor type described and disclosed herein may be a sensor in a given plurality of sensors.

In some embodiments, the interconnections between sensors of the plurality of sensors may be flexible, but not elastic/stretchable.

In some embodiments, the sensors of the plurality of sensors may be without any antennas; however, the plurality of sensors may be physical linked communication with the at least one antenna.

In some embodiments, the at least one antenna and the at least one processing circuitry may be in and/or of first-sensor-tag 1020, second-sensor-tag 1021, and/or monitoring-sensor-tag 120. In some embodiments, the plurality of sensors may be configured to sense the at least one property of the material-of-interest 1028. In some embodiments, the plurality of sensors may include the at least one sensor of the one or more electronic sensor circuits and may include at least one other sensor. In some embodiments, the at least one antenna (e.g., an antenna of first-sensor-tag 1020, second-sensor-tag 1021, and/or monitoring-sensor-tag 120) may be configured to receive electromagnetic energy. In some embodiments, the at least one processing circuitry may be operatively coupled (e.g., via wiring and/or via a printed circuit) to both the plurality of sensors and the at least one antenna. In some embodiments, when the at least one antenna receives the electromagnetic energy, the at least one processing circuitry may use at least a portion of that received electromagnetic energy to: power the given lattice-of-sensors 1023, cause the plurality of sensors to take at least one reading, and to then wirelessly transmit (broadcast) that at least one reading out through the at least one antenna. Another separate device, such as, but not limited to, device 1807, reader-and-calibration-member 1109, and/or mobile-computing-device 3450 may receive that transmitted (broadcast) signal, with the at least one reading information.

In some embodiments, spacing between two adjacent sensors (e.g., sensor spacing 1026) selected from the plurality of sensors may be initially known (e.g., known because can be measured when output from manufacturing; and/or determinable through calibration); and subsequent changes in that spacing (e.g., sensor spacing 1026) over time may be determinable (e.g., positional determination techniques and/or methods as described herein). In some embodiments, spacing (e.g., initial predetermined spacing 1025) between two or more distinct (different) lattice-of-sensors 1023 may be initially predetermined and known; and subsequent changes in that spacing over time may be determinable (e.g., positional determination techniques and/or methods as described herein). Such spacing (e.g., sensor spacing 1026 and/or initial predetermined spacing 1025) may be initially known because the given spacing may be predetermined (and verified) upon being manufactured; and/or may be calibrated (as discussed herein). In some embodiments, "known" in this context may be with respect to devices, systems, and/or software that receive and/or utilize the at least one readings generated by the various sensors disclosed and described herein. "Known" may be also be with respect to mapping spacing and/or changes in spacing to given coordinate system. See e.g., FIG. 10D.

Note, distances/spacing (such as, but not limited to, 1025, 1026, 3535, and/or the like) while initially known, may change over time through wear-and-tear and/or the result of forces acting on the sensors; however, distances/spacing may be measured and/or calculated by various techniques discussed herein.

In some embodiments, each lattice-of-sensors 1023 selected from the two or more distinct lattice-of-sensors 1023 may be a substantially two-dimensional layer, such that the two or more distinct lattice-of-sensors 1023 may be a substantially three-dimensional structure. That three-dimensional structure may be predetermined in some embodiments. That three-dimensional structure may be initially fixed, but may alter over time (e.g., from the accumulation of forces and/or stresses upon the three-dimensional structure of two or more lattice-of-sensors 1023). See e.g., FIG. 10D, FIG. 34E, FIG. 35H, FIG. 35I, and/or FIG. 35J.

In some embodiments, each sensor of the plurality of sensors, a sensor of first-sensor-tag 1020, a sensor of second-sensor-tag 1021, a sensor of monitoring-sensor-tag 120, may generate its own readings. These reading(s) may be transmitted (broadcast) from the at least one antenna. These readings(s) may be received and via software used to construct various visual or analytical representations of what has and/or is being sensed/monitored, such as, but not limited to, in the form of three-dimensional structure maps, two-dimensional structure maps, contour maps, grade-based images, using color gradients, combinations thereof, and/or the like. For example, and without limiting the scope of the present application, from such readings a three-dimensional map of the given material-of-interest 1028 may be built/constructed (and visually outputted to a viewing screen); and changes in time to that given material-of-interest 1028, captured by further readings, may also be tracked and visualized in a continually updated three-dimensional map of the given material-of-interest 1028.

Figure 11A:
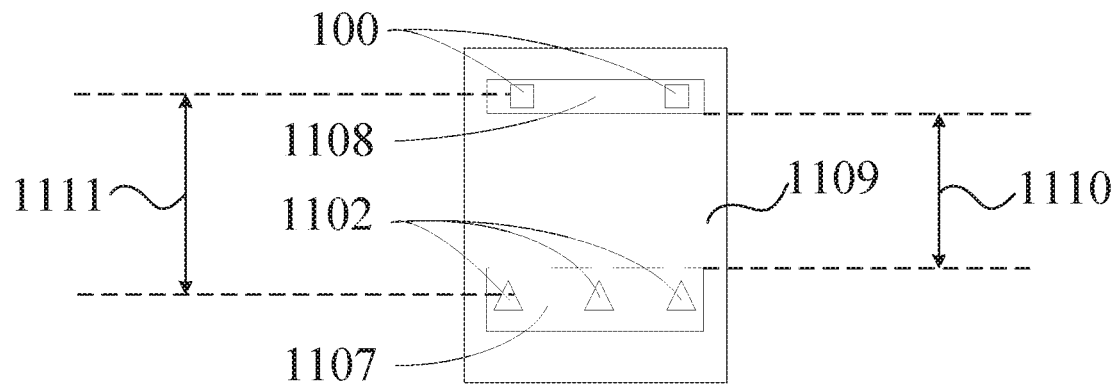
FIG. 11A may be a diagrammatical top view of a reader-and-calibration-member, in accordance with some embodiments of the present invention.

FIG. 11A may be a diagrammatical top view (or a side view in some embodiments) of a reader-and-calibration-member 1109, in accordance with some embodiments of the present invention. In some embodiments, reader-and-calibration-member 1109 may comprise one or more readers 100. In some embodiments, reader-and-calibration-member 1109 may comprise one or more reference-sensor-tags 1102. In some embodiments, reader-and-calibration-member 1109 may comprise a reader-housing-member 1108. In some embodiments, reader-and-calibration-member 1109 may comprise a reference-housing-member 1107. In some embodiments, reader-and-calibration-member 1109 may comprise one or more of: reader-housing-member 1108, reader 100, reference-housing-member 1107, and reference-sensor-tags 1102. In some embodiments, reader-and-calibration-member 1109 may house reader-housing-member 1108 and reference-housing-member 1107. In some embodiments, reader-housing-member 1108 may house one or more readers 100. In some embodiments, reference-housing-member 1107 may house one or more reference-sensor-tags 1102. In some embodiments, reader-and-calibration-member 1109 may be a structural member. In some embodiments, reader-housing-member 1108 may be a structural member. In some embodiments, reference-housing-member 1107 may be a structural member. In some embodiments, reader-and-calibration-member 1109 may be rigid to semi-rigid. In some embodiments, reader-housing-member 1108 may be rigid to semi-rigid. In some embodiments, reference-housing-member 1107 may be rigid to semi-rigid. In some embodiments reader-housing-member 1108 may be separated from reference-housing-member 1107 by a member-separation-distance 1110. In some embodiments, a given reader 100 may be separated from a given reference-sensor-tag 1102 by a reader-tag-separation-distance 1111. In some embodiments, member-separation-distance 1110 and/or reader-tag-separation-distance 1111 may be known (predetermined) and fixed distances. In some embodiments, member-separation-distance 1110 and/or reader-tag-separation-distance 1111 may be changed to a number of different known distances.

In some embodiments, a given reference-sensor-tag 1102 may be a backscatter sensor tag. In some embodiments, a given reference-sensor-tag 1102 may be a RFID (radio frequency identification) sensor tag. In some embodiments, a given reference-sensor-tag 1102 may be a NFC (near field communication) sensor tag.

Continuing discussing FIG. 11A, in some embodiments, a given reference-sensor-tag 1102 may be structurally the same or substantially the same as a given monitoring-sensor-tag 120, except that reference-sensor-tags 1102 are not attached to the given material-of-interest. Rather, in some embodiments, reference-sensor-tags 1102 may be attached to reader-and-calibration-member 1109, reference-housing-member 1107, and/or fixed with respect to a given set of at least one antennas 110 of readers 100. Thus, for the structures of reference-sensor-tags 1102, refer back to disclosed and discussed structures for monitoring-sensor-tags 120. That is, in some embodiments, each reference-sensor-tag 1102 may comprise at least one second-electric-circuit (which may be structurally the same or substantially the same to electric circuit 140 or processing circuitry 204). In some embodiments, each reference-sensor-tag 1102 may comprise at least one second-sensor (which may be structurally the same or substantially the same to various sensors discussed and disclosed herein, such as, but not limited to capacitive-based sensor 202 and/or resistance-based sensor 203). In some embodiments, each reference-sensor-tag 1102 may comprise at least one fourth-antenna (which may be structurally the same or substantially the same to at least one antenna 130). In some embodiments, the at least one fourth-antenna may be in communication with the at least one second-electric-circuit. In some embodiments, the at least one second-electric-circuit may be in communication with the at least one second-sensor. In some embodiments, when at least one fourth-antenna may receive electromagnetic signaling (e.g., radio waves from at least one antenna 110 of a given reader 100), then the at least one second-electric-circuit may take (or cause to be taken) one or more "calibration-readings" from the at least one second-sensor and then the at least one second-electric-circuit may cause transmission of such one or more calibration-readings using the at least one fourth-antenna, back to the at least one antenna 110 of that given reader 100.

Note, in terms of terminology nomenclature, when the term "fourth-antenna" may be used (which may be an antenna of a reference-sensor-tags 1102), then antenna 130 may be a "first-antenna," and antenna 110 may be a "second-antenna," and a "third-antenna" may be an antenna of position-reference-tag 1203 to be discussed below in a FIG. 12 discussion below.

Continuing discussing FIG. 11A, in some embodiments, each reader 100 (of reader-and-calibration-member 1109) may comprise at least one antenna 110. In some embodiments, each reference-sensor-tag 1102 may be fixed with respect to each at least one antenna 110 of reader 100. In some embodiments, each reference-sensor-tag 1102 may be fixed with respect to each at least one antenna 110 of reader 100 at predetermined distance(s). In some embodiments, a minimum of such predetermined distance may be substantially reader-tag-separation-distance 1111 or approximated by reader-tag-separation-distance 1111. In some embodiments, each reference-sensor-tag 1102 may comprise the at least one fourth-antenna. In some embodiments, each at least one fourth-antenna may be fixed with respect to each at least one antenna 110 of each reader of each reader-and-calibration-member 1109.

Figure 11B:
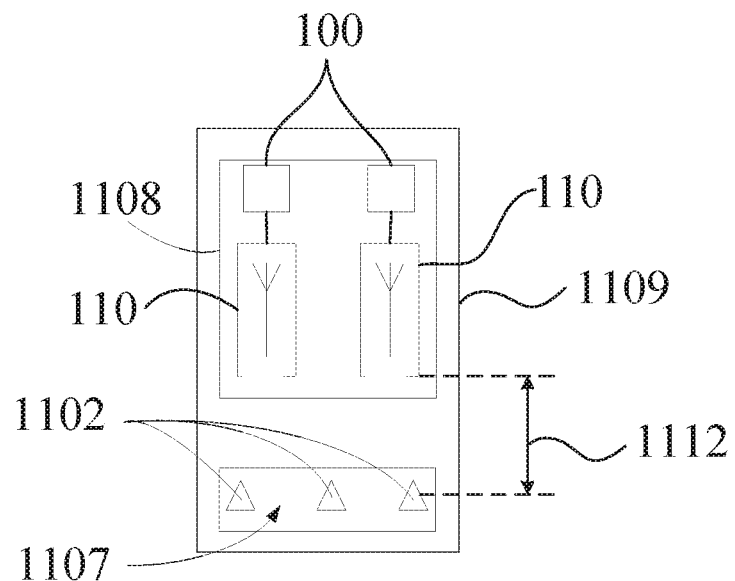
FIG. 11B may be a diagrammatical top view of a reader-and-calibration-member, in accordance with some embodiments of the present invention.

FIG. 11B may be a diagrammatical top view of a reader-and-calibration-member 1109, in accordance with some embodiments of the present invention. Reader-and-calibration-member 1109 shown in FIG. 11B, as compared against FIG. 11A discussed above, may depict additional detail, in that in FIG. 11B the at least one antennas 110 of each reader 100 of reader-and-calibration-member 1109 may be shown. In FIG. 11B, reader-antenna-tag-separation-distance 1112 may be depicted. In some embodiments, reader-antenna-tag-separation-distance 1112 may be a predetermined and fixed distance between a given at least one antenna 110 and a given reference-sensor-tag 1102. In some embodiments, reader-antenna-tag-separation-distance 1112 may be a predetermined and fixed distance between a given at least one antenna 110 and a given at least one fourth-antenna of a given reference-sensor-tag 1102. In some embodiments, each at least one antenna 110 of each reader 100 (of reader-and-calibration-member 1109) may be fixed with respect to each reference-sensor-tags 1102. In some embodiments, reader-antenna-tag-separation-distance 1112 may be changed to a number of different known distances.

Figure 11C:
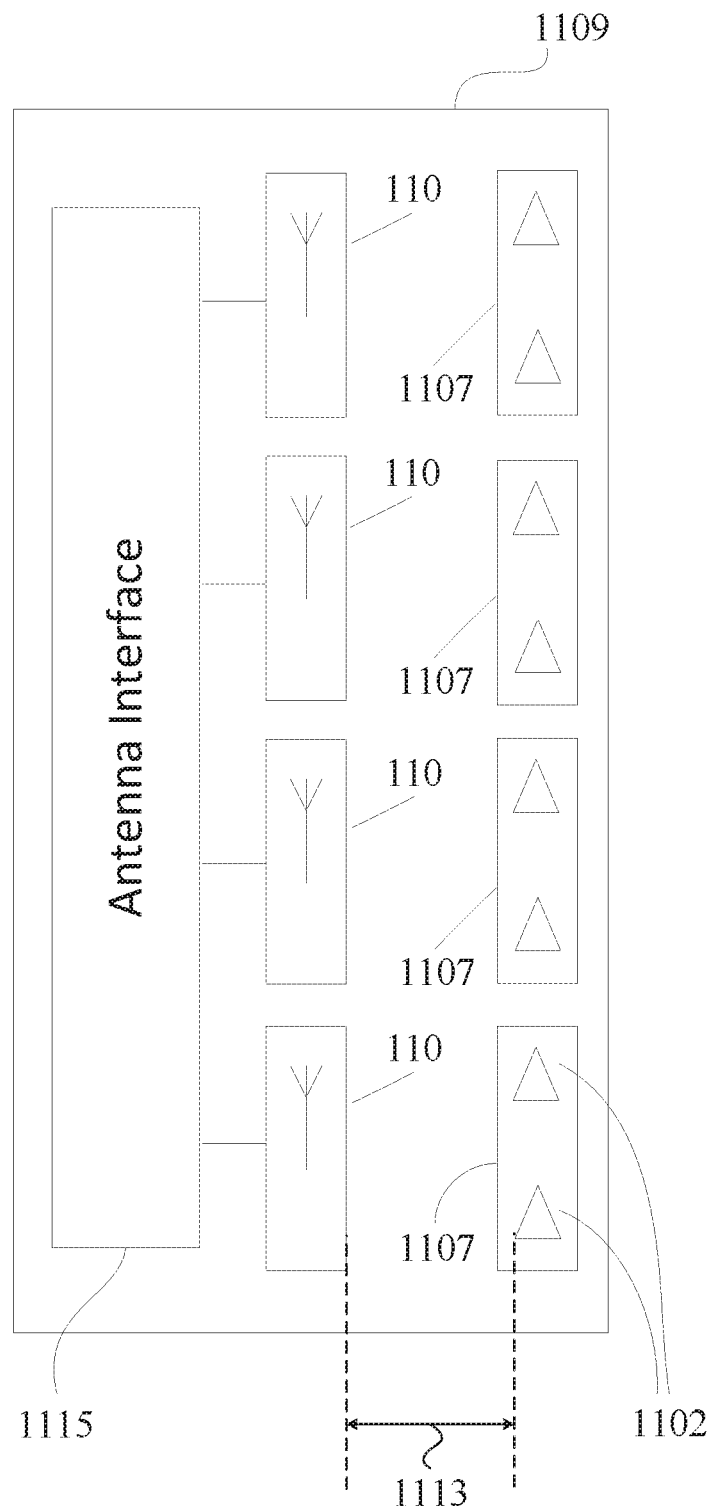
FIG. 11C may be a diagrammatical top view of a reader-and-calibration-member with an antenna interface, in accordance with some embodiments of the present invention.

FIG. 11C may be a diagrammatical top view of a reader-and-calibration-member 1109 with an antenna-interface 1115, in accordance with some embodiments of the present invention. Reader-and-calibration-member 1109 shown in FIG. 11C, as compared against FIG. 11A discussed above, may depict additional detail, in that in FIG. 11C the at least one antennas 110 of each reader 100 of reader-and-calibration-member 1109 may be shown. In FIG. 11C, reader-antenna-tag-separation-distance 1113 may be depicted. In some embodiments, reader-antenna-tag-separation-distance 1113 may be a predetermined and fixed distance between a given at least one antenna 110 and a given reference-sensor-tag 1102. In some embodiments, reader-antenna-tag-separation-distance 1113 may be a predetermined and fixed distance between a given at least one antenna 110 and a given at least one fourth-antenna of a given reference-sensor-tag 1102. In some embodiments, each at least one antenna 110 of each reader 100 (of reader-and-calibration-member 1109) may be fixed with respect to each reference-sensor-tags 1102.

Reader-and-calibration-member 1109 shown in FIG. 11C, as compared against FIG. 11B discussed above, may depict additional detail, in that in FIG. 11C antenna-interface 1115 may be shown. In some embodiments, a given reader 100 may comprise antenna-interface 1115 and at least one antenna 110. In some embodiments, antenna-interface 1115 may be in communication with each at least one antenna 110 for that given reader 100. In some embodiments, antenna-interface 1115 may be hardware block. In some embodiments, antenna-interface 1115 may facilitate communications between at least one antenna 110 and one or more of: a control circuit and/or a processor 1801 (or processing module) (see e.g., FIG. 18). Continuing discussing FIG. 11C, in some embodiments, antenna-interface 1115 may function in communication routing and/or function as a duplex. In some embodiments, antenna-interface 1115 may translate data and/or commands from the control circuit and/or processor 1801 (or processing module) into signals for transmission via at least one antenna 110. In some embodiments, antenna-interface 1115 may translate signals received via at least one antenna 110 into data (e.g., the one or more readings and/or the one or more calibration-readings) and/or commands destined for the control circuit and/or for processor 1801 (or processing module).

With respect to FIG. 11A, FIG. 11B, and/or FIG. 11C, in a given reader-and-calibration-member 1109, locations of all included reference-sensor-tags 1102 relative to all included readers 100 and all included at least one antennas 110, may be known parameters, or may be mathematically determined, thus allowing a calibration process to increase precision of the one or more readings from monitoring-sensor-tag 120 attached to a given material-of-interest.

Note in some embodiments, disclosed structures and functions for a given reader-and-calibration-member 1109 may apply to a given reader 100. That is, in some embodiments, a given reader 100 may be the given reader-and-calibration-member 1109.

Figure 12:
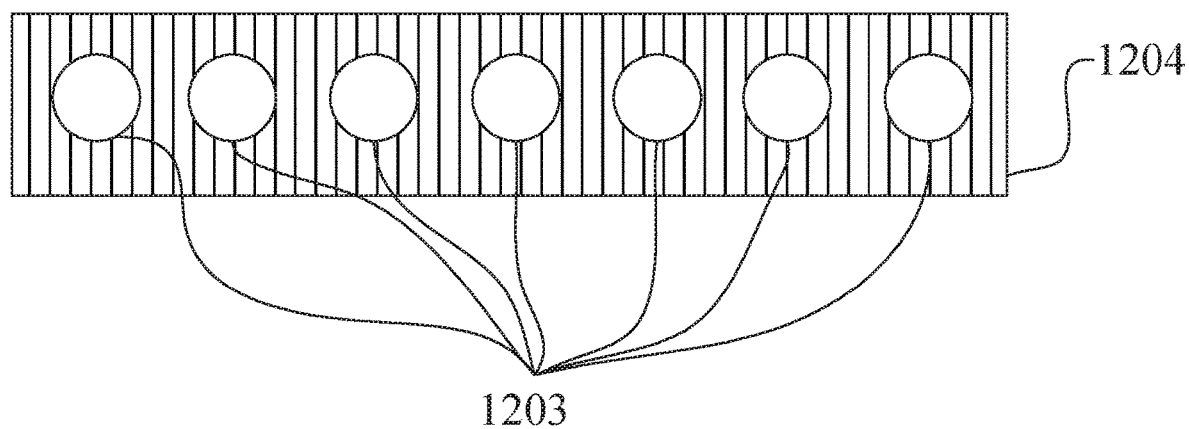
FIG. 12 may be a diagrammatical side view (or a top view) of a position-reference-member, in accordance with the present invention.

FIG. 12 may be a diagrammatical side view (or a top view or a bottom view, in some embodiments) of a position-reference-member 1204, in accordance with the present invention. In some embodiments, position-reference-member 1204 may be a structural member. In some embodiments, position-reference-member 1204 may be rigid to semi-rigid. In some embodiments, during use, position-reference-member 1204 may be fixed with respect to patient 1328. In some embodiments, position-reference-member 1204 may comprise one or more position-reference-tags 1203. In some embodiments, position-reference-member 1204 may house one or more position-reference-tags 1203. In some embodiments, one or more position-reference-tags 1203 located on position-reference-member 1204 may be arranged in known and/or predetermined positions (i.e., configurations and/or patterns). For example, and without limiting the scope of the present invention, as shown in FIG. 12, the position-reference-tags 1203 may be arranged in a substantially linear (straight) arrangement in (on) position-reference-member 1204. The position-reference-tags 1203 may also be arranged in an arbitrary arrangement in (on) position-reference-member 1204.

In some embodiments, a given position-reference-tag 1203 may be a backscatter sensor tag. In some embodiments, a given position-reference-tag 1203 may be a RFID (radio frequency identification) sensor tag. In some embodiments, a given position-reference-tag 1203 may be a NFC (near field communication) sensor tag.

Continuing discussing FIG. 12, in some embodiments, a given position-reference-tag 1203 may be structurally the same or substantially the same as a given monitoring-sensor-tag 120, except that position-reference-tags 1203 are not attached to the given material-of-interest. And in some embodiments, position-reference-tags 1203 may not comprise a sensor. Rather, in some embodiments, position-reference-tags 1203 may be attached to position-reference-member 1204. Thus for the structures of position-reference-tags 1203 refer back to disclosed and discussed structures for monitoring-sensor-tags 120. That is, in some embodiments, each position-reference-tag 1203 may comprise their own electric-circuit (which may be structurally the same or substantially the same to electric circuit 140, but without elements to handle processing from a sensor). In some embodiments, each position-reference-tag 1203 may comprise at least one third-antenna (which may be structurally the same or substantially the same to at least one antenna 130). In some embodiments, the at least one third-antenna may be in communication with its own electric-circuit. In some embodiments, when at least one third-antenna may receive electromagnetic signaling (e.g., radio waves from at least one antenna 110 of a given reader 100), then the electric-circuit of position-reference-tag 1203 may cause transmission of "calibration-signals" from the at least one third-antenna to be transmitted back to the at least one antenna 110 of that given reader 100.

Note, in terms of terminology nomenclature, when the term "fourth-antenna" may be used (which may be an antenna of a reference-sensor-tags 1102), then antenna 130 may be a "first-antenna," and antenna 110 may be the "second-antenna," and the "third-antenna" may be the antenna of position-reference-tag 1203.

Also note, any antenna disclosed herein, in some embodiments, may be selected from one or more of: monostatic, bistatic, or multistatic. Further note, any antenna disclosed herein, in some embodiments, may be selected from one or more of: only for receiving, only for transmitting, or for both receiving and transmitting. And further note, receiving and/or transmitting may comprise signals for communication purposes, but also signals for energy transmission, harvesting, and usage.

Continuing discussing FIG. 12, in some embodiments, positions (locations) of position-reference-tags 1203 may be known with respect to a given origin (e.g., origin 1325 of FIG. 13A and FIG. 13C) and/or a given coordinate system (e.g., a three-dimensional coordinate system, a Cartesian coordinate system, a radial coordinate system, or other well-known coordinate system). Because positions (locations) of position-reference-tags 1203 may be known, positions (locations) of reader(s) 100 may be determined relative to the position-reference-tags 1203 associated with the position-reference-member 1204. Because positions (locations) of position-reference-tags 1203 may be known, positions (locations) of antennas 110 of reader(s) 100 may be determined relative to the position-reference-tags 1203 associated with the position-reference-member 1204. The positions (locations) of readers 100 (or their antennas 110) may then be specified relative to a chosen three-dimensional coordinate system. See e.g., FIG. 13A and FIG. 13C.

Figure 13A:
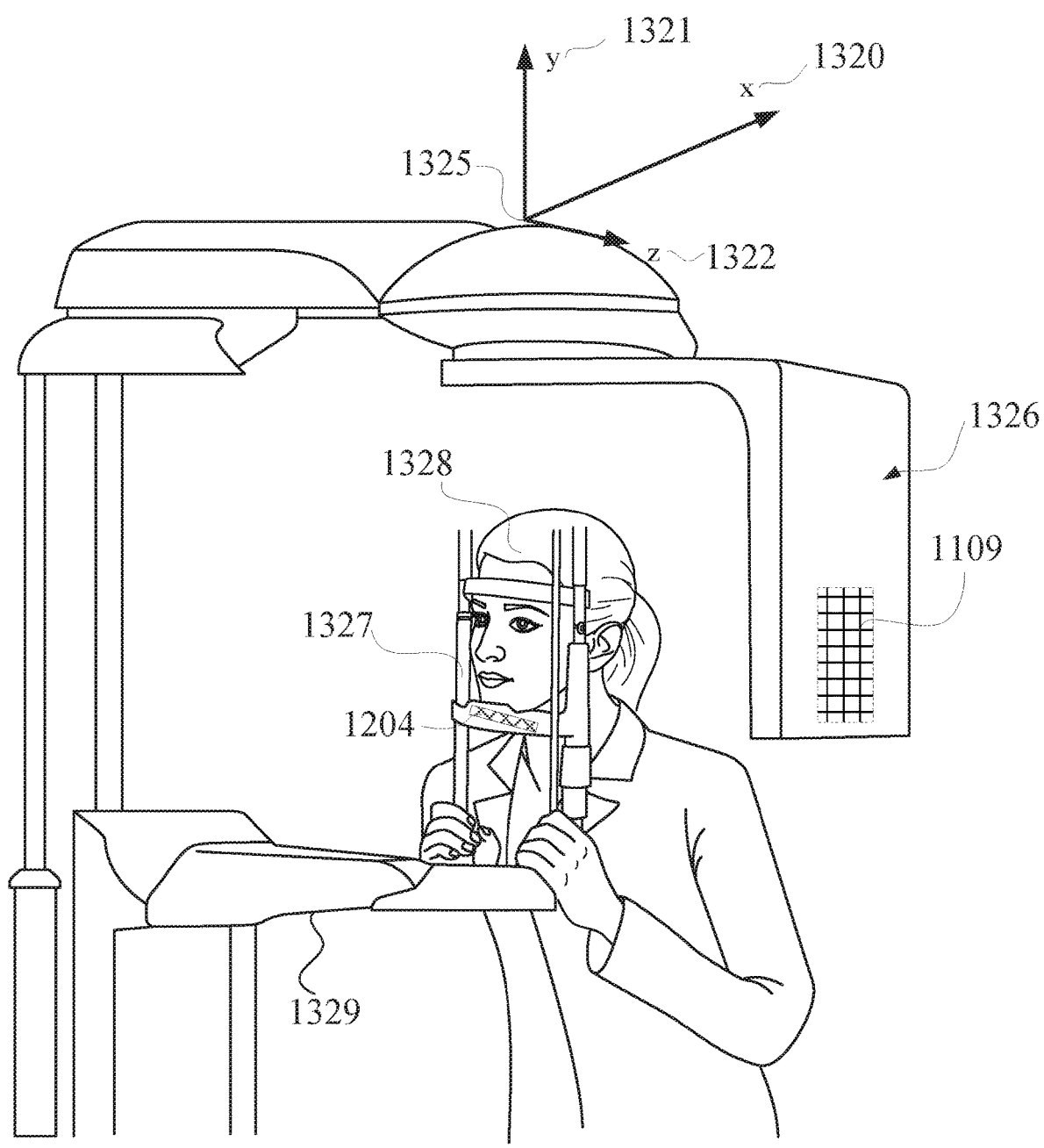
FIG. 13A may depict a system for non-invasive monitoring of a material-of-interest with one or more monitoring-sensor-tags that may be in and/or on a patient; wherein the system comprises a translating-scan-member that may translate along a predetermined path of motion.

FIG. 13A may depict a system for non-invasive monitoring of a material-of-interest with one or more monitoring-sensor-tags 120 that may be in and/or on patient 1328; wherein the system comprises a translating-scan-member 1326 that may translate along a predetermined path of motion.

In some embodiments, FIG. 13A may depict a three-dimensional Cartesian coordinate system chosen to determine three-dimensional coordinates of a plurality of position-reference-tags 1203 connected to position-reference-member 1204, relative to which the positions (locations) of readers 100 may then be determined. In some embodiments, three dimensional coordinates of at least some of the plurality of position-reference-tags 1203 may be specified relative to the chosen Cartesian coordinate system defined by known origin 1325, Imaginary x-axis 1320, Imaginary y-axis 1321, and Imaginary z-axis 1322. Positions (locations) of reference-sensor-tags 1102 connected to reader-and-calibration-member 1109 and the positions of the monitoring-sensor-tag 120 may also be specified relative to the chosen coordinate system.

Continuing discussing FIG. 13A, in some embodiments, translating-scan-member 1326 may comprise reader-and-calibration-member 1109. In some embodiments, reader-and-calibration-member 1109 may be attached to translating-scan-member 1326. In some embodiments, reader-and-calibration-member 1109 may comprise one or more reference-sensor-tags 1102. In some embodiments, reader-and-calibration-member 1109 may comprise one or more readers 100. In some embodiments, reference-sensor-tags 1102, readers 100, and/or antenna-interface 1115 (where antenna-interface 1115 may be in electrical communication with the readers 100) may be in electrical communication with translating-scan-member 1326. In some embodiments, translating-scan-member 1326 may be in electrical communication with a processor 1801.

Continuing discussing FIG. 13A, in some embodiments, the one or more monitoring-sensor-tags 120 may be located on or in the given material-of-interest, which may be on or in patient 1328. In some embodiments, the material-of-interest, may be on or in a head of patient 1328. In some embodiments, the material-of-interest, may be on or in a mouth of patient 1328. In some embodiments, the material-of-interest, may be on or in: tooth 1000, dental-filling 1001, gum 1002, root-canal-cavity 1003, root-canal-post 1004, dental-crown 1005, dental-implant 1007, and/or implant-post 1008 of patient 1328. Note in some embodiments, at least some of the one or more monitoring-sensor-tags 120 utilized in the system shown in FIG. 13A may comprise one or more standalone-strain-sensor 1006. See e.g., FIG. 18 which may be applied to the system shown in FIG. 13A.

Continuing discussing FIG. 13A, in some embodiments, the system may comprise patient-fixation-member 1327. In some embodiments, patient-fixation-member 1327 may removably support at least a portion of patient 1328. In some embodiments, patient-fixation-member 1327 may be a structural member. In some embodiments, patient-fixation-member 1327 may be substantially rigid to semi-rigid, not including any portions with padding. In some embodiments, patient-fixation-member 1327 may be supported structurally by support 1329. In some embodiments, support 1329 may attach to patient-fixation-member 1327. In some embodiments, support 1329 may be a structural member. In some embodiments, support 1329 may be a rigid to semi-rigid. In some embodiments, patient-fixation-member 1327 may removably support the at least the portion of patient 1328 such that the supported portion of patient 1328 may be held relatively (sufficiently) fixed (with respect to origin 1325) during scanning, when translating-scan-member 1326 may be translating and travelling along the predetermined path of motion and the readers 100 (of reader-and-calibration-member 1109) may be scanning. In some embodiments, patient 1328 may breathe normally and blink normally, as a scanning frequency may be comparatively faster that such normal motions of patient 1328 may not adversely affect processing of received readings and transmissions from monitoring-sensor-tag 120 and/or from position-reference-tags 1203. In some embodiments, patient-fixation-member 1327 may comprise a chin rest to removably support a chin of patient 1328. In some embodiments, patient-fixation-member 1327 may comprise position-reference-member 1204; and position-reference-member 1204 may comprise one or more position-reference-tags 1203. In some embodiments, position-reference-member 1204 may be attached to patient-fixation-member 1327. In some embodiments, position-reference-member 1204 may be attached to patient-fixation-member 1327 at the chin rest. During scanning, position-reference-member 1204 may be fixed with respect to origin 1325 and the chosen coordinate system. During scanning, the one or more position-reference-tags 1203 of position-reference-member 1204 may be fixed with respect to origin 1325 and the chosen coordinate system. Recall, in some embodiments, position-reference-member 1204 may house the one or more position-reference-tags 1203.

Continuing discussing FIG. 13A, in some embodiments, the predetermined path of motion of translating-scan-member 1326 may translate substantially around patient-fixation-member 1327, which may be removably supporting the at least the portion of patient 1328. In some embodiments, this predetermined path of motion may be curved, sinuous, arcing, ellipsoidal, circular, semi-circular, and/or the like. In some embodiments, translating-scan-member 1326 may be a rotating-scan-member.

Figure 13B:
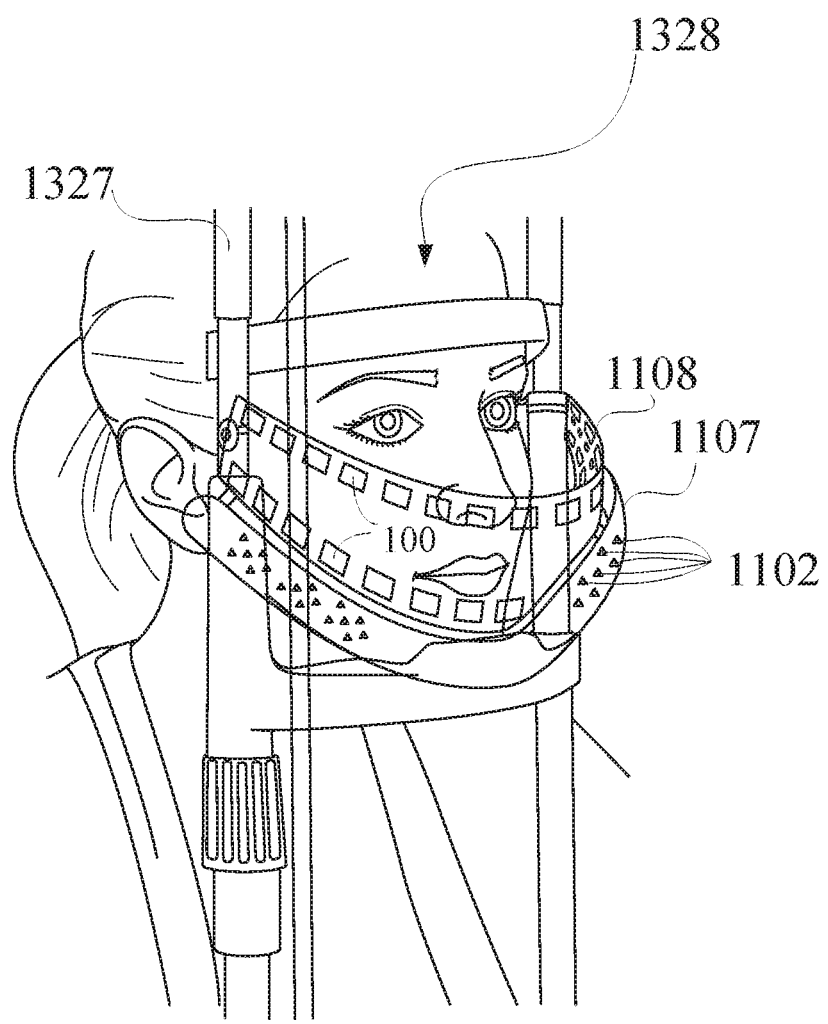
FIG. 13B may depict a system for non-invasive monitoring of a material-of-interest with one or more monitoring-sensor-tags that may be in and/or on a patient; wherein the system comprise a reader-housing-member with one or more readers that may communicate with the one or monitoring-sensor-tags.
Figure 13C:
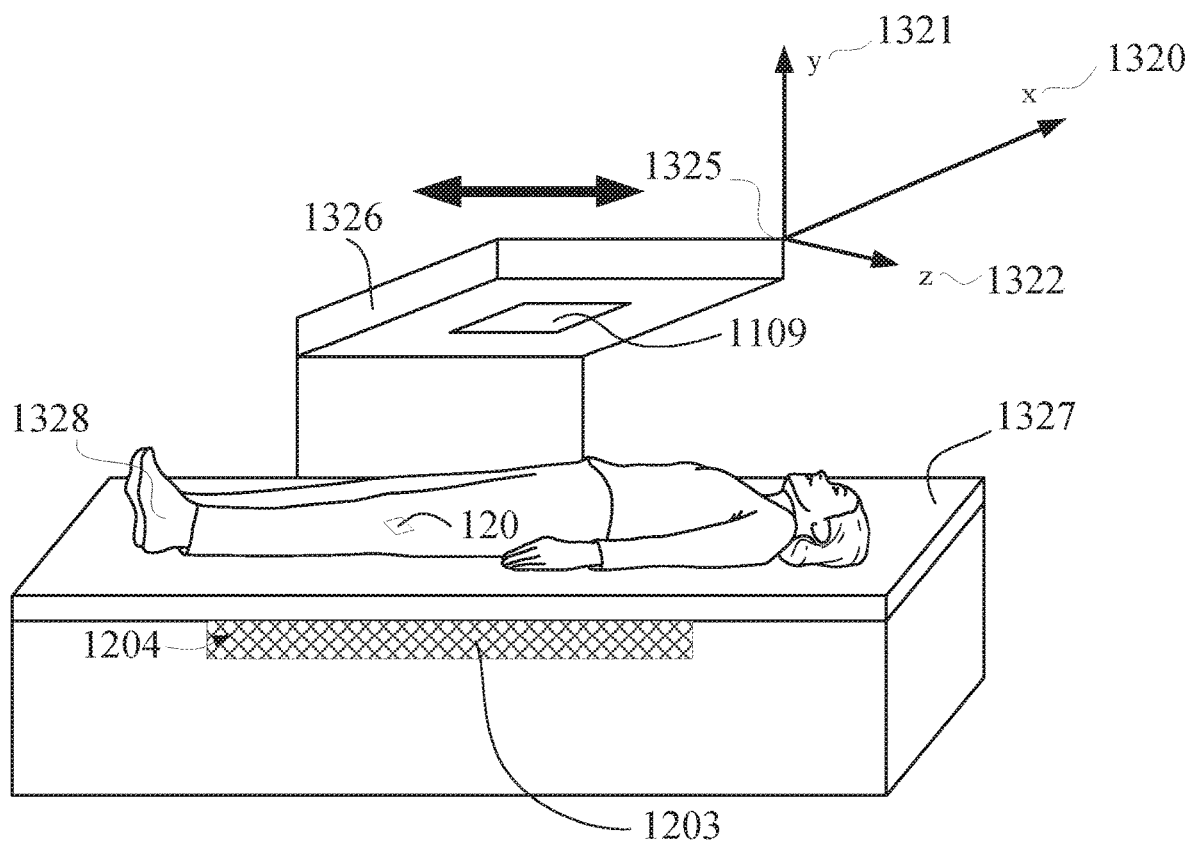
FIG. 13C may depict a system for non-invasive monitoring of a material-of-interest with one or more monitoring-sensor-tags that may be in and/or on a patient; wherein the system comprises a translating-scan-member that may translate along a predetermined path of motion.

FIG. 13B may depict a system for non-invasive monitoring of a material-of-interest with one or more monitoring-sensor-tags 120 that may be in and/or on patient 1328; wherein the system comprise a reader-housing-member 1108 with one or more readers 100 that may communicate with the one or monitoring-sensor-tags 120. The system shown in FIG. 13B may differ fundamentally from the system shown in FIG. 13A, by the system in FIG. 13B not utilizing a translating-scan-member 1326; that is, scanning in the system in FIG. 13B, may be accomplished without translation mechanics; that is, the scanning in the system of FIG. 13B may be accomplished statically (fixedly).

Continuing discussing FIG. 13B, in some embodiments, the one or more monitoring-sensor-tags 120 may be located on or in the given material-of-interest, which may be on or in patient 1328. In some embodiments, the material-of-interest, may be on or in a head of patient 1328. In some embodiments, the material-of-interest, may be on or in a mouth of patient 1328. In some embodiments, the material-of-interest, may be on or in: tooth 1000, dental-filling 1001, gum 1002, root-canal-cavity 1003, root-canal-post 1004, dental-crown 1005, dental-implant 1007, and/or implant-post 1008 of patient 1328. Note in some embodiments, at least some of the one or more monitoring-sensor-tags 120 utilized in the system shown in FIG. 13B may comprise one or more standalone-strain-sensor 1006. See e.g., FIG. 18 which may be applied to the system shown in FIG. 13B.

Continuing discussing FIG. 13B, in some embodiments, the system may comprise patient-fixation-member 1327. In some embodiments, patient-fixation-member 1327 may removably supports at least a portion of patient 1328. In some embodiments, patient-fixation-member 1327 may be a structural member. In some embodiments, patient-fixation-member 1327 may be substantially rigid to semi-rigid, not including any portions with padding. In some embodiments, patient-fixation-member 1327 may be supported structurally by support 1329 (not shown in FIG. 13B). In some embodiments, support 1329 may attach to patient-fixation-member 1327. In some embodiments, support 1329 may be a structural member. In some embodiments, support 1329 may be a rigid to semi-rigid. In some embodiments, patient-fixation-member 1327 may removably supports the at least the portion of patient 1328 such that the supported portion of patient 1328 may be held relatively (sufficiently) fixed (with respect to origin 1325) during scanning, when readers 100 and/or reference-sensor-tags 1102 may be wirelessly transmitting and/or wirelessly receiving transmissions. In some embodiments, patient 1328 may breathe normally and blink normally, as a scanning frequency may be comparatively faster that such normal motions of patient 1328 may not adversely affect processing of received readings and transmissions from monitoring-sensor-tag 120 and/or from reference-sensor-tags 1102. In some embodiments, patient-fixation-member 1327 may comprise a chin rest to removably support a chin of patient 1328. In some embodiments, patient-fixation-member 1327 may comprise reader-housing-member 1108; and reader-housing-member 1108 may comprise one or more readers 100. In some embodiments, reader-housing-member 1108 may be attached to patient-fixation-member 1327. In some embodiments, reader-housing-member 1108 may be attached to patient-fixation-member 1327 at the chin rest (now shown in FIG.

13B). In some embodiments, reader-housing-member 1108 may be at least partially curved so as to arrange readers 100 at least partially around target regions to be scanned, i.e., the material(s)-of-interest with the one or more monitoring-sensor-tags 120 to be scanned. In some embodiments, arrangement of readers 100, via geometry of reader-housing-member 1108 may also locate at least some readers 100 above and below the material(s)-of-interest with the one or more monitoring-sensor-tags 120 to be scanned.

Continuing discussing FIG. 13B, in some embodiments, patient-fixation-member 1327 may comprise reference-housing-member 1107; and reference-housing-member 1107 may comprise one or more reference-sensor-tags 1102. In some embodiments, reference-housing-member 1107 may be attached to patient-fixation-member 1327. In some embodiments, reference-housing-member 1107 may be attached to patient-fixation-member 1327 at the chin rest. In some embodiments, reference-housing-member 1107 may be at least partially curved so as to arrange reference-sensor-tags 1102 at least partially around target regions to be scanned, i.e., the material(s)-of-interest with the one or more monitoring-sensor-tags 120 to be scanned by readers 100. In some embodiments, arrangement of reference-sensor-tags 1102, via geometry of reference-housing-member 1107 may also locate at least some reference-sensor-tags 1102 above and/or below the material(s)-of-interest with the one or more monitoring-sensor-tags 120 to be scanned. In some embodiments, reference-housing-member 1107 may be substantially parallel with reader-housing-member 1108. In some embodiments, reference-housing-member 1107 may be located below, above, or both below and above reader-housing-member 1108. During scanning, readers 100 and/or reference-sensor-tags 1102 may be fixed with respect to patient-fixation-member 1327. Recall, in some embodiments, positions (locations) of reference-sensor-tags 1102 may be known or mathematically determined (derived).

FIG. 13C may depict a system for non-invasive monitoring of a material-of-interest with one or more monitoring-sensor-tags 120 that may be in and/or on patient 1328; wherein the system comprises a translating-scan-member 1326 that may translate along a predetermined path of motion. The system shown in FIG. 13C may be more akin to the system of FIG. 13A, in that both systems may utilize a type of translating-scan-member 1326 but with different predetermined paths of motion. In some embodiments, translating-scan-member 1326 of FIG. 13C may be a reciprocating translating member, wherein the predetermined path may be substantially linear (straight). Also, the patient-fixation-member 1327 utilized in the system of FIG. 13C may also be structurally different from the patient-fixation-member 1327 shown in FIG. 13A. In some embodiments, patient-fixation-member 1327 of FIG. 13C may be a platform for supporting up to all of patient 1328 upon such a platform. In some embodiments, patient 1328 may lay (in various positions) upon this platform embodiment of patient-fixation-member 1327. In some embodiments, the predetermined path may have a length that substantially matches a length of this platform embodiment of patient-fixation-member 1327. In some embodiments, the predetermined path may have a width that substantially matches a width of this platform embodiment of patient-fixation-member 1327; in which case, translating-scan-member 1326 may also translate in a side to side motion as well as reciprocating along the length of the predetermined path. Or in some embodiments, a width of reader-and-calibration-member 1109 may be sufficient wide to accommodate scanning the width of this platform embodiment of patient-fixation-member 1327.

Continuing discussing FIG. 13C, the material(s)-of-interest with the one or more monitoring-sensor-tags 120 may be located on or in patient 1328. In some embodiments, the material(s)-of-interest with the one or more monitoring-sensor-tag 120 may be located anywhere on or in patient 1328. In some embodiments, the material(s)-of-interest with the one or more monitoring-sensor-tag 120 need not be constrained to a head region (nor to a mouth region) of patient 1328. For example, and without limiting the scope of the present invention, as shown in FIG. 13C, the material-of-interest with the one or more monitoring-sensor-tags 120 may be located in (or on) a left leg region of patient 1328. Note in some embodiments, at least some of the one or more monitoring-sensor-tags 120 utilized in the system shown in FIG. 13C may comprise one or more standalone-strain-sensor 1006. See e.g., FIG. 18 which may be applied to the system shown in FIG. 13C.

Figure 14A:
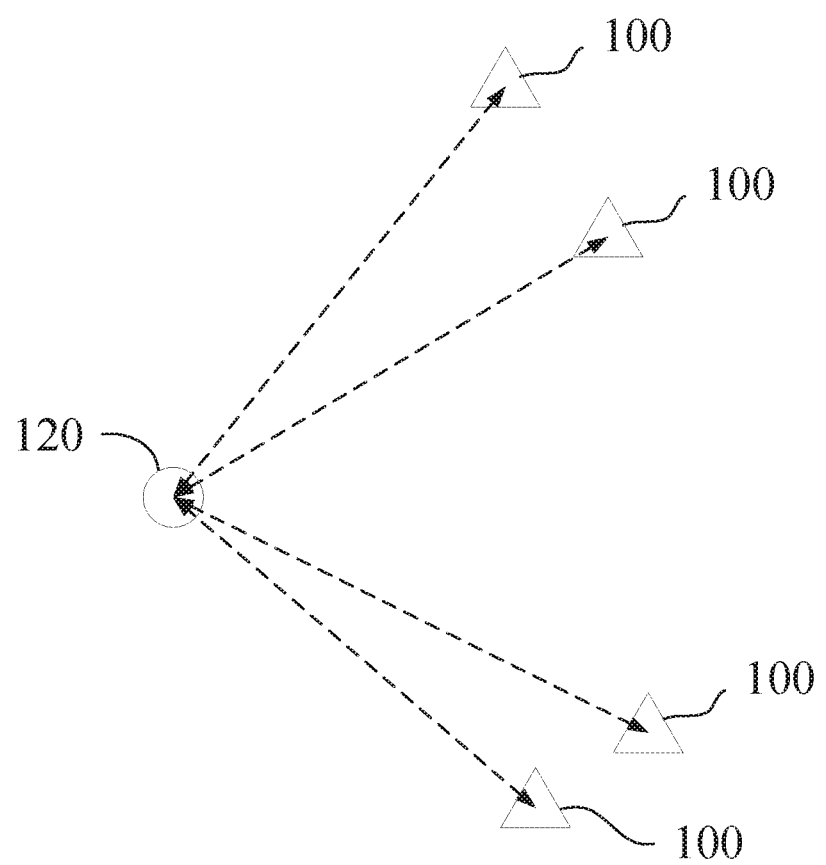
FIG. 14A may be a schematic view of a single monitoring-sensor-tag and a plurality of readers that may communicate (wirelessly) with the single monitoring-sensor-tag.

FIG. 14A may be a schematic view of a single monitoring-sensor-tag 120 and a plurality of readers 100 that may communicate (wirelessly) with the single monitoring-sensor-tag 120. Thus, the arrangement of FIG. 14A may be applicable to the system of FIG. 13B. Knowing the positions (locations) of the readers 100, then a position (location) of the single monitoring-sensor-tag 120 may be determined. Prior to such position (location) determination, the single monitoring-sensor-tag 120 may have unknown coordinates (e.g., x, y, and z in a Cartesian coordinate system). Whereas, in some embodiments, the readers 100 may have known (or determinable) coordinates relative to the chosen coordinate system, which may include a known origin. A process (method) for determining the coordinates of the single monitoring-sensor-tag 120 may be utilized to determine position (location) of all such monitoring-sensor-tags 120 in use in a given system. And thus, positions (locations) corresponding to the readings from sensors (e.g., 202, 203, 1006, and/or the like) of the given monitoring-sensor-tags 120 may be determined and analyzed, with respect to the given material-of-interest that is associated with the monitoring-sensor-tags 120.

Figure 14B:
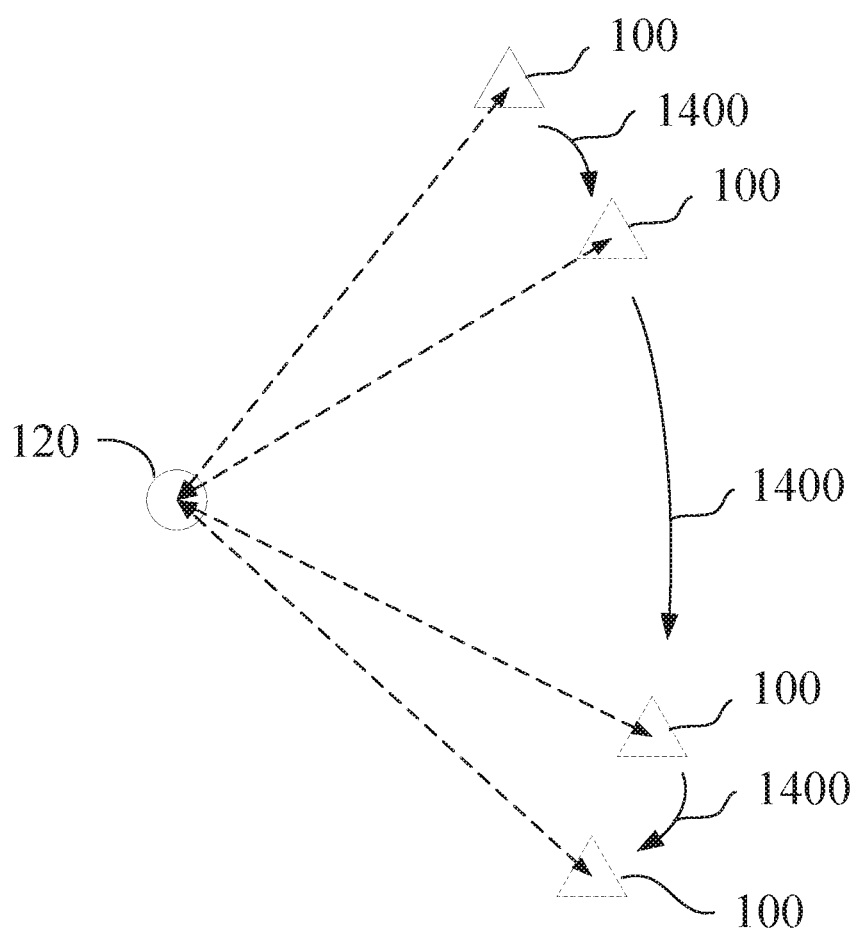
FIG. 14B may be a schematic view of a single monitoring-sensor-tag and a single reader; wherein the single reader may translate with respect to the single monitoring-sensor-tag; and wherein the single reader and the single monitoring-sensor-tag may be in wireless communication.

FIG. 14B may be a schematic view of a single monitoring-sensor-tag 120 and a single reader 100; wherein the single reader 100 may translate (in direction-of-motion 1400) with respect to the single monitoring-sensor-tag 120; and wherein the single reader 100 and the single monitoring-sensor-tag 120 may be in wireless communication. Thus, the arrangement of FIG. 14B may be applicable to the system of FIG. 13A (and/or the system of FIG. 13C).

In some embodiments, knowing the positions (locations) of the single reader 100 as a function of time, a position (location) of the single monitoring-sensor-tag 120 (which may be fixed during scanning) may be determined. Prior to such position (location) determination, the single monitoring-sensor-tag 120 may have unknown coordinates (e.g., x, y, and z in a Cartesian coordinate system). Whereas, in some embodiments, the translating single reader 100 may have known (or determinable) coordinates relative to the chosen coordinate system and as a function of time, which may include a known origin or known starting position at a starting time. A process (method) for determining the coordinates of the single monitoring-sensor-tag 120 may be utilized to determine position (location) of all such monitoring-sensor-tags 120 in use in a given system. And thus, positions (locations) corresponding to the readings from sensors (e.g., 202, 203, 1006, and/or the like) of the given monitoring-sensor-tags 120 may be determined and analyzed, with respect to the given material-of-interest that is associated with the monitoring-sensor-tags 120.

Determining positions (locations) of any given monitoring-sensor-tag 120, and/or determination of any given reader 100, may involve well-known local position systems (LPS) techniques; that may utilize one or more of the following mathematical techniques: triangulation, trilateration, multilateration, combinations thereof, and/or the like. Additionally, such information may be utilized in such positional calculations: known reference points (e.g., origin 1325 and/or known locations of position-reference-tags 1203); direct paths (line of sight or LoS); angle of incidence (or angle of arrival or AoA); phase difference of arrival (PDoA); received signal strength indicator (RSSI); time of arrival (ToA); time of flight (ToF); and/or time difference of arrival (TDoA).

For example, the following discussion presents one method for determining position (location) information of a given monitoring-sensor-tag 120 according to the configuration of FIG. 14A. Let us stipulate that reader 100 number i has coordinates $(x_i, y_i, z_i)$. The actual distance (range) between the given monitoring-sensor-tag 120 $n,m$ with coordinates $\bar{x}=[x\ y\ z]$ and reader 100 number i is $r_{(m,n),i}$. The distance measured between the given monitoring-sensor-tag 120 $n,m$ and reader 100 number i is $h_{(m,n),i}$. The range measurement error is assumed to be a random variable $w_{(m,n),i}$ with variance $\sigma_{(m,n),i}^2$. $h_{(m,n),i}$ can be expressed as follows:

$$h_{(m,n),i} = r_{(m,n),i} + w_{(m,n),i} \quad (5)$$

Let us assume that the number (quantity) of readers 100 used to determine position (location) of the given monitoring-sensor-tag 120 $n,m$ is s. The distance (range) between the given monitoring-sensor-tag 120 $n,m$ and reader 100 number i, denoted as $r_{(m,n),i}$ may be expressed as:

$$r_{(m,n),i} = \sqrt{(x_i-x)^2+(y_i-y)^2+(z_i-z)^2}\ i=1,2,\ldots,s \quad (6)$$

We can therefore express the measured distance between the given monitoring-sensor-tag 120 $n,m$ and reader 100 number i as:

$$h_{(m,n),i} = \sqrt{(x_i-x)^2+(y_i-y)^2+(z_i-z)^2} + w_{(m,n),i} \quad (7)$$

In vector form, the vector $\bar{r}_{(n,m)}(\bar{x})$ of distances (ranges) between the given monitoring-sensor-tag 120 $n,m$ with coordinates $x=[x\ y\ z]$ and the readers 100 where number i may be 1, 2, 3, ..., s is:

$$\bar{r}_{(n,m)}(\bar{x}) = \begin{bmatrix} \sqrt{(x_1-x)^2+(y_1-y)^2+(z_1-z)^2} \\ \sqrt{(x_2-x)^2+(y_2-y)^2+(z_2-z)^2} \\ \vdots \\ \sqrt{(x_s-x)^2+(y_s-y)^2+(z_s-z)^2} \end{bmatrix} \quad (8)$$

In vector form, the vector $\bar{h}_{(n,m)}$ of measured distances between the given monitoring-sensor-tag 120 $n,m$ and the readers 100 where number i may be 1, 2, 3, ..., s is:

$$\bar{h}_{(n,m)} = [h_{(m,n),1} h_{(m,n),2} \ldots h_{(m,n),s}]^T \quad (9)$$

where T is a symbol for a vector or a matrix transpose.

In vector form, the vector $\bar{w}_{(n,m)}$ of measurement errors of the distances between the given monitoring-sensor-tag 120 $n,m$ and the readers 100 where number i may be 1, 2, 3, ..., s is:

$$\bar{w}_{(n,m)} = [w_{(m,n),1} w_{(m,n),2} \ldots w_{(m,n),s}]^T \quad (10)$$

We may express equation (5) in vector form, expressing the vector of distance measurements $\bar{h}_{(n,m)}$ as follows:

$$\bar{h}_{(n,m)}(\bar{x}) = \bar{r}_{(n,m)}(\bar{x}) + \bar{w}_{(n,m)} \quad (11)$$

$$\bar{h}_{(n,m)}(\bar{x}) = \begin{bmatrix} \sqrt{(x_1-x)^2+(y_1-y)^2+(z_1-z)^2} \\ \sqrt{(x_2-x)^2+(y_2-y)^2+(z_2-z)^2} \\ \vdots \\ \sqrt{(x_s-x)^2+(y_s-y)^2+(z_s-z)^2} \end{bmatrix} + \bar{w}_{(n,m)} \quad (12)$$

We need to estimate location coordinate $\bar{x}=[x\ y\ z]^T$ for each monitoring-sensor-tag 120 $n,m$ given the vector of distance measurements $\bar{h}_{(n,m)}$ between the given monitoring-sensor-tag 120 $n,m$ and the readers 100 where i may be 1, 2, 3, ..., s.

Alternatively (or in addition to), in conformity with the arrangement shown in FIG. 14B, a single moving reader 100 number i may be used to obtain a series of coordinates $(x_i, y_i, z_i)$ of this reader 100 number i, assuming the movement of this reader 100 number i may be controlled and its coordinates known, and as a function of time.

There are numerous well-known methods (techniques and/or algorithms) to estimate $\bar{x}$ in equation (11). Based on the results of a calibration process described below, one may optionally use Nonlinear Least Squares (NLS) or Maximum Likelihood (ML) estimators among other available optimization techniques.

An optional Nonlinear Least Squares (NLS) approach minimizes the least squares cost function derived from equation (7). It is a widely used and well-known method, that is discussed below. Based on equation (7) one may denote the NLS cost function CM of the given monitoring-sensor-tag 120 $n,m$ position estimate $\bar{x}=[x\ y\ z]^T$ as:

$$C(\bar{x}) = \sum_{i=1}^{s}(h_{(m,n),i} - \sqrt{(x_i-x)^2+(y_i-y)^2+(z_i-z)^2})^2$$

$$= (\bar{h}-\bar{r}(\bar{x}))^T(\bar{h}-\bar{r}(\bar{x})) \quad (13)$$

where:
- $(x_i, y_i, z_i)$ are coordinates of Reader 100 number i, where i may be 1, 2, ..., s; and
- $h_{(m,n),i}$ the measured distance between the given monitoring-sensor-tag 120 $n,m$ and reader 100 number i.

The NLS position estimate $\hat{x}$ will correspond to the smallest value of the cost function $C(\bar{x})$:

$$\hat{x} = \underset{\bar{x}}{\mathrm{argmin}}\ C(\bar{x}) \quad (14)$$

Levenberg-Marquardt Algorithm (LMA), Newton-Raphson Algorithm (NRA), Gauss-Newton Algorithm (GNA) are some methods widely used for solving optimization problem in equation (14).

An optional Maximum Likelihood (ML) approach is a widely used and well-known method for solving non-linear equations by means of maximizing the Probability Density Function (PDF) of the function in question.

A probability density function $\rho(\bar{h}_{(n,m)})$ for the vector of measured distances $\bar{h}_{(n,m)}$ from equation (11) may be expressed as:

$$\rho(\bar{h}_{(n,m)}) = \frac{1}{(2\pi)^{\frac{s}{2}}|R|^{\frac{1}{2}}} \exp\left(-\frac{1}{2}(\bar{h}_{(n,m)} - \bar{r}_{(n,m)})^T R^{-1} (\bar{h}_{(n,m)} - \bar{r}_{(n,m)})\right) \quad (15)$$

where R is the covariance matrix of $\bar{h}_{(n,m)}$ wherein R may be defined as:

$$R = E\{(\bar{h}_{(n,m)} - \bar{r}_{(n,m)})(\bar{h}_{(n,m)} - \bar{r}_{(n,m)})^T\} = \mathrm{diag}(\sigma_1^2, \sigma_2^2, \ldots, \sigma_s^2) \quad (16)$$

where $\sigma_i^2$ is the variance of the range measurement error from above equation (6). $R^{-1}$ is matrix inverse of the matrix R and $|R|$ is determinant of matrix R Maximization of the probability density function $\rho(\bar{h}_{(n,m)})$ of the vector of measured distances $\bar{h}_{(n,m)}$ in equation (12) may be expressed as the following minimization problem:

$$\hat{x} = \underset{\bar{x}}{\mathrm{argmin}}\, C(\bar{x}) \quad (17)$$

where $C(\bar{x})$ is a cost function of the position estimate $x=[x\ y\ z]^T$ of the given monitoring-sensor-tag 120 n,m expressed as:

$$C(\bar{x}) = (\bar{h}_{(n,m)} - \bar{r}_{(n,m)})^T R^{-1} (\bar{h}_{(n,m)} - \bar{r}_{(n,m)}) = \sum_{i=1}^{s} \frac{\left(h_{(m,n),i} - \sqrt{(x_i - x)^2 + (y_i - y)^2 + (z_i - z)^2}\right)}{\sigma_i^2} \quad (18)$$

where:
- $(x_i, y_i, z_i)$ are coordinates of Reader 100 number i, wherein number i may be 1, 2, ..., s;
- $h_{(m,n),i}$ is the measured distance between the given monitoring-sensor-tag 120 n,m and reader 100 number i; and
- $\bar{x}=[x\ y\ z]^T$ is the position estimate of the given monitoring-sensor-tag 120 n,m.

Levenberg-Marquardt Algorithm (LMA), Newton-Raphson Algorithm (NRA), Gauss-Newton Algorithm (GNA) are some methods widely used for solving optimization problem in equation (17).

Linear approaches for initial coordinate estimate. Many approaches have been used to convert non-linear equations (12) copied below:

$$\bar{h}_{(n,m)}(\bar{x}) = \begin{bmatrix} \sqrt{(x_1 - x)^2 + (y_1 - y)^2 + (z_1 - z)^2} \\ \sqrt{(x_2 - x)^2 + (y_2 - y)^2 + (z_2 - z)^2} \\ \vdots \\ \sqrt{(x_s - x)^2 + (y_s - y)^2 + (z_s - z)^2} \end{bmatrix} + \bar{w}_{(n,m)} \quad (12)$$

to set of linear equations, direct solution of which may provide a start point for an optimization process employed for finding the coordinates of the given monitoring-sensor-tag 120 n,m in above equations (14) and (17). Some embodiments may employ widely described and well-known Linear Least Squares (LLS) and Weighted Linear Least Squares (WLLS) approaches in order to convert non-linear equation (12) into a linear forma; and then to find $\bar{x}=[x\ y\ z]^T$ which is used as a start point for subsequent optimization processes in determining coordinates of the given monitoring-sensor-tag 120 n,m.

Figure 15:
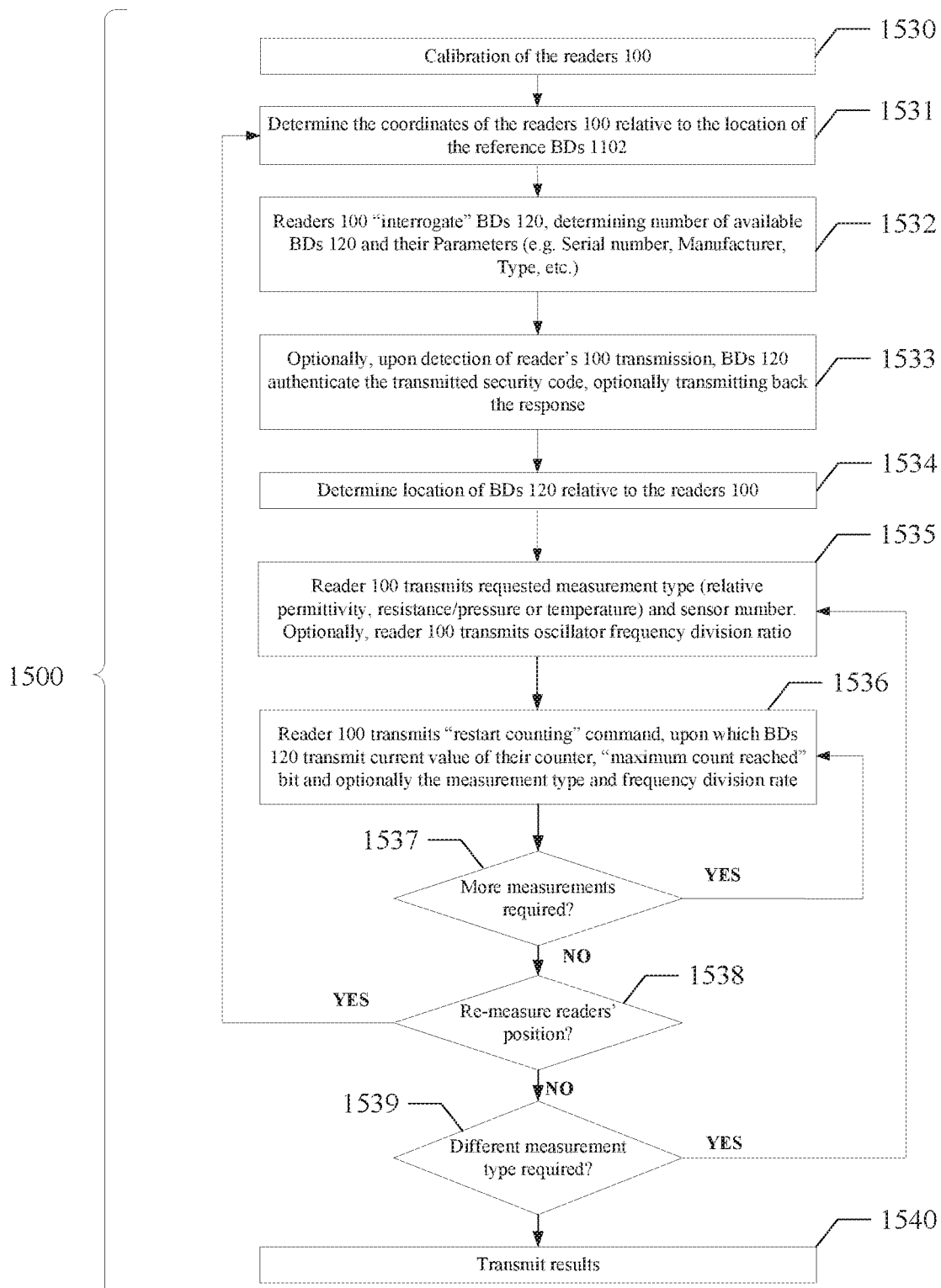
FIG. 15 may depict a flow diagram illustrating steps in a method for non-invasive monitoring of a material-of-interest with one or more monitoring-sensor tag using one or more readers.

FIG. 15 may depict a flow diagram illustrating steps in a method 1500 for non-invasive monitoring of a material-of-interest with one or more monitoring-sensor tag 120 using one or more readers 100.

Continuing discussing FIG. 15, in some embodiments method 1500 may comprise step 1530; wherein step 1530 may be a step of calibrating readers 100 that are to be used. That is in some embodiments, method 1500 may begin with step 1530 of calibrating the readers 100. Reader 100 calibration in step 1530 may involve wireless communication between readers 100 and reference-sensor-tags 1102. Recall, in some embodiments, reference-sensor-tags 1102 may have known locations (positions, coordinates). In some embodiments, reference-sensor-tags 1102 may comprise stress (deformation) sensor resistors (such as 700 and/or 703) with known parameters. In some embodiments, reference-sensor-tags 1102 may comprise capacitor-based relative permittivity sensors (such as 402, 404, 405, 406, 407, and/or 408) with known parameters. In some embodiments, reference-sensor-tags 1102 may comprise one or more of: stress (deformation) sensor resistors (such as 700 and/or 703); and/or capacitor-based relative permittivity sensors (such as 402, 404, 405, 406, 407, and/or 408) with known parameters. Such sensors of reference-sensor-tags 1102 may provide the one or more "calibration-readings" back to readers 100; which may then provide for various reference (or foundational) qualities to assist in calibrating readers 100. In some embodiments, reference-sensor-tags 1102 sensors may also sense local (ambient) temperature to aid in temperature calibration while the local (ambient) temperature in vicinity of said sensors is known.

Continuing discussing FIG. 15, in some embodiments, method 1500 may comprise step 1531. In some embodiments, successful conclusion of step 1530 may then transition into step 1531. In some embodiments, step 1531 may be a step of determining a location (i.e., position and/or coordinates) of the one or more readers 100. Step 1531 may be accomplished by wireless communication between readers 100 and reference-sensor-tags 1102, wherein locations of reference-sensor-tags 1102 may be known and thus locations of readers 100 may be determined relative to these known locations of reference-sensor-tags 1102.

Continuing discussing FIG. 15, in some embodiments, method 1500 may comprise step 1532. In some embodiments, successful conclusion of step 1531 may then transition into step 1532. In some embodiments, step 1532 may be a step of reader 100 interrogation of the one or more monitoring-sensor-tags 120 that are associated with the material-of-interest. In some embodiments, in this interrogation step 1532, a number (quantity) of available one or more monitoring-sensor-tags 120 may be transmitted back to the readers 100 and determined. In some embodiments, in this interrogation step 1532, "additional information" of the one or more monitoring-sensor-tags 120 may be transmitted back to the readers 100 and determined. In some embodiments, this "additional information" may comprise one or more of: identification information for a given monitoring-sensor-tag 120 that is transmitting (e.g., an ID for each monitoring-sensor-tag 120 that is transmitting); model number for the given monitoring-sensor-tag 120 that is transmitting; serial number for the given monitoring-sensor-tag 120 that is transmitting; manufacturer of the given monitoring-sensor-tag 120 that is transmitting; year of manufacture of the given monitoring-sensor-tag 120 that is transmitting; or a request for a security code associated with that given monitoring-sensor-tag 120 that is transmitting; a public security key; a cyclic redundancy check code for the given monitoring-sensor-tag 120 that is transmitting; a parity check code for the given monitoring-sensor-tag 120 that is transmitting; and receipt of a disable instruction for the given monitoring-sensor-tag 120 that is transmitting; wherein the given monitoring-sensor-tag 120 that is transmitting is selected from the one or more monitoring-sensor-tags 120.

The cyclic redundancy check code and/or the parity check code for the given monitoring-sensor-tag 120 that may be transmitting may be known approaches to generate additional data based on the transmitted information. That additional data, once received by the readers 100 and further analyzed by a processor 1801 (see e.g., FIG. 18) may be used to validate correct transmission of said transmitted information.

The model number for the given monitoring-sensor-tag 120 that may be transmitting; the serial number for the given monitoring-sensor-tag 120 that may be transmitting; and/or the manufacturer of the given monitoring-sensor-tag 120 may be information used for identifying the type of the given monitoring-sensor-tag 120 to be used in subsequent steps including but not limited to calibration.

Continuing discussing FIG. 15, in some embodiments, step 1532 may progress into step 1534 or into step 1533. In some embodiments, method 1500 may comprise step 1533. In some embodiments, step 1533 may be an authentication step, to ensure that only authorized readers 100 (and not some other RFID type of reading/scanning device) may be accessing the one or more monitoring-sensor-tags 120. For example, and without limiting the scope of the present invention, in some embodiments, the one or more monitoring-sensor-tags 120 may not transmit useful information, such as the one or more readings, unless the given monitoring-sensor-tag 120 first receives a proper security code (e.g., password) from the given reader 100. In some embodiments, the given monitoring-sensor-tag 120 may transmit a request for this security code to the readers 100. In some embodiments, the given monitoring-sensor-tag 120 may transmit its public security key in addition for the request for the said security code to the readers 100. In some embodiments, where step 1533 is required in method 1500, successful completion of the authentication step 1533 may then transition into step 1534.

Some applications of method 1500 may not include step 1533, in which case, step 1532 may transition into step 1534.

Continuing discussing FIG. 15, in some embodiments, method 1500 may comprise step 1534. In some embodiments, step 1534 may follow step 1532 or may follow step 1533. In some embodiments, step 1534 may be a step of determining locations (positions and/or coordinates) of the one or more monitoring-sensor-tags 120. Such location determination may proceed via LPS (local positioning systems) techniques as discussed above in the FIG. 14A and FIG. 14B discussion.

Continuing discussing FIG. 15, in some embodiments, method 1500 may comprise step 1535. In some embodiments, step 1535 may follow step 1534. In some embodiments, step 1535 may be a step of the reader 100 instructing (i.e., commanding and/or requesting) the one more monitoring-sensor-tags 120. In some embodiments, such instructions from the readers 100 may initiate a process in the one or more monitoring-sensor-tags 120 such that the given monitoring-sensor-tag 120 may generate the one or more readings from their one or more sensors and then transmit the resulting one or more readings back to the readers 100 via the antennas 130 of the given monitoring-sensor-tag 120. For example, and without limiting the scope of the present invention, the readers 100 may request a specific measurement type to provide information (one or more readings) that may correlate with specific state information of the given material-of-interest that may be monitored and/or tracked by using one or more monitoring-sensor-tags 120 attached to (associated with) the given material-of-interest. Recall the one or more readings from the sensors of the one or more monitoring-sensor-tags 120 may yield state information such as, but not limited to: structural integrity of a current state of the material-of-interest; structural integrity changes of the material-of-interest; pressure received at the material-of-interest; force received at the material-of-interest; stress received at the material-of-interest; shear-stress received in the material of interest; torsion received at the material-of-interest; twisting imparted to the material-of-interest; tension in the material-of-interest; compression of the material-of-interest; deformation received at the material-of-interest; temperature at some portion of the material-of-interest; positional changes of a given monitoring-sensor-tag 120 attached to the material-of-interest with respect to position of another monitoring-sensor-tag 120 attached to the material-of-interest, wherein the given monitoring-sensor-tag 120 and the other monitoring-sensor-tag are 120 selected from the one or more monitoring-sensor-tags 120 attached to the material-of-interest; or positional changes of at least one monitoring-sensor-tag 120 attached to the material-of-interest with respect to time, wherein the at least one monitoring-sensor-tag 120 is selected from the one or more monitoring-sensor-tags 120. For example, and without limiting the scope of the present invention, the readers 100 may request a specific measurement type from a specific sensor type. For example, and without limiting the scope of the present invention, the readers 100 may request one or more readings from specific sensors, wherein the specific sensors may be identified by a sensor-specific-ID (e.g., a unique sensor number for that specific sensor). In some embodiments, the sensor-specific-ID (sensor number) may serve to choose a specific sensor from a number of sensors of a given monitoring-sensor-tag 120. For example, and without limiting the scope of the present invention, as shown in FIG. 8, a number of different sensors may exist for a given monitoring-sensor-tag 120. For example, and without limiting the scope of the present invention, the readers 100 may transmit an oscillator frequency division ratio to the given monitoring-sensor-tag 120. For example, and without limiting the scope of the present invention, sensors (of monitoring-sensor-tags 120) may belong to different ring oscillator circuits; and such different ring oscillator circuits may be selected sequentially or in parallel. That is, any given independent ring oscillators in a given monitoring-sensor-tag 120 may be engaged either sequentially or in parallel.

Continuing discussing FIG. 15, in some embodiments, method 1500 may comprise step 1536. In some embodiments, step 1536 may follow step 1535. Alternatively, in some embodiments, step 1536 may be a sub-step of step 1535. In some embodiments, step 1536 may be a step of the readers 100 transmitting the "restart counting" command to the one or more monitoring-sensor-tags 120. Recall RESTART_COUNT signal 931 of FIG. 9 and the FIG. 9 discussion above. A monitoring-sensor-tag 120 receiving RESTART_COUNT signal 931 may then cause that monitoring-sensor-tag 120 to transmit one or more of the following: their current value of their counter; "maximum count reached" bit; the measurement type (sensor type); the sensor-specific-ID; the sensor's one or more readings; and/or frequency division rate.

Continuing discussing FIG. 15, in some embodiments, method 1500 may comprise step 1537. In some embodiments, step 1537 may follow step 1536. In some embodiments, step 1537 may be a step of determining if additional measurements to be taken from the sensors of the one or more monitoring-sensor-tags 120. If yes, then method 1500 may progress back to step 1536. If no, then method 1500 may progress to step 1538. In some embodiments, criteria for evaluating step 1537 may comprise, but may not be limited to, either achieving the pre-determined mathematical variance of the series of obtained measurements or reaching a pre-defined maximal number of measurements.

Continuing discussing FIG. 15, in some embodiments, method 1500 may comprise step 1538. In some embodiments, step 1538 may follow a "no" outcome of step 1537. In some embodiments, step 1538 may be a step of determining if the reader 100 locations are to be re-determined per step 1531. If yes, then method 1500 may progress back to step 1531. If no, then method 1500 may progress to step 1539. In some embodiments, criteria for evaluating step 1538 may be defined by the settings provided by the user, matching the type of environment in which the specific embodiment is used. For example, in the case of a static set of readers as related to patient 1328, like the one depicted in FIG. 13B, step 1538 may not be required. In case of a system, like the one shown in FIG. 13C, comprising a translating-scan-member 1326 that may translate along a predetermined path of motion, step 1538 may be performed either each time or at predetermined time intervals to ensure that the location of the translating-scan-member 1326 is determined correctly.

Continuing discussing FIG. 15, in some embodiments, method 1500 may comprise step 1539. In some embodiments, step 1539 may follow a "no" outcome of step 1538. In some embodiments, step 1539 may be a step of determining if different measurement types are be taken from the sensors of the one or more monitoring-sensor-tags 120. If yes, then method 1500 may progress back to step 1535. If no, then method 1500 may progress to step 1540. In some embodiments, criteria for evaluating step 1539 may be provided by the settings in the specific embodiment. For example, if monitoring-sensor-tags 120 of different types are used (e.g., measuring stress, temperature, humidity, liquid penetration, etc.) step 1539 may determine that additional measurement types have to be performed.

Continuing discussing FIG. 15, in some embodiments, method 1500 may comprise step 1540. In some embodiments, step 1540 may follow a "no" outcome of step 1539. In some embodiments, step 1540 may be a step of readers 100 transmitting "received monitoring-sensor-tag 120 transmissions." In some embodiments, the received monitoring-sensor-tag 120 transmissions may comprise one or more of the following: the one or more readings; the sensor-specific-ID; the additional information; and/or any other information and/or data transmitted from antennas 130 of the one or more monitoring-sensor-tags 120. In some embodiments, the readers 100 may transmit this "received monitoring-sensor-tag 120 transmissions" to processor 1801 (see e.g., FIG. 18) for processing and analysis. In some embodiments, the readers 100 may transmit this "received monitoring-sensor-tag 120 transmissions" to memory 1803, where processor 1801 (see e.g., FIG. 18) may then access for processing and analysis. In some embodiments, the readers 100 may transmit this "received monitoring-sensor-tag 120 transmissions" to antenna-interface 1115; wherein antenna-interface 1115 may route (transmit) to memory 1803, where processor 1801 (see e.g., FIG. 18) may then access for processing and analysis. In some embodiments, the readers 100 may transmit this "received monitoring-sensor-tag 120 transmissions" to antenna-interface 1115; wherein antenna-interface 1115 may route (transmit) to processor 1801 (see e.g., FIG. 18) which may then access the said "received monitoring-sensor-tag 120 transmissions" for processing and analysis. In some embodiments, the readers 100 may pre-process some of "received monitoring-sensor-tag 120 transmissions" via an electric circuit of the reader 100 prior to transmission to: antenna-interface 1115, memory 1803, or processor 1801.

Overall broadly speaking, calibration may mean adjusting precision based on known facts (i.e., known data and/or known information). For example, positioning a reference tag at a known distance before start of using a device may permit fine-tuning of the system. For example, it may be known what electromagnetic wave phase delay should be at a distance of 1 m (i.e., one meter). The extra phase which may be measured may be due to phase distortion, introduced by tag, antenna, reader 100, cable and; may be filtered out (accounted for) thanks to a calibration process.

It is natural that in the specific system 1800 there may be a need for more than one calibration method based on the type of monitoring-sensor-tags 120, readers 100, antennas 110 as well as other elements of the system 1800. Below, for example, may describe one such possible calibration method 1600. In some embodiments, FIG. 16 may depict a flow diagram illustrating a method 1600 for calibrating the system 1800 (see FIG. 18) based on one or more reference-sensor-tags 1102. In some embodiments, FIG. 16 may depict a flow diagram illustrating a method 1600 for calibrating one or more readers 100. In some embodiments, step 1530 of method 1500 shown in FIG. 15 may be method 1600. That is, in some embodiments, method 1600 shown in FIG. 16 may depict how step 1530 may proceed. In some embodiments, method 1600 may comprise steps: step 1680, step 1681, step 1682, and step 1683.

Figure 16:
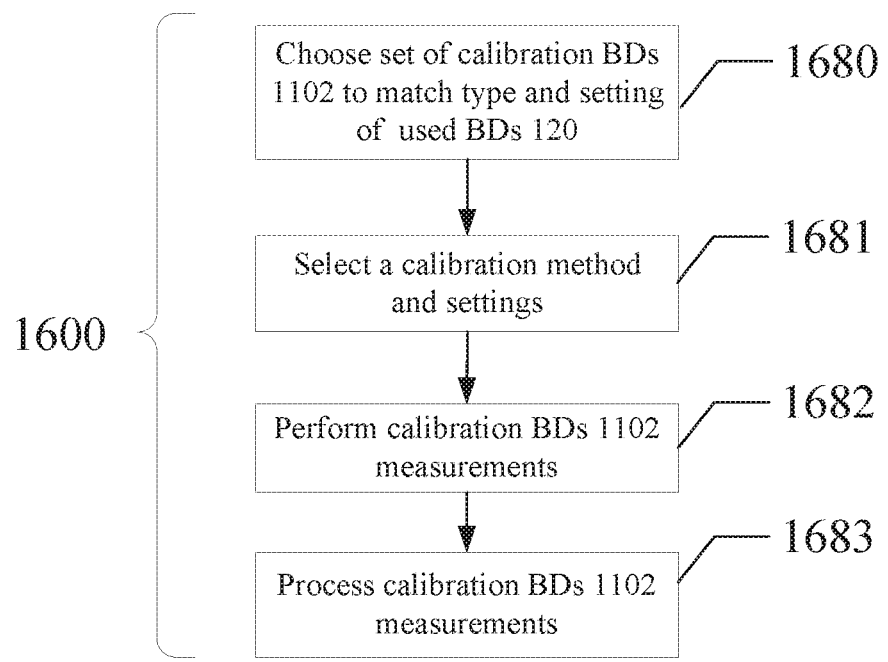
FIG. 16 may depict a flow diagram illustrating a method for calibrating a system (shown in FIG. 18) based on one or more reference-sensor-tags.

Discussing FIG. 16, in some embodiments, step 1680 may choose a set of reference-sensor-tags 1102 to match a type and an environmental setting of used (or to be used) monitoring-sensor-tags 120. As noted below, in order to filter out possible measurement distortions from the measurements and to fine-tune the system 1800, the type of the reference-sensor-tags 1102 needs to match or to be as close as possible to the type of monitoring-sensor-tag 120.

Continuing discussing FIG. 16, in some embodiments, step 1681 may be a stage at which a calibration method and its settings are chosen based on the specific system 1800 in place, and based on the user-provided options and preferences. For example, and without limiting the scope of the present invention, a specific range of the reader 100 frequencies may be selected, reader 100 transmitting power may be adjusted, reader 100 transmitting mode can be selected, among other settings, during step 1681.

Determining range, using one of the techniques above, such as phase difference of arrival (PDoA), is based on measuring the phase difference of arrival $\phi$ of the electromagnetic wave emitted by reader 100, backscattered by a given monitoring-sensor-tag 120, and received by reader 100, according to the configuration of FIG. 14A, as an example.

Continuing discussing FIG. 16, in some embodiments, step 1682 may perform phase measurements of monitoring-sensor-tags 120. For each reader 100 number $a_j$ take N measurements of the phase $\varphi(f_s)_k^{a_j,c_i}$ (where k=1 ... N) between $a_j$ and each reference-sensor-tag 1102 number $c_i$ allocated to reader 100 number $a_j$ in the software settings. The said phase measurements may be taken at a number of different frequencies $f_s$ where s=1 ... M.

In some embodiments, instead of performing a predefined number N of phase measurements, a number of phase measurements may be limited by the number at which the mathematical variance of $\varphi(f_s)_k^{a_j,c_i}$ falls below a pre-determined value for each pair $a_j$, $c_i$ and each frequency $f_s$ where s=1 ... M.

In some embodiments, the phase difference of arrival φ between the electromagnetic wave emitted by reader 100, backscattered by a given monitoring-sensor-tag 120, and received by reader 100, according to the configuration of FIG. 14A may be expressed as:

$$\varphi(f_s)_k^{a_j,c_i} = \varphi_{wave} + \varphi_{reader} + \varphi_{tag}$$

Where:

$\varphi_{wave}$ is the phase difference due to the propagation of the emitted electromagnetic wave;

$\varphi_{reader}$ is the phase difference introduced by but not limited to reader 100, antenna 110, and cables connecting reader 100 and antenna 110; and $\varphi_{tag}$ is the phase difference introduced by a given monitoring-sensor-tag 120.

Continuing discussing FIG. 16, in some embodiments, step 1683 calibration of reference-sensor-tags 1102 measurements may be processed as follows:

For each reader 100 number $a_j$ and each reference-sensor-tag 1102 number $c_i$ allocated to the reader 100, calculate:

Mean $\overline{\varphi}(f_s)^{a_j,c_i}$ of the phase measurements $\varphi(f_s)_k^{a_j,c_i}$ between $a_j$ and $c_i$, k=1 ... N for each frequency $f_s$ where s=1 ... M;

Difference $\varphi_{delta}(f_s)^{a_j,c_i}$ between the calculated phase $\varphi_{wave}(f_s)^{a_j,c_i}$ and $\overline{\varphi}(f_s)^{a_j,c_i}$ where:

$$\varphi_{delta}(f_s)^{a_j,c_i} = \varphi_{wave}(f_s)^{a_j,c_i} - \overline{\varphi}(f_s)^{a_j,c_i} \qquad (20)$$

where $\varphi_{wave}(f_s)^{a_j,c_i}$ is the phase difference, due to the propagation of the emitted electromagnetic wave, mentioned above, is calculated as:

$$\varphi_{wave}(f_s)^{a_j,c_i} = \left(\frac{4\pi r_{j,i} f_s}{c}\right) \bmod 2\pi$$

where c is the speed of light constant, mod is modulo (remainder) function, and as $r_{j,i}$ is the known distance (range) from reader 100 number $a_j$ and reference-sensor-tag 1102 number $c_i$.

Thus, the correction $\varphi_{delta}(f_s)^{a_j,c_i}$ to be applied to the reported phase $\varphi(f)_k^{a_j,c_i}$ has been calculated.

Figure 17:
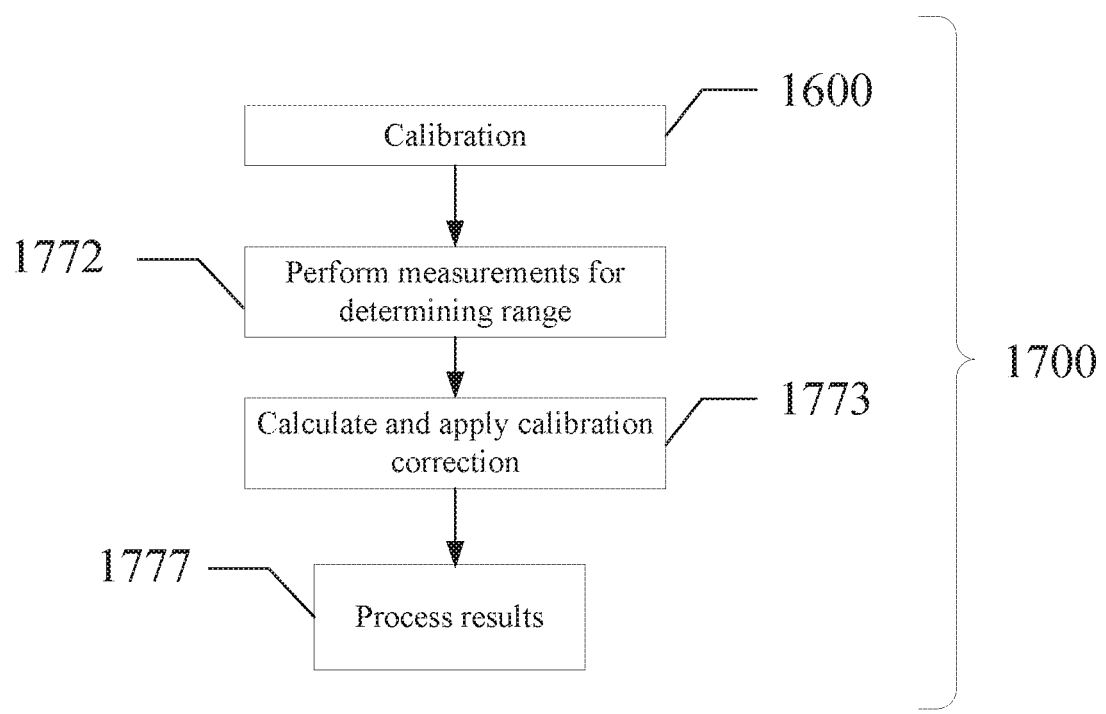
FIG. 17 may depict a flow diagram for determining location of one or more monitoring-sensor-tags associated with a material-of-interest.

FIG. 17 may depict a flow diagram for determining location of one or more monitoring-sensor-tags 120 associated with (e.g., attached to) the given material-of-interest. FIG. 17 may depict method 1700. In some embodiments, method 1700 may be a method for determining location of one or more monitoring-sensor-tags 120 associated with (e.g., attached to) the given material-of-interest. In some embodiments, method 1700 may provide additional details of step 1534 from FIG. 15.

For example, and without limiting the scope of the present invention, method 1700 may be employed to determine locations of one or more monitoring-sensor-tags 120 located in or on: dental-filling 1001 (FIG. 10A); root-canal-cavity 1003 (FIG. 10B); root-canal-post 1004 (FIG. 10B); dental-crown 1005 (FIG. 10B); dental-implant 1007 (FIG. 10C); implant-post 1008 (FIG. 10C); and/or the like.

For example, and without limiting the scope of the present invention, method 1700 may be employed to determine locations of one or more monitoring-sensor-tags 120 located in or on the given material-of-interest in the systems of FIG. 13A, FIG. 13B, or FIG. 13C.

In some embodiments, method 1700 may comprise method 1600, step 1772, step 1773, and step 1777. See e.g., FIG. 17.

Continuing discussing FIG. 17, in some embodiments, method 1700 may comprise method 1600 as discussed above, which may be a calibration method. In some embodiments, method 1700 may begin with method 1600.

Continuing discussing FIG. 17, in some embodiments, method 1700 may comprise step 1772. In some embodiments, successful calibration under method 1600 may then transition into step 1772. In some embodiments, step 1772 may be a step of obtaining measurements for determining ranges (distance) of the one or more monitoring-sensor tags 120 between readers 100. As mentioned before, one of well-known techniques for location and range (distance) measurement may include phase difference of arrival (PDoA); received signal strength indicator (RSSI); time of arrival (ToA); time of flight (ToF); and/or time difference of arrival (TDoA). For example, for the phase difference of arrival (PDoA) technique, the measurements may include phase difference of arrival. In some embodiments, such range measuring may be between each operational monitoring-sensor tag 120 selected from the one or more monitoring-sensor tags 120; and from a predetermined number (quantity) of operational readers 100. In some embodiments, the predetermined number (quantity) of operational readers 100 may be selected by a user engaging with software settings; wherein the software may be non-transitorily stored in memory 1803. In some embodiments, the predetermined number (quantity) of operational readers 100 may be those readers 100 closest to the given monitoring-sensor-tag 120. In some embodiments, the predetermined number (quantity) of operational readers 100 may be readers 100 determined under method 1600. In some embodiments of step 1772, measurements for determining of the range (distance) between each monitoring-sensor-tag 120 to each reader 100 from the group of readers 100 allocated to the given monitoring-sensor-tag 120 may be performed. In some embodiments, measurements of phase difference of arrival (PDoA) $\varphi(f_s)_k^{a_j,c_i}$ from each monitoring-sensor-tag 120 number $s_u$ to each reader 100 number $a_j$ in its vicinity may be performed. In some embodiments, "in its vicinity" may be dependent upon a frequency (or a wavelength) of wireless communication utilized by antennas 110 and/or antennas 130 for a given application (for a given use). For example, and without limiting the scope of the present invention, when radio waves may be used by antennas 110 and/or antennas 130, then "in its vicinity" may be selected from the group of 1 mm (millimeter) to 50 meters or less. In some embodiments, for each reader 100 number $a_j$ step 1772 may take M measurements of phase difference of arrival (PDoA) $\varphi(f_s)_k^{a_j,c_i}$ (where k=1 ... M) between reader 100 number $a_j$ and each monitoring-sensor-tag 120 number $s_u$ allocated to reader 100 number $a_j$. The said phase measurements may be taken at a number of different frequencies $f_s$ where s=1 ... L. In some embodiments, as noted above, allocation of readers 100 to monitoring-sensor-tags 120 may be predetermined and/or set by a user engaging with the software setting of the software.

Continuing discussing FIG. 17 and step 1772 in particular, in some embodiments, the above range phase difference of arrival (PDoA) $\varphi(f_s)_k^{a_j,c_i}$ measurements may be processed by calculating a mean and a variance for each of the frequencies $f_s$ where s=1 . . . L. For example, and without limiting the scope of the present invention, for each reader 100 number $a_j$ and each monitoring-sensor-tag 120 number $s_u$ allocated to that reader 100, calculate for each of the frequencies $f_s$ where s=1 . . . L:

Mean $\overline{\varphi}$ $(f_s)^{a_j,s_u}$ of the phase measurements $\varphi(f_s)_k^{a_j,s_u}$ between $a_j$ and $s_u$, k=1 . . . M; and Variance $\sigma^2(\varphi(f_s)_k^{a_j,s_u})$ of the phase measurements $\varphi(f_s)_k^{a_j,s_u}$ between $a_j$ and $s_u$, k=1 . . . M.

Continuing discussing FIG. 17, in some embodiments, method 1700 may comprise step 1773. In some embodiments, step 1773 may follow step 1772. In some embodiments, step 1773 may be a step of applying calibration-based corrections (adjustments) to the measurements and/or calculations of step 1772. For example, and without limiting the scope of the present invention, if monitoring-sensor-tags 120 locations have not been determined (calculated), then step 1773 may apply correction $\varphi_{delta}(f_s)^{a_j,c_i}$ calculated in equation (20) during described calibration process of method 1600, to the phase $\varphi(f_s)^{a_j,s_u}$ calculated above, such a corrected phase may be:

$$\varphi_{corrected}(f_s)^{a_j,s_u} = \overline{\varphi}(f_s)^{a_j,s_u} + \varphi_{delta}(f_s)^{a_j,c_i} \quad (21)$$

wherein the reference-sensor-tags 1102 number $c_i$ in equation (21) may be the one closest to reader 100 number $a_j$. In some embodiments, the reference-sensor-tags 1102 number $c_i$ in equation (21) may be the one closest in type to monitoring-sensor-tag 120 number $s_u$.

In some embodiments, reader 100 may emit electromagnetic waves at a number of pre-set frequencies $f_s$. It is well known and shown that it is possible to range estimate (distance) $h^{a_j,s_u}$ between each reader 100 number $a_j$ and each monitoring-sensor-tag 120 number $s_u$ by:

$$h^{a_j,s_u} = \frac{c}{4\pi} \frac{\Delta\varphi^{a_j,s_u}}{\Delta f^{a_j,s_u}} \quad (22)$$

where $\Delta\ddot{o}^{a_j,s_u}$ is a phase difference between two values of phase $\varphi_{corrected}(f_s)^{a_j,s_u}$ corresponding to two different frequencies from the set of frequencies $f_s$, and $\Delta f^{a_j,s_u}$ is the difference between the said two different frequencies. In some embodiments, equation (22) is used to calculate the range estimate (distance) $h^{a_j,s_u}$ between each reader 100 number $a_j$ and each monitoring-sensor-tag 120 number $s_u$. Continuing discussing FIG. 17, in some embodiments, method 1700 may comprise step 1777. In some embodiments, step 1777 may follow step 1773. In some embodiments, step 1777 may be a step of (non-transitory) saving determined (calculated) locations for the one or more monitoring-sensor-tags 120 to memory 1803.

Figure 18:
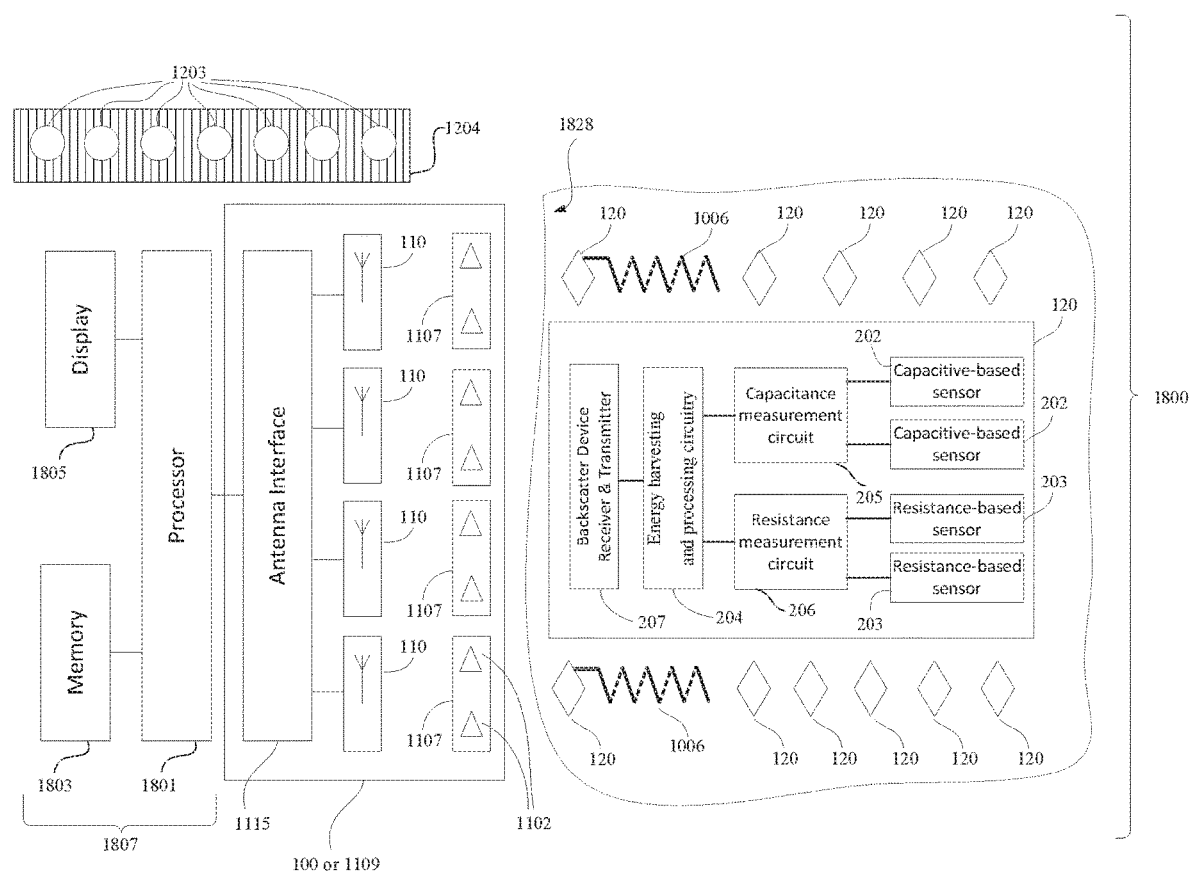
FIG. 18 may depict a block diagram of a device, a reader, a processor, memory, a display, a position-reference-member, and a material-of-interest with one or more monitoring-sensor-tags.

Note, in some embodiments, calculations carried out in methods 1500, 1600, and/or 1700 may be carried out by processor 1801 (see e.g., FIG. 18).

FIG. 18 may depict a block diagram of reader 100 (or of reader-and-calibration-member 1109), processor 1801, memory 1803, a display 1805, a position-reference-member 1204, and a material-of-interest 1828 with one or more monitoring-sensor-tags 120. In some embodiments, FIG. 18 may depict a system 1800 for non-invasive monitoring of material-of-interest 1828 with one or more monitoring-sensor tag 120 using one or more readers 100 (or using at least one reader-and-calibration-member 1109 with one or more readers 100).

Continuing discussing FIG. 18, in some embodiments, system 1800 may comprise one or more monitoring-sensor-tags 120 and one or more readers 100. In some embodiments, the one or more readers 100 and the one or more monitoring-sensor-tags 120 may be in wireless communications with each other.

Continuing discussing FIG. 18, the one or more monitoring-sensor-tags 120 may be as discussed previously above for monitoring-sensor-tags 120. For example, and without limiting the scope of the present invention, the one or more monitoring-sensor-tags 120 may be "attached to" material-of-interest 1828, wherein "attached to" has been described above.

Continuing discussing FIG. 18, the one or more readers 100 may be as discussed previously above for readers 100. In some embodiments, each of the one or more readers 100 may comprise one or more second-antennas 110; whereas a term of "first-antennas 130" may be antennas of the one or more monitoring-sensor-tags 120. In some embodiments, the one or more readers 100 using their one or more second-antennas 110 may transmits electromagnetic radiation (e.g., radio waves) of a predetermined characteristic. Such a transmission may be directed to the one or more monitoring-sensor-tags 120, specifically to their first-antennas 130. Such that first-antennas 130 (of the one or more monitoring-sensor-tags 120) may receive this electromagnetic radiation of the predetermined characteristic as an input. In some embodiments, this input may cause the at least one electric circuit 140 (of the one or more monitoring-sensor-tags 120) to take the one or more readings from the at least one sensor (e.g., 202 and/or 203); and to then transmit the one or more readings using the first-antennas 130 back to the one or more second-antennas 110 of the one or more readers 100. In some embodiments, at least one of the second-antennas 110 selected from the one or more second-antennas 110 then receives the one or more readings; and the one or more readers 100 or a device 1807 in communication with the one or more readers 100 may then use the one or more readings to determine a "current state" (as them term has been discussed previously) of material-of-interest 1828.

In some embodiments, material-of-interest 1828 shown in FIG. 18 may be representative of any materials-of-interest discussed previously herein, such as, but not limited to: dental-filling 1001; root-canal-post 1004; dental-crown 1005; an article implantable within a body of an organism; the article attachable to the body of the organism; specific tissue of the organism; and/or the construction member. As noted, in some embodiments, the article may be selected from: a medical device; a tissue graft; a bone graft; an artificial tissue; a bolus with time-release medication; and/or a medication. As noted, in some embodiments, the medical device may be dental-implant 1007 and/or implant-post 1008. As noted, in some embodiments, the organism may be a human, such as patient 1328. As noted, in some embodiments, the tissue may be tooth 1000, gum 1002, and/or root-canal-cavity 1003 and/or any other tissue of the organism.

Continuing discussing FIG. 18, in some embodiments, system 1800 may further comprise device 1807 that may be in communication with the one or more readers 100 and that may then use the one or more readings to determine a current state of material-of-interest 1828. In some embodiments, this device 1807 may comprise processor 1801 and memory

1803. In some embodiments, device 1807 may be a computing device and/or a computer. In some embodiments, processor 1801 may be in communication with the one or more second-antennas 110. In some embodiments, disposed between processor 1801 and the one or more second-antennas 110 may be antenna-interface 1115, as that component has been discussed previously. In some embodiments, antenna-interface 1115 may be in communication with both the one or more second-antennas 110 and processor 1801. In some embodiments, memory 1803 may be in communication with processor 1801. In some embodiments, memory 1803 may be in communication with processor 1801 as well as with antenna-interface 1115 and/or the one or more second-antennas 110. In some embodiments, non-transitorily stored in memory 1803 may be code (i.e., the software) for instructing processor 1801 how to interpret the current state by processing the one or more readings received at the at least one of the second-antennas 110 selected from the one or more second-antennas 110. In some embodiments, data; information, the one or more readings; measurement results; calculation results; the "additional information"; and/or the like may be non-transitorily stored in memory 1803.

Note, in some embodiments, instead of a separate device 1807 as noted above, each reader 100 may itself comprise antenna-interface 1115, processor 1801, and memory 1803. Whereas, in other embodiments, device 1807 may be integrated with the one more readers 100.

In some embodiments, memory 1803 may store (hold) information on a volatile or non-volatile medium, and may be fixed and/or removable. In some embodiments, memory 1803 may include a tangible computer readable and computer writable non-volatile recording medium, on which signals are stored that define a computer program (i.e., the code or the software) or information to be used by the computer program. The recording medium may, for example, be hard drive, disk memory, flash memory, and/or any other article(s) of manufacture usable to record and store information (in a non-transitory fashion). In some embodiments, in operation, processor 1801 may cause(s) data (such as, but not limited to, information, the one or more readings; measurement results; calculation results; the "additional information"; and/or the like) to be read from the nonvolatile recording medium into a volatile memory (e.g., a random access memory, or RAM) that may allow for more efficient (i.e., faster) access to the information by processor 1801 as compared against the nonvolatile recording medium. Memory 1803 may be located in device 1807 and in communication with processor 1801. See e.g., FIG. 18. In some embodiments, processor 1801 may manipulate(s) the data and/or information within integrated circuit memory (e.g., RAM) and may then copy the data to the nonvolatile recording medium (e.g., memory 1803) after processing may be completed. A variety of mechanisms are known for managing data movement between the nonvolatile recording medium and the integrated circuit memory element, and the invention is not limited to any mechanism, whether now known or later developed. The invention is also not limited to a particular processing unit (e.g., processor 1801) or storage unit (e.g., memory 1803).

Continuing discussing FIG. 18, in some embodiments of system 1800 the one or more second-antennas 110 may have known (or determinable) positional locations. As previously discussed, locations of the one or more readers 100 (or locations of the second-antennas 110) may be determined via wireless communications between the one or more readers 100 (via their one or more second-antennas 110) and one or more reference-sensor-tags 1102 (via their at least one fourth-antennas). And/or as previously discussed, locations of the one or more readers 100 (or locations of the second-antennas 110) may be determined via wireless communications between the one or more readers 100 (via their one or more second-antennas 110) and one or more position-reference-tag 1203 (via their at least one third-antennas). That is in some embodiments, system 1800 may further comprise one or more reference-sensor-tags 1102 and/or system 1800 may further comprise one or more position-reference-tag 1203. See e.g., FIG. 18. As discussed previously, reference-sensor-tags 1102 may be housed in reference-housing-member 1107. As discussed previously, reference-sensor-tags 1102 may be fixed with respect to second-antennas 110; even in embodiments where the second-antennas 110 may be translating with respect to origin 1325 (e.g., the systems of FIG. 13A and of FIG. 13C) (because the reader-and-calibration-member 1109 housing the second-antennas 110 may be translating together as a unit). As previously discussed, in some embodiments, position-reference-tags 1203 may be housed in position-reference-member 1204. As previously discussed, in some embodiments, position-reference-tags 1203 and position-reference-member 1204 may be stationary; i.e., fixed with respect to an origin 1325; even when second-antennas 110 may be translating as shown in FIG. 13A and in FIG. 13C (because the reader-and-calibration-member 1109 housing the second-antennas 110 may be translating while position-reference-member 1204 remains stationary). Note, in some embodiments of system 1800, position-reference-member 1204 (with position-reference-tags 1203) may be optional or not included. In any event, because locations (positions) of second-antennas 110 (or readers 100) may be determinable and thus known; then processor 1801 running the code (i.e., the software or the computer program) non-transitorily stored in memory 1803 may be instructed by that code, using these known positional locations of the one or more second-antennas 110 and using communications from the first-antennas 130, may then determine (calculate) positional locations of the one or more monitoring-sensor-tags 120.

Continuing discussing FIG. 18, in some embodiments, reader 100 may comprise the one or more second-antennas 110; one or more reference-sensor-tags 1102; and antenna-interface 1115. In some embodiments, the one or more reference-sensor-tags 1102 may be fixed relative to the one or more second-antennas 110. In some embodiments, reader 100 may comprise one or more reference-housing-member 1107; wherein each reference-housing-member 1107 may comprise the one or more reference-sensor-tags 1102. Thus, reader 100 may function as reader-and-calibration-member 1109; which is why reader 100 in FIG. 18 is also noted as reader-and-calibration-member 1109. In some embodiments, one or more second-antennas 110 may have known (or determinable) positional locations relative to: a known origin (e.g., origin 1325), known reference-sensor-tags 1102 locations, and/or known position-reference-tag 1203 locations.

In some embodiments, one or more readers 100 may be disposed within reader-and-calibration-member 1109 and the one or more second-antennas 110 may have known positional locations relative to: a known origin (e.g., origin 1325), known reference-sensor-tags 1102 locations, and/or known position-reference-tag 1203 locations. See e.g., FIG. 11A, FIG. 11B, and FIG. 18.

Note, structures shown in cross-hatch in FIG. 19 through FIG. 32 may correspond to one or more monitoring-sensor-tags 120.

Figure 19:
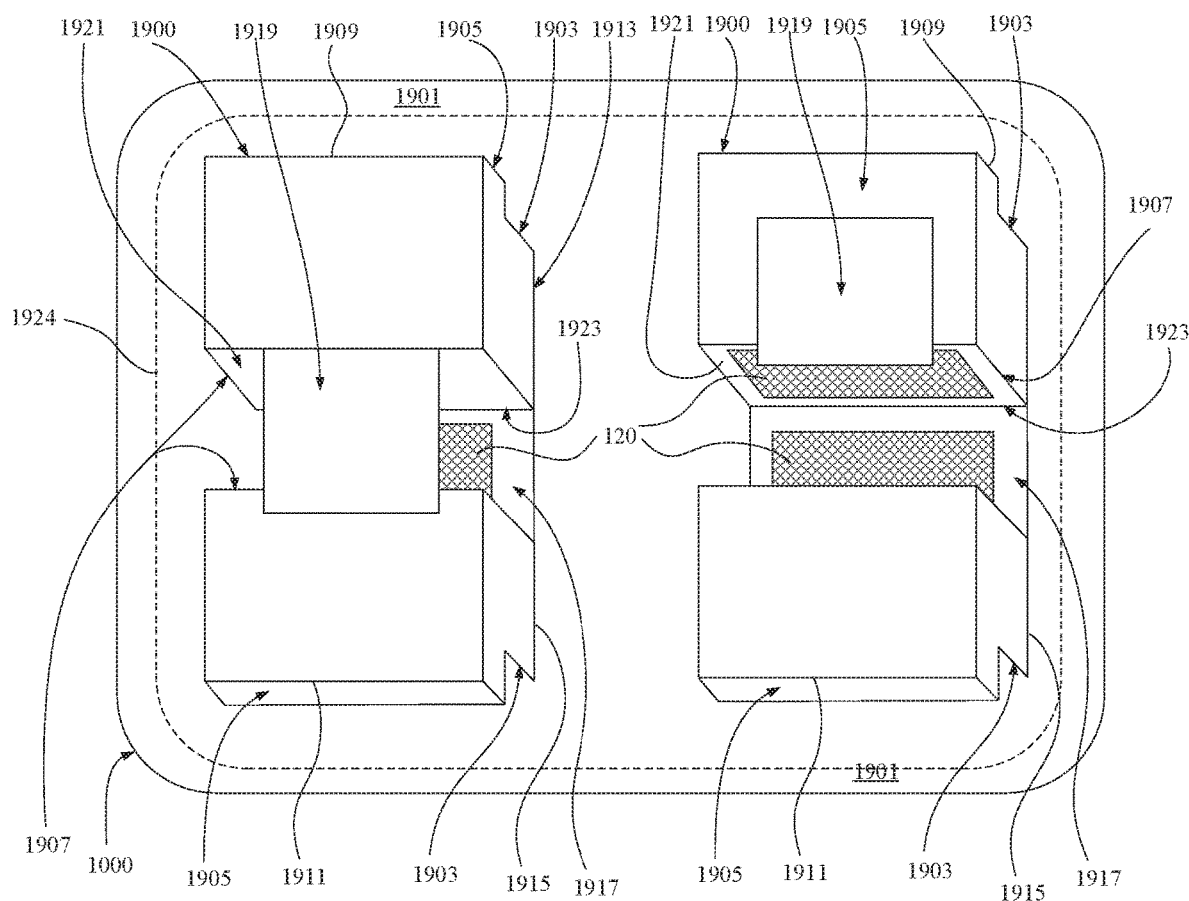
FIG. 19 may depict orthodontic-brackets connected to a tooth-surface, from a front perspective view; wherein the given orthodontic-bracket may have one or more monitoring-sensor-tags attached to the given orthodontic-bracket.

FIG. 19 may depict orthodontic-brackets 1900 connected to a tooth-surface 1901 of a tooth 1000, from a front perspective view; wherein the given orthodontic-bracket 1900 may have one or more monitoring-sensor-tags 120 attached to the given orthodontic-bracket 1900. In some embodiments, disposed between a given orthodontic-bracket 1900 and a given tooth-surface 1901 of a given tooth 1000, may be a substrate 1924. In some embodiments, substrate 1924 may be connected to the given tooth-surface 1901; and the given orthodontic-bracket 1900 may be connected to the substrate 1924. A plurality of such orthodontic-brackets 1900 attached to a plurality of teeth (e.g., tooth 1000) may form orthodontic-braces. In some embodiments, orthodontic-bracket 1900 may be rigid to substantially semi-rigid. In some embodiments, a given orthodontic-bracket 1900 may comprise a base 1903 and a head 1905; wherein the head may be bifurcated with an orthodontic-bracket-receiving-cavity 1907; and the base 1903 may be the portion of 1900 that may be attached to tooth-surface 1901. In some embodiments, base 1903 and head 1905 may be integral with each other. In some embodiments, orthodontic-bracket-receiving-cavity 1907 may be a channel and/or a cavity that may run substantially through a middle of a given head 1905. In some embodiments, orthodontic-bracket-receiving-cavity 1907 bifurcating head 1905 may create an upper-head 1909 and a lower-head 1911 (where "upper" and "lower" in this context may be with respect to a given patient; i.e., "upper" closer to top of the patient's head and "lower" further away from the top of the head of the patient). In some embodiments, upper-head 1909 may be integral with an upper-base 1913. In some embodiments, lower-head 1911 may be integral with lower-base 1915. In some embodiments, base 1903 may comprise upper-base 1913 and lower-base 1915; and upper-base 1913 and lower-base 1915 may be integral with each other. In some embodiments, orthodontic-bracket-receiving-cavity 1907 may be for receiving a longitudinal portion of an orthodontic-archwire 2401 (see e.g., FIG. 24).

Continuing discussing FIG. 19, in some embodiments, orthodontic-bracket-receiving-cavity 1907 may comprise interior-side 1917. In some embodiments, interior-side 1917 may be a side of orthodontic-bracket-receiving-cavity 1907 that may be closest to base 1903. In some embodiments, interior-side 1917 may be a side of orthodontic-bracket-receiving-cavity 1907 that may be closest to tooth-surface 1901. In some embodiments, a top surface or a top side of orthodontic-bracket-receiving-cavity 1907 may be top-interior 1921. In some embodiments, interior-side 1917 and top-interior 1921 may meet at interior-seam 1923.

Continuing discussing FIG. 19, in some embodiments, orthodontic-bracket 1900 may comprise one or more orthodontic-bracket-locks 1919. In some embodiments, orthodontic-bracket-lock 1919 may be for covering, sealing, partially covering, or partially sealing over an opening to orthodontic-bracket-receiving-cavity 1907. In some embodiments, orthodontic-bracket-lock may run from upper-head 1909 over orthodontic-bracket-receiving-cavity 1907 to lower-head 1911.

Continuing discussing FIG. 19, in some embodiments, one or more monitoring-sensor-tags 120 may be attached to one or more orthodontic-elements, and/or portions of such orthodontic-elements. In some embodiments, the orthodontic-elements may comprise one or more of: orthodontic-bracket 1900, an orthodontic-bracket-hook 2301 (see e.g., FIG. 23), an orthodontic-bracket-receiving-cavity 1907, an orthodontic-bracket-lock 1919, an orthodontic-archwire 2401 (see e.g., FIG. 24), an orthodontic-spring 2403 (see e.g., FIG. 24), an orthodontic-expander 3000 (see e.g., FIG. 30), an orthodontic elastic-band 2501 (see e.g., FIG. 25), an orthodontic-power-chain 3100 (see e.g., FIG. 31 and FIG. 32), or an orthodontic-band 3001 (see e.g., FIG. 30), and/or portions thereof. The orthodontic-elements, due to their very nature and function, often intentionally put forces upon teeth to achieve certain results (e.g., corrected bite, straighter teeth, and/or the like); and thus, such orthodontic-elements are ideal hardware elements to utilize one or more monitoring-sensor-tags 120.

Continuing discussing FIG. 19, in some embodiments, one or more monitoring-sensor-tags 120 may be attached to one or more surfaces that make up orthodontic-bracket-receiving-cavity 1907; such as, but not limited to interior-side 1917 and/or top-interior 1921.

In some embodiments, the given orthodontic-element with the one or more monitoring-sensor-tags 120 may be monitored and/or tracked to provide one or more of: structural integrity of a current state of the given orthodontic-element; structural integrity changes of the given orthodontic-element; pressure received at the given orthodontic-element; force received at the given orthodontic-element; stress received at the given orthodontic-element; shear-stress received in the given orthodontic-element; torsion received at the given orthodontic-element; compression of the given orthodontic-element; tension in the given orthodontic-element; twisting received of the given orthodontic-element; deformation received at the given orthodontic-element; temperature at some portion of the given orthodontic-element; positional changes of a given monitoring-sensor-tag 120 attached to the given orthodontic-element with respect to position of another monitoring-sensor-tag 120 attached to the given orthodontic-element, wherein the given monitoring-sensor-tag 120 and the other monitoring-sensor-tag are 120 selected from the one or more monitoring-sensor-tags 120 attached to the given orthodontic-element; or positional changes of at least one monitoring-sensor-tag 120 attached to the given orthodontic-element with respect to time, wherein the at least one monitoring-sensor-tag 120 is selected from the one or more monitoring-sensor-tags 120.

Figure 20:
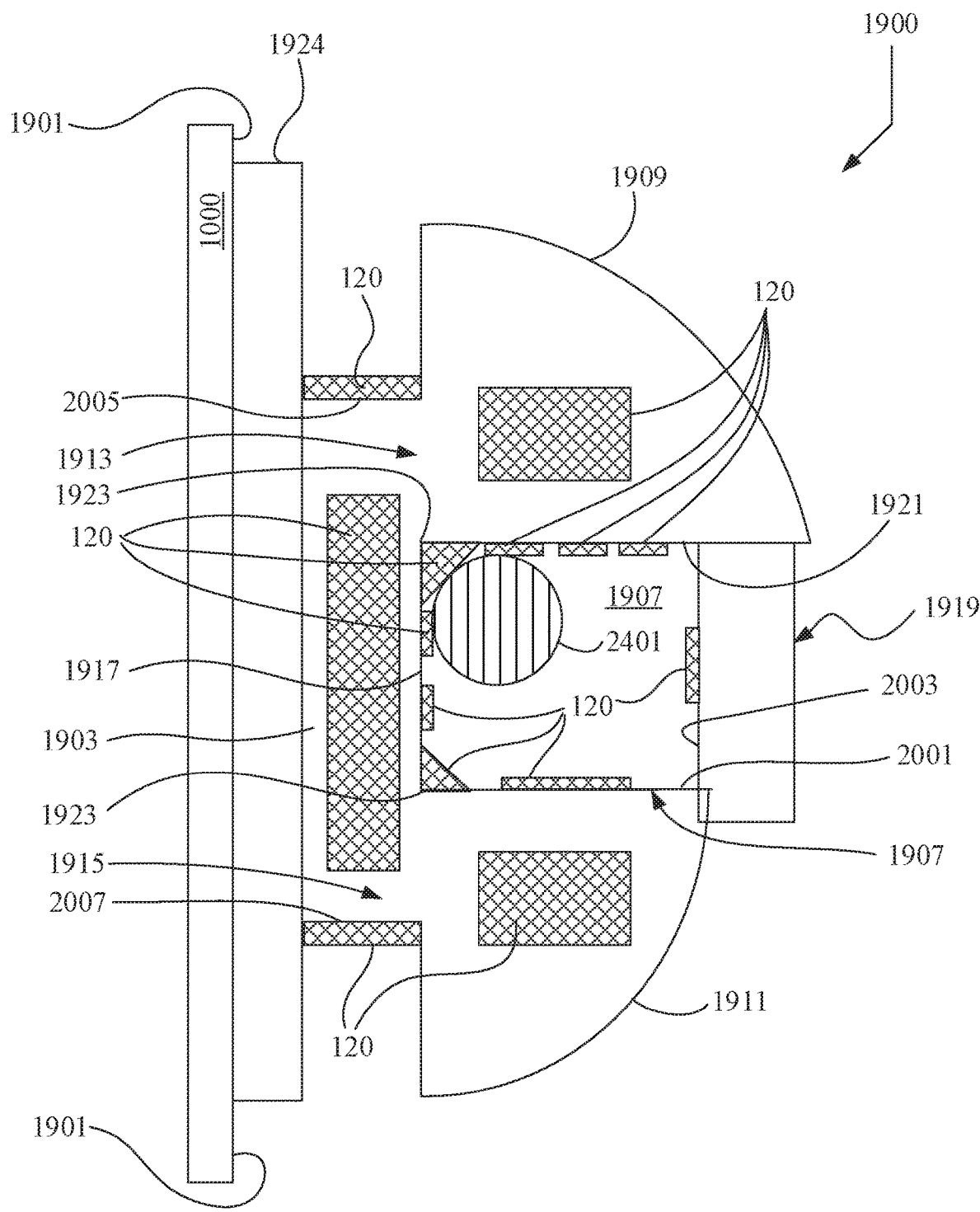
FIG. 20 may depict an orthodontic-bracket connected to a tooth-surface, from a side view; wherein the orthodontic-bracket may have one or more monitoring-sensor-tags attached to the orthodontic-bracket.

FIG. 20 may depict orthodontic-bracket 1900 connected to tooth-surface 1901, from a side view; wherein orthodontic-bracket 1900 may have one or more monitoring-sensor-tags 120 attached to orthodontic-bracket 1900 and/or to portions thereof. In some embodiments, orthodontic-bracket-receiving-cavity 1907 may be substantially bounded on three sides by portions of orthodontic-bracket 1900. In some embodiments, these three sides may be top-interior 1921, interior-side 1917, and bottom-interior 2001; wherein top-interior 1921 may be connected to interior-side 1917 at an interior-seam 1923; and wherein interior-side 1917 may be connected to bottom-interior 2001 at another interior-seam 1923. In some embodiments, an opening to orthodontic-bracket-receiving-cavity 1907 may be covered, sealed, partially covered, and/or partially sealed by orthodontic-bracket-lock 1919. In some embodiments, a surface of orthodontic-bracket-lock 1919 that may be facing orthodontic-bracket-receiving-cavity 1907 may be lock-interior 2003. In some embodiments, one or more monitoring-sensor-tags 120 may be attached to: top-interior 1921, interior-seam 1923, interior-side 1917, another interior-seam 1923, bottom-interior 2001, lock-interior 2003, and/or portions thereof.

Continuing discussing FIG. 20, in some embodiments one or more monitoring-sensors-tags 120 may be attached to (including located within such structures) upper-head 1909, lower-head 1911, base 1903, and/or portions thereof.

Continuing discussing FIG. 20, in some embodiments upper-base 1913 may comprise a top portion, designated top-base 2005. In some embodiments, lower-base 1915 may comprise a bottom portion, designated bottom-base 2007. In some embodiments, one or more monitoring-sensor-tags 120 may be attached to top-base 2005, to bottom-base 2007, to base 1903, and/or portions thereof.

Figure 21:
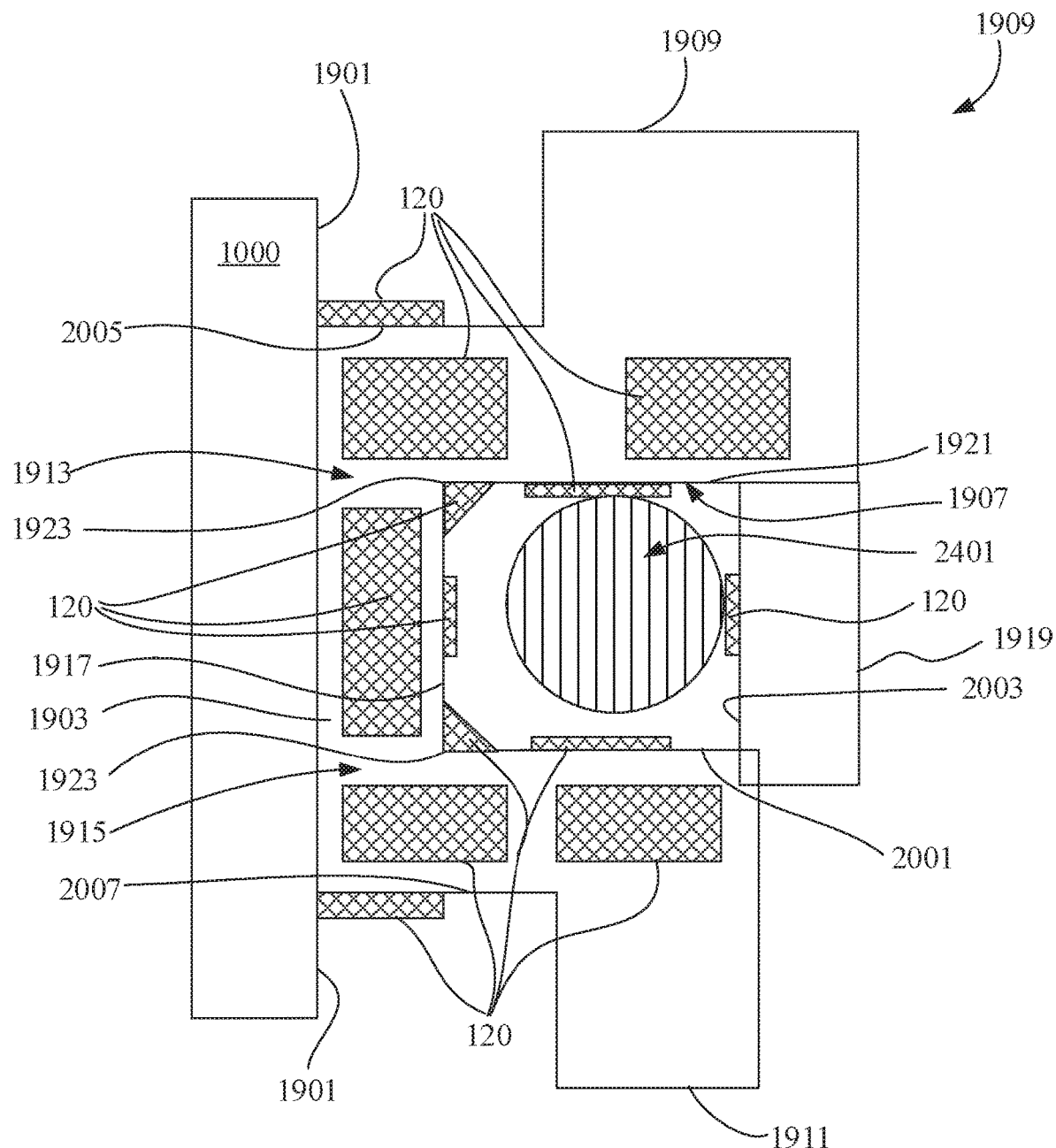
FIG. 21 may depict an orthodontic-bracket connected to a tooth-surface, from a side view; wherein the orthodontic-bracket may have one or more monitoring-sensor-tags attached to the orthodontic-bracket.

FIG. 21 may depict orthodontic-bracket 1900 connected to tooth-surface 1901, from a side view; wherein orthodontic-bracket 1900 may have one or more monitoring-sensor-tags 120 attached to orthodontic-bracket 1900 and/or to portions thereof. The orthodontic-bracket 1900 of FIG. 21 may be substantially similar to the orthodontic-bracket 1900 shown in FIG. 20, in terms of structural features and functions; except the orthodontic-bracket 1900 of FIG. 20 may be more rounded (e.g., bulbous) as compared against the more angular orthodontic-bracket 1900 of FIG. 21 (and FIG. 19).

Figure 22:
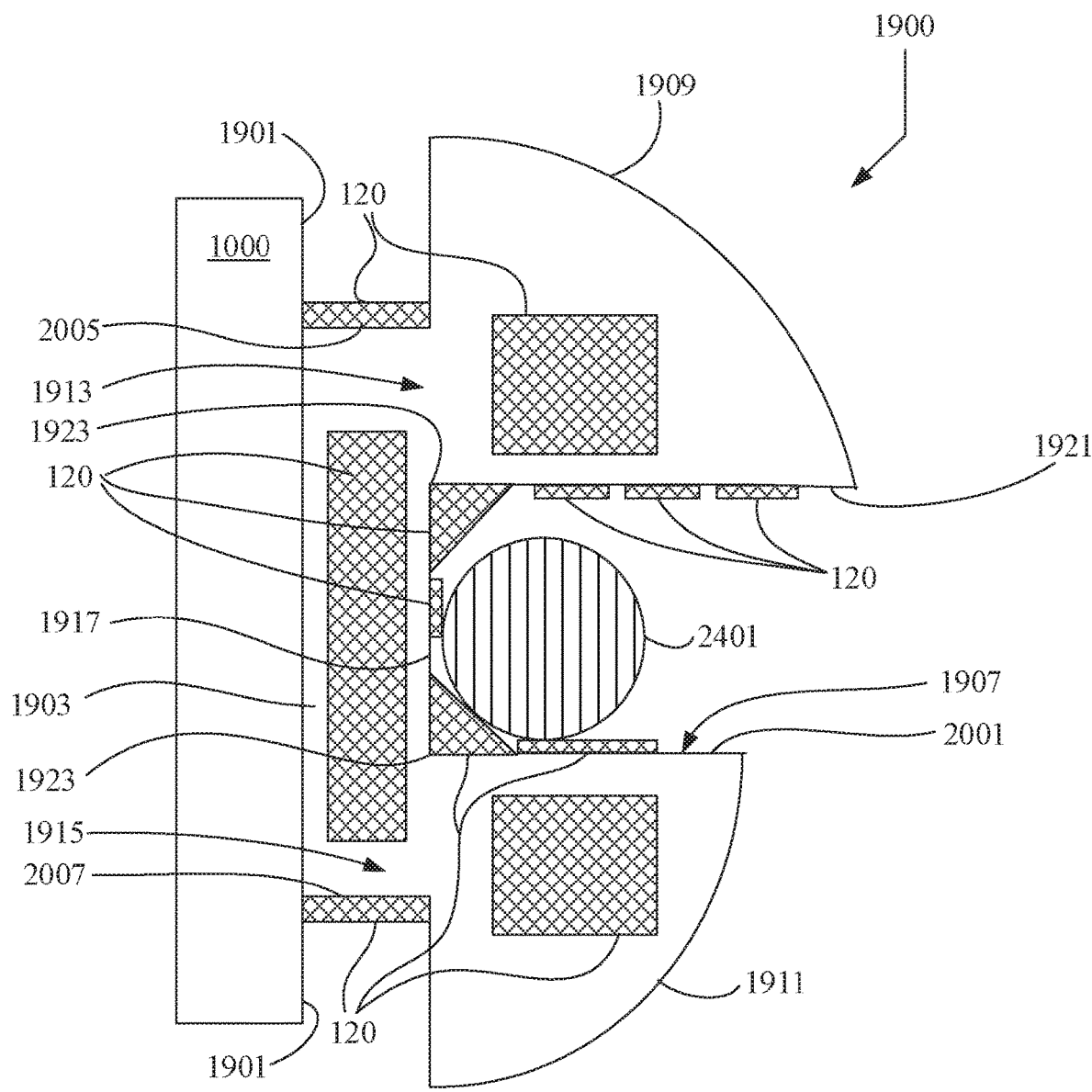
FIG. 22 may depict an orthodontic-bracket connected to a tooth-surface, from a side view; wherein the orthodontic-bracket may have one or more monitoring-sensor-tags attached to the orthodontic-bracket.

FIG. 22 may depict orthodontic-bracket 1900 connected to tooth-surface 1901, from a side view; wherein orthodontic-bracket 1900 may have one or more monitoring-sensor-tags 120 attached to orthodontic-bracket 1900. The orthodontic-bracket 1900 of FIG. 22 may be substantially similar to the orthodontic-bracket 1900 shown in FIG. 20, in terms of structural features and functions; except the orthodontic-bracket 1900 of FIG. 22 may be shown without orthodontic-bracket-lock 1919.

Figure 23:
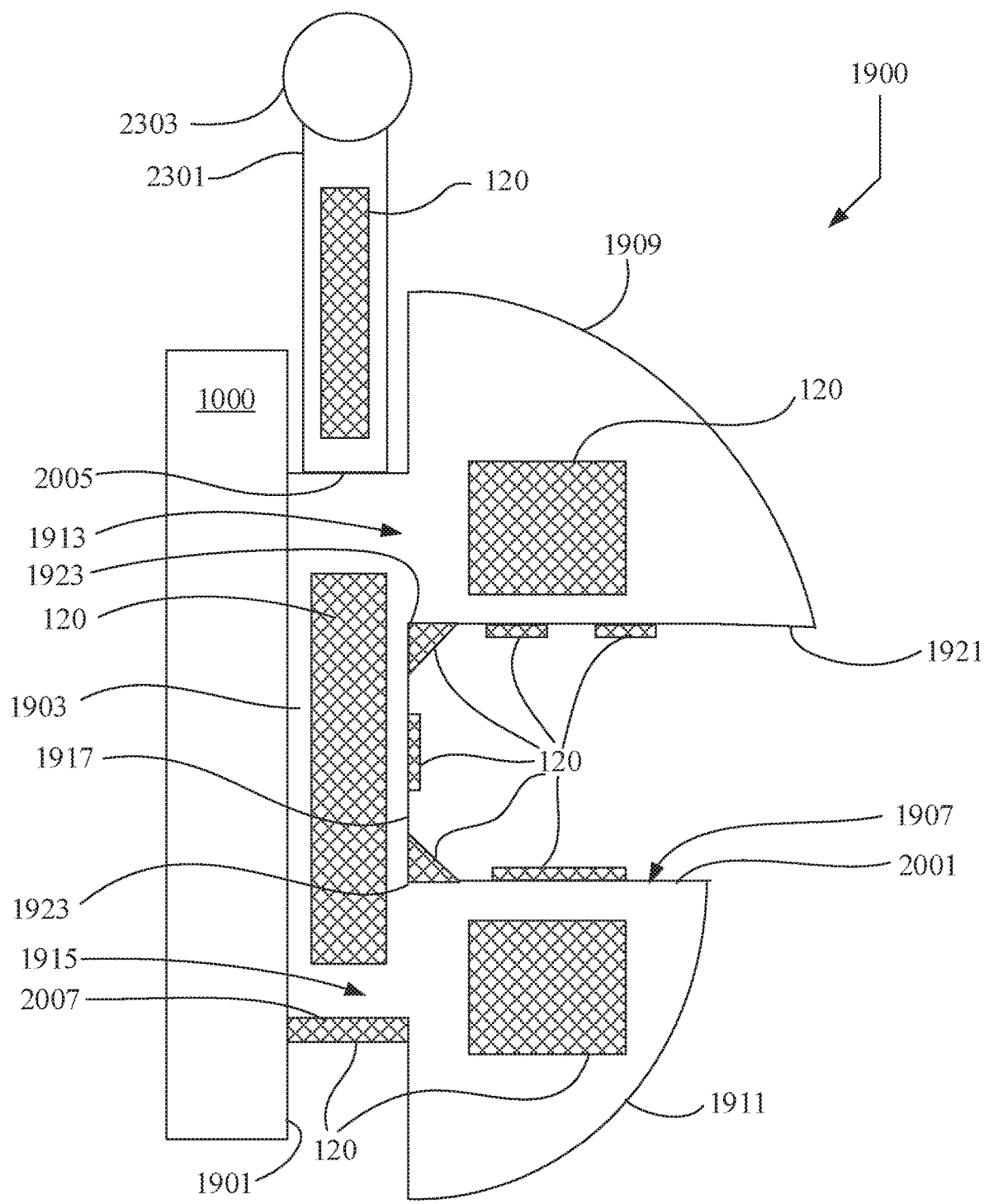
FIG. 23 may depict an orthodontic-bracket connected to a tooth-surface, from a side view; wherein the orthodontic-bracket may have one or more monitoring-sensor-tags attached to the orthodontic-bracket.

FIG. 23 may depict orthodontic-bracket 1900 connected to tooth-surface 1901, from a side view; wherein orthodontic-bracket 1900 may have one or more monitoring-sensor-tags 120 attached to orthodontic-bracket 1900. The orthodontic-bracket 1900 of FIG. 23 may be substantially similar to the orthodontic-bracket 1900 shown in FIG. 22, in terms of structural features and functions; except the orthodontic-bracket 1900 of FIG. 23 may be shown with orthodontic-bracket-hook 2301. In some embodiments, orthodontic-bracket-hook 2301 may function as an anchor to receive an orthodontic-elastic-band 2501 (see e.g., FIG. 25).

Continuing discussing FIG. 23, in some embodiments, orthodontic-bracket-hook 2301 may be an elongate member that may extend from a top portion of orthodontic-bracket 1900. In some embodiments, orthodontic-bracket-hook 2301 may be an elongate member that may extend from a top portion of upper-head 1909. In some embodiments, orthodontic-bracket-hook 2301 may be an elongate member that may extend from a top portion of upper-base 1913. In some embodiments, orthodontic-bracket-hook 2301 may be an elongate member that may extend from top-base 2005 (embodiment shown in FIG. 23). In some embodiments, orthodontic-bracket-hook 2301 may be an elongate member that may be rigid to substantially semi-rigid.

Continuing discussing FIG. 23, in some embodiments, a free end of this elongate member of orthodontic-bracket-hook 2301 may terminate in and at hook-stop 2303. In some embodiments, hook-stop 2303 may be terminal end structure for preventing orthodontic-elastic-band 2501 from slipping off of orthodontic-bracket-hook 2301. In some embodiments, hook-stop 2303 may have a greater width or a greater diameter than a transverse-width of the elongate member portion of orthodontic-bracket-hook 2301. In some embodiments, hook-stop 2303 may be a bulbous member.

Continuing discussing FIG. 23, in some embodiments, the one or more monitoring-sensor-tags 120 may be attached to one or more of orthodontic-bracket-hook 2301 and/or hook-stop 2303.

Continuing discussing FIG. 23, in some embodiments, the one or more monitoring-sensor-tags 120 may be attached to (or integrated into) one or more of orthodontic-bracket-hook 2301, hook-stop 2303, combinations thereof, portions thereof, and/or the like. In some embodiments, one or more of orthodontic-bracket-hook 2301, hook-stop 2303, combinations thereof, portions thereof, may be examples of various orthodontic-elements.

Figure 24:
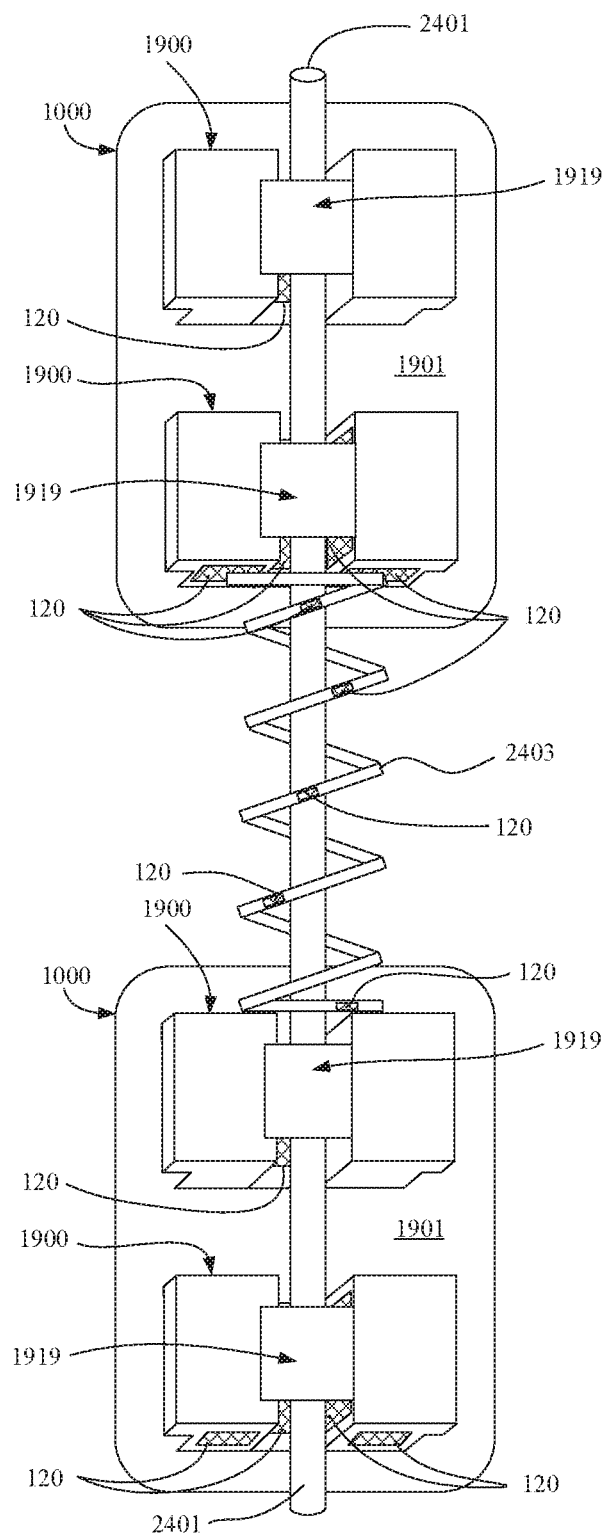
FIG. 24 may depict orthodontic-brackets attached to different teeth but linked via an orthodontic-archwire; wherein one or more monitoring-sensor-tags may be attached to various orthodontic-elements.

FIG. 24 may depict orthodontic-brackets 1900 attached to different teeth 1000 but linked via an orthodontic-archwire 2401; wherein one or more monitoring-sensor-tags 120 may be attached to various orthodontic-elements. In some embodiments, orthodontic-archwire 2401 may be an elongate member. In some embodiments, orthodontic-archwire 2401 may be substantially cylindrical. In some embodiments, orthodontic-archwire 2401 may be flexible to semi-rigid. In some embodiments, orthodontic-archwire 2401 may be substantially metallic. In some embodiments, portions of a longitude (length) of orthodontic-archwire 2401 may be captured (received) by a plurality of orthodontic-bracket-receiving-cavities 1907 of different orthodontic-brackets 1900.

Continuing discussing FIG. 24, in some embodiments, disposed between different teeth 1000, may be one or more orthodontic-springs 2403; wherein a length portion of orthodontic-archwire 2401 may pass through an axial center of orthodontic-spring 2403, such that a longitude of orthodontic-archwire 2401 and a longitude of orthodontic-spring 2403 may be substantially coaxial (concentric) with respect to each other over this length portion of orthodontic-archwire 2401. In some embodiments, force or changes in the force of the orthodontic-spring 2403 on such adjacent teeth 1000 may be measured, tracked, and/or monitored by placement of one or more monitoring-sensor-tags 120 on orthodontic-spring 2403 and/or on orthodontic-brackets 1900 in communication with orthodontic-spring 2403.

Continuing discussing FIG. 24, in some embodiments, the one or more monitoring-sensor-tags 120 may be attached to (or integrated into) one or more of orthodontic-archwire 2401, orthodontic-spring 2403, combinations thereof, portions thereof, and/or the like. In some embodiments, one or more of orthodontic-archwire 2401, orthodontic-spring 2403, combinations thereof, portions thereof, may be examples of various orthodontic-elements.

Figure 25:
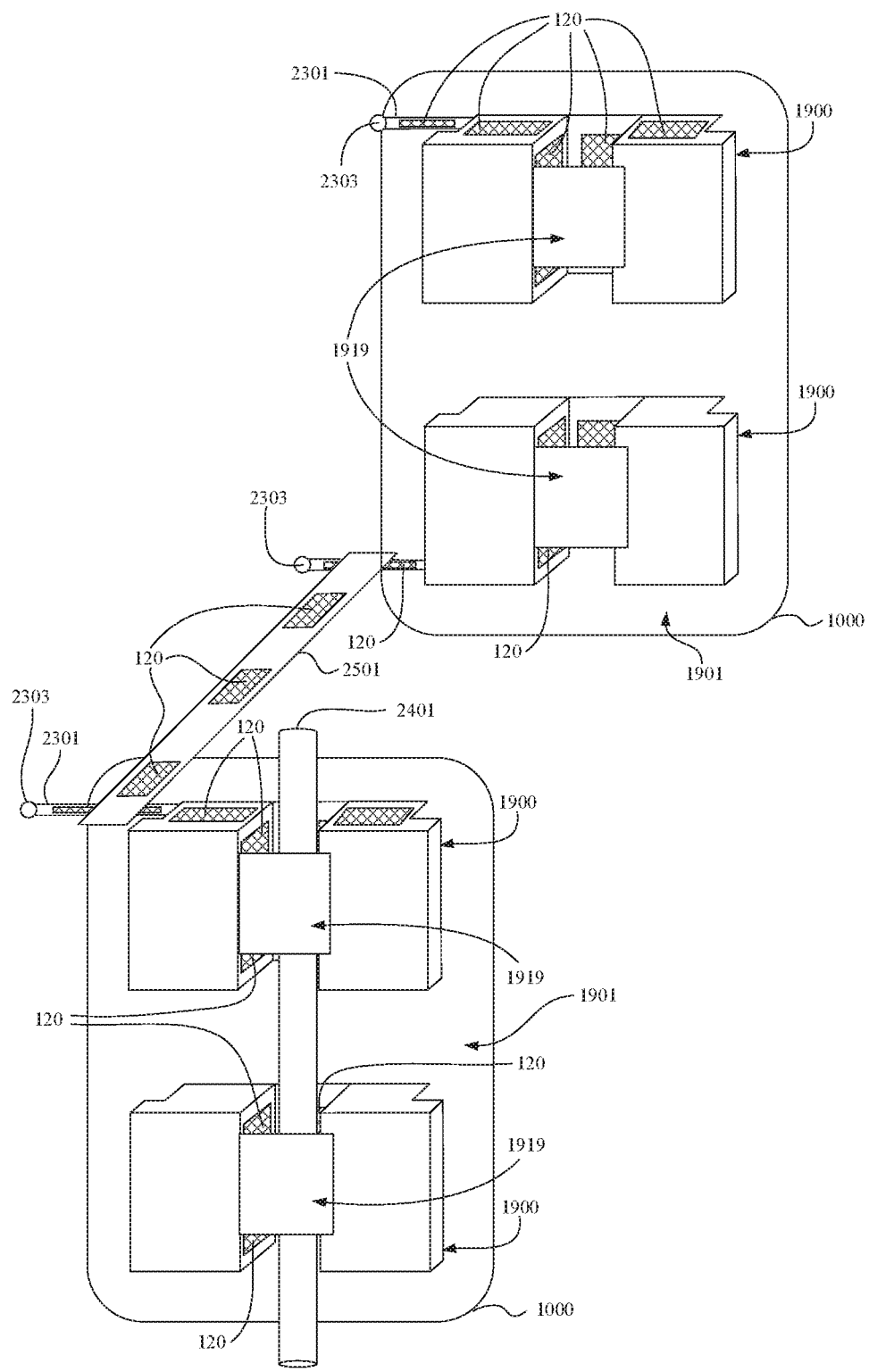
FIG. 25 may depict orthodontic-brackets attached to upper teeth and orthodontic-brackets attached to lower teeth; wherein such "upper" and such "lower" orthodontic-brackets may be linked via an orthodontic-elastic-band; wherein one or more monitoring-sensor-tags may be attached to various orthodontic-elements.

FIG. 25 may depict orthodontic-brackets 1900 attached to upper teeth 1000 and orthodontic-brackets 1900 attached to lower teeth 1000; wherein such "upper" and such "lower" orthodontic-brackets 1900 may be linked via an orthodontic-elastic-band 2501; wherein one or more monitoring-sensor-tags 120 may be attached to various orthodontic-elements. In some embodiments, orthodontic-elastic-band 2501 may be an elastic member. In some embodiments, orthodontic-elastic-band 2501 may be a substantially elongate member. In some embodiments, orthodontic-elastic-band 2501 may be attached to two different orthodontic-bracket-hook 2301; wherein each orthodontic-bracket-hook 2301 may be of a different orthodontic-bracket 1900, attached to a different tooth 1000.

Continuing discussing FIG. 25, in some embodiments, the various orthodontic-elements, that may have the one or more monitoring-sensor-tags 120 attached thereto, may comprise orthodontic-elastic-band 2501. In some embodiments, substantially elongate and elastic orthodontic-elastic-band 2501 may comprise the one or more monitoring-sensor-tags 120. In some embodiments, the one or more monitoring-sensor-tags 120 may be attached to or integral with orthodontic-elastic-band 2501.

FIG. 25, may also show other of the various orthodontic-elements, that may have the one or more monitoring-sensortags 120 attached thereto. For example, and without limiting the scope of the present invention, the orthodontic-brackets 1900 may have the one or more monitoring-sensor-tags 120 attached thereto. And/or the orthodontic-archwire 2401 may have the one or more monitoring-sensor-tags 120 attached thereto. One possible usage or application of the configuration shown in FIG. 25 may be monitoring forces exercised by orthodontic-elastic-band 2501 on the different orthodontic-brackets 1900 that are in communication with orthodontic-elastic-band 2501 by using the one or more monitoring-sensor-tags 120 attached to one or more of: orthodontic-elastic-band 2501, orthodontic-bracket-hook 2301, the different orthodontic-brackets 1900 that are in communication with orthodontic-elastic-band 2501, and/or other orthodontic-elements.

Figure 26:
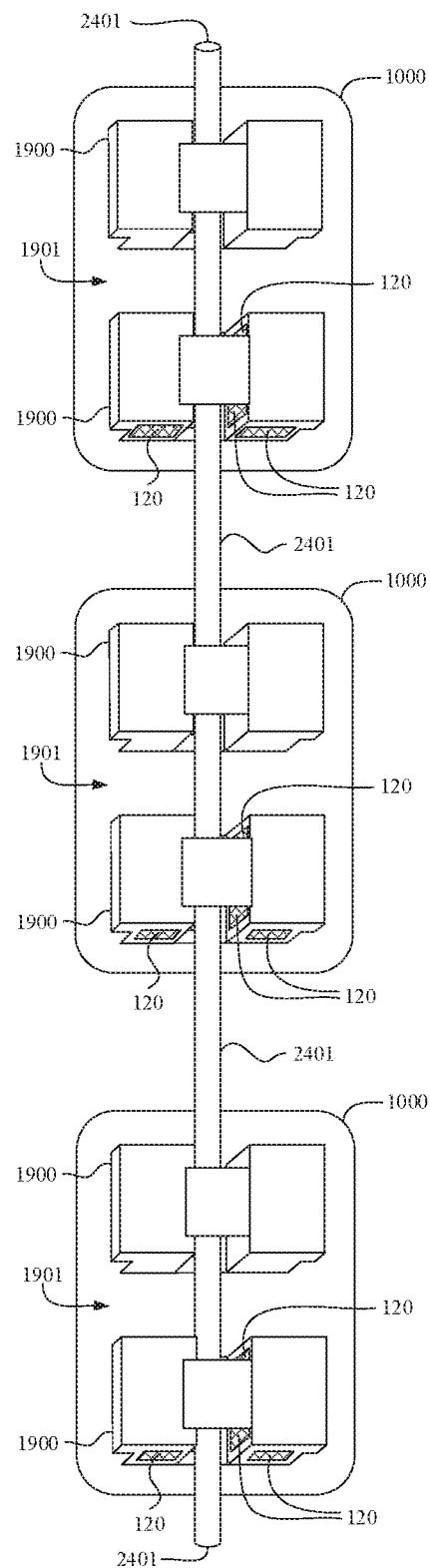
FIG. 26 may depict orthodontic-brackets attached to different teeth but linked via an orthodontic-archwire; wherein one or more monitoring-sensor-tags may be attached to various orthodontic-elements.

FIG. 26 may depict orthodontic-brackets 1900 attached to different teeth 1000 but linked via an orthodontic-archwire 2401; wherein one or more monitoring-sensor-tags 120 may be attached to various orthodontic-elements. FIG. 26, may show the various orthodontic-elements, that may have the one or more monitoring-sensor-tags 120 attached thereto. For example, and without limiting the scope of the present invention, the orthodontic-brackets 1900 may have the one or more monitoring-sensor-tags 120 attached thereto. And/or the orthodontic-archwire 2401 may have the one or more monitoring-sensor-tags 120 attached thereto.

Figure 27:
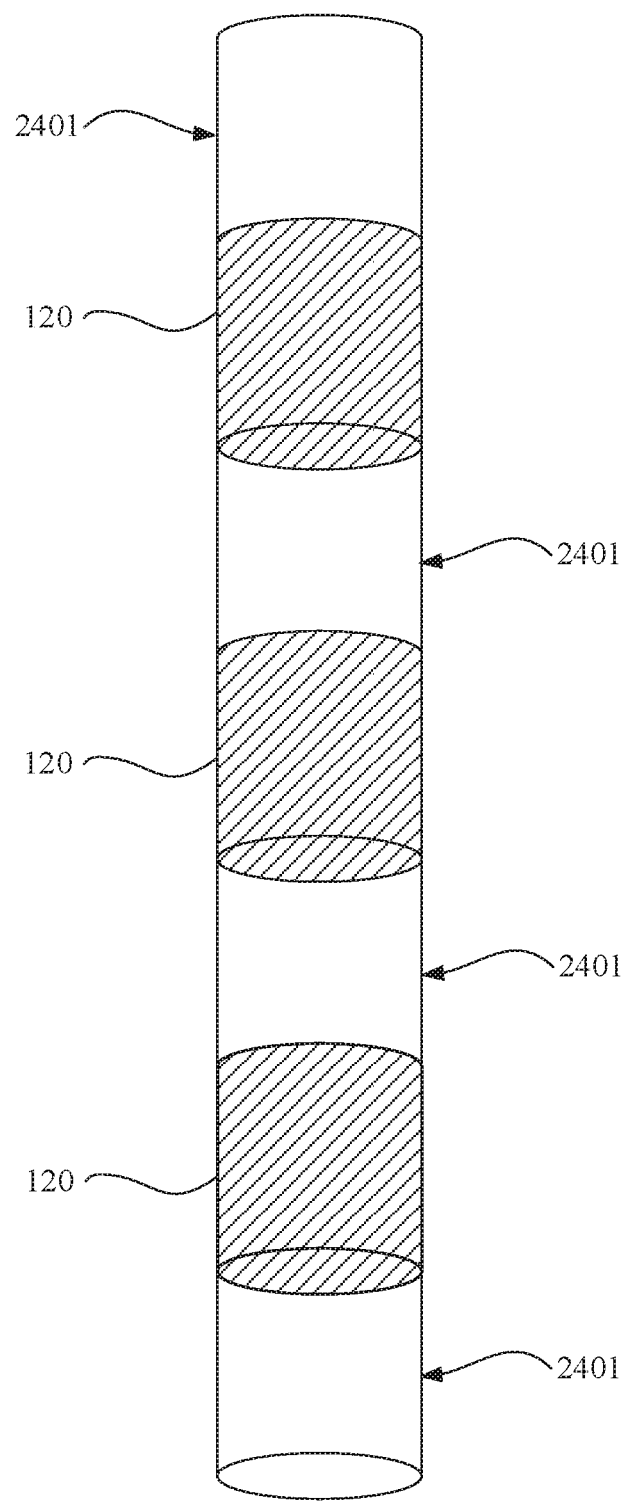
FIG. 27 may depict a portion an orthodontic-archwire; wherein one or more monitoring-sensor-tags may be attached to and/or integrated into the orthodontic-archwire.

FIG. 27 may depict a portion of an orthodontic-archwire 2401; wherein one or more monitoring-sensor-tags 120 may be attached to and/or integrated into the orthodontic-archwire 2401. That is, in some embodiments, portions of a given orthodontic-archwire 2401 may comprise one or more monitoring-sensor-tags 120, that may be integral with the given orthodontic-archwire 2401.

Figure 28:
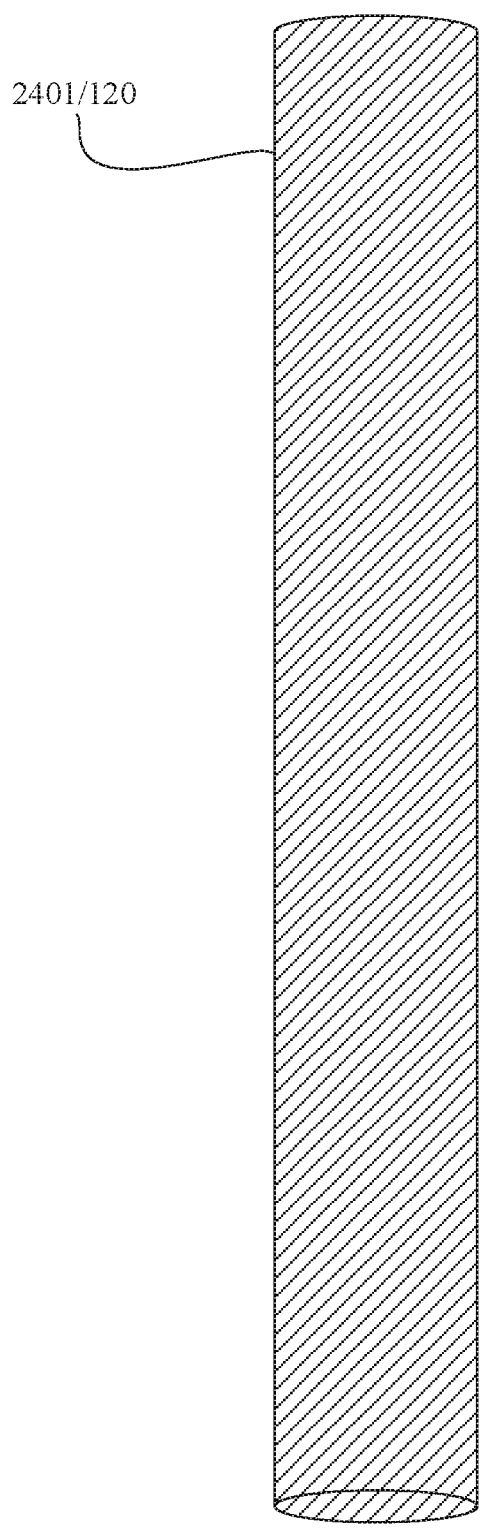
FIG. 28 may depict a portion of an orthodontic-archwire that is also a monitoring-sensor-tag.

FIG. 28 may depict a portion of an orthodontic-archwire 2401 that is also a monitoring-sensor-tag 120. In some embodiments, substantially all of a core of a given orthodontic-archwire 2401 may be also be configured as a given monitoring-sensor-tag 120. In some embodiments, at least some predetermined length of a core of orthodontic-archwire 2401 may be also be configured as a given monitoring-sensor-tag 120.

Figure 29:
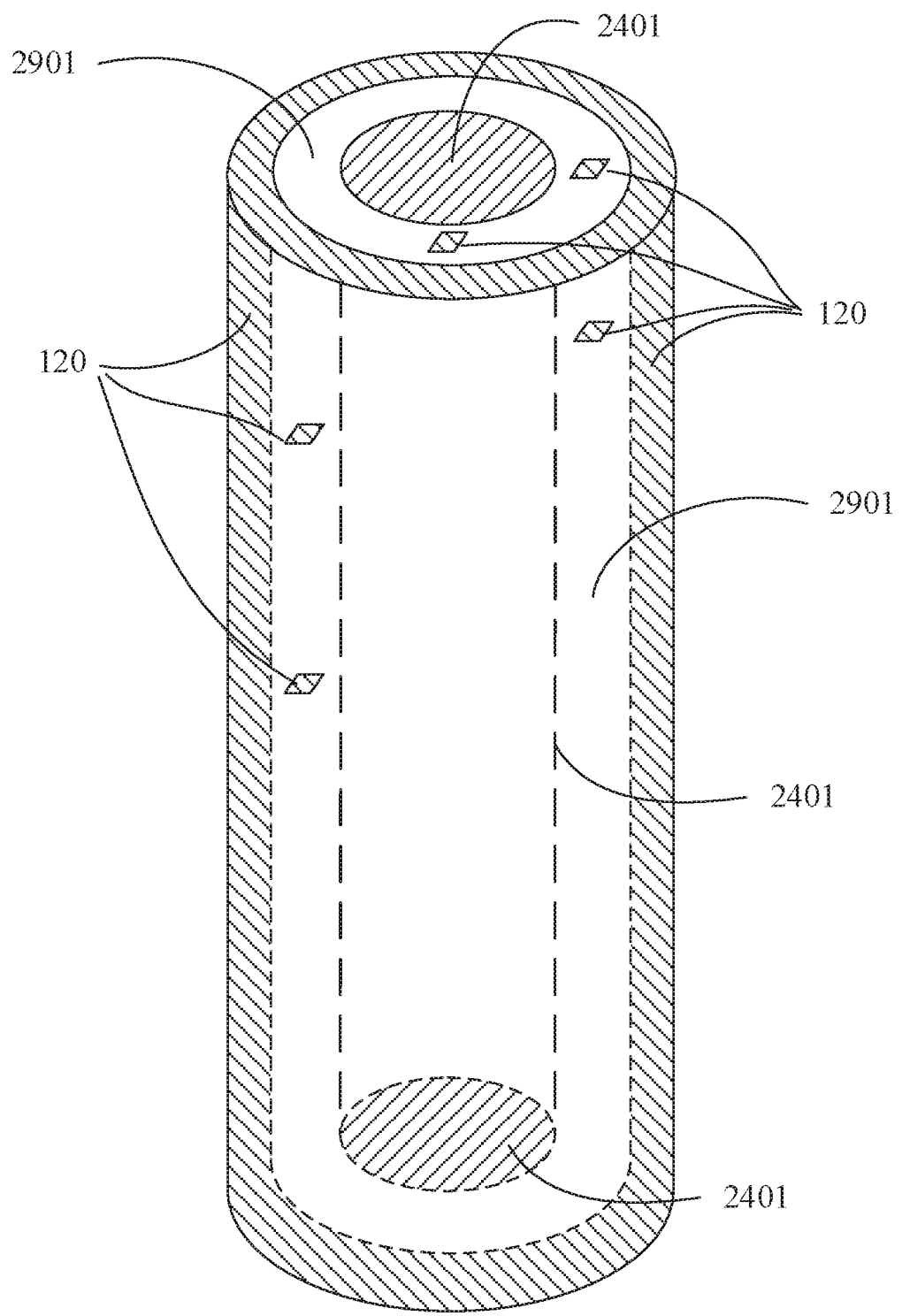
FIG. 29 may depict a portion of an orthodontic-archwire that is also a monitoring-sensor-tag; wherein the monitoring-sensor-tag may be substantially sheathed in an isolation-layer.

FIG. 29 may depict a portion of an orthodontic-archwire 2401 and one or more monitoring-sensor-tags 120; wherein these monitoring-sensor-tags 120 may be substantially sheathed within an isolation-layer 2901; and/or may be located outside of isolation-layer 2901 and not physically touching orthodontic-archwire 2401. In some embodiments, orthodontic-archwire 2401 may be substantially sheathed in isolation-layer 2901. A reason such an arrangement may be important, may be to physically separate the monitoring-sensor-tags 120 from the orthodontic-archwire 2401; because, in some embodiments, orthodontic-archwire 2401 may be made from electrically conductive alloys, which might interfere with operation of the one or more monitoring-sensor-tags 120. In some embodiments, isolation-layer 2901 may be substantially non-electrically conductive. The orthodontic-archwire 2401 shown in FIG. 29, may be substantially similar to the stress sensor shown in FIG. 7B. The discussion of the FIG. 7B stress sensor may apply to FIG. 29. In some embodiments, the arrangement of orthodontic-archwire 2401 and its isolation-layer 2901 sheathing shown in FIG. 29, may be applied to any orthodontic-archwire 2401 shown in the other figures herein.

Continuing discussing FIG. 29, in some embodiments, isolation-layer 2901 may contain one or more monitoring-sensor-tags 120. In some embodiments, isolation-layer 2901 may have one or more of the following properties, characteristics: flexible, semi-rigid, electrically inert (e.g., electrically non-conductive), act as an electrical insulator, waterproof, and/or the like.

Figure 30:
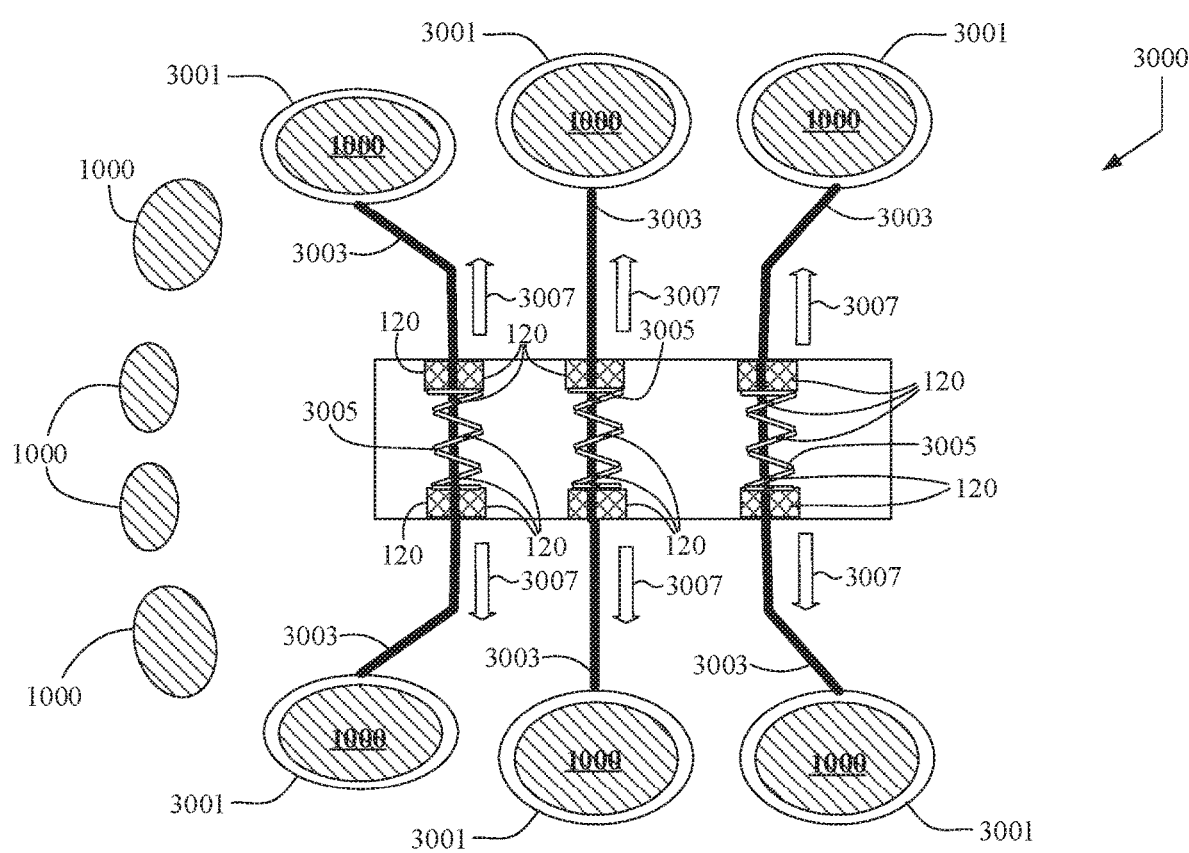
FIG. 30 may depict a top view (or top cross-sectional view) diagramming use of an orthodontic-expander with one or more monitoring-sensor-tags.

FIG. 30 may depict a top view (or top cross-sectional view) diagramming use of an orthodontic-expander 3000 with one or more monitoring-sensor-tags 120. In some embodiments, orthodontic-expander 3000 may be used to widen the jaw (e.g., widen the upper jaw). In some embodiments, orthodontic-expander 3000 may comprise at least two paired and opposing orthodontic-bands 3001, an expander-arm 3003 disposed the at least two paired and opposing orthodontic-bands 3001; and a force-generating-means 3005 within or between the expander-arm 3003. In some embodiments, a given orthodontic-band 3001 may be secured to a given tooth 1000. In some embodiments, a given orthodontic-band 3001 may substantially circumscribed an outer perimeter of the given tooth 1000. In some embodiments, force-generating-means 3005 may be a spring(s) or similar force generating device. In some embodiments, direction-of-force 3007 may show a direction of generated force from force-generating-means 3005.

Continuing discussing FIG. 30, in some embodiments, the orthodontic-elements may comprise the orthodontic-expander 3000 and/or its components. In some embodiments, at least a portion of orthodontic-expander 3000 may comprise one or more monitoring-sensor-tags 120. In some embodiments, the one or more monitoring-sensor-tags 120 may be attached to the at least the portion of orthodontic-expander 3000. In some embodiments, at least a portion of orthodontic-band 3001 may comprise one or more monitoring-sensor-tags 120. In some embodiments, the one or more monitoring-sensor-tags 120 may be attached to the at least the portion of orthodontic-band 3001. In some embodiments, at least a portion of expander-arm 3003 may comprise one or more monitoring-sensor-tags 120. In some embodiments, the one or more monitoring-sensor-tags 120 may be attached to the at least the portion of expander-arm 3003. In some embodiments, at least a portion of force-generating-means 3005 may comprise one or more monitoring-sensor-tags 120. In some embodiments, the one or more monitoring-sensor-tags 120 may be attached to the at least the portion of force-generating-means 3005. The inclusion of such one or more monitoring-sensor-tags 120 with orthodontic-expander 3000 and/or its components, as shown in FIG. 30 may permit the monitoring of forces acting on teeth 1000 by orthodontic-expander 3000 and/or its components.

Figure 31:
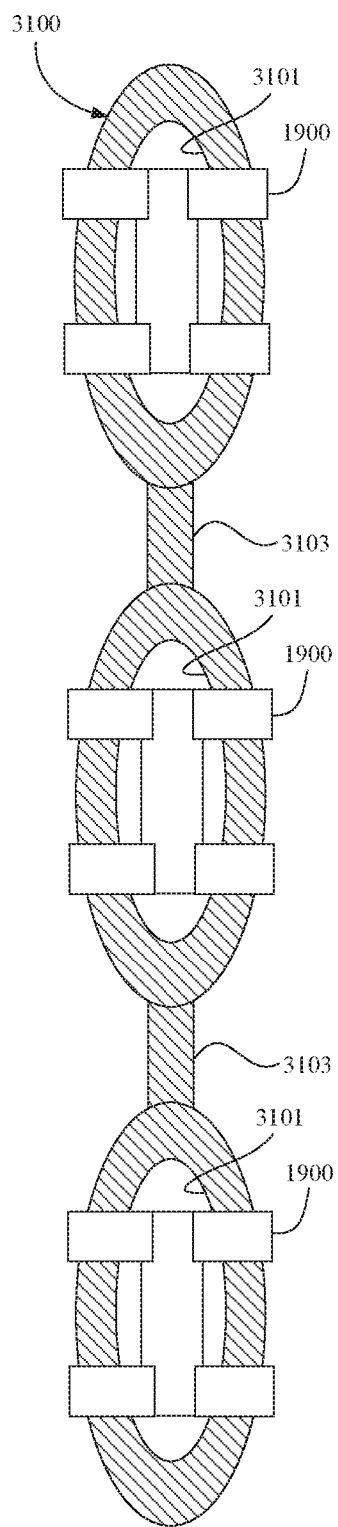
FIG. 31 may depict use of an orthodontic-power-chain used along with orthodontic-brackets.

FIG. 31 may depict use of an orthodontic-power-chain 3100 used along with orthodontic-brackets 1900. In some embodiments, orthodontic-power-chain 3100 may be used in place of or in addition to archwire 2401 on orthodontic-brackets 1900. In some embodiments, orthodontic-power-chain 3100 may function as a series of linked ligatures, linking a given orthodontic-bracket 1900 of a given tooth 1000 to an adjacent orthodontic-bracket 1900 of the adjacent tooth 1000, with respect to upper teeth or with respect to lower teeth. In some embodiments, orthodontic-power-chain 3100 may be substantially elastomeric. In some embodiments, orthodontic-power-chain 3100 may be flexible to semi-rigid. In some embodiments, orthodontic-power-chain 3100 may be comprised of a capture-portion 3101 and a linkage-portion 3103. In some embodiments, a given linkage-portion 3103 may be disposed between and connected to two different capture-portions 3101. In some embodiments, a given capture-portion 3101 may be removably capture (e.g., removably attach to) a given orthodontic-bracket 1900.

Figure 32:
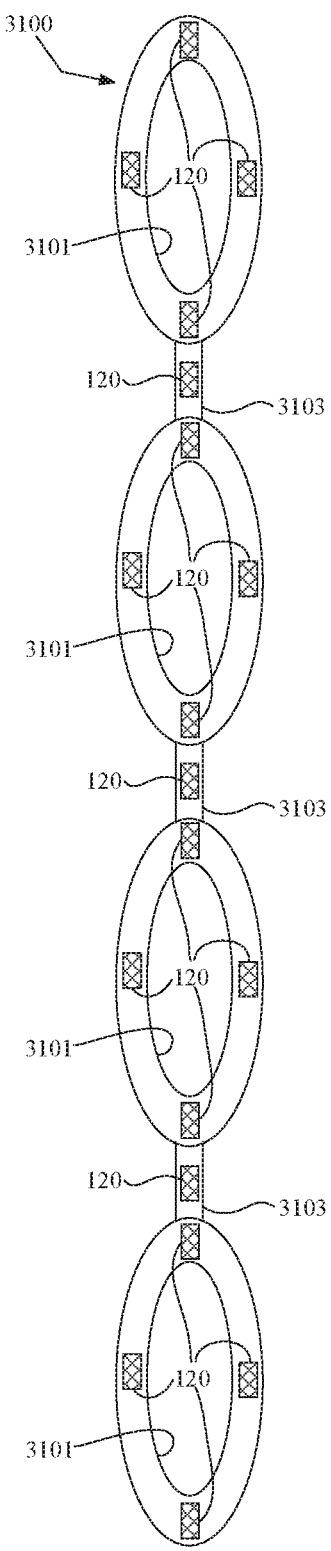
FIG. 32 depict an orthodontic-power-chain with one or more monitoring-sensor-tags.

FIG. 32 may depict an orthodontic-power-chain 3100 with one or more monitoring-sensor-tags 120. In some embodiments, at least some portions of orthodontic-power-chain 3100 may comprise one or more monitoring-sensor-tags 120. In some embodiments, one or more monitoring-sensor-tags 120 may be attached to at least some portion of orthodontic-power-chain 3100. In some embodiments, at least some portions of capture-portion 3101 may comprise one or more monitoring-sensor-tags 120. In some embodiments, one or more monitoring-sensor-tags 120 may be attached to at least some portion of capture-portion 3101. In some embodiments, at least some portions of linkage-portion 3103 may comprise one or more monitoring-sensor-tags 120. In some embodiments, one or more monitoring-sensor-tags 120 may be attached to at least some portion of linkage-portion 3103. In some embodiments, such use of the one or more monitoring-sensor-tags 120 with orthodontic-power-chain 3100 and/or its components, as shown in FIG. 32, may permit monitoring forces acting on teeth 1000 by orthodontic-power-chain 3100 and/or its components.

In some embodiments, a system for non-invasive monitoring of an orthodontic-element may comprise one or more monitoring-sensor-tags 120 and one or more orthodontic-elements. In some embodiments, the one or more monitoring-sensor-tags 120 may be attached to the one or more orthodontic-elements. In some embodiments, a given orthodontic-element may be selected from an orthodontic-bracket 1900, an orthodontic-bracket-hook 2301, an orthodontic-bracket-receiving-cavity 1907, an orthodontic-bracket-lock 1919, an orthodontic-archwire 2401, an orthodontic-spring 2403, an orthodontic-expander 3000, an orthodontic elastic-band 2501, an orthodontic-power-chain 3100, an orthodontic-band 3001, combinations thereof, and/or the like.

In some embodiments, such a system may further comprise one or more readers 100; wherein each of the one or more readers 100 may comprise one or more second-antennas 110. In some embodiments, the one or more readers 100, using the one or more second-antennas 110 may transmit electromagnetic radiation of a predetermined characteristic. In some embodiments, the first-antenna 130 (e.g., of at least one of the one or more monitoring-sensor-tags 120) may receive this electromagnetic radiation of the predetermined characteristic as an input. In some embodiments, this input may cause the at least one electric circuit (e.g., of at least one of the one or more monitoring-sensor-tags 120) to take one or more readings from the at least one sensor (e.g., of at least one of the one or more monitoring-sensor-tags 120) and to then transmit the one or more readings using the first-antenna 130 back to the one or more second-antennas 110. In some embodiments, at least one of the second-antennas 110 selected from the one or more second-antennas 110 may then receive the one or more readings; and the one or more readers 100 or a device in communication with the one or more readers 100 may use the one or more readings to determine the current state of the given orthodontic-element with the one or more monitoring-sensor-tags 120.

For example, and without limiting the scope of the present invention, in some embodiments, the current state of the given orthodontic-element may be used at least in part to provide a course of treatment to a patient (e.g., patient 1328) that has the given orthodontic-element (with the one or more monitoring-sensor-tags 120) installed upon the patient.

Figure 33:
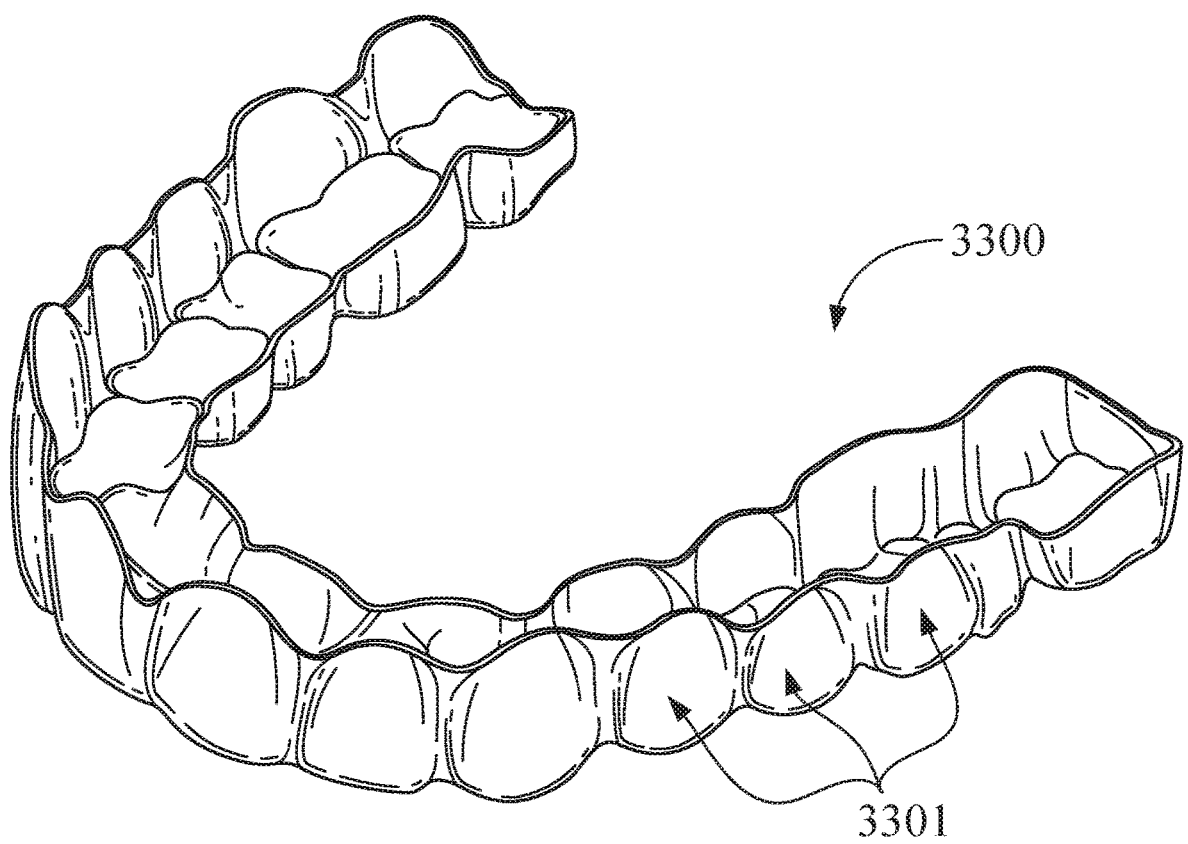
FIG. 33 may depict an example of typical prior art "clear" or "invisible" orthodontic braces, showing clear braces aligner.

FIG. 33 may depict an example of typical prior art "clear" or "invisible" orthodontic braces, showing clear braces aligner 3300. Within the orthodontics industry aligner 3300 may also be referred to as a "tray." Some brands of such "clear" or "invisible" braces may include, but may not be limited to, Invisalign, ClearSmile, Inman Aligner, ClearPath, Eon, and the like. Aligner 3300 may be substantially clear and/or substantially transparent (with respect to normal/typical non-aided human vision). Aligner 3300 is comprised of a plurality of linearly linked tooth-wells 3301, wherein each such tooth-well 3301 is supposed to be sized and shaped to fit onto a specific tooth of the given patient. Generally, the patient will wear one aligner 3300 for bottom teeth and one aligner 3300 for top teeth, at a time, as needed, wherein such aligners 3300 are custom built to be sized to the patient's current teeth geometry and teeth spacing. The geometry of the given aligner 3300 exerts pressure on the patient's teeth and over time causes the patient's teeth to shift into a more desirable position for biting and/or smiling. For full corrective re-positioning of the patient's teeth, a series of slightly different dimensioned aligners 3300 is sequentially worn over months or years, wherein each sequential aligner 3300 in the series is only of slightly (but important) different dimensions from the immediately preceding sequential aligner 3300 in the series.

A problem is that the patient's teeth need to be measured accurately to determine the appropriate sized custom built aligner 3300 to be built for those specific teeth. Then the given aligner 3300 needs to be built per those custom measurements, which introduces another level of potential error as the manufacturing process may not be perfect. And this problem of measuring the patient's teeth and building a given custom built aligner 3300 may happen for each one of the aligners 3300 needed in the series, which thus requires a significant amount of time of the given orthodontist and thus significantly increases the cost of using such "clear" or "invisible" braces. An additional issue is that the different dimensions of the series of aligners 3300 are based on a prediction (estimation) of the patient's teeth correction progress; whereas, the actual teeth correction progress may deviate from such estimates, rendering the therapeutic effect less effective in this preexisting process. (Note, similar problems occur with traditional [preexisting] feet orthotics, and the improved invention is discussed below.) It would be desirable to measure changes in teeth positioning and/or pressure and/or forces on teeth, in a passive manner; in a manner free from discomfort; in a fast or quick manner; and/or in real-time or near real-time when so desired, so as to minimize such problems and errors. FIG. 34A through FIG. 34E may depict embodiments directed to such objectives.

Figure 34A:
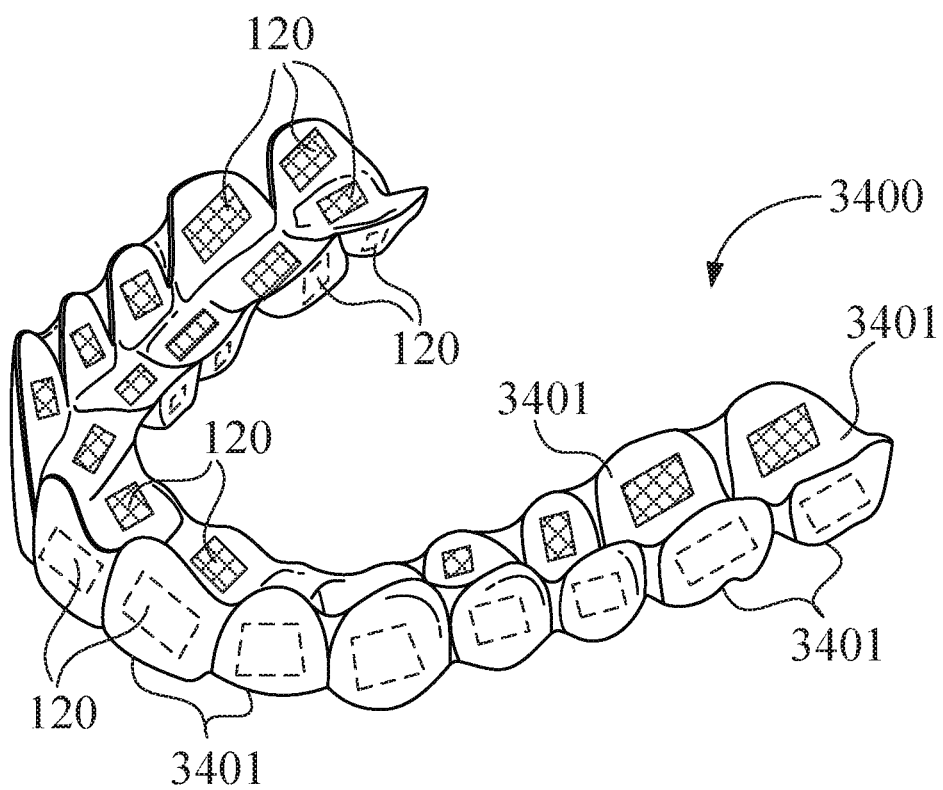
FIG. 34A may depict a perspective view of an aligner fitted with sensor tags.
Figure 34B:
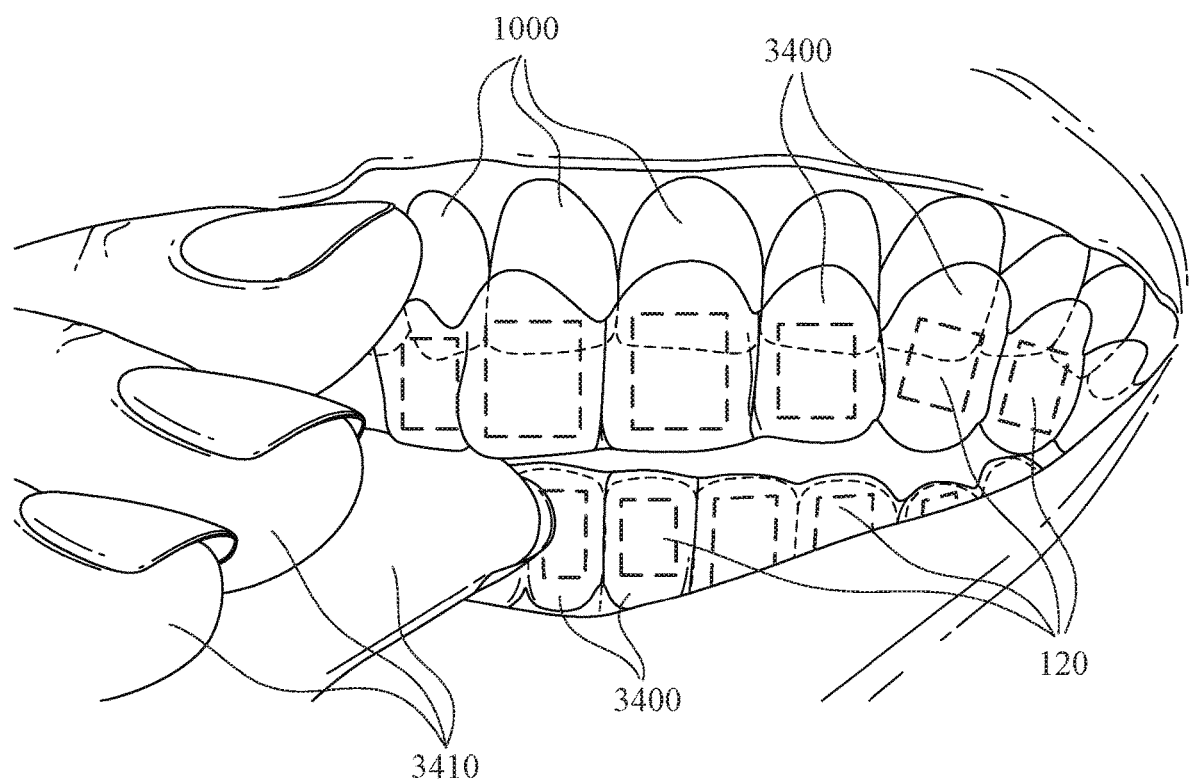
FIG. 34B may depict a front view showing portions of two (upper and lower) aligners (with sensor tags) fitted onto teeth, in a mouth, of a given user.
Figure 34C:
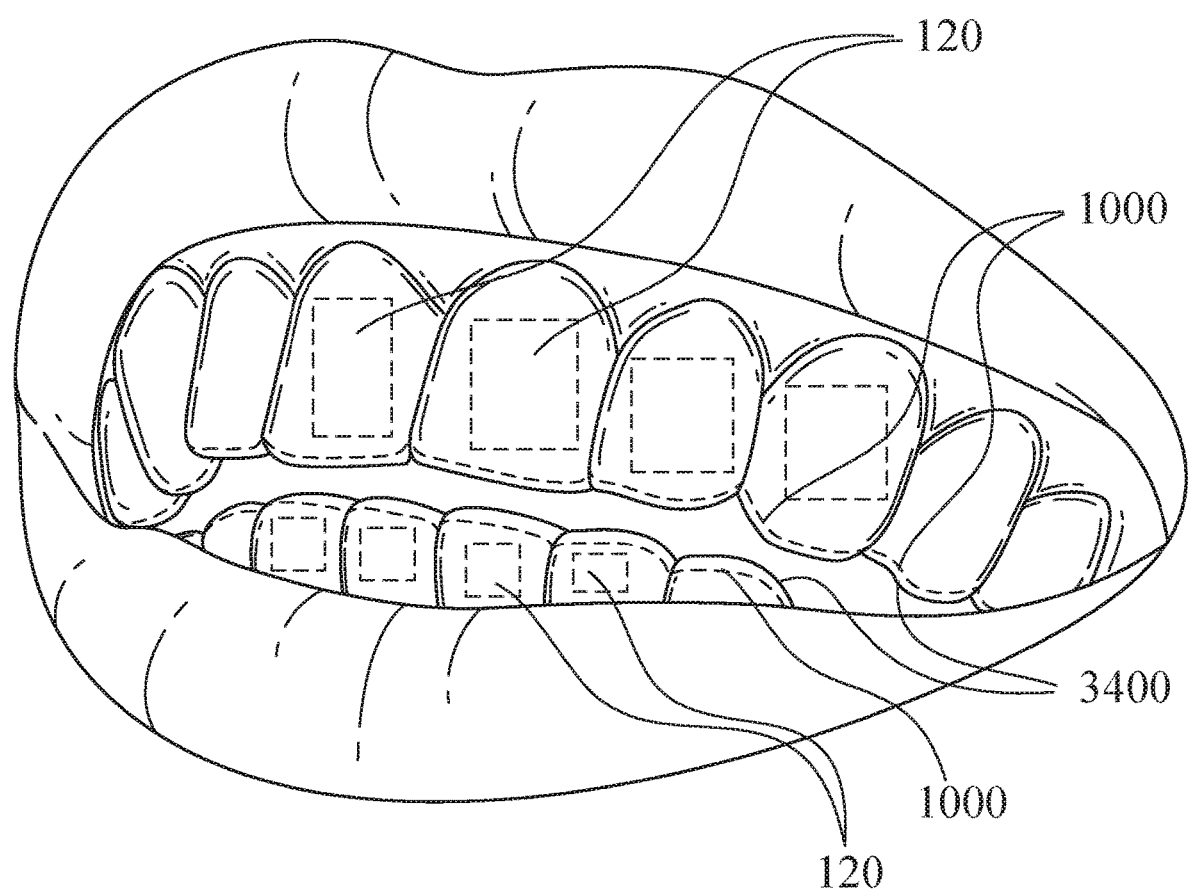
FIG. 34C may depict a front view showing portions of two (upper and lower) aligners (with sensor tags) fitted onto teeth, in a mouth, of a given user.
Figure 34D:
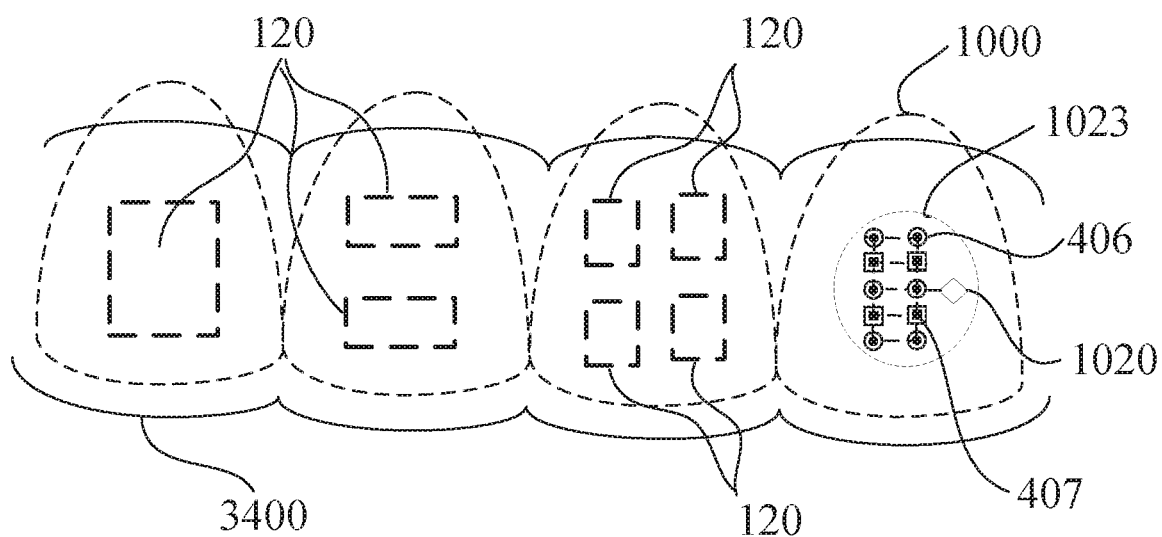
FIG. 34D may depict a front view showing a portion of a given aligner, which may be fitted with at least one monitoring-sensor-tags and/or fitted with at least one lattice-of-sensors, wherein this aligner may fitted onto teeth and be in wireless communication with a reader-and-calibration-member.
Figure 34D:
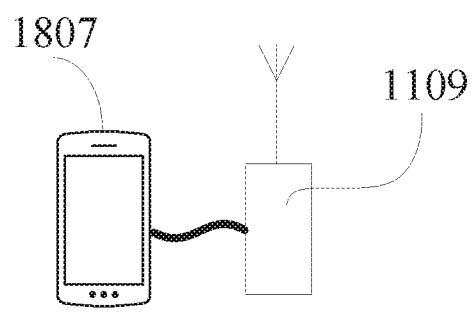
Figure 34E:
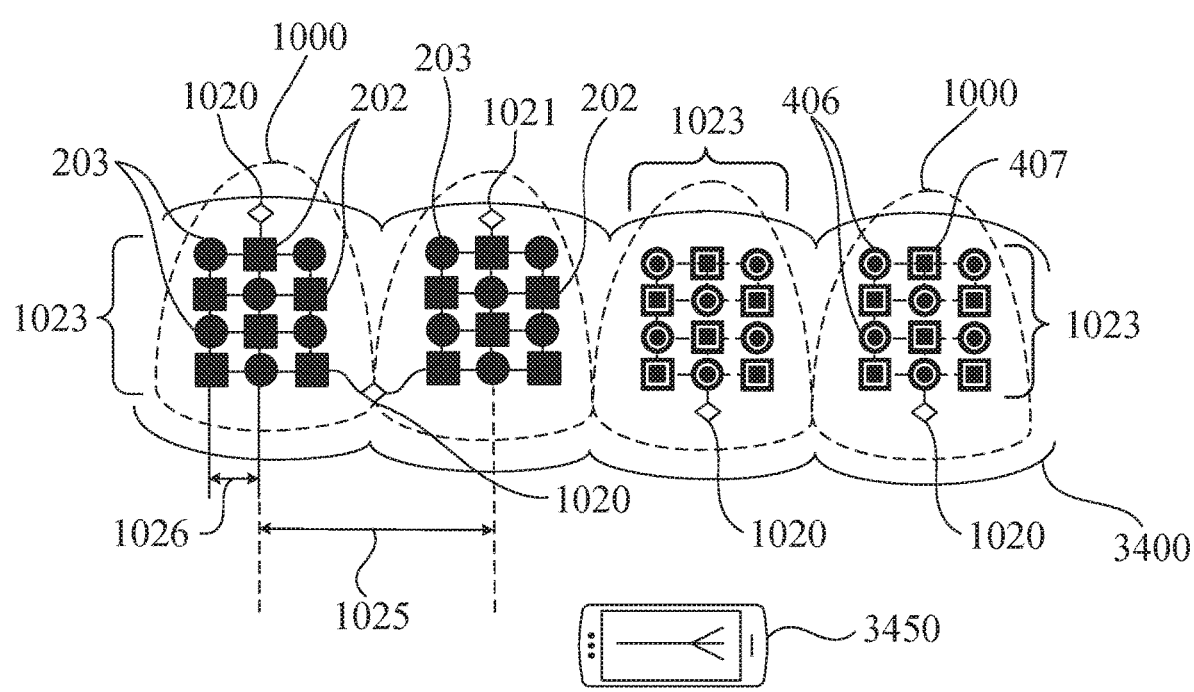
FIG. 34E may depict a front view showing a portion of a given aligner (with sensor tags) fitted onto teeth and in wireless communication with a mobile-computing-device.

FIG. 34A may depict a perspective view of an aligner 3400. FIG. 34B may depict a front view showing portions of two (upper and lower) aligners 3400 fitted onto teeth 1000, in a mouth, of a given user (patient, e.g., patient 1328). FIG. 34B may also show fingers 3410 in proximity to the mouth and the teeth 1000. (Note, such fingers 3410 could be fingers of the patient or could be fingers of a practitioner [e.g., an orthodontist, a dentist, an oral surgeon, etc.].) FIG. 34C may depict a slightly different front view showing portions of two (upper and lower) aligners 3400 fitted onto teeth 1000, in a mouth, of a given user (patient, e.g., patient 1328). FIG. 34D may depict a front view showing a portion of a given aligner 3400 fitted onto teeth 1000 and in wireless communication with a reader-and-calibration-member 1109. The aligner 3400 shown in FIG. 34D may be fitted with at least one monitoring-sensor-tags 120 and/or fitted with at least one lattice-of-sensors 1023. FIG. 34E may depict a front view showing a portion of a given aligner 3400 fitted onto teeth 1000 and in wireless communication with a mobile-computing-device 3450.

In some embodiments, aligner 3400 may be an orthodontics braces/aligner that may be configured to fit onto teeth 1000 for a purpose of changing an alignment of the 1000 over time. In some embodiments, a given aligner 3400 may be substantially U-shaped when viewed from above, if the given aligner 3400 may be lying flat on a surface. In some embodiments, aligner 3400 may be substantially similar to aligner 3300, except that aligner 3400 may comprise: one or more electronic sensor circuits; one or more monitoring-sensor-tags 120; and/or one or more lattice-of-sensors 1023. Herein, electronics sensor circuit(s) may be used interchangeably with monitoring-sensor-tag(s) 120. Herein, electronics sensor circuit(s) may be used interchangeably with lattice-of-sensors 1023. In some embodiments, the one or more electronic sensor circuits, the one or more monitoring-sensor-tags 120, and/or the one or more lattice-of-sensors 1023 may be attached to at least one tooth-well 3401 selected from the plurality of linearly linked tooth-wells 3401. In some embodiments, the one or more electronic sensor circuits, the one or more monitoring-sensor-tags 120, and/or the one or more lattice-of-sensors 1023 may comprise at least one sensor configured to sense at least one property of material-of-interest 1028. In some embodiments, the at least one sensor of a given aligner 3400 (or of a given tooth-well 3401 of that aligner 3400) may be configured to measure at least one of: capacitance, resistance, inductance, combinations thereof, and/or the like, of material-of-interest 1028. In some embodiments, material-of-interest 1028 may be at least one tooth-well 3401 that the one or more electronic sensor circuits, the one or more monitoring-sensor-tags 120, and/or the one or more lattice-of-sensors 1023 may be attached to. In some embodiments, material-of-interest 1028 may be a given tooth 1000, wherein that tooth 1000 may be fitted into at least one tooth-well 3401 that the one or more electronic sensor circuits, the one or more monitoring-sensor-tags 120, and/or the one or more lattice-of-sensors 1023 may be attached to. In some embodiments, material-of-interest 1028 may be combination of at least one tooth-well 3401 and tooth 1000.

In some embodiments, aligner 3400 may be aligning orthodontic braces for shifting positioning of teeth 1000 over time. In some embodiments, aligner 3400 may be comprised of a plurality of linearly linked tooth-wells 3401, wherein each such tooth-well 3401 may be sized and shaped to fit onto a specific tooth of the given patient (e.g., patient 1328). In some embodiments, each tooth-well 3401 may be custom shaped and sized from measurements of a specific tooth 1000 of the patient. In some embodiments, aligner 3400 may be for upper or for lower teeth 1000. In some embodiments, aligner 3400 may be substantially optically clear and/or substantially optically transparent (with respect to normal/typical non-aided human vision). See e.g., FIG. 34A through FIG. 34E. In some embodiments, aligner 3400 may be substantially opaque.

In figures FIG. 34A through FIG. 34E, any shown monitoring-sensor-tag 120 may be replaced with a given lattice-of-sensors 1023 and/or a plurality of given lattice-of-sensors 1023. See e.g., FIG. 34A through FIG. 34E.

In figures FIG. 34A through FIG. 34E, any shown lattice-of-sensors 1023 may be replaced with a given monitoring-sensor-tag 120 and/or with a plurality of given monitoring-sensor-tag 120. See e.g., FIG. 34A through FIG. 34E.

In some embodiments, the one or more monitoring-sensor-tags 120 may be located on and/or within a given aligner 3400. See e.g., FIG. 34A through FIG. 34E.

In some embodiments, the one or more lattice-of-sensors 1023 may be located on and/or within a given aligner 3400. See e.g., FIG. 34A through FIG. 34E.

In some embodiments, a given tooth-well 3401 may comprise the one or more monitoring-sensor-tags 120. In some embodiments, the one or more monitoring-sensor-tags 120 may be located on and/or within the given tooth-well 3401. In some embodiments, the one or more monitoring-sensor-tags 120 may be located at a side, both opposing sides (e.g., tongue side or lip side), a bottom, and/or a top of the given tooth-well 3401. In some embodiments, each monitoring-sensor-tag 120 may be uniquely identified (e.g., with a unique number), wherein such a unique identifier may reflect the specific tooth-well 3401 that has that given monitoring-sensor-tag 120. In some embodiments, each monitoring-sensor-tag 120 may be uniquely identified, wherein such a unique identifier may reflect the specific tooth-well 3401 that has that given monitoring-sensor-tag 120 and may reflect a general location of that given monitoring-sensor-tag 120 in/on that specific tooth-well 3401, such as inner side (tongue side), outer side (lip side), top, or bottom of the specific tooth-well 3401. See e.g., FIG. 34A through FIG. 34E.

In some embodiments, a given tooth-well 3401 may comprise the one or more lattice-of-sensors 1023. In some embodiments, the one or more lattice-of-sensors 1023 may be located on and/or within the given tooth-well 3401. In some embodiments, the one or more lattice-of-sensors 1023 may be located at a side, both opposing sides, a bottom, and/or a top of the given tooth-well 3401. In some embodiments, each lattice-of-sensors 1023 may be uniquely numbered, wherein such a unique number may reflect the specific tooth-well 3401 that has that given lattice-of-sensors 1023. In some embodiments, each lattice-of-sensors 1023 may be uniquely numbered, wherein such a unique number may reflect the specific tooth-well 3401 that has that given lattice-of-sensors 1023 and may reflect a general location of that given lattice-of-sensors 1023 in that specific tooth-well 3401, such as inner side, outer side, top, or bottom of the specific tooth-well 3401. Similarly, in some embodiments, each sensor from the given lattice-of-sensors 1023 may be uniquely identified (with a unique identifier, such as, but not limited to, a unique number). See e.g., FIG. 34A through FIG. 34E.

In some embodiments, at least a portion of the one or more electronic sensor circuits, the one or more monitoring-sensor-tags 120, and/or the one or more lattice-of-sensors 1023 may be physically contacting a given tooth 1000, wherein that tooth 1000 may be fitted into the at least one tooth-well 3401 that the one or more electronic sensor circuits, the one or more monitoring-sensor-tags 120, and/or the one or more lattice-of-sensors 1023 may be attached to.

In some embodiments, at least a portion of the one or more electronic sensor circuits, the one or more monitoring-sensor-tags 120, and/or the one or more lattice-of-sensors 1023 may be in close proximity of a given tooth 1000, wherein that tooth 1000 may be fitted into the at least one tooth-well 3401 that the one or more electronic sensor circuits, the one or more monitoring-sensor-tags 120, and/or the one or more lattice-of-sensors 1023 may be attached to. In this context, close proximity may be one centimeter (cm) or less than one cm; or one millimeter (mm) or less than one mm.

In some embodiments, the one or more electronic sensor circuits, the one or more monitoring-sensor-tags 120, and/or the one or more lattice-of-sensors 1023 may be embedded entirely within the at least one tooth-well 3401 that the one or more electronic sensor circuits, the one or more monitoring-sensor-tags 120, and/or the one or more lattice-of-sensors 1023 may be attached to.

In some embodiments, the one or more electronic sensor circuits, the one or more monitoring-sensor-tags 120, and/or the one or more lattice-of-sensors 1023 may be on an exterior surface of the at least one tooth-well 3401 that the one or more electronic sensor circuits, the one or more monitoring-sensor-tags 120, and/or the one or more lattice-of-sensors 1023 may be attached to.

In some embodiments, the one or more electronic sensor circuits, the one or more monitoring-sensor-tags 120, and/or the one or more lattice-of-sensors 1023 may be partially on an exterior surface of the at least one tooth-well 3401 that the one or more electronic sensor circuits, the one or more monitoring-sensor-tags 120, and/or the one or more lattice-of-sensors 1023 may be attached to and a remainder of the one or more electronic sensor circuits, the one or more monitoring-sensor-tags 120, and/or the one or more lattice-of-sensors 1023 may be partially embedded within the at least one tooth-well 3401 that the one or more electronic sensor circuits, the one or more monitoring-sensor-tags 120, and/or the one or more lattice-of-sensors 1023 may be attached to.

In some embodiments, the one or more electronic sensor circuits, the one or more monitoring-sensor-tags 120, and/or the one or more lattice-of-sensors 1023 may be located at a predetermined location of the at least one tooth-well 3401 that the one or more electronic sensor circuits, the one or more monitoring-sensor-tags 120, and/or the one or more lattice-of-sensors 1023 may be attached to. In some embodiments, this predetermined location of the at least one tooth-well 3401 may be selected from one or more of: a side towards a tongue, a side towards a lip, a bottom, a top, combinations thereof, and/or the like.

In some embodiments, each tooth-well 3401 selected from the plurality of linearly linked tooth-wells 3401 may have attached at least one electronic sensor circuit, at least one monitoring-sensor-tag 120, at least one lattice-of-sensors 1023, combinations thereof, and/or the like. See e.g., FIG. 34A, through FIG. 34E.

In some embodiments, before a given patient wears a given aligner 3400, the one or more monitoring-sensor-tags 120 may be read (scanned/interrogated) to determine baseline locations of the one or more monitoring-sensor-tags 120 and/or to determine baseline stresses/pressure upon the sensors of the one or more monitoring-sensor-tags 120. See e.g., FIG. 34A, FIG. 34D, and FIG. 34E.

In some embodiments, before a given patient wears a given aligner 3400, the one or more lattice-of-sensors 1023 may be read (scanned/interrogated) to determine baseline locations of the one or more lattice-of-sensors 1023 and/or to determine baseline stresses/pressure upon the sensors of the one or more lattice-of-sensors 1023. See e.g., FIG. 34A, FIG. 34D, and FIG. 34E.

In some embodiments, the sensors from the one or more monitoring-sensor-tags 120 may measure stresses and/or pressure that the teeth 1000 exert upon these sensors. Such measurements may be used to direct the shape and sizes of each given tooth-well 3401 to be manufactured to form a given aligner 3400. Over time such measurements may correspond to trends in positional shifting of teeth 1000, and of a specific tooth 1000; and thus, used to direct the shape and sizes of a next given tooth-well 3401 to be manufactured to form a given next aligner 3400. See e.g., FIG. 34A through FIG. 34E.

In some embodiments, the sensors from the one or more lattice-of-sensors 1023 may measure stresses and/or pressure that the teeth 1000 exert upon these sensors. Such measurements may be used to direct the shape and sizes of each given tooth-well 3401 to be manufactured to form a given aligner 3400. Over time such measurements may correspond to trends in positional shifting of teeth 1000, and of a specific tooth 1000; and thus, used to direct the shape and sizes of a next given tooth-well 3401 to be manufactured to form a given next aligner 3400. See e.g., FIG. 34A through FIG. 34E.

In some embodiments, each monitoring-sensor-tag 120 of the one or more monitoring-sensor-tags 120 of a given aligner 3400 or of a given tooth-well 3401, may comprise at least one antenna (e.g., antenna 130) for wireless (e.g., radio frequency) communication with reading/scanning/interrogating devices, such as, but not limited to, reader 100, reader-and-calibration-member 1109 (shown in FIG. 34D) and/or mobile-computing-device 3450 (shown in FIG. 34E). In some embodiments, the one or more monitoring-sensor-tags 120 may be passive, i.e., receiving the necessary power for such wireless communication from the given reading/scanning/interrogating device. In some embodiments, the one or more monitoring-sensor-tags 120 may be actively powered with its own battery power source.

In some embodiments, each first-sensor-tag 1020 of a given lattice-of-sensors 1023 may be a monitoring-sensor-tag 120, with its at least one antenna 130. In some embodiments, each second-sensor-tag 1021 of a given lattice-of-sensors 1023 may be a monitoring-sensor-tag 120, with its at least one antenna 130. See e.g., FIG. 34E.

In some embodiments, the device that may be reading/scanning/interrogating the sensors of the monitoring-sensor-tags 120 and/or of the sensors of the lattice-of-sensors 1023, may be reader 100, reader-and-calibration-member 1109 (see e.g., FIG. 34E), and/or mobile-computing-device 3450 (see e.g., FIG. 34E). As shown in FIG. 34D, reader-and-calibration-member 1109 may be a standalone device that may be in communication (wired or wireless) with device 1807. Recall, in some embodiments, device 1807 may comprise processor 1801 and memory 1803 (and display 1805, in some embodiments); and, device 1807 may be a computing device and/or a computer, such as, but not limited, to a smartphone, tablet computer, laptop, and/or the like. In some embodiments, reader-and-calibration-member 1109 shown in FIG. 34D may be replaced with reader 100. In FIG. 34E, the functionality of reader-and-calibration-member 1109 and/or of reader 100 may be integral and incorporated into mobile-computing-device 3450. In some embodiments, mobile-computing-device 3450 may be a mobile computing device, such as a computer. In some embodiments, mobile-computing-device 3450 may comprise processor 1801 and memory 1803 (and display 1805, in some embodiments). In some embodiments, mobile-computing-device 3450 may be a smartphone, a tablet computer, a laptop, and/or the like. In some embodiments, mobile-computing-device 3450 may comprise one or more antennas for reading, scanning, and/or interrogating antennas of monitoring-sensor-tag 120 for getting sensor data. In some embodiments, mobile-computing-device 3450 may comprise one or more antennas for reading, scanning, and/or interrogating antennas of lattice-of-sensors 1023 for getting sensor data. In some embodiments, mobile-computing-device 3450 may comprise one or more RFID readers and/or NFC readers. In some embodiments, mobile-computing-device 3450 may comprise one or more readers 100.

In some embodiments, a patient may use their own mobile-computing-device 3450 (e.g., their own smartphone) to read/scan/interrogate sensors of the one or more monitoring-sensor-tags 120 or of the sensors of the lattice-of-sensors 1023, of the patient's in use aligner 3400, and at the convenience of the patient (e.g., at home); wherein the received measurement data, received at the mobile-computing-device 3450, may then be transmitted (e.g., across the internet) to the patient's practitioner (e.g., an orthodontist, a dentist, an oral surgeon, etc.).

Use of aligner(s) 3400 may prevent and/or correct problems associated with prior art aligners 3300. With use of aligner(s) 3400, teeth positioning, teeth movement, teeth forces/pressures may all be measured, passively, in real-time (or near real-time), to generate aligner(s) 3400 with better fits; to generate proper aligner(s) 3400 at clinical optimal frequency; and/or to minimize generation of aligners with improper sizes/shapes.

In some embodiments the invention may be a system for monitoring aligner 3400 performance. In some embodiments, this system may comprise aligner 3400. In some embodiments, aligner 3400 may be as described above, e.g., aligner 3400 may comprise one or more monitoring-sensor-tags 120/1020. In some embodiments, this system may further comprise one or more reader(s) for receiving the one or more readings, wherein such a reader may be an electronic computing device. For example, and without limiting the scope of the present invention, in some embodiments, this reader may be reader 100, reader-and-calibration-member 1109, device 1807, mobile-computing-device 3450, and/or the like.

In some embodiments, this reader may be in wireless communication with the least one antenna 130 of the one or more monitoring-sensor-tags 120/1020, wherein this reader may comprise its own antenna (such as, but not limited to, antenna 110) for such wireless communications with the one or more monitoring-sensor-tags 120/1020. In some embodiments, such wireless communications may be RFID, NFC, WiFi, Bluetooth, and/or the like.

In some embodiments, this reader (e.g., reader-and-calibration-member 1109) may be in wired communication with device 1807. See e.g., FIG. 34D. In some embodiments, mobile-computing-device 3450 may be an example of device 1807.

In some embodiments, this system may comprise a set of programmed computer instructions that may be non-transitorily stored within memory (e.g., memory 1803) of a computing device that may be separate (different) from aligner 3400; wherein this set of programmed computer instructions may be executable by a processor (e.g., processor 1801) of the computing device that may be operationally linked to this memory; wherein the set of programmed computer instructions may govern communications between this reader and the aligner 3400 and how the one or more readings obtained from the at least one monitoring-sensor-tag 120/1020 may be handled. For example, and without limiting the scope of the present invention, this set of programmed computer instructions may perform steps from FIG. 36, FIG. 37, FIG. 38, and/or the like. In this paragraph, this computing device may be the reader and/or may be mobile-computing-device 3450. Note, in some embodiments, mobile-computing-device 3450 may be an example of a reader; whereas, in other embodiments, mobile-computing-device 3450 may not be a reader, but may be in communication with the reader.

Figure 34F:
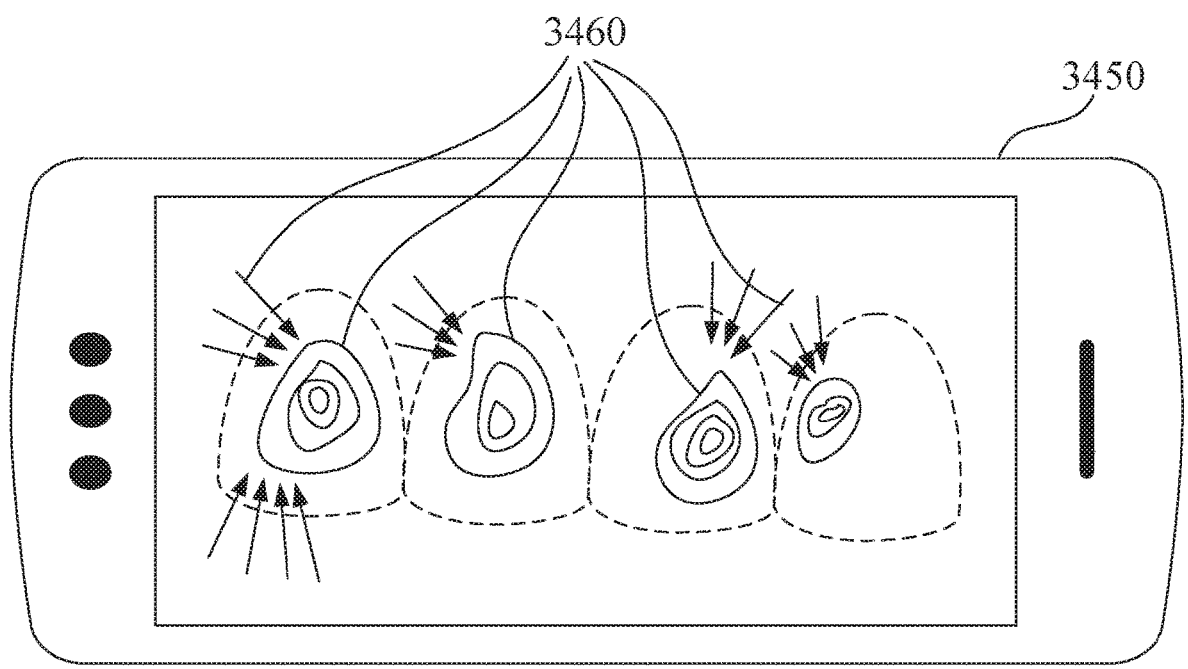
FIG. 34F may depict a schematic view of a given mobile-computing-device may be displaying a particular image, wherein the particular image may be a visual interpretation of sensor information from sensors associated with measuring teeth and/or aligners (e.g., clear braces) used with teeth.

FIG. 34F may depict a given mobile-computing-device 3450 showing a particular image displayed on a screen of mobile-computing-device 3450. In some embodiments, this particular image may be "visual interpretation of sensor information 3460." In some embodiments, visual interpretation of sensor information 3460 may comprise visual representations of one or more elements shown in FIG. 34E. In some embodiments, visual interpretation of sensor information 3460 may comprise visual representations of one or more of: capacitive-based sensor 202 information/data (e.g., from monitoring a given region of a given tooth 1000 that may be physically touching a portion of aligner 3400); resistance-based sensor 203 information/data (e.g., from monitoring a given region of a given tooth 1000 that may be physically touching a portion of aligner 3400); conductive surface type "D" sensor 406 (e.g., from monitoring a given region of a given tooth 1000 that may be physically touching a portion of aligner 3400); conductive surface type "E" sensor 407 (e.g., from monitoring a given region of a given tooth 1000 that may be physically touching a portion of aligner 3400); first-sensor-tag 1020 information/data (e.g., from monitoring a given region of a given tooth 1000 that may be physically touching a portion of aligner 3400); second-sensor-tag 1021 information/data (e.g., from monitoring a given region of a given tooth 1000 that may be physically touching a portion of aligner 3400); lattice-of-sensors 1023 information/data (e.g., from monitoring a given region of a given tooth 1000 that may be physically touching a portion of aligner 3400); capacitive-based sensor 202 information/data (e.g., from monitoring a given region of aligner 3400); resistance-based sensor 203 information/data (e.g., from monitoring a given region of aligner 3400); conductive surface type "D" sensor 406 (e.g., from monitoring a given region of aligner 3400); conductive surface type "E" sensor 407 (e.g., from monitoring a given region of aligner 3400); first-sensor-tag 1020 information/data (e.g., from monitoring a given region of aligner 3400); second-sensor-tag 1021 information/data (e.g., from monitoring a given region of aligner 3400); lattice-of-sensors 1023 information/data (e.g., from monitoring a given region of aligner 3400); initial predetermined spacing 1025 information/data; sensor-spacing 1026 information/data; sensor information/data from a particular sensor that may be in communication with first-sensor-tag 1020; sensor information/data from a particular sensor that may be in communication with second-sensor-tag 1021; sensor information/data from a particular sensor that may be in communication with lattice-of-sensors 1023; changes in such information/data; combinations thereof; and/or the like. In some embodiments, visual interpretation of sensor information 3460 may comprise display of visual representations of differences in such sensor information/data. In some embodiments, visual interpretation of sensor information 3460 may comprise use of contour maps, color gradients, combinations thereof, and/or the like to display visual representations of differences in such sensor information/data. In some embodiments, visual interpretation of sensor information 3460 may comprise display of visual representations of problems and/or potential problems with respect to aligner 3400 and/or tooth 1000.

In some embodiments, at least some of the sensors mentioned above, such as, but not limited to, capacitive-based sensors, may readily still provide their readings if the sensor is not in direct physical contact with tooth 1000 or touch tooth 1000 in a partial way.

Orthotics may also be known as insoles or inserts, and may refer to an insole/insert that goes into a shoe 3503 (disposed between a bottom of a foot 3505 and a sole of the shoe 3503 [the foot 3505 may or may not be covered in a sock]), wherein this insole/insert was custom manufactured to fit a topography, shape, size, geometry, and/or dimensions of a bottom of a specific foot 3505 of a given patient; wherein when such an orthotic is correctly manufactured, that orthotic may reduce discomfort and/or pain in the patient when the patient wears the correctly manufactured custom orthotic with shoes 3503.

However, manufacturing such a proper fitting orthotic is not easy, as measuring for this highly custom and specific bottom topography, shape, size, geometry, and/or dimensions of a specific foot 3505 involves many different and subtle measurements and dimensions. Errors may incur in the measuring and/or in the manufacture of the custom orthotic. And even when such measurements may be done properly and translated into a properly manufactured orthotic (at least according to the measurements), there is no guarantee that the resulting custom manufactured orthotic will alleviate discomfort and/or pain associated with the patient wearing shoes 3503. In part because of such problems, orthotics are relatively expensive. Thus, it would be desirable to outfit or manufacture a given orthotic 3501 with one or more monitoring-sensor-tags 120 and/or with one or more lattice-of-sensors 1023, to aid in both custom orthotic manufacturing and/or to aid in pinpointing problematic geometry of a given orthotic to be fixed/corrected by having access to better measurements from the one or more monitoring-sensor-tags 120 and/or from the one or more lattice-of-sensors 1023.

Figures FIG. 35A through FIG. 35J may depict use of orthotics 3501 with one or more monitoring-sensor-tags 120; and/or with one or more lattice-of-sensors 1023.

In some embodiments, orthotic 3501 may be a component of shoe 3503. In some embodiments, orthotic 3501 may be an insole (and/or sock liner [also sometimes known as a footsock] of shoe 3503. In some embodiments, the insole, the sock liner, and/or the footsock may be components of shoe 3503. In some embodiments, orthotic 3501 may be insertable in shoe 3503. In some embodiments, orthotic 3501 may be removably insertable in shoe 3503. In some embodiments, orthotic 3501 may be insertable into shoe 3503 onto the insole of shoe 3503.

Figure 35A:
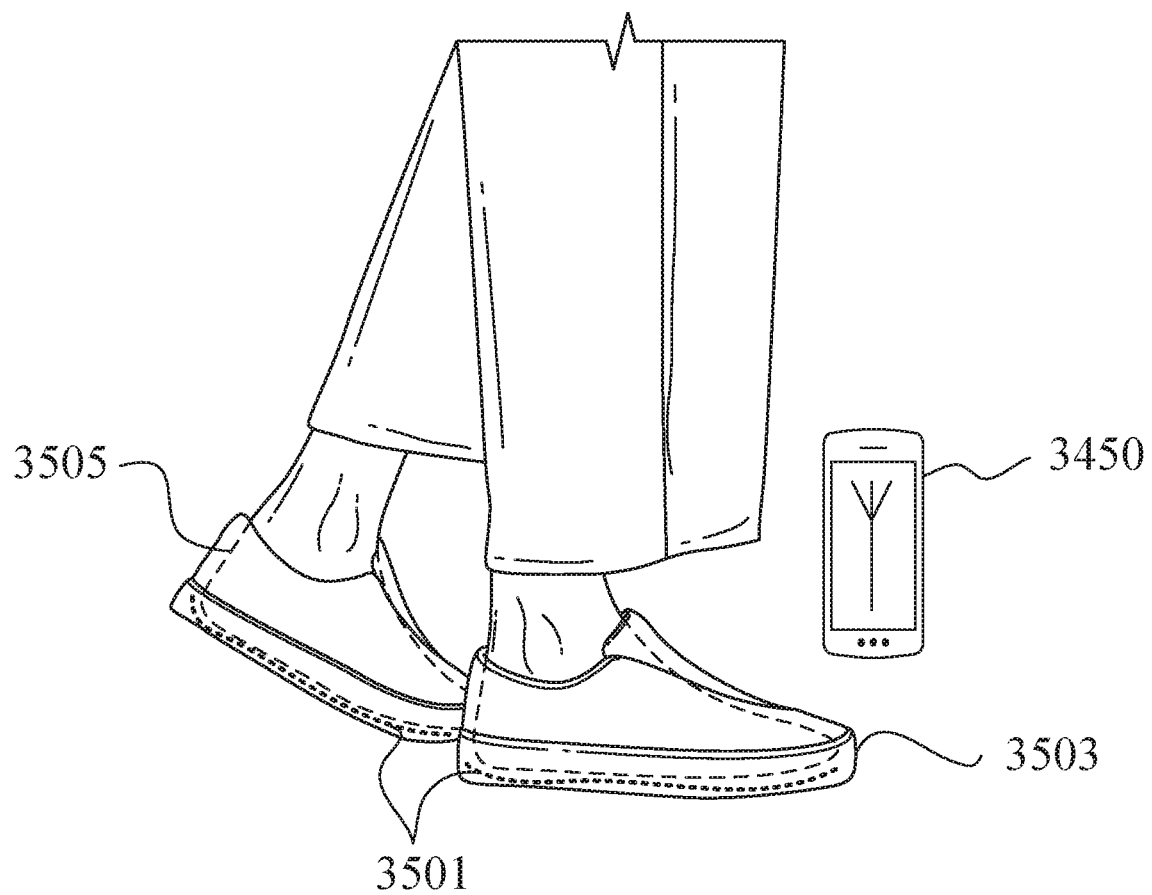
FIG. 35A may depict a partial side view of a patient walking, wearing shoes, in which in these shoes may be "orthotics" disposed beneath the patient's feet.

FIG. 35A may depict a partial side view of a patient walking, wearing shoes 3503, in which in these shoes may be orthotics 3501 disposed beneath the patient's feet 3505. In some embodiments, either or both of these orthotics 3501 may be fitted (and/or built) with one or more monitoring-sensor-tags 120; and/or with one or more lattice-of-sensors 1023 (which may not be expressly called out in FIG. 35A).

Also shown in FIG. 35A may be at least one mobile-computing-device 3450. As noted above, in some embodiments, mobile-computing-device 3450 may be a mobile computing device, such as a computer. In some embodiments, mobile-computing-device 3450 may comprise processor 1801 and memory 1803 (and display 1805, in some embodiments). In some embodiments, mobile-computing-device 3450 may be a smartphone, a tablet computer, a laptop, and/or the like. In some embodiments, mobile-computing-device 3450 may be in wireless communication with orthotic 3501. In some embodiments, mobile-computing-device 3450 may be in wireless communication with the one or more monitoring-sensor-tags 120. In some embodiments, mobile-computing-device 3450 may be in wireless communication with the one or more lattice-of-sensors 1023. Such wireless communications may permit mobile-computing-device 3450 to receive data from the sensors of the one or more monitoring-sensor-tags 120; and/or from the one or more lattice-of-sensors 1023. In some embodiments, this wireless communication may be characterized as NFC (near field communication) and/or as wireless communication characteristic for RFID (radio frequency ID), and/or as Bluetooth, and/or as Wi-Fi (WiFi). In some embodiments, these characteristics and/or properties of mobile-computing-device 3450 noted herein in this paragraph may apply to any mobile-computing-device 3450 shown in figures FIG. 35A through FIG. 35J.

Figure 35B:
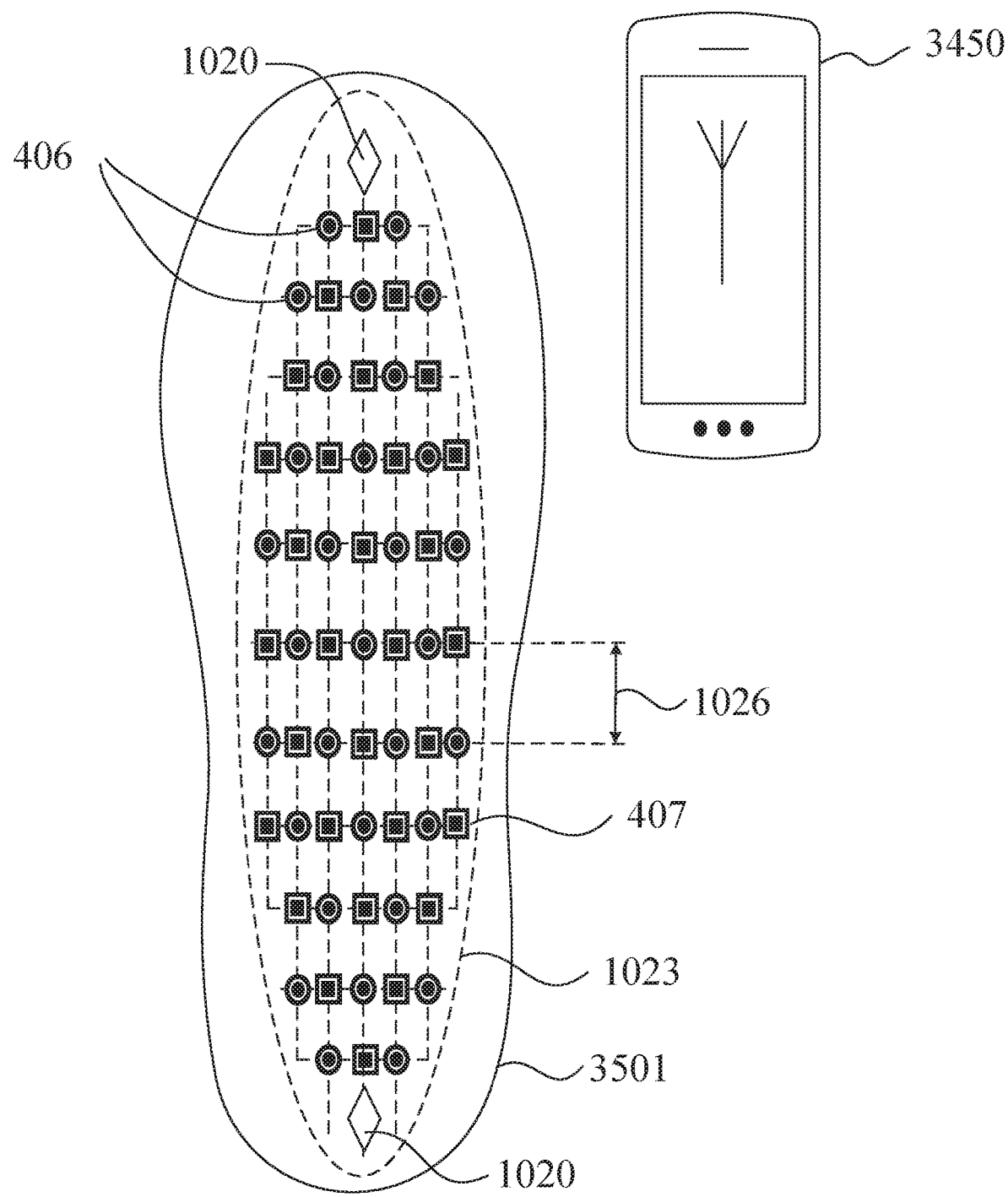
FIG. 35B may depict a schematic top view of an orthotic fitted with at least one lattice-of-sensors and shown "proximate" to (and in wireless communication with) at least one mobile-computing-device.

FIG. 35B may depict a schematic top view of an orthotic 3501 fitted with at least one lattice-of-sensors 1023 and shown "proximate" to at least one mobile-computing-device 3450. "Proximate" in this context may be close enough such that at least one mobile-computing-device 3450 may be in wireless communication with at least one of the first-sensor-tags 1020 (which may have an antenna) of the at least one lattice-of-sensors 1023. As noted, in some embodiments, this wireless communication may be characterized as NFC (near field communication) and/or as wireless communication characteristic for RFID (radio frequency ID), and/or as Bluetooth, and/or as Wi-Fi (WiFi). In some embodiments, when the lattice-of-sensors 1023 may not have its own internal power source (or its own internal power source may be depleted), then this "proximate" distance may be close enough for mobile-computing-device 3450 to power lattice-of-sensors 1023 through transmission of electromagnetic wireless energy from mobile-computing-device 3450 to lattice-of-sensors 1023. In some embodiments, this wireless communication may be characterized as the mobile-computing-device 3450 scanning, reading, and/or interrogating the various sensors of lattice-of-sensors 1023.

Continuing discussing FIG. 35B, in some embodiments, the at least one lattice-of-sensors 1023 may in, on, on top of, under, or combinations thereof, the given orthotic 3501. In some embodiments, the at least one lattice-of-sensors 1023 may be in communication with the orthotic 3501. In some embodiments, the at least one lattice-of-sensors 1023 may be in physical communication with the orthotic 3501. In some embodiments, the at least one lattice-of-sensors 1023 may be attached to the orthotic 3501. For example, and without limiting the scope of the present invention, the at least one lattice-of-sensors 1023 may be embedded within a given orthotic 3501. In some embodiments, the at least one lattice-of-sensors 1023 may be configured substantially as a planar sheet that may be substantially parallel with a major plane of a given orthotic 3501.

Continuing discussing FIG. 35B, in some embodiments, the at least one lattice-of-sensors 1023 shown in FIG. 35B (and shown in the figures FIG. 35B through FIG. 35J) may be as discussed per above. For example and without limiting the scope of the present invention, a given lattice-of-sensors 1023 may comprise at least one first-sensor-tag 1020 (with an antenna) and a plurality of sensors (e.g., the plurality of sensors comprising sensors 406 and 407) (e.g., the plurality of sensors without their own antennas), wherein this plurality of sensors may be in electrical communication with the at least one first-sensor-tag 1020, and wherein the sensors of plurality of sensors are arranged in a fixed manner, with predetermined sensor spacing 1026.

In some embodiments, the sensors from the one or more monitoring-sensor-tags 120 may measure stresses and/or pressure that the bottoms of feet 3505 may exert upon these sensors. Such measurements may be used to direct the shape and sizes of a given orthotic 3501 to be manufactured.

In some embodiments, the sensors from the one or more lattice-of-sensors 1023 may measure stresses and/or pressure that the bottoms of feet 3505 may exert upon these sensors. Such measurements may be used to direct the shape and sizes of each a given orthotic 3501 to be manufactured.

Since predetermined sensor spacing 1026 may be known (or may be determined), relative location of each sensor in lattice-of-sensors 1023 with respect to any other sensor in the lattice-of-sensors 1023 may also known or may be determined (e.g., calculated). Therefore, a high-precision representation of the impact/forces/pressures of a given orthotic 3501 on foot 3505 of a given patient and/or conversely of the impact of the foot 3505 of a given patient on a given orthotic 3501 may be readily, continually, and consistently found.

Advances in technology miniaturization, which already make possible sizes of semiconductor-based elements to be of the order of several nanometers (e.g., 7 nm semiconductor processes), may allow placing millions of sensors per square millimeter. The practical precision requirements and costs considerations may reduce the density of sensors from the maximum allowed by technology, reducing the density to thousands, hundreds, dozens, or single units per square or cubic millimeter.

The number of sensors placed per area or per volume unit may allow translating the measurements (readings) results from such sensors into two-dimensional images (maps), three-dimensional images (maps), four-dimensional images/maps with time, and/or other visual or numerical forms, and in real-time or near real-time, allowing professionals and practitioners, such as, but not limited to, podiatrists, chiropodists, and/or the like to assess the manufactured orthotics and its impact on the patient in the ways which have been previously possible. These above principals are equally applicable to aligners 3400 and orthodontists.

Figure 35C:
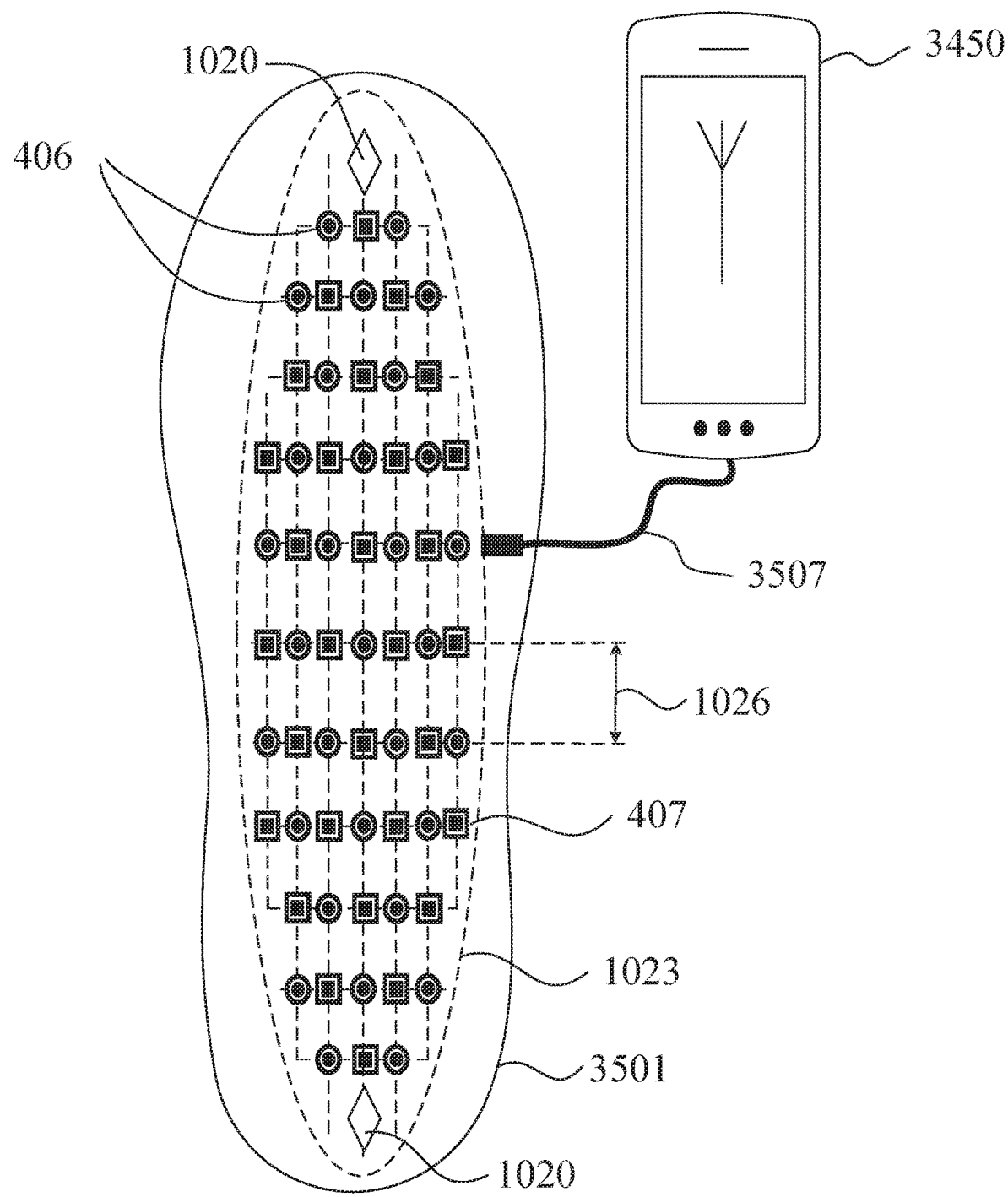
FIG. 35C may depict a schematic top view of an orthotic fitted with at least one lattice-of-sensors that may be in wired connection with a mobile-computing-device FIG. 35D may depict a schematic top view of an orthotic fitted with at least one lattice-of-sensors that may be in wired connection with a reader.

FIG. 35C may depict a schematic top view of an orthotic 3501 fitted with at least one lattice-of-sensors 1023 that may be in wired connection 3507 with mobile-computing-device 3450. In FIG. 35C, mobile-computing-device 3450 may in wired electrical communication with lattice-of-sensors 1023 via a wired connection shown as wired connection 3507 in FIG. 35C. In some embodiments, wireless communication between mobile-computing-device 3450 and lattice-of-sensors 1023 need not be occurring in the configuration shown in FIG. 35C, although such wireless communications may be still be possible in some embodiments of the configuration shown in FIG. 35C. In some embodiments, wired connection 3507 may permit electrical power to be transmitted from mobile-computing-device 3450 to lattice-of-sensors 1023. In some embodiments, wired connection 3507 may permit mobile-computing-device 3450 to scan, read, and/or interrogate the various sensors of lattice-of-sensors 1023. In some embodiments, orthotic 3501 and/or lattice-of-sensors 1023 may be fitted with at least one port for removably receiving wired connection 3507. In some embodiments, this port may be a standard sized and configured industry port, such as, but not limited to, USB, micro-USB, other USB port versions, serial port, parallel port, Firewire, Thunderbolt, Ethernet, 1-Wire, and/or the like.

Figure 35D:
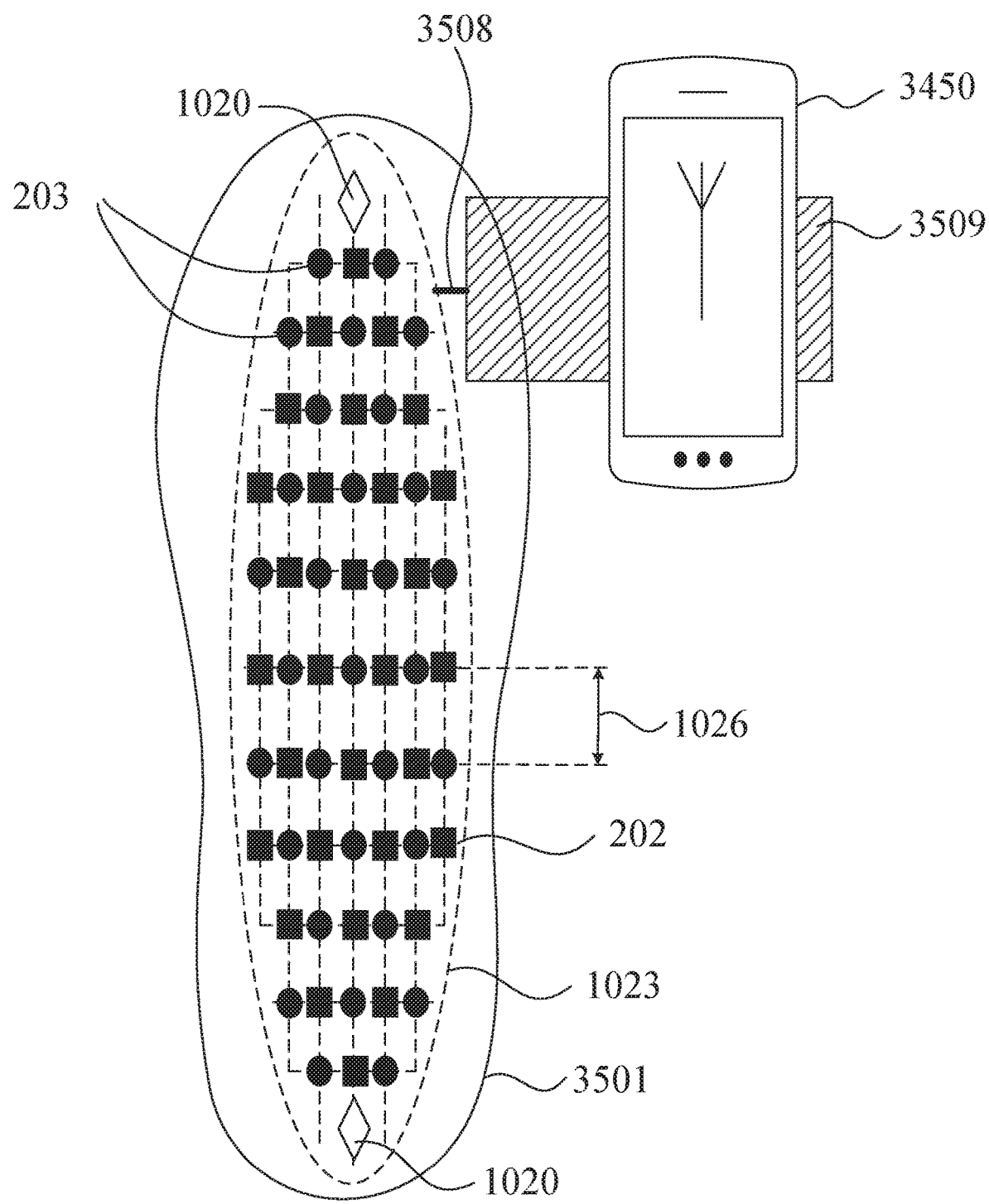
FIG. 35E may depict a schematic top view of an orthotic fitted with at least one lattice-of-sensors and shown "proximate" to at least one mobile-computing-device, wherein the at least one lattice-of-sensors may comprise one or more of: a wireless charging source, a power source, a memory, and/or a WiFi antenna, any one of which may be in wired electrical communication with a lattice-of-sensors of the orthotic.
FIG. 35F may depict a schematic top view of an orthotic fitted with at least one lattice-of-sensors, on top of a mat-reader, and wherein this mat-reader may be "proximate" to at least one mobile-computing-device which may be in wireless communication with this mat-reader. In some embodiments, this mat-reader may comprise as least one WiFi-antenna for wireless communications.
FIG. 35G may depict a perspective view of a foot of a patient within a shoe, in physical contact with the orthotic (with sensor tags). The patient may be standing on a mat-reader with one or more antennas that may be reading, scanning, and/or interrogating the various antennas of the sensor tags of the orthotic to obtain sensor data.
FIG. 35H may depict a partial exploded perspective view of a foot of a patient disposed above the orthotic (with sensor tags), which may be standing on a mat-reader. One or more antennas of the mat-reader may be reading, scanning, and/or interrogating the various antennas the sensor tags of the orthotic to obtain sensor data. Such sensor data received at the mat-reader may then be wirelessly transmitted to a mobile-computing-device depicted in FIG. 35H via WiFi-antenna of the mat-reader.
FIG. 35I may depict a partial exploded perspective view of how two or more lattice-of-sensors may be layered (stacked) on top of each other in a given orthotic.
FIG. 35J may depict a perspective view of two or more lattice-of-sensors that may be layered (stacked) on top of each other in a given orthotic and showing the initial predetermined spacing between the two or more lattice-of-sensors.
FIG. 35K may depict a schematic view of a given mobile-computing-device may be displaying a particular image, wherein the particular image may be a visual interpretation of sensor information from sensors associated with measuring feet and/or orthotics used with feet.

FIG. 35D may depict a schematic top view of an orthotic 3501 fitted with at least one lattice-of-sensors 1023 that may be in wired connection 3508 with a reader 3509. In some embodiments, wired connection 3508 may permit electrical power to be transmitted from reader 3509 to lattice-of-sensors 1023. In some embodiments, wired connection 3508 may permit reader 3509 to scan, read, and/or interrogate the various sensors of lattice-of-sensors 1023. In some embodiments, orthotic 3501 and/or lattice-of-sensors 1023 may be fitted with at least one port for removably receiving wired connection 3508. In some embodiments, this port may be a standard sized and configured industry port, such as, but not limited to, USB, micro-USB, other USB port versions, serial port, parallel port, Firewire, Thunderbolt, Ethernet, 1-Wire, and/or the like.

Continuing discussing FIG. 35D, in some embodiments, reader 3509 may be shown "proximate" to at least one mobile-computing-device 3450. "Proximate" in this context may be close enough such that at least one mobile-computing-device 3450 may be in wireless communication with reader 3509 (which may have an antenna). For example, and without limiting the scope of the present invention, mobile-computing-device 3450 may be laying on top of reader 3509 with wireless communications occurring between the two devices. In some embodiments, this wireless communication may be characterized as NFC (near field communication) and/or as wireless communication characteristic for RFID (radio frequency ID). In some embodiments, when the lattice-of-sensors 1023 and/or reader 3509 may not have their own internal power source (or their own internal power source may be depleted), then this "proximate" distance may be close enough for mobile-computing-device 3450 to power reader 3509 and lattice-of-sensors 1023 through transmission of electromagnetic wireless energy from mobile-computing-device 3450 to reader 3509. In some embodiments, this wireless communication may be characterized as the mobile-computing-device 3450 scanning, reading, and/or interrogating reader 3509. That is, reader 3509 may receive sensor data from the various sensors of lattice-of-sensors 1023 via wired connection 3508; and then reader 3509 may wirelessly transmit this sensor data to mobile-computing-device 3450.

In some embodiments, reader 3509 may share purposes, structures, and/or components with that of monitoring-sensor-tag 120, comprising antenna 130 and electric circuit 140. Using antenna 130, wireless communications from the mobile-computing-device 3450 may both power electric circuit 140 and transmit information to and from lattice-of-sensors 1023.

In some embodiments, reader 3509 may comprise one or more RFID tag(s) or NFC tag(s), which may harvest (receive) power to supply itself and lattice-of-sensors 1023 with electricity required to provide exchange of information between mobile-computing-device 3450 and lattice-of-sensors 1023.

In some embodiments, reader 3509 and lattice-of-sensors 1023 may share purposes, structures, and/or components with that of monitoring-sensor-tag 120, harvesting electrical power from wireless communications from the mobile-computing-device 3450 to supply itself and lattice-of-sensors 1023 with electricity required to provide exchange of information between mobile-computing-device 3450 and lattice-of-sensors 1023.

In some embodiments, mobile-computing-device 3450 may comprise reader 100 and antenna 110 in order to power reader 3509 and lattice-of-sensors 1023 and communicate with reader 3509 and lattice-of-sensors 1023.

Figure 35E:
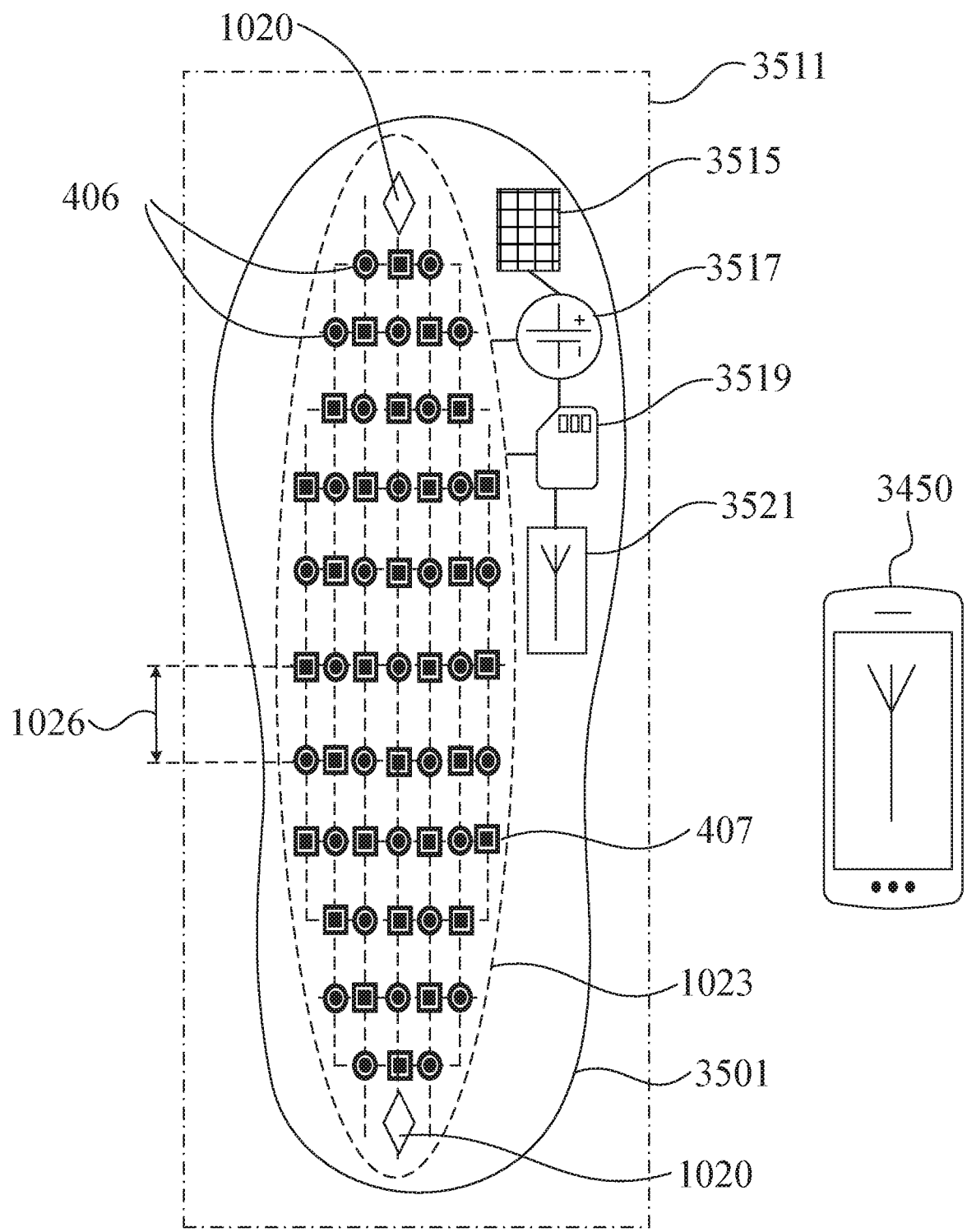

FIG. 35E may depict a schematic top view of an orthotic 3501 fitted with at least one lattice-of-sensors 1023 and shown "proximate" to at least one mobile-computing-device 3450. "Proximate" in this context may be close enough such that at least one mobile-computing-device 3450 may be in wireless communication with the at least one of lattice-of-sensors 1023.

Continuing discussing FIG. 35E, in some embodiments, the at least one lattice-of-sensors 1023 may comprise one or more of: a wireless charging source 3515, a power source 3517, a memory 3519, and/or a WiFi antenna 3521, any one of which may be in wired electrical communication with lattice-of-sensors 1023.

Continuing discussing FIG. 35E, in some embodiments, wireless charging source 3515 may be an electrical hardware component for receiving electromagnetic energy (e.g., from a magnetic field and/or from radio waves) and for distributing electrical energy to other electrical components of lattice-of-sensors 1023.

Continuing discussing FIG. 35E, in some embodiments, power source 3517 may be one or more batteries. In some embodiments, power source 3517 may be one or more rechargeable batteries. In some embodiments, power source 3517 may power the various electrical components/hardware of lattice-of-sensors 1023. In some embodiments, power source 3517 may receive electrical power from wireless charging source 3515. In some embodiments, power source 3517 may be charged from wireless charging source 3515. Some embodiments may not include power source 3517 and may receive required electrical power directly from wireless charging source 3515.

Continuing discussing FIG. 35E, in some embodiments, memory 3519 may be for non-transitory storage of data and/or software (such as, but not limited to, firmware, code, computer programs, and/or the like). In some embodiments, memory 3519 may be for non-transitory storage of data received from the various sensors of lattice-of-sensors 1023. In some embodiments, memory 3519 may store (hold) information on a volatile or on a non-volatile medium, and may be fixed and/or removable. In some embodiments, memory 3519 may include a tangible computer readable and computer writable non-volatile recording medium, on which signals are stored that define a computer program (i.e., the code or the software) or information (e.g., data) to be used by the computer program. The recording medium may, for example, be hard drive, disk memory, flash memory, and/or any other article(s) of manufacture usable to record and store information (in a non-transitory fashion). In some embodiments, memory 3519 may receive electrical power from power source 3517.

Continuing discussing FIG. 35E, in some embodiments, WiFi antenna 3521 may wirelessly communicate with mobile-computing-device 3450. In some embodiments, WiFi antenna 3521 may communicate sensor data received from the sensors of lattice-of-sensors 1023 to mobile-computing-device 3450. In some embodiments, WiFi antenna 3521 may communicate sensor data received from memory 3519 to mobile-computing-device 3450. In some embodiments, WiFi antenna 3521 may be configured for wireless communications according to industry accepted communication protocols and/or standards, such as, but not limited to, WiFi, Bluetooth, Bluetooth Low Energy (BLE), ZigBee, and/or the like. In some embodiments, WiFi antenna 3521 may receive electrical power from power source 3517.

FIG. 35E may also show mat-reader 3511 positioned beneath orthotic 3501. In some embodiments, mat-reader 3511 may be a mat intended to be stepped on by users (e.g., patients). In some embodiments, mat-reader 3511 may be a mat imbedded with various electronic hardware components, such as one or more antennas. In some embodiments, mat-reader 3511 may comprise one or more antennas for scanning, reading, and/or interrogating the various sensors of lattice-of-sensors 1023. In some embodiments, the one or more antennas of mat-reader 3511 may be in wireless communication with the antenna(s) of first-sensor-tag(s) 1020 of lattice-of-sensors 1023. In some embodiments, when a given orthotic 3501 with at least one lattice-of-sensors 1023 may be placed on top of mat-reader 3511, the one or more antennas of mat-reader 3511 may scan, read, and/or interrogate the antenna(s) of first-sensor-tag(s) 1020 of lattice-of-sensors 1023. In some embodiments, mat-reader 3511 may be shown "proximate" to at least one mobile-computing-device 3450. "Proximate" in this context may be close enough such that at least one mobile-computing-device 3450 may be in wireless communication with mat-reader 3511 (which may have an antenna). In some embodiments, mat-reader 3511 may share purposes, structures, and components with that of reader 3509, or reader-and-calibration-member 1109.

Figure 35F:
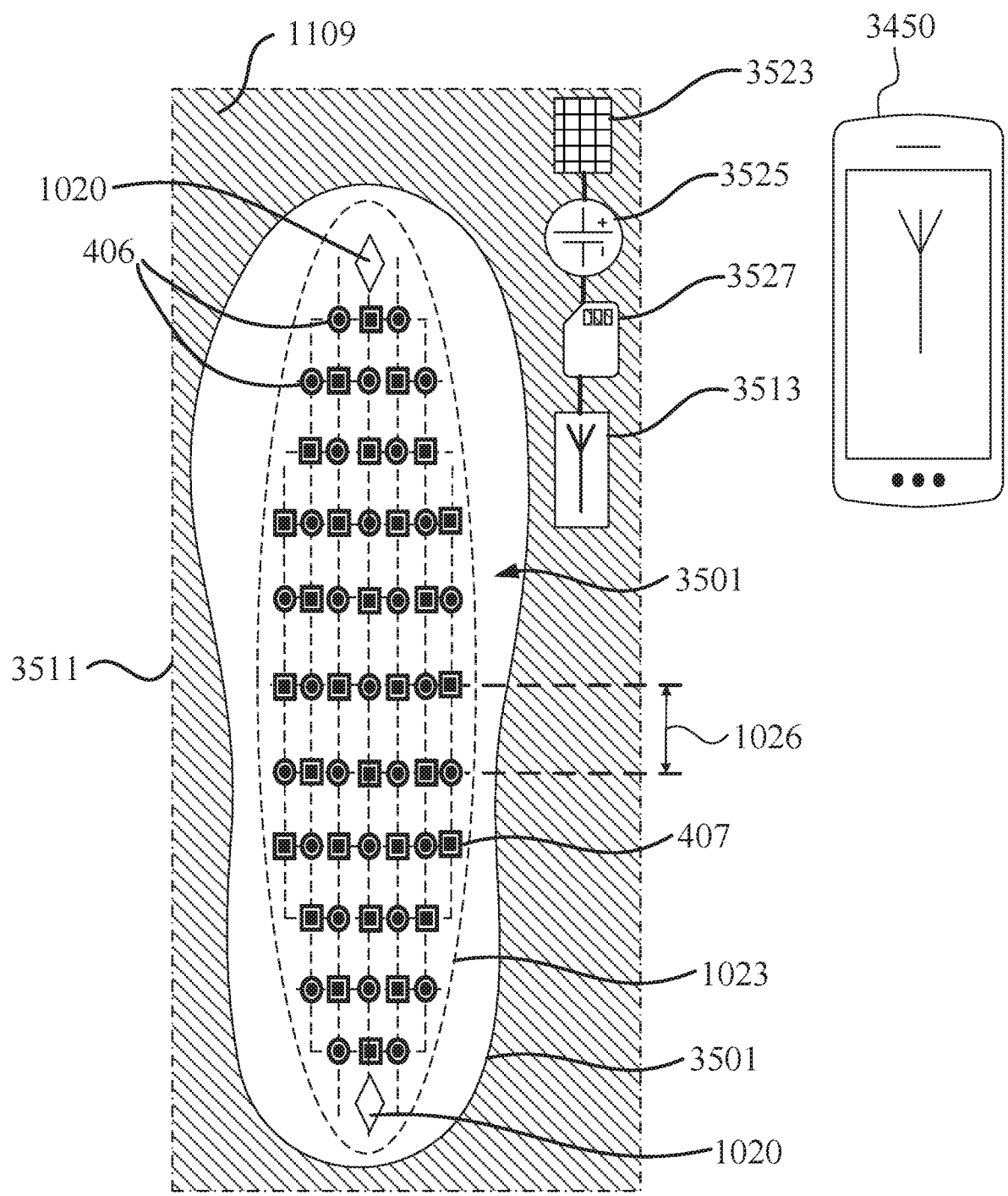

FIG. 35F may depict a schematic top view of an orthotic 3501 fitted with at least one lattice-of-sensors 1023, on top of mat-reader 3511, and wherein mat-reader 3511 may be "proximate" to at least one mobile-computing-device 3450. "Proximate" in this context may be close enough such that at least one mobile-computing-device 3450 may be in wireless communication with mat-reader 3511. In some embodiments, mat-reader 3511 may comprise as least one WiFi-antenna 3513 for wireless communications. In some embodiments, WiFi-antenna 3513 may be configured for wireless communications according to industry accepted communication protocols and/or standards, such as, but not limited to, WiFi, Bluetooth, Bluetooth Low Energy (BLE), ZigBee, and/or the like. In some embodiments, mat-reader 3511 may use WiFi-antenna 3513 for wireless communications with mobile-computing-device 3450. In some embodiments, mat-reader 3511 may use WiFi-antenna 3513 for wireless communications with lattice-of-sensors 1023. In some embodiments, mat-reader 3511 may use at least one antenna other than WiFi-antenna 3513 for wireless communications with lattice-of-sensors 1023. In some embodiments, WiFi-antenna 3513 may be termed, a "second antenna." In some embodiments, WiFi-antennas discussed herein may be termed, a "second antenna."

Continuing discussing FIG. 35F, in some embodiments, at least one antenna of mat-reader 3511 may scan, read, and/or interrogate antennas from lattice-of-sensors 1023 (e.g., antenna(s) of first-sensor-tag(s) 1020) to receive sensor data from the sensors of lattice-of-sensors 1023. In some embodiments, mat-reader 3511 may then use WiFi-antenna 3513 to wirelessly transmit this received sensor data to mobile-computing-device 3450.

Continuing discussing FIG. 35F, in some embodiments, when a patient wearing a given orthotic 3501 with one or more lattice-of-sensors 1023 steps onto mat-reader 3511, mat-reader 3511 may be activated to scan, read, and/or interrogate sensors from lattice-of-sensors 1023. In some embodiments, a mobile app (i.e., software) running on mobile-computing-device 3450 may initiate scanning, reading, and/or interrogation activities of mat-reader 3511 of the sensors of lattice-of-sensors 1023.

In some embodiments, mat-reader 3511 may comprise one or more of: a wireless charging source 3523, a power source 3525, a memory 3527, and/or a WiFi antenna 3513. In some embodiments, wireless charging source 3523 may be an electrical hardware component for receiving electromagnetic energy (e.g., from a magnetic field and/or from radio waves) and for distributing electrical energy to other electrical components of mat-reader 3511.

Continuing discussing FIG. 35F, in some embodiments, power source 3525 may be one or more batteries. In some embodiments, power source 3525 may be one or more rechargeable batteries. In some embodiments, power source 3525 may power the various electrical components/hardware of mat-reader 3511. In some embodiments, power source 3525 may receive electrical power from wireless charging source 3523. In some embodiments, power source 3525 may be charged from wireless charging source 3523.

Continuing discussing FIG. 35F, in some embodiments, memory 3527 may be for non-transitory storage of data and/or software (such as, but not limited to, firmware, code, computer programs, and/or the like). In some embodiments, memory 3527 may be for non-transitory storage of data received from the various sensors of lattice-of-sensors 1023. In some embodiments, memory 3527 may store (hold) information on a volatile or on a non-volatile medium, and may be fixed and/or removable. In some embodiments, memory 3527 may include a tangible computer readable and computer writable non-volatile recording medium, on which signals are stored that define a computer program (i.e., the code or the software) or information (e.g., data) to be used by the computer program. The recording medium may, for example, be hard drive, disk memory, flash memory, and/or any other article(s) of manufacture usable to record and store information (in a non-transitory fashion). In some embodiments, memory 3527 may receive electrical power from power source 3525.

Figure 35G:
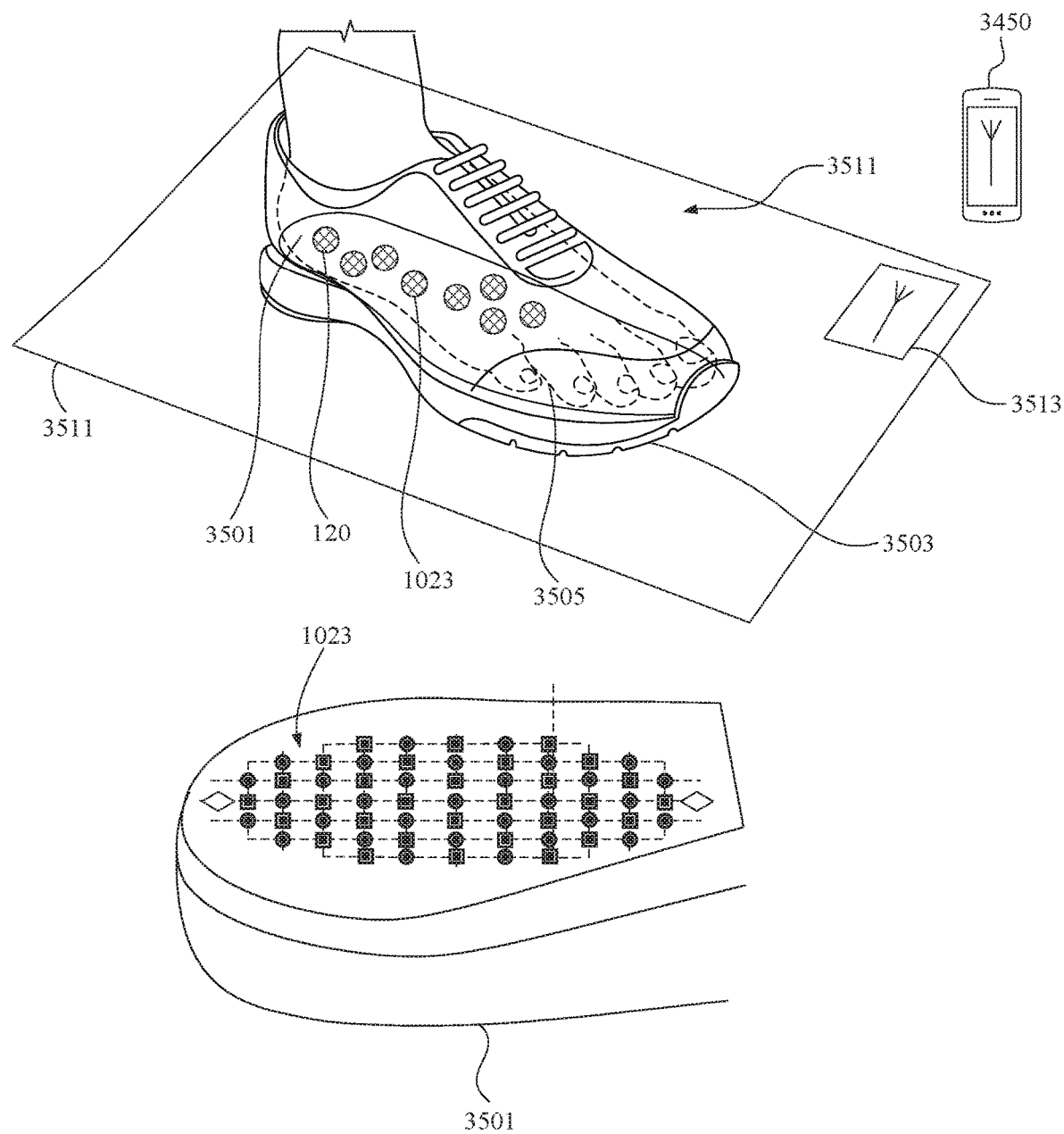

FIG. 35G may depict a perspective view of foot 3505 of a patient within shoe 3503, wherein that foot 3505 may be disposed above, but in physical contact with an orthotic 3501, wherein orthotic 3501 may comprise at least one monitoring-sensor-tag 120 and/or at least one lattice-of-sensors 1023. The shoe 3503, along with foot 3505 and orthotic 3501, may be standing on mat-reader 3511. One or more antennas of mat-reader 3511 may be reading, scanning, and/or interrogating the various antennas of the at least one monitoring-sensor-tag 120 and/or the at least one lattice-of-sensors 1023 to obtain sensor data. Such sensor data received at mat-reader 3511 may then be wirelessly transmitted to mobile-computing-device 3450 via WiFi-antenna 3513 of mat-reader 3511.

Continuing discussing FIG. 35G, in some embodiments, orthotic 3501 may comprise a plurality of distinct lattice-of-sensors 1023. In some embodiments, orthotic 3501 may comprise a plurality of distinct monitoring-sensor-tag 120.

Continuing discussing FIG. 35G, in some embodiments, when a patient wearing a given orthotic 3501 with one or more lattice-of-sensors 1023 and/or one or more monitoring-sensor-tag 120 steps onto mat-reader 3511, mat-reader 3511 may be activated to scan, read, and/or interrogate sensors from lattice-of-sensors 1023 and/or monitoring-sensor-tags 120. In some embodiments, a mobile app (e.g., software) running on mobile-computing-device 3450 may initiate scanning, reading, and/or interrogation activities of mat-reader 3511 of the sensors of lattice-of-sensors 1023 and/or monitoring-sensor-tags 120.

Figure 35H:
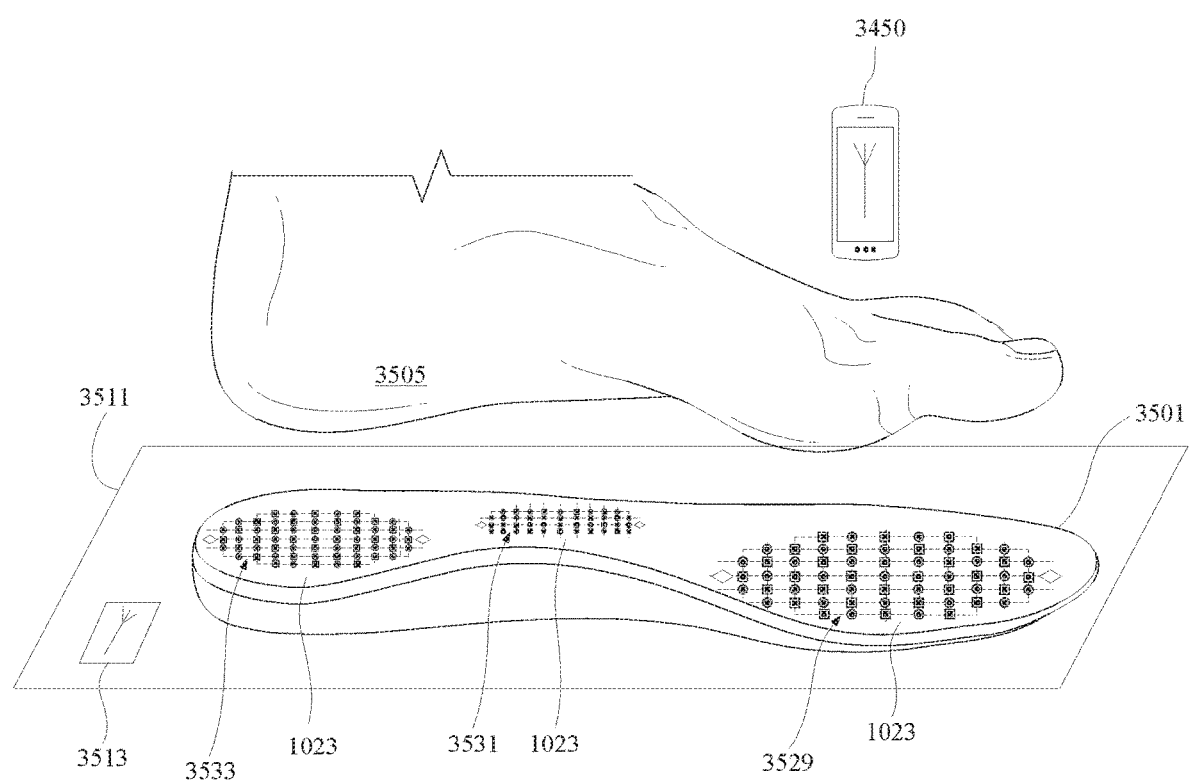

FIG. 35H may depict a partial exploded perspective view of foot 3505 of a patient disposed above orthotic 3501, wherein orthotic 3501 may comprise at least one monitoring-sensor-tags 120 and/or at least one lattice-of-sensors 1023. As shown in FIG. 35H, the above orthotic 3501 may be positioned above mat-reader 3511. One or more antennas of mat-reader 3511 may be reading, scanning, and/or interrogating the various antennas of the at least one monitoring-sensor-tag 120 and/or the at least one lattice-of-sensors 1023 to obtain sensor data. Such sensor data received at mat-reader 3511 may then be wirelessly transmitted to mobile-computing-device 3450 via WiFi-antenna 3513 of mat-reader 3511. In some embodiments, orthotic 3501 may comprise distinct regions, wherein each such distinct region has separate at least one monitoring-sensor-tags 120 and/or at least one lattice-of-sensors 1023. For example, and without limiting the scope of the present invention, these distinct regions may be a ball-region 3529, an arch-region 3531, and/or a heal-region 3533. In some embodiments, ball-region 3529 may correspond and be located where a ball of foot 3505 and/or of where toes of foot 3505 may rest on orthotic 3501. In some embodiments, arch-region 3531 may correspond and be located where an arch of foot 3505 may rest on orthotic 3501. In some embodiments, heal-region 3533 may correspond and be located where a heal of foot 3505 may rest on orthotic 3501. In some embodiments, ball-region 3529 may comprise at least one monitoring-sensor-tags 120 and/or at least one lattice-of-sensors 1023. In some embodiments, arch-region 3531 may comprise at least one monitoring-sensor-tags 120 and/or at least one lattice-of-sensors 1023. In some embodiments, heal-region 3533 may comprise at least one monitoring-sensor-tags 120 and/or at least one lattice-of-sensors 1023. Thus, common hot zones, pressure points, and/or commonly complained about locations of foot 3505 may be regularly and easily monitored and with great locational detail/fidelity.

Figure 35I:
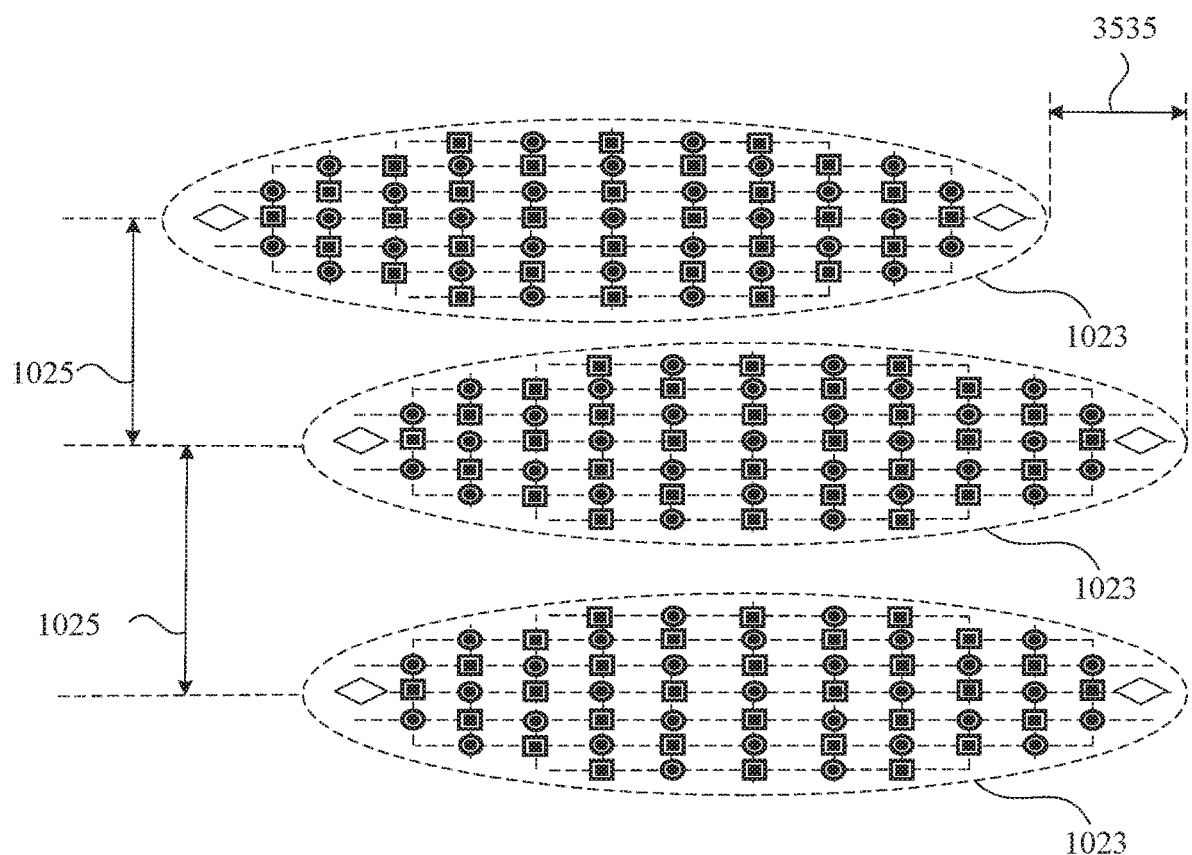

FIG. 35I may depict a partial exploded perspective view of how two or more lattice-of-sensors 1023 may be layered (stacked) on top of each other in a given orthotic 3501. With respect to a patient standing in a typical Earth gravitational field, wherein the patient's soles of the patient's shoes 3503 may be substantially horizontal and orthogonal with respect to that typical Earth gravitational field, then initial predetermined spacing 1025 may represent a substantially vertical distance between any two adjacent lattice-of-sensors 1023, wherein such substantially vertical distance(s) may be fixed within the given medium (material of construction) for the orthotic 3501; and lateral spacing 3535 may represent a substantially lateral distance between any two adjacent lattice-of-sensors 1023, wherein such substantially lateral distance(s) may be fixed within the given medium (material of construction) for the orthotic 3501. Such layering and/or stacking of lattice-of-sensors 1023 in a given orthotic 3501 may increase sensor density providing increased measurement sensitivity. Such layering and/or stacking of lattice-of-sensors 1023 in a given orthotic 3501 may provide a three-dimensional (3D) data and/or imaging capacity enabling podiatrists, chiropodists, orthopedic surgeons and/or other professionals to obtain multi-dimensional representation of the impact of a given orthotic 3501 on foot 3505 of a given patient and/or conversely of the impact of the foot 3505 of a given patient on a given orthotic 3501. Since lateral spacing 3535 and initial predetermined spacing 1025 and predetermined sensor spacing 1026 may be known (or may be determined), relative location of each sensor in lattice-of-sensors 1023 in respect to any other sensor in the same or other lattice-of-sensors 1023 may be known or may be determined (e.g., calculated). Therefore, a high-precision representation of the impact/forces/pressures of a given orthotic 3501 on foot 3505 of a given patient and/or conversely of the impact of the foot 3505 of a given patient on a given orthotic 3501 may be found.

Without limiting the scope of the present invention, each of the lateral spacing 3535 and initial predetermined spacing 1025 and predetermined sensor spacing 1026 may be knowingly varied in a pre-determined way across a given orthotic 3501 or/and across any geometrical dimension of a given orthotic 3501. For example, and without limiting the scope of the present invention, predetermined sensor spacing 1026 may vary across the surface of a given orthotic 3501.

Note in FIG. 35I, any shown lattice-of-sensor 1023 may be replaced with a monitoring-sensor-tag 120.

Figure 35J:
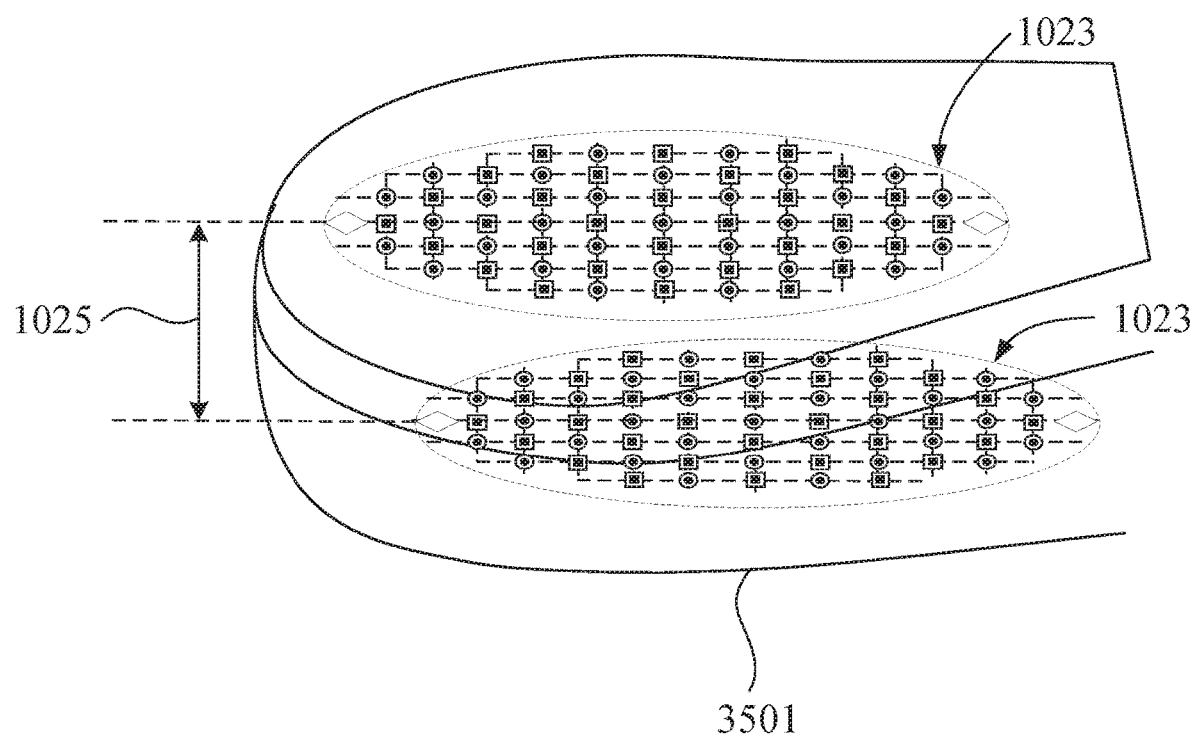

FIG. 35J may depict a perspective view of two or more lattice-of-sensors 1023 that may be layered (stacked) on top of each other in a given orthotic 3501 and showing the initial predetermined spacing 1025 between the two or more lattice-of-sensors 1023.

Note in FIG. 35J, any shown lattice-of-sensor 1023 may be replaced with a monitoring-sensor-tag 120.

For example, and without limiting the scope of the present invention, the described use of lattice-of-sensors 1023 and/or monitoring-sensor-tags 120 in a given orthotic 3501, feet positioning, feet movement, feet forces/pressures may all be measured, in real-time (or near real-time), to assess and/or generate (manufacture) a given orthotic 3501 with better fits; to generate proper orthotic 3501 at clinical optimal frequency; and/or to minimize generation of orthotic 3501 with improper sizes/shapes or qualities.

In some embodiments, the given orthotic 3501 with the one or more monitoring-sensor-tags 120 may be monitored and/or tracked to provide one or more of: structural integrity of a current state of the given orthotic 3501; structural integrity changes of the given orthotic 3501; pressure received at the given orthotic 3501; force received at the given orthotic 3501; stress received at the given orthotic 3501; shear-stress received in the given orthotic 3501; torsion received at the given orthotic 3501; compression of the given orthotic 3501; tension in the given orthotic 3501; twisting received of the given orthotic 3501; deformation received at the given orthotic 3501; temperature at some portion of the given orthotic 3501; positional changes of a given monitoring-sensor-tag 120 attached to the given orthotic 3501 with respect to position of another monitoring-sensor-tag 120 attached to the given orthotic 3501, wherein the given monitoring-sensor-tag 120 and the other monitoring-sensor-tag are 120 selected from the one or more monitoring-sensor-tags 120 attached to the given orthotic 3501; or positional changes of at least one monitoring-sensor-tag 120 attached to the given orthotic 3501 with respect to time, wherein the at least one monitoring-sensor-tag 120 is selected from the one or more monitoring-sensor-tags 120.

Figure 35K:
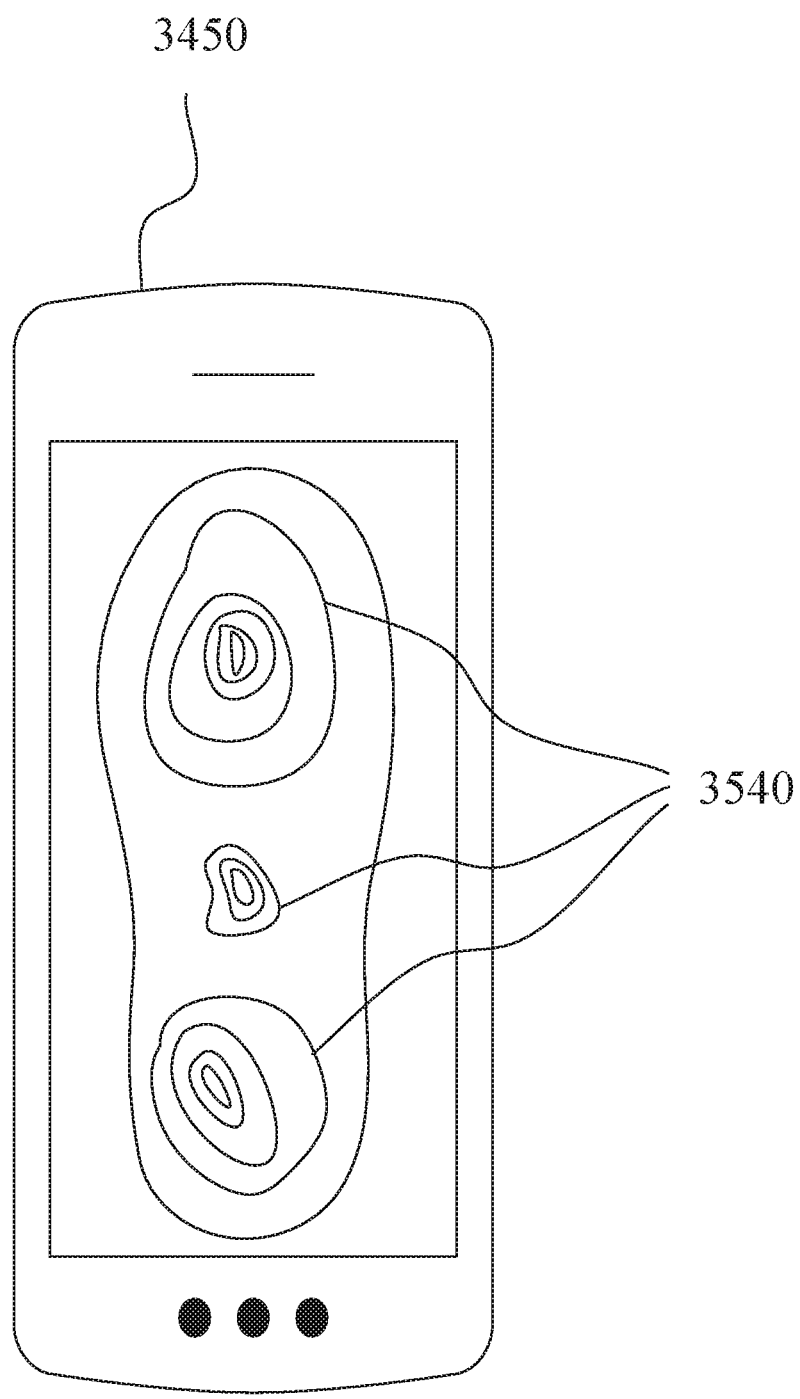

FIG. 35K may depict a given mobile-computing-device 3450 showing a particular image displayed on a screen of mobile-computing-device 3450. In some embodiments, this particular image may be "visual interpretation of sensor information 3540." In some embodiments, visual interpretation of sensor information 3540 may comprise visual representations of one or more elements shown in FIG. 35H, FIG. 35I, FIG. 35J, combinations thereof, and/or the like. In some embodiments, visual interpretation of sensor information 3540 may comprise visual representations of one or more of: capacitive-based sensor 202 information/data (e.g., from monitoring a given region of a given foot 3505 that may be physically touching a portion of orthotic 3501); resistance-based sensor 203 information/data (e.g., from monitoring a given region of a given foot 3505 that may be physically touching a portion of orthotic 3501); conductive surface type "D" sensor 406 (e.g., from monitoring a given region of a given foot 3505 that may be physically touching a portion of orthotic 3501); conductive surface type "E" sensor 407 (e.g., from monitoring a given region of a given foot 3505 that may be physically touching a portion of orthotic 3501); first-sensor-tag 1020 information/data (e.g., from monitoring a given region of a given foot 3505 that may be physically touching a portion of orthotic 3501); second-sensor-tag 1021 information/data (e.g., from monitoring a given region of a given foot 3505 that may be physically touching a portion of orthotic 3501); lattice-of-sensors 1023 information/data (e.g., from monitoring a given region of a given foot 3505 that may be physically touching a portion of orthotic 3501); capacitive-based sensor 202 information/data (e.g., from monitoring a given region of orthotic 3501); resistance-based sensor 203 information/data (e.g., from monitoring a given region of orthotic 3501); conductive surface type "D" sensor 406 (e.g., from monitoring a given region of orthotic 3501); conductive surface type "E" sensor 407 (e.g., from monitoring a given region of orthotic 3501); first-sensor-tag 1020 information/data (e.g., from monitoring a given region of orthotic 3501); second-sensor-tag 1021 information/data (e.g., from monitoring a given region of orthotic 3501); lattice-of-sensors 1023 information/data (e.g., from monitoring a given region of orthotic 3501); capacitive-based sensor 202 information/data (e.g., from monitoring a given ball-region 3529 of orthotic 3501); resistance-based sensor 203 information/data (e.g., from monitoring a given ball-region 3529 of orthotic 3501); conductive surface type "D" sensor 406 (e.g., from monitoring a given ball-region 3529 of orthotic 3501); conductive surface type "E" sensor 407 (e.g., from monitoring a given ball-region 3529 of orthotic 3501); first-sensor-tag 1020 information/data (e.g., from monitoring a given ball-region 3529 of orthotic 3501); second-sensor-tag 1021 information/data (e.g., from monitoring a given ball-region 3529 of orthotic 3501); lattice-of-sensors 1023 information/data (e.g., from monitoring a given ball-region 3529 of orthotic 3501); capacitive-based sensor 202 information/data (e.g., from monitoring a given arch-region 3531 of orthotic 3501); resistance-based sensor 203 information/data (e.g., from monitoring a given arch-region 3531 of orthotic 3501); conductive surface type "D" sensor 406 (e.g., from monitoring a given arch-region 3531 of orthotic 3501); conductive surface type "E" sensor 407 (e.g., from monitoring a given arch-region 3531 of orthotic 3501); first-sensor-tag 1020 information/data (e.g., from monitoring a given arch-region 3531 of orthotic 3501); second-sensor-tag 1021 information/data (e.g., from monitoring a given arch-region 3531 of orthotic 3501); lattice-of-sensors 1023 information/data (e.g., from monitoring a given arch-region 3531 of orthotic 3501); capacitive-based sensor 202 information/data (e.g., from monitoring a given heal-region 3533 of orthotic 3501); resistance-based sensor 203 information/data (e.g., from monitoring a given heal-region 3533 of orthotic 3501); conductive surface type "D" sensor 406 (e.g., from monitoring a given heal-region 3533 of orthotic 3501); conductive surface type "E" sensor 407 (e.g., from monitoring a given heal-region 3533 of orthotic 3501); first-sensor-tag 1020 information/data (e.g., from monitoring a given heal-region 3533 of orthotic 3501); second-sensor-tag 1021 information/data (e.g., from monitoring a given heal-region 3533 of orthotic 3501); lattice-of-sensors 1023 information/data (e.g., from monitoring a given heal-region 3533 of orthotic 3501); initial predetermined spacing 1025 information/data; sensor-spacing 1026 information/data; lateral spacing 3535 information/data; sensor information/data from a particular sensor that may be in communication with first-sensor-tag 1020; sensor information/data from a particular sensor that may be in communication with second-sensor-tag 1021; sensor information/data from a particular sensor that may be in communication with lattice-of-sensors 1023; changes in such information/data; combinations thereof; and/or the like. In some embodiments, visual interpretation of sensor information 3540 may comprise display of visual representations of differences in such sensor information/data. In some embodiments, visual interpretation of sensor information 3540 may comprise use of contour maps, color gradients, combinations thereof, and/or the like to display visual representations of differences in such sensor information/data. In some embodiments, visual interpretation of sensor information 3540 may comprise display of visual representations of problems and/or potential problems with respect to orthotic 3501 and/or foot 3505.

In some embodiments, at least some of the sensors mentioned above, such as, but not limited to, capacitive-based sensors, may readily still provide their readings if the sensor is not in direct physical contact with a surface of foot 3505 or touching a surface of foot 3505 in a partial way.

Figure 36:
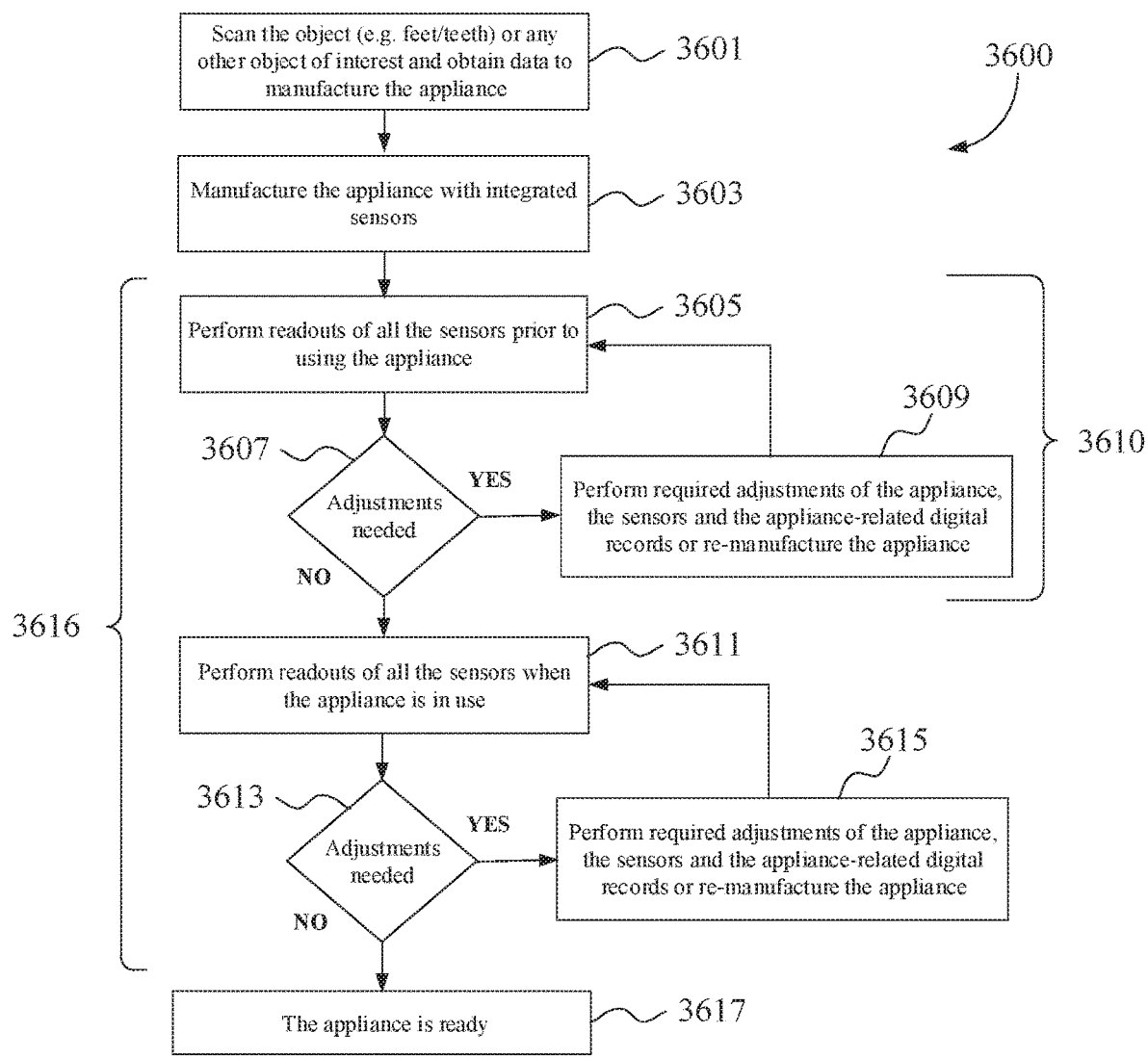
FIG. 36 may depict a flow diagram illustrating steps in a method for initial manufacturing of a given appliance of interest (such as, but not limited to, an orthodontics bracers aligner with sensor tags and/or a foot orthotic with sensor tags).

FIG. 36 may depict a flow diagram illustrating steps in a method 3600 for initial manufacturing of a given appliance of interest. In some embodiments, an appliance of interest may be aligner 3400 with at least one monitoring-sensor-tag 120 and/or with at least one lattice-of-sensor 1023 as shown and discussed in figures FIG. 34A through FIG. 34E. In some embodiments, an appliance of interest may be orthotic 3501 with at least one monitoring-sensor-tag 120 and/or with at least one lattice-of-sensor 1023 as shown and discussed in figures FIG. 35A through FIG. 35J.

Continuing discussing FIG. 36, in some embodiments method 3600 may comprise step 3601; wherein step 3601 may be a step of scanning the organ or objects. That is, in some embodiments, method 3600 may begin with scanning the organ or objects for which the appliances of interest are to be manufactured, e.g., feet 3505 or teeth 1000, or any other object of interest, and obtain data to manufacture the appliance, which may be a given orthotic 3501 or a given aligner 3400.

Continuing discussing FIG. 36, in some embodiments, method 3600 may comprise step 3603. In some embodiments, successful conclusion of step 3601 may then transition into step 3603. In some embodiments, step 3603 may be a step of manufacturing the appliance of interest (e.g., the given orthotic 3501 or the given aligner 3400) with integrated and/or embedded sensors (e.g., at least one monitoring-sensor-tag 120 and/or at least one lattice-of-sensor 1023) according to the measurements obtained from the scanning step 3601. In some embodiments the step 3603 may be done using the data obtained in step 3601.

Continuing discussing FIG. 36, in some embodiments, method 3600 may comprise step 3605. In some embodiments, successful conclusion of step 3603 may then transition into step 3605. In some embodiments, step 3605 may be a step of performing readouts (data outputs) of all (or a subset of) the sensors prior to using the appliance of interest. That is, step 3605 may be a step of scanning, reading, and/or interrogating all (or a subset of) the various sensors of the at least one monitoring-sensor-tag 120 and/or of the least one lattice-of-sensor 1023 that may be fitted with the given appliance of interest. This may be done to determine and/or verify functionality of the sensors from the at least one monitoring-sensor-tag 120 and/or of the least one lattice-of-sensor 1023.

Continuing discussing FIG. 36, in some embodiments, method 3600 may comprise step 3607. In some embodiments, step 3607 may follow step 3605. In some embodiments, step 3607 may be a step of determining if adjustments in the appliance of interest may be needed or desired. If yes adjustments may be needed or desired, then method 3600 may progress to step 3609. If no adjustments may be needed or desired, then method 3600 may progress to step 3611. In some embodiments, criteria for evaluating step 3607 may comprise, but may not be limited to, matching the embedded sensors readouts to the expected values for such sensors when the given appliance of interest may not be in use.

Continuing discussing FIG. 36, in some embodiments, method 3600 may comprise step 3609. In some embodiments, step 3609 may follow a "yes" outcome of step 3607. In some embodiments, step 3609 may be a step of performing required (or desired) adjustments of the appliance of interest. In some embodiments, step 3609 may include adjustment and/or calibration of the embedded or integrated sensors. In some embodiments, step 3609 may include adjustments or processing of the appliance of interest's related digital records. In some embodiments, step 3609 may include re-manufacturing of the appliance of interest if adjustments of the existing appliance of interest is not practically feasible and/or not desirable.

Continuing discussing FIG. 36, in some embodiments, following Step 3609 of the method 3600 may progress back to step 3605.

Continuing discussing FIG. 36, in some embodiments, method 3600 may comprise step 3611. In some embodiments, step 3611 may follow a "no" outcome of step 3607. In some embodiments, step 3611 may be a step of performing readouts of all the sensors when the appliance of interest may in use (e.g., aligner 3400 being worn on teeth 1000 or orthotics 3501 being used in shoes 3503 and/or with feet 3505). That is, step 3611 may be a step of scanning, reading, and/or interrogating all (or a subset of) the various sensors of the at least one monitoring-sensor-tag 120 and/or of the least one lattice-of-sensor 1023 that may be fitted with the given appliance of interest and while that appliance of interest may be in use with the given patient.

Continuing discussing FIG. 36, in some embodiments, method 3600 may comprise step 3613. In some embodiments, step 3613 may follow step 3611. In some embodiments, step 3613 may be a step of determining if adjustments in the appliance of interest may be needed or desired. If yes adjustments may be needed or desired, then method 3600 may progress to step 3615. If no adjustments may be needed or desired, then method 3600 may progress to step 3617. In some embodiments, criteria for evaluating step 3613 may comprise, but may not be limited to, matching the embedded sensors readouts (data outputs) to the expected values.

Continuing discussing FIG. 36, in some embodiments, method 3600 may comprise step 3615. In some embodiments, step 3615 may follow a "yes" outcome of step 3613. In some embodiments, step 3615 may be a step of performing required (or desired) adjustments of the appliance of interest. In some embodiments, step 3615 may include adjustment and/or calibration of the embedded or integrated sensors. In some embodiments, step 3615 may include adjustments or processing of the appliance of interest's related digital records. In some embodiments, step 3615 may include re-manufacturing of the appliance of interest if adjustments of the existing appliance of interest is not practically feasible and/or if not desirable.

Continuing discussing FIG. 36, in some embodiments, following Step 3615 of the method 3600 may progress back to step 3611.

Continuing discussing FIG. 36, in some embodiments, method 3600 may comprise step 3617. In some embodiments, step 3617 may follow a "no" outcome of step 3613. In some embodiments, step 3617 may be a final step of the method 3600 indicating that the appliance of interest is ready for its intended use.

Continuing discussing FIG. 36, in some embodiments, steps 3605, 3607, 3609, 3611, 3613, and 3615 of method 3600 may be designated as step 3616. In some embodiments, step 3616 may be a readout-and-adjustment loop step. In some embodiments, step 3616 may comprise steps 3605, 3607, 3609, 3611, 3613, and 3615. In some embodiments, step 3616 may play a role in method 3700 of FIG. 37.

Continuing discussing FIG. 36, in some embodiments, steps 3605 to 3609 (e.g., 3605, 3607, and 3609) of method 3600 may be designated as step 3610. In some embodiments, step 3610 may be a pre-use readout-and-adjustment loop step. In some embodiments, step 3610 may comprise steps 3605, 3607, and 3609. In some embodiments, step 3610 may play a role in method 3800 of FIG. 38.

Figure 37:
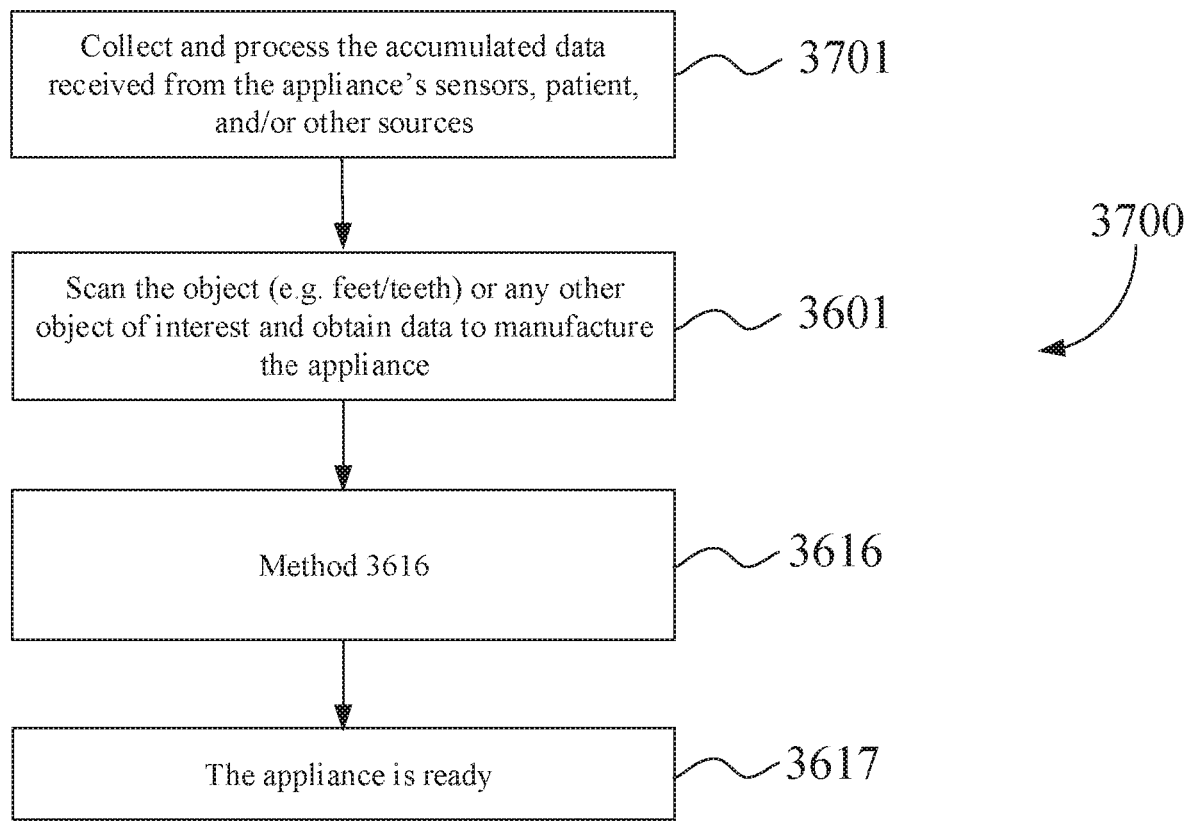
FIG. 37 may depict a flow diagram illustrating steps in a method which may target a case wherein a patient is at the practitioner's office for the patient's checkup or for a checkup of the appliance of interest or a planned update or re-manufacturing of the appliance of interest; and therefore the practitioner may have a physical access (as opposed to access to remotely transmitted data from out-of-office locations) to the given appliance of interest and the patient. In some embodiments, the above method in FIG. 37 may be a method of assessing performance of the given appliance of interest in the presence or proximity of the given practitioner.

FIG. 37 may depict a flow diagram illustrating steps in method 3700. In some embodiments method 3700 may target a case wherein a patient is at the practitioner's office for patient's checkup or for a checkup of the appliance of interest (e.g., from method 3600 of FIG. 36) or a planned update or re-manufacturing of appliance of interest (e.g., from method 3600 of FIG. 36); and therefore the practitioner may have a physical access (as opposed to access to remotely transmitted data from out-of-office locations) to the given appliance of interest and the patient. In some embodiments, method 3700 may a method of assessing performance of the given appliance of interest in the presence or proximity of the given practitioner. In some embodiments, the appliance of interest in method 3700 may be the appliance of interest manufactured in method 3600 discussed above. In some embodiments, the appliance of interest may be aligner 3400 with at least one monitoring-sensor-tag 120 and/or with at least one lattice-of-sensor 1023 as shown and discussed in figures FIG. 34A through FIG. 34E. In some embodiments, the appliance of interest may be orthotic 3501 with at least one monitoring-sensor-tag 120 and/or with at least one lattice-of-sensor 1023 as shown and discussed in figures FIG. 35A through FIG. 35J.

Continuing discussing FIG. 37, in some embodiments method 3700 may comprise step 3701. In some embodiments, step 3701 may be a step of collecting (and processing in some embodiments) the accumulated data received: from the appliance of interest's sensors; from the patient for whom the appliance of interest is intended; and/or from other sources. In some embodiments step 3701 may include collecting the data received from the appliance of interest's sensors while in practitioner's office. In some embodiments step 3701 may include collecting the data received from the appliance of interest's sensors while outside of the practitioner's office. In some embodiments step 3701 may include processing data collected throughout an effective lifetime of the appliance of interest and/or data collected throughout the lifetime of scanning the patient; and/or data collected from other sources. For example, and without limiting the scope of the present invention, data from other sources could be previous dental records that may be of assistance to an orthodontist or a specialist, so that such additional data could be taken into consideration in the process of assessing, updating, repairing or re-manufacturing appliance of interest by the specialist.

Continuing discussing FIG. 37, in some embodiments, method 3700 may comprise step 3601 from method 3600. In some embodiments, successful conclusion of step 3701 may then transition into step 3601 of method 3700. In some embodiments, step 3601 of method 3700 may operate as step 3601 was discussed above for method 3600.

Continuing discussing FIG. 37, in some embodiments, method 3700 may comprise step 3616 from method 3600. In some embodiments, successful conclusion of step 3601 may then transition into step 3616 of method 3700. In some embodiments, step 3616 of method 3700 may operate as step 3616 was discussed above for method 3600.

In some embodiments, successful conclusion of step 3616 in method 3700 may then transition into step 3617 of method 3700. In some embodiments, step 3617 may be a final step of the method 3700 indicating that the appliance of interest is ready for its intended use.

Figure 38:
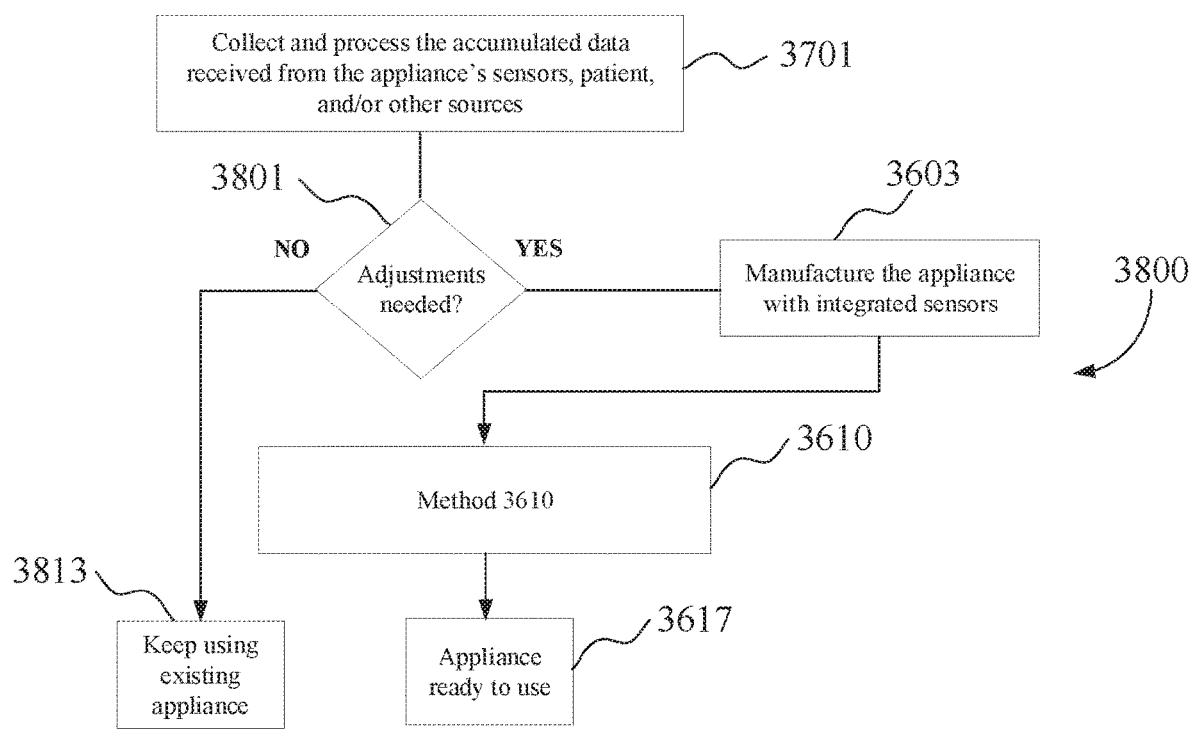
FIG. 38 may depict a flow diagram illustrating steps in a method which may target a case wherein a patient is away from the practitioner's office and the practitioner only has access to remotely transmitted data from the appliance of interest and/or from the patient.

FIG. 38 may depict a flow diagram illustrating steps in method 3800. In some embodiments method 3800 may target a case wherein a patient is away from the practitioner's office and the practitioner only has access to remotely transmitted data from the appliance of interest and/or from the patient. In some embodiments, the appliance of interest in method 3800 may be the appliance of interest manufactured in method 3600 and/or the appliance of interest altered or manufactured in method 3700. In some embodiments, the appliance of interest may be aligner 3400 with at least one monitoring-sensor-tag 120 and/or with at least one lattice-of-sensor 1023 as shown and discussed in figures FIG. 34A through FIG. 34E. In some embodiments, the appliance of interest may be orthotic 3501 with at least one monitoring-sensor-tag 120 and/or with at least one lattice-of-sensor 1023 as shown and discussed in figures FIG. 35A through FIG. 35J.

Continuing discussing FIG. 38, in some embodiments method 3800 may comprise step 3701 of method 3800. In some embodiments, step 3701 of method 3800 may operate as step 3701 was discussed above for method 3700; in step 3701 of method 3800 this data may be coming from a remote location with respect to the practitioner's location and then being transmitted from that remote location to the practitioner's location using at least portions of one or more data networks, such as, but not limited to, LANs (local area networks), WANs (wide area networks), the Internet, cellular networks, and/or the like.

Continuing discussing FIG. 38, in some embodiments method 3800 may comprise step 3801. In some embodiments, step 3801 may follow step 3701. In some embodiments, step 3801 may be a step of determining if adjustments in the appliance of interest may be needed or desired. If yes adjustments may be needed or desired, then method 3800 may progress to step 3603 of method 3800. In some embodiments, step 3603 may be a step of having a new appliance of interest manufactured. In some embodiments, step 3603 of method 3800 may operate as step 3603 was discussed above for method 3600. If no adjustments may be needed or desired, then method 3800 may progress to step 3813 from step 3801. In some embodiments, criteria for evaluating step 3801 may comprise, but may not be limited to, matching the embedded sensors readouts to the expected values for such sensors for the given patient.

Continuing discussing FIG. 38, in some embodiments, step 3813 may be a final step of the method 3800 indicating that no changes in the appliance of interest are necessary and the patient may continue using the existing appliance of interest.

Continuing discussing FIG. 38, in some embodiments, method 3800 may comprise step 3610 of method 3800. In some embodiments, successful conclusion of step 3603 may then transition into step 3610. In some embodiments, step 3610 of method 3800 may operate as step 3610 was discussed above for method 3600.

In some embodiments, successful conclusion of step 3610 in method 3800 may then transition into step 3617. In some embodiments, step 3617 may be a final step of the method 3800 indicating that the appliance of interest is ready for its intended use and may be provided to the patient (e.g., shipped or picked up by the patient).

In some embodiments, the lattice-of-sensors 1023 may not have any antennas other than an antenna associated with first-sensor-tag 1020. That is, in some embodiments, the plurality of sensors that may be a region of lattice-of-sensors 1023 may have no antennas.

In some embodiments, the lattice-of-sensors 1023 may have one or more antennas that may be in addition to an antenna associated with first-sensor-tag 1020. That is, in some embodiments, the plurality of sensors that may be a region of lattice-of-sensors 1023 may have its own one or more antennas. Such antennas may be for wireless communications, such as using radio frequencies, such as RFID, such as NFC, such as WiFi, such as Bluetooth, and/or the like.

In some embodiments the invention may be a system for monitoring orthotic performance. In some embodiments, this system may comprise orthotic 3501 for use within shoe 3503. In some embodiments, orthotic 3501 may be as described above, e.g., orthotic 3501 may comprise one or more monitoring-sensor-tags 120/1020. In some embodiments, this system may further comprise one or more reader(s) for receiving the one or more readings, wherein such a reader may be an electronic computing device. For example, and without limiting the scope of the present invention, in some embodiments, this reader may be reader 100, reader-and-calibration-member 1109, mobile-computing-device 3450, reader 3509, mat-reader 3511, and/or the like.

In some embodiments, this reader may be in wireless communication with the at least one antenna 130 of the one or more monitoring-sensor-tags 120/1020, wherein this reader may comprise its own antenna (such as, but not limited to, antenna 110) for such wireless communications with the one or more monitoring-sensor-tags 120/1020. In some embodiments, such wireless communications may be RFID, NFC, WiFi, Bluetooth, and/or the like.

In some embodiments, this reader may be in wired communication with the at least one circuit (e.g., 140) of the one or more monitoring-sensor-tags 120/1020. See e.g., FIG. 35C and FIG. 35D.

In some embodiments, this reader may be a mat (e.g., mat-reader 3511) configured to be stood upon by shoe 3503 with orthotic 3501; wherein such a mat may be in wireless communication with the at least one antenna 130 of the one or more monitoring-sensor-tags 120/1020, wherein such a mat may comprise an antenna (e.g., WiFi-antenna 3513) for such wireless communications with the one or more monitoring-sensor-tags 120/1020. In some embodiments, this reader may use its antenna to wirelessly communicate with mobile-computing-device 3450. In some embodiments, this reader may comprise a WiFi antenna (e.g., WiFi-antenna 3513) for wireless communications with an electrical computing device (e.g., mobile-computing-device 3450) that is separate (different) from this reader.

In some embodiments, this reader may comprise a memory (e.g., memory 1803) for the non-transitory storage of the one or more readings obtained from the one or more monitoring-sensor-tags 120/1020.

In some embodiments, this reader comprises a power-source (e.g., power-source 3517) for electrically powering electronic components of this reader. In some embodiments, this reader may comprise a wireless charging source (e.g., wireless charging source 3515) that may be operationally linked to this power-source; wherein upon the wireless charging source receiving electromagnetic energy of a predetermined quality, the wireless charging source may convert at least a portion of this received electromagnetic energy for electrical power use by the power-source.

In some embodiments, this system may comprise a set of programmed computer instructions that may be non-transitorily stored within memory (e.g., memory 1803) of a computing device that may be separate (different) from orthotic 3501; wherein this set of programmed computer instructions may be executable by a processor (e.g., processor 1801) of the computing device that may be operationally linked to this memory; wherein the set of programmed computer instructions may govern communications between this reader and the orthotic 3501 and how the one or more readings obtained from the at least one monitoring-sensor-tag 120/1020 may be handled. For example, and without limiting the scope of the present invention, this set of programmed computer instructions may perform steps from FIG. 36, FIG. 37, FIG. 38, and/or the like. In this paragraph, this computing device may be the reader and/or may be mobile-computing-device 3450. Note, in some embodiments, mobile-computing-device 3450 may be an example of a reader; whereas, in other embodiments, mobile-computing-device 3450 may not be a reader, but may be in communication with the reader.

Note, monitoring-sensor-tag 120 may be referred to herein as an electronic sensor circuit; and/or monitoring-sensor-tags 120 may be referred to herein as an electronic sensor circuits. Herein, electronics sensor circuit(s) may be used interchangeably with monitoring-sensor-tag(s) 120.

Note, lattice-of-sensors 1023 may be referred to herein as an electronic sensor circuit; and/or two or more lattice-of-sensors 1023 may be referred to herein as an electronic sensor circuits. Herein, electronics sensor circuit(s) may be used interchangeably with lattice-of-sensors 1023.

Any of the sensors described herein and/or shown in the figures may be configured to take at least one reading. Any of the sensors described herein and/or shown in the figures may be configured to take at least one reading of the material-of-interest 1028.

Note, the sensors discussed herein may not use wells, analytes, chemistry, nor biochemistry as a basis for their sensing/measuring capability; but rather, may use electrics, electrical circuits, and/or electromagnetic radiation (e.g., radio waves) for their sensing/measuring capabilities.

Monitoring-sensor-tags, systems for utilizing such, and methods of use have been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching without departing from the spirit of the invention.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. An orthodontic aligner that is configured to fit onto teeth for a purpose of changing an alignment of the teeth over time, wherein the orthodontic aligner comprises:
    a plurality of linearly linked tooth-wells, wherein each tooth-well selected from the plurality of linearly linked tooth-wells is configured to fit onto a specific tooth of the teeth; and two or more distinct lattice-of-sensors, wherein each distinct lattice-of-sensors selected from the two or more distinct lattice-of-sensors comprises:
  a plurality of sensors made up of at least two different types of sensors, wherein the plurality of sensors are configured to sense at least one property of a material-of-interest;
  at least one antenna configured to receive electromagnetic energy;
  at least one processing circuitry that is operatively coupled to both the plurality of sensors and to the at least one antenna;
  wherein the at least one processing circuitry and the plurality of sensors for a given distinct lattice-of-sensors selected from the two or more distinct lattice-of-sensors both occupy a same tooth-well selected from the plurality of linearly linked tooth-wells;
  wherein when the at least one antenna, from the given distinct lattice-of-sensors selected from the two or more distinct lattice-of-sensors, receives the electromagnetic energy, the at least one processing circuitry, of the given distinct lattice-of-sensors selected from the two or more distinct lattice-of-sensors, uses at least a portion of that received electromagnetic energy to: (a) power that given distinct lattice-of-sensors selected from the two or more distinct lattice-of-sensors; (b) cause at least one of the plurality of sensors, from the given distinct lattice-of-sensors selected from the two or more distinct lattice-of-sensors, to take at least one reading; and (c) to then wirelessly transmit that at least one reading out through the at least one antenna, of that given distinct lattice-of-sensors selected from the two or more distinct lattice-of-sensors;
  wherein each distinct lattice-of-sensors selected from the two or more distinct lattice-of-sensors is passively powered from the electromagnetic energy and not from an internal power source;
  wherein each distinct lattice-of-sensors selected from the two or more distinct lattice-of-sensors is attached to at least one tooth-well selected from the plurality of linearly linked tooth-wells.

2. The orthodontic aligner of claim 1, wherein the plurality of linearly linked tooth-wells is substantially optically transparent.

3. The orthodontic aligner of claim 1, wherein a sensor selected from plurality of sensors is configured to measure at least one of: capacitance, resistance, or inductance, of the material-of-interest.

4. The orthodontic aligner of claim 1, wherein the material-of-interest is the at least one tooth-well that at least one of the distinct lattice-of-sensors selected from the two or more distinct lattice-of-sensors is attached to.

5. The orthodontic aligner of claim 1, wherein the material-of-interest is a tooth, wherein the tooth is configured to fit into the at least one tooth-well that at least one of distinct lattice-of-sensors selected from the two or more distinct lattice-of-sensors is attached to.

6. The orthodontic aligner of claim 1, wherein at least a portion of a distinct lattice-of-sensors selected from the two or more distinct lattice-of-sensors is configured to physically contact a tooth, wherein the tooth is fitted into the at least one tooth-well that the distinct lattice-of-sensors selected from the two or more distinct lattice-of-sensors is attached to.

7. The orthodontic aligner of claim 1, wherein at least one distinct lattice-of-sensors selected from the two or more distinct lattice-of-sensors is embedded entirely within the at least one tooth-well that the at least one distinct lattice-of-sensors selected from the two or more distinct lattice-of-sensors is attached to.

8. The orthodontic aligner of claim 1, wherein at least one distinct lattice-of-sensors selected from the two or more distinct lattice-of-sensors is on an exterior surface of the at least one tooth-well that the at least one distinct lattice-of-sensors selected from the two or more distinct lattice-of-sensors is attached to.

9. The orthodontic aligner of claim 1, wherein at least one distinct lattice-of-sensors selected from the two or more distinct lattice-of-sensors is at least partially on an exterior surface of the at least one tooth-well that the at least one distinct lattice-of-sensors selected from two or more distinct lattice-of-sensors is attached to; and another of the distinct lattice-of-sensors is at least partially embedded within the at least one tooth-well that another of the distinct lattice-of-sensors selected from the two or more distinct lattice-of-sensors is attached to.

10. The orthodontic aligner of claim 1, wherein a distinct lattice-of-sensors selected from the two or more distinct lattice-of-sensors is located at a predetermined location of the at least one tooth-well that the distinct lattice-of-sensors selected from the two or more distinct lattice-of-sensors is attached to.

11. The orthodontic aligner of claim 10, wherein the predetermined location is selected from one or more of: a side of the at least one tooth-well towards a tongue, a side of the at least one tooth-well towards a lip, a bottom of the at least one tooth-well, or a top of the at least one tooth-well.

12. The orthodontic aligner of claim 1, wherein a distinct lattice-of-sensors selected from the two or more distinct lattice-of-sensors is assigned a predetermined unique identifier that corresponds with the at least one tooth-well that the distinct lattice-of-sensors selected from the two or more distinct lattice-of-sensors is attached to.

13. The orthodontic aligner of claim 1, wherein the at least one reading is of one or more of: inductance, capacitance, or resistance.

14. The orthodontic aligner of claim 1, wherein the at least one reading provides information to determine one or more of: structural integrity current state of the orthodontic aligner; structural integrity changes of the orthodontic aligner; pressure received at the orthodontic aligner; force received at the orthodontic aligner; stress received at the orthodontic aligner; torsion received at the orthodontic aligner; deformation received at the orthodontic aligner; temperature at the orthodontic aligner; positional changes of a first distinct lattice-of-sensors selected from the two or more distinct lattice-of-sensors with respect to position of a second distinct lattice-of-sensors selected from the two or more distinct lattice-of-sensors; or positional changes of at least one distinct lattice-of-sensors selected from the two or more distinct lattice-of-sensors with respect to time.

15. The orthodontic aligner of claim 1, wherein when the at least one processing circuitry causes the at least one antenna to transmit the at least one reading, the at least one processing circuitry also causes the at least one antenna to transmit additional information.

16. The orthodontic aligner of claim 15, wherein
  the additional information is selected from one or more of: identification information for a distinct lattice-of-sensors selected from the two or more distinct lattice-of-sensors that is transmitting; model number for the distinct lattice-of-sensors selected from the two or more distinct lattice-of-sensors that is transmitting; serial number for the distinct lattice-of-sensors selected from the two or more distinct lattice-of-sensors that is transmitting; manufacturer of the distinct lattice-of-sensors selected from the two or more distinct lattice-of-sensors that is transmitting; year of manufacture of the distinct lattice-of-sensors selected from the two or more distinct lattice-of-sensors that is transmitting; a request for a security code associated with that distinct lattice-of-sensors selected from the two or more distinct lattice-of-sensors that is transmitting; a cyclic redundancy check code for the distinct lattice-of-sensors selected from the two or more distinct lattice-of-sensors that is transmitting; a parity check code for the distinct lattice-of-sensors selected from the two or more distinct lattice-of-sensors that is transmitting; or receipt of a disable instruction for the distinct lattice-of-sensors selected from the two or more distinct lattice-of-sensors that is transmitting.

17. The orthodontic aligner of claim 1, wherein spacing between two adjacent sensors selected from the plurality of sensors of the given distinct lattice-of-sensors selected from the two or more distinct lattice-of-sensors is initially known by a system that utilizes the orthodontic aligner; and wherein changes in that spacing over time is determinable by the system.

18. The orthodontic aligner of claim 1, wherein spacing between at least two of the two or more distinct lattice-of-sensors is initially predetermined and known by a system that utilizes the orthodontic aligner; and wherein changes in that spacing over time is determinable by the system.

19. The orthodontic aligner of claim 1, wherein each lattice-of-sensors selected from the two or more distinct lattice-of-sensors is a substantially two-dimensional layer, such that the two or more distinct lattice-of-sensors is a substantially three-dimensional structure.

* * * * *